US010544212B2

(12) United States Patent
Bloom et al.

(10) Patent No.: US 10,544,212 B2
(45) Date of Patent: Jan. 28, 2020

(54) ANTI-IL-33 ANTIBODIES, COMPOSITIONS, METHODS AND USES THEREOF

(71) Applicant: Pfizer Inc., New York, NY (US)

(72) Inventors: Laird Bloom, Needham, MA (US); Karl Henry Nocka, Harvard, MA (US); James Reasoner Apgar, Newton, MA (US); Matthew Allister Lambert, Dublin (IE); Mark A. Farmer, North Reading, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/495,172

(22) Filed: Apr. 24, 2017

(65) Prior Publication Data

US 2018/0037644 A1 Feb. 8, 2018

Related U.S. Application Data

(60) Provisional application No. 62/328,294, filed on Apr. 27, 2016, provisional application No. 62/483,781, filed on Apr. 10, 2017.

(51) Int. Cl.
*C07K 16/24* (2006.01)
*A61K 39/395* (2006.01)
*A61K 39/00* (2006.01)

(52) U.S. Cl.
CPC ........ *C07K 16/244* (2013.01); *A61K 39/3955* (2013.01); *A61K 2039/505* (2013.01); *A61K 2039/55527* (2013.01); *C07K 2317/33* (2013.01); *C07K 2317/35* (2013.01); *C07K 2317/515* (2013.01); *C07K 2317/56* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS 5,624,821 A 4/1997 Winter

FOREIGN PATENT DOCUMENTS

| | | |
|---|---|---|
| EP | 17255261 | 1/2011 |
| WO | 2003048731 | 6/2003 |
| WO | 2005079844 | 9/2005 |
| WO | 2008144610 | 11/2008 |
| WO | 2009124090 | 10/2009 |
| WO | 2011031600 | 3/2011 |
| WO | 2012083132 | 6/2012 |
| WO | 2012113813 | 8/2012 |
| WO | 2012113927 | 8/2012 |
| WO | 2013126834 | 8/2013 |
| WO | 2013173761 | 11/2013 |
| WO | 2014044681 | 3/2014 |
| WO | 2014062621 | 4/2014 |
| WO | 2014152195 | 9/2014 |
| WO | 2014164959 | 10/2014 |
| WO | 2015099175 | 7/2015 |
| WO | 2015106080 | 7/2015 |
| WO | 2015164354 | 10/2015 |
| WO | 2016077366 | 5/2016 |
| WO | 2016077381 | 6/2016 |
| WO | 2016156440 | 10/2016 |
| WO | 2017062456 | 4/2017 |
| WO | 2017124110 | 7/2017 |

OTHER PUBLICATIONS

Lloyd et al; Protein Engineering, Design & Selection 2009, 22:159-168.*
MacCallum et al. Journal of Molecular Biology, 1996; 262:732-745.*
Casset et al. (Biochemical and Biophysical Research Communications, 2003; vol. 307, pp. 198-205.*
Rudikoff et al ; Proceeding of the National Academy of Sciences, 1982; 79(6):1979-1983.*
Brekke et al.; "Therapeutic Antibodies for Human Diseases at the Dawn of the Twenty-First Century"; Nature Reviews; vol. 2; pp. 52-62; 2003.
Cayrol et al.; "IL-33: an alarmin cytokine with crucial roles in innate immunity, inflammation and allergy"; Current Opinion in Immunology, vol. 31; pp: 31-37; 2014.
Chelius et al.; "Identification and Characterization of Deamidation Sites in the Conserved Regions of Human Immunoglobulin Gamma Antibodies"; Anal. Chem.; vol. 77; pp. 6004-6011; 2005.
Chu et al.; "IL-33, but not thymic stromal lymphopoietin or IL-25, is central to mite and peanut allergic sensitization" American Academy of Allergy, Asthma & Immunology; vol. 131; pp. 187-200.e8.
Cohen et al.; "Oxidation of the alarmin IL-33 regulates ST2-dependent inflammation" Nature Communi.; vol. 8; pp. 1-10; 2015; doi:10.1038/ncomms9327.
Coyle et al. "Crucial Role of the Interleukin 1 Receptor Family Member T1/ST2 in T Helper Cell Type 2—mediated Lung Mucosal Immune Responses" J. Exp. Med.; vol. 190; No. 7; pp. 895-902; 1999.
Hara et al.; "Airway Uric Acid is a Sensor of Inhaled Protease Allergens and Initiates Type 2 Immune Responses in Respiratory Mucosa" J. Immunol.; vol. 192; pp. 4032-4042; 2014.
Maier et al.; "Human Th2 but Not Th9 Cells Release IL-31 in a STAT6/NF-kB—Dependent Way" J Immunol.; vol. 193; pp. 645-654; 2014.
Molofsky et al.; "Interleukin-33 in Tissue Homeostasis, Injury, and Inflammation" Immunity; vol. 42; pp. 1005-1019.
Rivellese et al.; "IgE and IL-33-mediated triggering of human basophils inhibits TLR4-induced monocyte activation" Eur J. Immunol.; vol. 44; pp. 3045-3055; 2014.

(Continued)

*Primary Examiner* — Bridget E Bunner
*Assistant Examiner* — Fozia Hamud

(57) ABSTRACT

The invention provides antibodies, and antigen-binding fragments thereof, that specifically bind to IL-33, as well as uses, and associated methods thereof.

18 Claims, 3 Drawing Sheets

Specification includes a Sequence Listing.

(56) References Cited

OTHER PUBLICATIONS

Singh et al. Developability of Biotherapeutics: Computational Approaches; CRC Press; chapter 5 "Application of mechanistic pharmacokinetic-pharmacodynamic modeling towards the development of biologics"; pp. 109-134; 2015.
Suzukawa et al. "An IL-1 Cytokine Member, IL-33, Induces Human Basophil Activation via its ST2 Receptor" J. Immunol.; vol. 181; pp. 5981-5989; 2008.
Vocca et al. "IL-33/ST2 axis controls Th2/IL-31 and Th17 immune response inallergic airway diseases" Immunobiology; vol. 220; pp. 954-963; 2015.
Zalevsky et al. "Enhanced antibody half-life improves in vivo activity" Nature Biotechnology; vol. 28; No. 2; pp. 157-159; 2010.
Chu et al.; "IL-33, but not thymic stromal lymphopoietin or IL-25, is central to mite and peanut allergic sensitization" American Academy of Allergy, Asthma & Immunology; vol. 131; pp. 187-200.e8, 2013.
Molofsky et al.; "Interleukin-33 in Tissue Homeostasis, Injury, and Inflammation" Immunity; vol. 42; pp. 1005-1019, Jun. 2015.

* cited by examiner

```
DP54JK4      1 EVQLVESGGGLVQPGGSLRLSCAASGFTFSSYWMSWVRQAPGKGLEWVANIKQDGSEKYY 60
               ||||||||||||||||||||||||||||||||.|||||||||.|||||||.|..|.|.||
IL33-158_VH  1 EVQLVESGGGLVQPGGSLRLSCAASGFTFSSYWMSWVRQAPGKGLEWVASITPNAGKDIY 60

DP54JK4     57 VDSVKGRFTISRDNAKNSLYLQMNSLRAEDTAVYYCAR--------YFDYWGQGTLVTVSS 113
               ..||||||||||||||||||||||||||||||||||||        ...||||||||||||
IL33-158_VH 57 PDSVKGRFTISRDNAKNSLYLQMNSLRAEDTAVYYCARGHYYTSYSLGYWGQGTLVTVSS 121

DPK9JK4      1 DIQMTQSPSSLSASVGDRVTITCRASQSISSYLNWYQQKPGKAPKLLIYAASSLQSGVPS 60
               |||||||||||||||||||||||||||.|||....|.||||||||||||....||||||
IL33-158_VL  1 DIQMTQSPSSLSASVGDRVTITCRASQNINKHLDWYQQKPGKAPKLLIYFTNNLQTGVPS 60

DPK9JK4     61 RFSGSGSGTDFTLTISSLQPEDFATYYCQQSYSTPLTFGGGTKVEIK 107
               ||||||||||||||||||||||||||||.|.|....|||||||||||
IL33-158_VL 61 RFSGSGSGTDFTLTISSLQPEDFATYYCFQ-YNQGWTFGGGTKVEIK 106
```

FIG. 2A

```
DP54JK4      1 EVQLVESGGGLVQPGGSLRLSCAASGFTFSSYWMSWVRQAPGKGLEWVANIKQDGSEKYY 60
               ||||||||||||||||||||||||||||||||.|||||||||.|||||||.|..|.|.||
IL33-167_VH  1 EVQLVESGGGLVQPGGSLRLSCAASGFTFSSYNMSWVRQAPGKGLEWVASITPNAGKDIY 60

DP54JK4     57 VDSVKGRFTISRDNAKNSLYLQMNSLRAEDTAVYYCAR--------YFDYWGQGTLVTVSS 113
               ..||||||||||||||||||||||||||||||||||||        ...||||||||||||
IL33-167_VH 57 PDSVKGRFTISRDNAKNSLYLQMNSLRAEDTAVYYCARGHYYTSYSLGYWGQGTLVTVSS 121

DPK9JK4      1 DIQMTQSPSSLSASVGDRVTITCRASQSISSYLNWYQQKPGKAPKLLIYAASSLQSGVPS 60
               |||||||||||||||||||||||||||.|||....|.||||||||||||....||||||
IL33-167_VL  1 DIQMTQSPSSLSASVGDRVTITCRASQNINEHLDWYQQKPGKAPKLLIYFTNNLQTGVPS 60

DPK9JK4     54 RFSGSGSGTDFTLTISSLQPEDFATYYCQQSYSTPLTFGGGTKVEIK 107
               ||||||||||||||||||||||||||||.|.|....|||||||||||
IL33-167_VL 54 RFSGSGSGTDFTLTISSLQPEDFATYYCFQ-YNQGWTFGGGTKVEIK 106
```

FIG. 2B

SEQUENCE LISTING

<160> NUMBER OF SEQ ID NOS: 410

<210> SEQ ID NO 1
<211> LENGTH: 159
<212> TYPE: PRT
<213> ORGANISM: Artificial Sequence
<220> FEATURE:
<223> OTHER INFORMATION: Synthetic Construct

<400> SEQUENCE: 1

```
Ser Ile Thr Gly Ile Ser Pro Ile Thr Glu Tyr Leu Ala Ser Leu Ser
1               5                   10                  15

Thr Tyr Asn Asp Gln Ser Ile Thr Phe Ala Leu Glu Asp Glu Ser Tyr
            20                  25                  30

Glu Ile Tyr Val Glu Asp Leu Lys Lys Asp Glu Lys Lys Asp Lys Val
        35                  40                  45

Leu Leu Ser Tyr Tyr Glu Ser Gln His Pro Ser Asn Glu Ser Gly Asp
    50                  55                  60

Gly Val Asp Gly Lys Met Leu Met Val Thr Leu Ser Pro Thr Lys Asp
65                  70                  75                  80

Phe Trp Leu His Ala Asn Asn Lys Glu His Ser Val Glu Leu His Lys
                85                  90                  95

Cys Glu Lys Pro Leu Pro Asp Gln Ala Phe Phe Val Leu His Asn Met
            100                 105                 110

His Ser Asn Cys Val Ser Phe Glu Cys Lys Thr Asp Pro Gly Val Phe
        115                 120                 125

Ile Gly Val Lys Asp Asn His Leu Ala Leu Ile Lys Val Asp Ser Ser
    130                 135                 140

Glu Asn Leu Cys Thr Glu Asn Ile Leu Phe Lys Leu Ser Glu Thr
145                 150                 155
```

<210> SEQ ID NO 2
<211> LENGTH: 553
<212> TYPE: PRT
<213> ORGANISM: Artificial Sequence
<220> FEATURE:
<223> OTHER INFORMATION: Synthetic Construct

<400> SEQUENCE: 2

```
Lys Phe Ser Lys Gln Ser Trp Gly Leu Glu Asn Glu Ala Leu Ile Val
1               5                   10                  15

Arg Cys Pro Arg Gln Gly Lys Pro Ser Tyr Thr Val Asp Trp Tyr Tyr
            20                  25                  30

Ser Gln Thr Asn Lys Ser Ile Pro Thr Gln Glu Arg Asn Arg Val Phe
        35                  40                  45

Ala Ser Gly Gln Leu Leu Lys Phe Leu Pro Ala Glu Val Ala Asp Ser
    50                  55                  60

Gly Ile Tyr Thr Cys Ile Val Arg Ser Pro Thr Phe Asn Arg Thr Gly
65                  70                  75                  80

Tyr Ala Asn Val Thr Ile Tyr Lys Lys Gln Ser Asp Cys Asn Val Pro
                85                  90                  95

Asp Tyr Leu Met Tyr Ser Thr Val Ser Gly Ser Glu Lys Asn Ser Lys
            100                 105                 110

Ile Tyr Cys Pro Thr Ile Asp Leu Tyr Asn Trp Thr Ala Pro Leu Glu
        115                 120                 125

Trp Phe Lys Asn Cys Gln Ala Leu Gln Gly Ser Arg Tyr Arg Ala His
    130                 135                 140

Lys Ser Phe Leu Val Ile Asp Asn Val Met Thr Glu Asp Ala Gly Asp
145                 150                 155                 160

Tyr Thr Cys Lys Phe Ile His Asn Glu Asn Gly Ala Asn Tyr Ser Val
                165                 170                 175

Thr Ala Thr Arg Ser Phe Thr Val Lys Asp Glu Gln Gly Phe Ser Leu
            180                 185                 190
```

Phe Pro Val Ile Gly Ala Pro Ala Gln Asn Glu Ile Lys Glu Val Glu
            195                 200                 205

Ile Gly Lys Asn Ala Asn Leu Thr Cys Ser Ala Cys Phe Gly Lys Gly
        210                 215                 220

Thr Gln Phe Leu Ala Ala Val Leu Trp Gln Leu Asn Gly Thr Lys Ile
225                 230                 235                 240

Thr Asp Phe Gly Glu Pro Arg Ile Gln Gln Glu Gly Gln Asn Gln
                245                 250                 255

Ser Phe Ser Asn Gly Leu Ala Cys Leu Asp Met Val Leu Arg Ile Ala
                260                 265                 270

Asp Val Lys Glu Glu Asp Leu Leu Leu Gln Tyr Asp Cys Leu Ala Leu
            275                 280                 285

Asn Leu His Gly Leu Arg Arg His Thr Val Arg Leu Ser Arg Lys Asn
        290                 295                 300

Pro Ser Lys Glu Cys Phe Ile Glu Gly Arg Met Asp Pro Lys Ser Cys
305                 310                 315                 320

Asp Lys Thr His Thr Cys Pro Pro Cys Pro Ala Pro Glu Leu Leu Gly
                325                 330                 335

Gly Pro Ser Val Phe Leu Phe Pro Pro Lys Pro Lys Asp Thr Leu Met
                340                 345                 350

Ile Ser Arg Thr Pro Glu Val Thr Cys Val Val Val Asp Val Ser His
        355                 360                 365

Glu Asp Pro Glu Val Lys Phe Asn Trp Tyr Val Asp Gly Val Glu Val
        370                 375                 380

His Asn Ala Lys Thr Lys Pro Arg Glu Glu Gln Tyr Asn Ser Thr Tyr
385                 390                 395                 400

Arg Val Val Ser Val Leu Thr Val Leu His Gln Asp Trp Leu Asn Gly
                405                 410                 415

Lys Glu Tyr Lys Cys Lys Val Ser Asn Lys Ala Leu Pro Ala Pro Ile
            420                 425                 430

Glu Lys Thr Ile Ser Lys Ala Lys Gly Gln Pro Arg Glu Pro Gln Val
        435                 440                 445

Tyr Thr Leu Pro Pro Ser Arg Asp Glu Leu Thr Lys Asn Gln Val Ser
450                 455                 460

Leu Thr Cys Leu Val Lys Gly Phe Tyr Pro Ser Asp Ile Ala Val Glu
465                 470                 475                 480

Trp Glu Ser Asn Gly Gln Pro Glu Asn Asn Tyr Lys Thr Thr Pro Pro
                485                 490                 495

Val Leu Asp Ser Asp Gly Ser Phe Phe Leu Tyr Ser Lys Leu Thr Val
                500                 505                 510

Asp Lys Ser Arg Trp Gln Gln Gly Asn Val Phe Ser Cys Ser Val Met
            515                 520                 525

His Glu Ala Leu His Asn His Tyr Thr Gln Lys Ser Leu Ser Leu Ser
        530                 535                 540

Pro Gly Lys His His His His His
545                 550

<210> SEQ ID NO 3
<211> LENGTH: 166
<212> TYPE: PRT
<213> ORGANISM: Artificial Sequence
<220> FEATURE:
<223> OTHER INFORMATION: Synthetic Construct

<400> SEQUENCE: 3

Met Ser Ile Thr Gly Ile Ser Pro Ile Thr Glu Tyr Leu Ala Ser Leu
1               5                   10                  15

Ser Thr Tyr Asn Asp Gln Ser Ile Thr Phe Ala Leu Glu Asp Glu Ser
            20                  25                  30

Tyr Glu Ile Tyr Val Glu Asp Leu Lys Lys Asp Glu Lys Lys Asp Lys
                35                  40                  45

Val Leu Leu Ser Tyr Tyr Glu Ser Gln His Pro Ser Asn Glu Ser Gly
50                  55                  60

Asp Gly Val Asp Gly Lys Met Leu Met Val Thr Leu Ser Pro Thr Lys
65                  70                  75                  80

Asp Phe Trp Leu His Ala Asn Asn Lys Glu His Ser Val Glu Leu His
                85                  90                  95

Lys Ser Glu Lys Pro Leu Pro Asp Gln Ala Phe Phe Val Leu His Asn
                100                 105                 110

Met His Ser Asn Ser Val Ser Phe Glu Ser Lys Thr Asp Pro Gly Val
            115                 120                 125

Phe Ile Gly Val Lys Asp Asn His Leu Ala Leu Ile Lys Val Asp Ser
            130                 135                 140

Ser Glu Asn Leu Ser Thr Glu Asn Ile Leu Phe Lys Leu Ser Glu Thr
145                 150                 155                 160

His His His His His His
                165

<210> SEQ ID NO 4
<211> LENGTH: 169
<212> TYPE: PRT
<213> ORGANISM: Artificial Sequence
<220> FEATURE:
<223> OTHER INFORMATION: Synthetic Construct

<400> SEQUENCE: 4

Ser Ile Thr Gly Ile Ser Pro Ile Thr Glu Tyr Leu Ala Ser Leu Ser
1               5                   10                  15

Thr Tyr Asn Asp Gln Ser Ile Thr Phe Ala Leu Glu Asp Glu Ser Tyr
            20                  25                  30

Glu Ile Tyr Val Glu Asp Leu Lys Lys Asp Glu Lys Lys Asp Lys Val
        35                  40                  45

Leu Leu Ser Tyr Tyr Glu Ser Gln His Pro Ser Asn Glu Ser Gly Asp
50                  55                  60

Gly Val Asp Gly Lys Met Leu Met Val Thr Leu Ser Pro Thr Lys Asp
65                  70                  75                  80

Phe Trp Leu His Ala Asn Asn Lys Glu His Ser Val Glu Leu His Lys
                85                  90                  95

Cys Glu Lys Pro Leu Pro Asp Gln Ala Phe Phe Val Leu His Asn Met
                100                 105                 110

His Ser Asn Cys Val Ser Phe Glu Cys Lys Thr Asp Pro Gly Val Phe
            115                 120                 125

Ile Gly Val Lys Asp Asn His Leu Ala Leu Ile Lys Val Asp Ser Ser
            130                 135                 140

Glu Asn Leu Cys Thr Glu Asn Ile Leu Phe Lys Leu Ser Glu Thr Leu
145                 150                 155                 160

Glu Asp Tyr Lys Asp Asp Asp Lys
                165

<210> SEQ ID NO 5
<211> LENGTH: 166

```
<212> TYPE: PRT
<213> ORGANISM: Artificial Sequence
<220> FEATURE:
<223> OTHER INFORMATION: Synthetic Construct

<400> SEQUENCE: 5

Met Ser Ile Thr Gly Ile Ser Pro Ile Thr Glu Ser Leu Ala Ser Leu
1               5                   10                  15

Ser Thr Tyr Asn Asp Gln Ser Ile Thr Phe Ala Leu Glu Asp Glu Ser
            20                  25                  30

Tyr Glu Ile Tyr Val Glu Asp Leu Lys Lys Asp Lys Lys Asp Lys
        35                  40                  45

Val Leu Leu Ser Tyr Tyr Glu Ser Gln His Pro Ser Ser Glu Ser Gly
    50                  55                  60

Asp Gly Val Asp Gly Lys Met Leu Met Val Thr Leu Ser Pro Thr Lys
65                  70                  75                  80

Asp Phe Trp Leu Gln Ala Asn Asn Lys Glu His Ser Val Glu Leu His
                85                  90                  95

Lys Ser Glu Lys Pro Leu Pro Asp Gln Ala Phe Val Leu His Asn
            100                 105                 110

Arg Ser Phe Asn Ser Val Ser Phe Glu Ser Lys Thr Asp Pro Gly Val
        115                 120                 125

Phe Ile Gly Val Lys Asp Asn His Leu Ala Leu Ile Lys Val Asp Tyr
    130                 135                 140

Ser Glu Asn Leu Gly Ser Glu Asn Ile Leu Phe Lys Leu Ser Glu Ile
145                 150                 155                 160

His His His His His His
                165

<210> SEQ ID NO 6
<211> LENGTH: 533
<212> TYPE: PRT
<213> ORGANISM: Artificial Sequence
<220> FEATURE:
<223> OTHER INFORMATION: Synthetic Construct

<400> SEQUENCE: 6

Lys Phe Ser Lys Gln Ser Trp Gly Leu Glu Asn Glu Ala Leu Ile Val
1               5                   10                  15

Arg Cys Pro Arg Gln Gly Lys Pro Ser Tyr Thr Val Asp Trp Tyr Tyr
            20                  25                  30

Ser Gln Thr Asn Lys Ser Ile Pro Thr Gln Glu Arg Asn Arg Val Phe
        35                  40                  45

Ala Ser Gly Gln Leu Leu Lys Phe Leu Pro Ala Ala Val Ala Asp Ser
    50                  55                  60

Gly Ile Tyr Thr Cys Ile Val Arg Ser Pro Thr Phe Asn Arg Thr Gly
65                  70                  75                  80

Tyr Ala Asn Val Thr Ile Tyr Lys Lys Gln Ser Asp Cys Asn Val Pro
                85                  90                  95

Asp Tyr Leu Met Tyr Ser Thr Val Ser Gly Ser Glu Lys Asn Ser Lys
            100                 105                 110

Ile Tyr Cys Pro Thr Ile Asp Leu Tyr Asn Trp Thr Ala Pro Leu Glu
        115                 120                 125

Trp Phe Lys Asn Cys Gln Ala Leu Gln Gly Ser Arg Tyr Arg Ala His
    130                 135                 140

Lys Ser Phe Leu Val Ile Asp Asn Val Met Thr Glu Asp Ala Gly Asp
145                 150                 155                 160
```

Tyr Thr Cys Lys Phe Ile His Asn Glu Asn Gly Ala Asn Tyr Ser Val
            165                 170                 175

Thr Ala Thr Arg Ser Phe Thr Val Lys Asp Glu Gln Gly Phe Ser Leu
        180                 185                 190

Phe Pro Val Ile Gly Ala Pro Ala Gln Asn Glu Ile Lys Glu Val Glu
            195                 200                 205

Ile Gly Lys Asn Ala Asn Leu Thr Cys Ser Ala Cys Phe Gly Lys Gly
210                 215                 220

Thr Gln Phe Leu Ala Ala Val Leu Trp Gln Leu Asn Gly Thr Lys Ile
225                 230                 235                 240

Thr Asp Phe Gly Glu Pro Arg Ile Gln Gln Glu Glu Gly Gln Asn Gln
                245                 250                 255

Ser Phe Ser Asn Gly Leu Ala Cys Leu Asp Met Val Leu Arg Ile Ala
                260                 265                 270

Asp Val Lys Glu Glu Asp Leu Leu Leu Gln Tyr Asp Cys Leu Ala Leu
            275                 280                 285

Asn Leu His Gly Leu Arg Arg His Thr Val Arg Leu Ser Arg Lys Asn
290                 295                 300

Pro Ser Lys Glu Cys Phe Val Glu Cys Pro Pro Cys Pro Ala Pro Pro
305                 310                 315                 320

Val Ala Gly Pro Ser Val Phe Leu Phe Pro Pro Lys Pro Lys Asp Thr
                325                 330                 335

Leu Met Ile Ser Arg Thr Pro Glu Val Thr Cys Val Val Val Asp Val
                340                 345                 350

Ser His Glu Asp Pro Glu Val Gln Phe Asn Trp Tyr Val Asp Gly Met
            355                 360                 365

Glu Val His Asn Ala Lys Thr Lys Pro Arg Glu Glu Gln Phe Asn Ser
        370                 375                 380

Thr Phe Arg Val Val Ser Val Leu Thr Val Val His Gln Asp Trp Leu
385                 390                 395                 400

Asn Gly Lys Glu Tyr Lys Cys Lys Val Ser Asn Lys Gly Leu Pro Ala
                405                 410                 415

Pro Ile Glu Lys Thr Ile Ser Lys Thr Lys Gly Gln Pro Arg Glu Pro
            420                 425                 430

Gln Val Tyr Thr Leu Pro Pro Ser Arg Glu Glu Met Thr Lys Asn Gln
        435                 440                 445

Val Ser Leu Thr Cys Leu Val Lys Gly Phe Tyr Pro Ser Asp Ile Ala
450                 455                 460

Val Glu Trp Glu Ser Asn Gly Gln Pro Glu Asn Asn Tyr Lys Thr Thr
465                 470                 475                 480

Pro Pro Met Leu Asp Ser Asp Gly Ser Phe Phe Leu Tyr Ser Lys Leu
                485                 490                 495

Thr Val Asp Lys Ser Arg Trp Gln Gln Gly Asn Val Phe Ser Cys Ser
            500                 505                 510

Val Met His Glu Ala Leu His Asn His Tyr Thr Gln Lys Ser Leu Ser
        515                 520                 525

Leu Ser Pro Gly Lys
    530

<210> SEQ ID NO 7
<211> LENGTH: 113
<212> TYPE: PRT
<213> ORGANISM: Artificial Sequence
<220> FEATURE:

<223> OTHER INFORMATION: Synthetic Construct

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Phe Asp Tyr Trp Gly Gln Gly Thr Leu Val Thr Val Ser
            100                 105                 110

Ser

<210> SEQ ID NO 8
<211> LENGTH: 11
<212> TYPE: PRT
<213> ORGANISM: Artificial Sequence
<220> FEATURE:
<223> OTHER INFORMATION: Synthetic Construct

<400> SEQUENCE: 8

Trp Gly Gln Gly Thr Leu Val Thr Val Ser Ser
1               5                   10

<210> SEQ ID NO 9
<211> LENGTH: 330
<212> TYPE: PRT
<213> ORGANISM: Artificial Sequence
<220> FEATURE:
<223> OTHER INFORMATION: Synthetic Construct

<400> SEQUENCE: 9

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

```
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 10
<211> LENGTH: 330
<212> TYPE: PRT
<213> ORGANISM: Artificial Sequence
<220> FEATURE:
<223> OTHER INFORMATION: Synthetic Construct

<400> SEQUENCE: 10

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 11
<211> LENGTH: 107
<212> TYPE: PRT
<213> ORGANISM: Artificial Sequence
<220> FEATURE:
<223> OTHER INFORMATION: Synthetic Construct

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 12
<211> LENGTH: 10
<212> TYPE: PRT
<213> ORGANISM: Artificial Sequence
<220> FEATURE:
<223> OTHER INFORMATION: Synthetic Construct

<400> SEQUENCE: 12

Phe Gly Gly Gly Thr Lys Val Glu Ile Lys
1               5                   10

<210> SEQ ID NO 13
<211> LENGTH: 107
<212> TYPE: PRT
<213> ORGANISM: Artificial Sequence
<220> FEATURE:
<223> OTHER INFORMATION: Synthetic Construct

<400> SEQUENCE: 13

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 14
<211> LENGTH: 121
<212> TYPE: PRT
<213> ORGANISM: Artificial Sequence
<220> FEATURE:
<223> OTHER INFORMATION: Synthetic Construct

<400> SEQUENCE: 14

Glu Val Gln Leu Val Glu Thr Gly Gly Gly Leu Val Gln Pro Gly Arg
1               5                   10                  15

Ser Leu Lys Leu Ser Cys Lys Thr Ser Gly Phe Thr Phe Ser Ser Tyr
            20                  25                  30

Trp Met Tyr Trp Ile Arg Gln Ala Pro Gly Lys Gly Leu Glu Trp Val
        35                  40                  45

Ser Ser Ile Thr Pro Asn Gly Gly Asn Thr Tyr Tyr Pro Asp Ser Val
    50                  55                  60

Lys Gly Arg Phe Thr Ile Ser Arg Asp Asn Ala Glu Asn Thr Ile Tyr
65                  70                  75                  80

Leu Gln Met Ser Ser Leu Arg Ser Glu Asp Thr Ala Thr Tyr Phe Cys
                85                  90                  95

Ala Lys Gly His Tyr Tyr Tyr Thr Ser Tyr Ser Leu Gly Tyr Trp Gly
            100                 105                 110

Gln Gly Ser Leu Val Thr Val Ser Ser
        115                 120

<210> SEQ ID NO 15
<211> LENGTH: 19
<212> TYPE: PRT
<213> ORGANISM: Artificial Sequence
<220> FEATURE:
<223> OTHER INFORMATION: Synthetic Construct

<400> SEQUENCE: 15

Met Gly Trp Ser Cys Ile Ile Leu Phe Leu Val Ala Thr Ala Thr Gly
1               5                   10                  15

Ala His Ser

<210> SEQ ID NO 16
<211> LENGTH: 10
<212> TYPE: PRT
<213> ORGANISM: Artificial Sequence
<220> FEATURE:

```
<223> OTHER INFORMATION: Synthetic Construct

<400> SEQUENCE: 16

Gly Phe Thr Phe Ser Ser Tyr Trp Met Tyr
1               5                   10

<210> SEQ ID NO 17
<211> LENGTH: 17
<212> TYPE: PRT
<213> ORGANISM: Artificial Sequence
<220> FEATURE:
<223> OTHER INFORMATION: Synthetic Construct

<400> SEQUENCE: 17

Ser Ile Thr Pro Asn Gly Gly Asn Thr Tyr Tyr Pro Asp Ser Val Lys
1               5                   10                  15

Gly

<210> SEQ ID NO 18
<211> LENGTH: 12
<212> TYPE: PRT
<213> ORGANISM: Artificial Sequence
<220> FEATURE:
<223> OTHER INFORMATION: Synthetic Construct

<400> SEQUENCE: 18

Gly His Tyr Tyr Tyr Thr Ser Tyr Ser Leu Gly Tyr
1               5                   10

<210> SEQ ID NO 19
<211> LENGTH: 106
<212> TYPE: PRT
<213> ORGANISM: Artificial Sequence
<220> FEATURE:
<223> OTHER INFORMATION: Synthetic Construct

<400> SEQUENCE: 19

Glu Ile Gln Met Thr Gln Ser Pro Ser Val Leu Ser Ala Ser Val Gly
1               5                   10                  15

Asp Arg Val Thr Leu Ser Cys Lys Ala Ser Gln Asn Ile Asn Lys His
            20                  25                  30

Leu Asp Trp Tyr Gln Gln Lys Leu Gly Glu Ala Pro Lys Leu Leu Ile
        35                  40                  45

Tyr Phe Thr Asn Asn Leu Gln Thr Gly Ile Pro Ser Arg Phe Ser Gly
    50                  55                  60

Ser Gly Ser Gly Thr Asp Cys Thr Leu Thr Ile Asn Ser Leu Gln Pro
65                  70                  75                  80

Gly Asp Val Ala Thr Tyr Phe Cys Phe Gln Tyr Asn Asn Gly Trp Thr
                85                  90                  95

Phe Gly Gly Gly Thr Lys Leu Glu Leu Asp
            100                 105

<210> SEQ ID NO 20
<211> LENGTH: 11
<212> TYPE: PRT
<213> ORGANISM: Artificial Sequence
<220> FEATURE:
<223> OTHER INFORMATION: Synthetic Construct

<400> SEQUENCE: 20

Lys Ala Ser Gln Asn Ile Asn Lys His Leu Asp
1               5                   10
```

<210> SEQ ID NO 21
<211> LENGTH: 7
<212> TYPE: PRT
<213> ORGANISM: Artificial Sequence
<220> FEATURE:
<223> OTHER INFORMATION: Synthetic Construct

<400> SEQUENCE: 21

Phe Thr Asn Asn Leu Gln Thr
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic Construct

<400> SEQUENCE: 22

Phe Gln Tyr Asn Asn Gly Trp Thr
1               5

<210> SEQ ID NO 23
<211> LENGTH: 11
<212> TYPE: PRT
<213> ORGANISM: Artificial Sequence
<220> FEATURE:
<223> OTHER INFORMATION: Synthetic Construct

<400> SEQUENCE: 23

Trp Gly Gln Gly Ser Leu Val Thr Val Ser Ser
1               5                   10

<210> SEQ ID NO 24
<211> LENGTH: 98
<212> TYPE: PRT
<213> ORGANISM: Artificial Sequence
<220> FEATURE:
<223> OTHER INFORMATION: Synthetic Construct

<400> SEQUENCE: 24

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 25
<211> LENGTH: 15
<212> TYPE: PRT
<213> ORGANISM: Artificial Sequence
<220> FEATURE:
<223> OTHER INFORMATION: Synthetic Construct

<400> SEQUENCE: 25

Glu Pro Lys Ser Cys Asp Lys Thr His Thr Cys Pro Pro Cys Pro
1               5                   10                  15

<210> SEQ ID NO 26
<211> LENGTH: 110
<212> TYPE: PRT
<213> ORGANISM: Artificial Sequence
<220> FEATURE:
<223> OTHER INFORMATION: Synthetic Construct

<400> SEQUENCE: 26

Ala Pro Glu Ala Ala Gly Ala Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 27
<211> LENGTH: 107
<212> TYPE: PRT
<213> ORGANISM: Artificial Sequence
<220> FEATURE:
<223> OTHER INFORMATION: Synthetic Construct

<400> SEQUENCE: 27

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 28
<211> LENGTH: 451
<212> TYPE: PRT
<213> ORGANISM: Artificial Sequence
<220> FEATURE:
<223> OTHER INFORMATION: Synthetic Construct

<400> SEQUENCE: 28

Glu Val Gln Leu Val Glu Thr Gly Gly Gly Leu Val Gln Pro Gly Arg
1               5                   10                  15

Ser Leu Lys Leu Ser Cys Lys Thr Ser Gly Phe Thr Phe Ser Ser Tyr

-continued

```
                    20                  25                  30
Trp Met Tyr Trp Ile Arg Gln Ala Pro Gly Lys Gly Leu Glu Trp Val
            35                  40                  45
Ser Ser Ile Thr Pro Asn Gly Gly Asn Thr Tyr Tyr Pro Asp Ser Val
    50                  55                  60
Lys Gly Arg Phe Thr Ile Ser Arg Asp Asn Ala Glu Asn Thr Ile Tyr
65                  70                  75                  80
Leu Gln Met Ser Ser Leu Arg Ser Glu Asp Thr Ala Thr Tyr Phe Cys
                85                  90                  95
Ala Lys Gly His Tyr Tyr Tyr Thr Ser Tyr Ser Leu Gly Tyr Trp Gly
            100                 105                 110
Gln Gly Ser Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Val Glu Pro Lys Ser Cys
    210                 215                 220
Asp Lys Thr His Thr Cys Pro Pro Cys Pro Ala Pro Glu Ala Ala Gly
225                 230                 235                 240
Ala Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Met Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
```

Pro Gly Lys
        450

<210> SEQ ID NO 29
<211> LENGTH: 10
<212> TYPE: PRT
<213> ORGANISM: Artificial Sequence
<220> FEATURE:
<223> OTHER INFORMATION: Synthetic Construct

<400> SEQUENCE: 29

Phe Gly Gly Gly Thr Lys Leu Glu Leu Asp
1               5                   10

<210> SEQ ID NO 30
<211> LENGTH: 107
<212> TYPE: PRT
<213> ORGANISM: Artificial Sequence
<220> FEATURE:
<223> OTHER INFORMATION: Synthetic Construct

<400> SEQUENCE: 30

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 31
<211> LENGTH: 213
<212> TYPE: PRT
<213> ORGANISM: Artificial Sequence
<220> FEATURE:
<223> OTHER INFORMATION: Synthetic Construct

<400> SEQUENCE: 31

Glu Ile Gln Met Thr Gln Ser Pro Ser Val Leu Ser Ala Ser Val Gly
1               5                   10                  15

Asp Arg Val Thr Leu Ser Cys Lys Ala Ser Gln Asn Ile Asn Lys His
            20                  25                  30

Leu Asp Trp Tyr Gln Gln Lys Leu Gly Glu Ala Pro Lys Leu Leu Ile
        35                  40                  45

Tyr Phe Thr Asn Asn Leu Gln Thr Gly Ile Pro Ser Arg Phe Ser Gly
    50                  55                  60

Ser Gly Ser Gly Thr Asp Cys Thr Leu Thr Ile Asn Ser Leu Gln Pro
65                  70                  75                  80

Gly Asp Val Ala Thr Tyr Phe Cys Phe Gln Tyr Asn Asn Gly Trp Thr
                85                  90                  95

Phe Gly Gly Gly Thr Lys Leu Glu Leu Asp Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
        210

<210> SEQ ID NO 32
<211> LENGTH: 121
<212> TYPE: PRT
<213> ORGANISM: Artificial Sequence
<220> FEATURE:
<223> OTHER INFORMATION: Synthetic Construct

<400> SEQUENCE: 32

Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Ser Asn Tyr
            20                  25                  30

Trp Met Tyr Trp Ile Arg Gln Ala Pro Gly Met Gly Leu Glu Trp Val
        35                  40                  45

Ser Ser Ile Asn Asn Asp Gly Gly Asn Thr Tyr Tyr Leu Asp Ser Val
    50                  55                  60

Lys Gly Arg Phe Thr Ile Ser Arg Asn Asn Ala Glu Asn Thr Val Tyr
65                  70                  75                  80

Leu Gln Met Asn Ser Leu Arg Ser Glu Asp Thr Ala Thr Tyr Tyr Cys
                85                  90                  95

Ala Lys Gly His Tyr Ser Tyr Ser Tyr Ser Phe Ser Tyr Trp Gly
            100                 105                 110

Gln Gly Thr Leu Val Thr Val Ser Ser
        115                 120

<210> SEQ ID NO 33
<211> LENGTH: 10
<212> TYPE: PRT
<213> ORGANISM: Artificial Sequence
<220> FEATURE:
<223> OTHER INFORMATION: Synthetic Construct

<400> SEQUENCE: 33

Gly Phe Thr Phe Ser Asn Tyr Trp Met Tyr
1               5                   10

<210> SEQ ID NO 34
<211> LENGTH: 17
<212> TYPE: PRT
<213> ORGANISM: Artificial Sequence
<220> FEATURE:
<223> OTHER INFORMATION: Synthetic Construct

<400> SEQUENCE: 34

Ser Ile Asn Asn Asp Gly Gly Asn Thr Tyr Tyr Leu Asp Ser Val Lys

<210> SEQ ID NO 35
<211> LENGTH: 12
<212> TYPE: PRT
<213> ORGANISM: Artificial Sequence
<220> FEATURE:
<223> OTHER INFORMATION: Synthetic Construct

<400> SEQUENCE: 35

Gly His Tyr Ser Tyr Ser Ser Tyr Ser Phe Ser Tyr
1               5                   10

<210> SEQ ID NO 36
<211> LENGTH: 106
<212> TYPE: PRT
<213> ORGANISM: Artificial Sequence
<220> FEATURE:
<223> OTHER INFORMATION: Synthetic Construct

<400> SEQUENCE: 36

Asp Ile Gln Met Thr Gln Ser Pro Ser Val Leu Ser Ala Ser Val Gly
1               5                   10                  15

Asp Arg Val Thr Leu Ser Cys Lys Ala Ser His Asn Ile Asn Lys His
                20                  25                  30

Leu Asp Trp Cys Gln Gln Lys Val Gly Glu Ala Pro Lys Leu Leu Ile
            35                  40                  45

Tyr Phe Thr Asn Asn Leu Gln Thr Gly Ile Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Phe Gln Tyr Asn Ser Gly Trp Thr
                85                  90                  95

Phe Gly Gly Gly Thr Lys Leu Glu Leu Lys
            100                 105

<210> SEQ ID NO 37
<211> LENGTH: 11
<212> TYPE: PRT
<213> ORGANISM: Artificial Sequence
<220> FEATURE:
<223> OTHER INFORMATION: Synthetic Construct

<400> SEQUENCE: 37

Lys Ala Ser His Asn Ile Asn Lys His Leu Asp
1               5                   10

<210> SEQ ID NO 38
<211> LENGTH: 8
<212> TYPE: PRT
<213> ORGANISM: Artificial Sequence
<220> FEATURE:
<223> OTHER INFORMATION: Synthetic Construct

<400> SEQUENCE: 38

Phe Gln Tyr Asn Ser Gly Trp Thr
1               5

<210> SEQ ID NO 39
<211> LENGTH: 11
<212> TYPE: PRT
<213> ORGANISM: Artificial Sequence
<220> FEATURE:
<223> OTHER INFORMATION: Synthetic Construct

<400> SEQUENCE: 39

Trp Gly Gln Gly Thr Leu Val Thr Val Ser Ser
1               5                   10

<210> SEQ ID NO 40
<211> LENGTH: 451
<212> TYPE: PRT
<213> ORGANISM: Artificial Sequence
<220> FEATURE:
<223> OTHER INFORMATION: Synthetic Construct

<400> SEQUENCE: 40

Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Ser Asn Tyr
                20                  25                  30

Trp Met Tyr Trp Ile Arg Gln Ala Pro Gly Met Gly Leu Glu Trp Val
            35                  40                  45

Ser Ser Ile Asn Asn Asp Gly Gly Asn Thr Tyr Tyr Leu Asp Ser Val
        50                  55                  60

Lys Gly Arg Phe Thr Ile Ser Arg Asn Asn Ala Glu Asn Thr Val Tyr
65                  70                  75                  80

Leu Gln Met Asn Ser Leu Arg Ser Glu Asp Thr Ala Thr Tyr Tyr Cys
                85                  90                  95

Ala Lys Gly His Tyr Ser Tyr Ser Tyr Ser Phe Ser Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile

```
                    325                 330                 335
Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
        450

<210> SEQ ID NO 41
<211> LENGTH: 10
<212> TYPE: PRT
<213> ORGANISM: Artificial Sequence
<220> FEATURE:
<223> OTHER INFORMATION: Synthetic Construct

<400> SEQUENCE: 41

Phe Gly Gly Gly Thr Lys Leu Glu Leu Lys
1               5                   10

<210> SEQ ID NO 42
<211> LENGTH: 213
<212> TYPE: PRT
<213> ORGANISM: Artificial Sequence
<220> FEATURE:
<223> OTHER INFORMATION: Synthetic Construct

<400> SEQUENCE: 42

Asp Ile Gln Met Thr Gln Ser Pro Ser Val Leu Ser Ala Ser Val Gly
1               5                   10                  15

Asp Arg Val Thr Leu Ser Cys Lys Ala Ser His Asn Ile Asn Lys His
                20                  25                  30

Leu Asp Trp Cys Gln Gln Lys Val Gly Glu Ala Pro Lys Leu Leu Ile
            35                  40                  45

Tyr Phe Thr Asn Asn Leu Gln Thr Gly Ile Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Phe Gln Tyr Asn Ser Gly Trp Thr
                85                  90                  95

Phe Gly Gly Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160
```

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 43
<211> LENGTH: 121
<212> TYPE: PRT
<213> ORGANISM: Artificial Sequence
<220> FEATURE:
<223> OTHER INFORMATION: Synthetic Construct

<400> SEQUENCE: 43

Glu Val Gln Leu Val Glu Ser Gly Gly Asp Leu Val Gln Pro Gly Arg
1               5                   10                  15

Ser Leu Lys Leu Ser Cys Val Thr Ser Gly Phe Ile Phe Lys Asn Tyr
            20                  25                  30

Trp Met Thr Trp Ile Arg Gln Val Pro Gly Lys Gly Leu Glu Trp Val
        35                  40                  45

Ala Ser Ile Thr Asn Thr Gly Gly Ala Thr Tyr Tyr Pro Asp Ser Val
    50                  55                  60

Lys Gly Arg Phe Thr Ile Ser Arg Asp Asn Ser Glu Asn Thr Leu Tyr
65                  70                  75                  80

Leu Gln Met Asn Ser Leu Arg Ser Glu Asp Thr Ala Thr Tyr Tyr Cys
                85                  90                  95

Ala Arg Asp Arg Arg Tyr Asn Ser Gly Ser Pro Phe Ala Tyr Trp Gly
            100                 105                 110

Gln Gly Thr Leu Val Thr Val Ser Ser
        115                 120

<210> SEQ ID NO 44
<211> LENGTH: 10
<212> TYPE: PRT
<213> ORGANISM: Artificial Sequence
<220> FEATURE:
<223> OTHER INFORMATION: Synthetic Construct

<400> SEQUENCE: 44

Gly Phe Ile Phe Lys Asn Tyr Trp Met Thr
1               5                   10

<210> SEQ ID NO 45
<211> LENGTH: 17
<212> TYPE: PRT
<213> ORGANISM: Artificial Sequence
<220> FEATURE:
<223> OTHER INFORMATION: Synthetic Construct

<400> SEQUENCE: 45

Ser Ile Thr Asn Thr Gly Gly Ala Thr Tyr Tyr Pro Asp Ser Val Lys
1               5                   10                  15

Gly

<210> SEQ ID NO 46
<211> LENGTH: 12
<212> TYPE: PRT
<213> ORGANISM: Artificial Sequence

```
<220> FEATURE:
<223> OTHER INFORMATION: Synthetic Construct

<400> SEQUENCE: 46

Asp Arg Arg Tyr Asn Ser Gly Ser Pro Phe Ala Tyr
1               5                   10

<210> SEQ ID NO 47
<211> LENGTH: 107
<212> TYPE: PRT
<213> ORGANISM: Artificial Sequence
<220> FEATURE:
<223> OTHER INFORMATION: Synthetic Construct

<400> SEQUENCE: 47

Asp Ile Gln Leu Thr Gln Ser Pro Ser Thr Leu Ala Ala Ser Leu Gly
1               5                   10                  15

Glu Arg Val Thr Ile Ser Cys Arg Ala Ser Gln Ser Ile Ser Asn Ser
            20                  25                  30

Leu Ile Trp Phe Gln Gln Lys Pro Asp Gly Thr Ile Lys Arg Leu Ile
        35                  40                  45

Tyr Ser Ser Ser Thr Leu Glu Ser Gly Val Pro Ser Arg Phe Ser Gly
    50                  55                  60

Ser Gly Ser Gly Thr Asp Tyr Ser Leu Ser Ile Ser Ser Leu Glu Ser
65                  70                  75                  80

Glu Asp Phe Ala Met Tyr Tyr Cys Leu Gln Tyr Ala Thr Tyr Pro Trp
                85                  90                  95

Thr Phe Gly Gly Gly Thr Lys Leu Glu Leu Arg
            100                 105

<210> SEQ ID NO 48
<211> LENGTH: 11
<212> TYPE: PRT
<213> ORGANISM: Artificial Sequence
<220> FEATURE:
<223> OTHER INFORMATION: Synthetic Construct

<400> SEQUENCE: 48

Arg Ala Ser Gln Ser Ile Ser Asn Ser Leu Ile
1               5                   10

<210> SEQ ID NO 49
<211> LENGTH: 7
<212> TYPE: PRT
<213> ORGANISM: Artificial Sequence
<220> FEATURE:
<223> OTHER INFORMATION: Synthetic Construct

<400> SEQUENCE: 49

Ser Ser Ser Thr Leu Glu Ser
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic Construct

<400> SEQUENCE: 50

Leu Gln Tyr Ala Thr Tyr Pro Trp Thr
1               5
```

<210> SEQ ID NO 51
<211> LENGTH: 451
<212> TYPE: PRT
<213> ORGANISM: Artificial Sequence
<220> FEATURE:
<223> OTHER INFORMATION: Synthetic Construct

<400> SEQUENCE: 51

```
Glu Val Gln Leu Val Glu Ser Gly Gly Asp Leu Val Gln Pro Gly Arg
1               5                   10                  15

Ser Leu Lys Leu Ser Cys Val Thr Ser Gly Phe Ile Phe Lys Asn Tyr
            20                  25                  30

Trp Met Thr Trp Ile Arg Gln Val Pro Gly Lys Gly Leu Glu Trp Val
        35                  40                  45

Ala Ser Ile Thr Asn Thr Gly Gly Ala Thr Tyr Tyr Pro Asp Ser Val
50                  55                  60

Lys Gly Arg Phe Thr Ile Ser Arg Asp Asn Ser Glu Asn Thr Leu Tyr
65                  70                  75                  80

Leu Gln Met Asn Ser Leu Arg Ser Glu Asp Thr Ala Thr Tyr Tyr Cys
                85                  90                  95

Ala Arg Asp Arg Arg Tyr Asn Ser Gly Ser Pro Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
```

```
                    370                 375                 380
Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 52
<211> LENGTH: 10
<212> TYPE: PRT
<213> ORGANISM: Artificial Sequence
<220> FEATURE:
<223> OTHER INFORMATION: Synthetic Construct

<400> SEQUENCE: 52

Phe Gly Gly Gly Thr Lys Leu Glu Leu Arg
1               5                   10

<210> SEQ ID NO 53
<211> LENGTH: 214
<212> TYPE: PRT
<213> ORGANISM: Artificial Sequence
<220> FEATURE:
<223> OTHER INFORMATION: Synthetic Construct

<400> SEQUENCE: 53

Asp Ile Gln Leu Thr Gln Ser Pro Ser Thr Leu Ala Ala Ser Leu Gly
1               5                   10                  15

Glu Arg Val Thr Ile Ser Cys Arg Ala Ser Gln Ser Ile Ser Asn Ser
                20                  25                  30

Leu Ile Trp Phe Gln Gln Lys Pro Asp Gly Thr Ile Lys Arg Leu Ile
            35                  40                  45

Tyr Ser Ser Ser Thr Leu Glu Ser Gly Val Pro Ser Arg Phe Ser Gly
50                  55                  60

Ser Gly Ser Gly Thr Asp Tyr Ser Leu Ser Ile Ser Ser Leu Glu Ser
65                  70                  75                  80

Glu Asp Phe Ala Met Tyr Tyr Cys Leu Gln Tyr Ala Thr Tyr Pro Trp
                85                  90                  95

Thr Phe Gly Gly Gly Thr Lys Leu Glu Leu Arg Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
    210

<210> SEQ ID NO 54
<211> LENGTH: 121
<212> TYPE: PRT
<213> ORGANISM: Artificial Sequence
<220> FEATURE:
<223> OTHER INFORMATION: Synthetic Construct

<400> SEQUENCE: 54

Glu Val Gln Leu Val Asp Ser Gly Gly Asp Gln Val Gln Pro Gly Arg
1               5                   10                  15

Ser Leu Lys Leu Ser Cys Val Ala Ser Gly Phe Ile Phe Lys Asn Tyr
            20                  25                  30

Trp Met Thr Trp Ile Arg Gln Val Pro Gly Lys Gly Leu Glu Trp Ile
        35                  40                  45

Ala Ser Ile Thr Asn Ser Gly Gly Asn Thr Tyr Tyr Pro Asp Ser Val
    50                  55                  60

Lys Gly Arg Phe Thr Ile Ser Arg Asp Asn Ala Lys Asp Thr Leu Tyr
65                  70                  75                  80

Leu Gln Met Asn Ser Leu Arg Ser Glu Asp Thr Ala Thr Tyr Tyr Cys
                85                  90                  95

Ala Arg Asp Arg Arg Tyr Asn Ser Gly Ser Pro Phe Ala Tyr Trp Gly
            100                 105                 110

Gln Gly Thr Leu Val Thr Val Ser Ser
        115                 120

<210> SEQ ID NO 55
<211> LENGTH: 17
<212> TYPE: PRT
<213> ORGANISM: Artificial Sequence
<220> FEATURE:
<223> OTHER INFORMATION: Synthetic Construct

<400> SEQUENCE: 55

Ser Ile Thr Asn Ser Gly Gly Asn Thr Tyr Tyr Pro Asp Ser Val Lys
1               5                   10                  15

Gly

<210> SEQ ID NO 56
<211> LENGTH: 107
<212> TYPE: PRT
<213> ORGANISM: Artificial Sequence
<220> FEATURE:
<223> OTHER INFORMATION: Synthetic Construct

<400> SEQUENCE: 56

Asp Ile Gln Leu Thr Gln Ser Pro Ser Thr Leu Pro Ala Ser Leu Gly
1               5                   10                  15

Glu Arg Val Thr Ile Ser Cys Arg Thr Ser Gln Ser Ile Asn Asn Asn
            20                  25                  30

Leu Cys Trp Tyr Gln Gln Lys Pro Asp Gly Thr Val Lys Arg Leu Ile
        35                  40                  45

Tyr Ser Thr Ser Thr Leu Glu Ser Gly Val Pro Ser Arg Phe Ser Gly
    50                  55                  60

Ser Gly Ser Gly Thr Asp Tyr Ser Leu Ser Ile Ser Ser Leu Glu Ser
65                  70                  75                  80

Gln Asp Phe Ala Met Tyr Tyr Cys Leu Gln Tyr Ala Thr Tyr Pro Trp
                85                  90                  95

Thr Phe Gly Gly Gly Thr Lys Leu Glu Leu Lys
            100                 105

<210> SEQ ID NO 57
<211> LENGTH: 11
<212> TYPE: PRT
<213> ORGANISM: Artificial Sequence
<220> FEATURE:
<223> OTHER INFORMATION: Synthetic Construct

<400> SEQUENCE: 57

Arg Thr Ser Gln Ser Ile Asn Asn Asn Leu Cys
1               5                   10

<210> SEQ ID NO 58
<211> LENGTH: 7
<212> TYPE: PRT
<213> ORGANISM: Artificial Sequence
<220> FEATURE:
<223> OTHER INFORMATION: Synthetic Construct

<400> SEQUENCE: 58

Ser Thr Ser Thr Leu Glu Ser
1               5

<210> SEQ ID NO 59
<211> LENGTH: 451
<212> TYPE: PRT
<213> ORGANISM: Artificial Sequence
<220> FEATURE:
<223> OTHER INFORMATION: Synthetic Construct

<400> SEQUENCE: 59

Glu Val Gln Leu Val Asp Ser Gly Gly Asp Gln Val Gln Pro Gly Arg
1               5                   10                  15

Ser Leu Lys Leu Ser Cys Val Ala Ser Gly Phe Ile Phe Lys Asn Tyr
            20                  25                  30

Trp Met Thr Trp Ile Arg Gln Val Pro Gly Lys Gly Leu Glu Trp Ile
        35                  40                  45

Ala Ser Ile Thr Asn Ser Gly Gly Asn Thr Tyr Tyr Pro Asp Ser Val
    50                  55                  60

Lys Gly Arg Phe Thr Ile Ser Arg Asp Asn Ala Lys Asp Thr Leu Tyr
65                  70                  75                  80

Leu Gln Met Asn Ser Leu Arg Ser Glu Asp Thr Ala Thr Tyr Tyr Cys
                85                  90                  95

Ala Arg Asp Arg Arg Tyr Asn Ser Gly Ser Pro Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 60
<211> LENGTH: 214
<212> TYPE: PRT
<213> ORGANISM: Artificial Sequence
<220> FEATURE:
<223> OTHER INFORMATION: Synthetic Construct

<400> SEQUENCE: 60

Asp Ile Gln Leu Thr Gln Ser Pro Ser Thr Leu Pro Ala Ser Leu Gly
1               5                   10                  15

Glu Arg Val Thr Ile Ser Cys Arg Thr Ser Gln Ser Ile Asn Asn Asn
            20                  25                  30

Leu Cys Trp Tyr Gln Gln Lys Pro Asp Gly Thr Val Lys Arg Leu Ile
        35                  40                  45

Tyr Ser Thr Ser Thr Leu Glu Ser Gly Val Pro Ser Arg Phe Ser Gly
    50                  55                  60

Ser Gly Ser Gly Thr Asp Tyr Ser Leu Ser Ile Ser Ser Leu Glu Ser
65                  70                  75                  80

Gln Asp Phe Ala Met Tyr Tyr Cys Leu Gln Tyr Ala Thr Tyr Pro Trp
                85                  90                  95

Thr Phe Gly Gly Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 61
<211> LENGTH: 122
<212> TYPE: PRT
<213> ORGANISM: Artificial Sequence
<220> FEATURE:
<223> OTHER INFORMATION: Synthetic Construct

<400> SEQUENCE: 61

Gln Val Asn Leu Leu Gln Ser Gly Ala Thr Leu Val Lys Pro Gly Ala
1               5                   10                  15

Ser Met Lys Met Ser Cys Lys Ala Ser Gly Tyr Ser Phe Thr Asp Tyr
            20                  25                  30

Trp Val Ser Trp Val Lys Gln Ser His Gly Lys Ser Leu Glu Trp Ile
        35                  40                  45

Gly Glu Ile Tyr Pro Asn Ser Gly Ala Asn Asn Phe Asn Lys Glu Phe
    50                  55                  60

Lys Asp Lys Ala Thr Leu Thr Val Asp Lys Ser Thr Ser Thr Ala Tyr
65                  70                  75                  80

Met Glu Leu Thr Arg Leu Thr Ser Glu Asp Ser Ala Val Tyr Tyr Cys
                85                  90                  95

Thr Arg Gly Pro Tyr Tyr Tyr Ser Ser Gln Ile Ile Phe Ala Tyr Trp
            100                 105                 110

Gly Gln Gly Thr Leu Val Thr Val Ser Ser
        115                 120

<210> SEQ ID NO 62
<211> LENGTH: 10
<212> TYPE: PRT
<213> ORGANISM: Artificial Sequence
<220> FEATURE:
<223> OTHER INFORMATION: Synthetic Construct

<400> SEQUENCE: 62

Gly Tyr Ser Phe Thr Asp Tyr Trp Val Ser
1               5                   10

<210> SEQ ID NO 63
<211> LENGTH: 17
<212> TYPE: PRT
<213> ORGANISM: Artificial Sequence
<220> FEATURE:
<223> OTHER INFORMATION: Synthetic Construct

<400> SEQUENCE: 63

Glu Ile Tyr Pro Asn Ser Gly Ala Asn Asn Phe Asn Lys Glu Phe Lys

```
                  1               5                  10                 15
Asp

<210> SEQ ID NO 64
<211> LENGTH: 13
<212> TYPE: PRT
<213> ORGANISM: Artificial Sequence
<220> FEATURE:
<223> OTHER INFORMATION: Synthetic Construct

<400> SEQUENCE: 64

Gly Pro Tyr Tyr Tyr Ser Ser Gln Ile Ile Phe Ala Tyr
1               5                   10

<210> SEQ ID NO 65
<211> LENGTH: 107
<212> TYPE: PRT
<213> ORGANISM: Artificial Sequence
<220> FEATURE:
<223> OTHER INFORMATION: Synthetic Construct

<400> SEQUENCE: 65

Ile Ile Val Met Thr Gln Ser Pro Lys Ser Met Ser Ile Ser Val Gly
1               5                   10                  15

Asp Arg Val Thr Met Asn Cys Lys Ala Ser Gln Asn Val Gly Asn Asn
            20                  25                  30

Ile Ala Trp Tyr Arg Gln Lys Pro Gly Gln Ser Pro Glu Leu Leu Ile
        35                  40                  45

Tyr Tyr Ala Ser Asn Arg Tyr Thr Gly Val Pro Asp Arg Phe Thr Gly
    50                  55                  60

Gly Gly Tyr Gly Thr Asp Phe Thr Leu Thr Ile Asn Ser Val Gln Ala
65                  70                  75                  80

Glu Asp Ala Ala Phe Tyr Tyr Cys Gln Arg Ile Tyr Asn Ser Pro Pro
                85                  90                  95

Thr Phe Gly Gly Gly Thr Lys Val Glu Leu Lys
            100                 105

<210> SEQ ID NO 66
<211> LENGTH: 11
<212> TYPE: PRT
<213> ORGANISM: Artificial Sequence
<220> FEATURE:
<223> OTHER INFORMATION: Synthetic Construct

<400> SEQUENCE: 66

Lys Ala Ser Gln Asn Val Gly Asn Asn Ile Ala
1               5                   10

<210> SEQ ID NO 67
<211> LENGTH: 7
<212> TYPE: PRT
<213> ORGANISM: Artificial Sequence
<220> FEATURE:
<223> OTHER INFORMATION: Synthetic Construct

<400> SEQUENCE: 67

Tyr Ala Ser Asn Arg Tyr Thr
1               5

<210> SEQ ID NO 68
<211> LENGTH: 9
<212> TYPE: PRT
<213> ORGANISM: Artificial Sequence
```

<220> FEATURE:
<223> OTHER INFORMATION: Synthetic Construct

<400> SEQUENCE: 68

Gln Arg Ile Tyr Asn Ser Pro Pro Thr
1               5

<210> SEQ ID NO 69
<211> LENGTH: 452
<212> TYPE: PRT
<213> ORGANISM: Artificial Sequence
<220> FEATURE:
<223> OTHER INFORMATION: Synthetic Construct

<400> SEQUENCE: 69

Gln Val Asn Leu Leu Gln Ser Gly Ala Thr Leu Val Lys Pro Gly Ala
1               5                   10                  15

Ser Met Lys Met Ser Cys Lys Ala Ser Gly Tyr Ser Phe Thr Asp Tyr
                20                  25                  30

Trp Val Ser Trp Val Lys Gln Ser His Gly Lys Ser Leu Glu Trp Ile
            35                  40                  45

Gly Glu Ile Tyr Pro Asn Ser Gly Ala Asn Asn Phe Asn Lys Glu Phe
        50                  55                  60

Lys Asp Lys Ala Thr Leu Thr Val Asp Lys Ser Thr Ser Thr Ala Tyr
65                  70                  75                  80

Met Glu Leu Thr Arg Leu Thr Ser Glu Asp Ser Ala Val Tyr Tyr Cys
                85                  90                  95

Thr Arg Gly Pro Tyr Tyr Tyr Ser Ser Gln Ile Ile Phe Ala Tyr Trp
            100                 105                 110

Gly Gln Gly Thr Leu Val Thr Val Ser Ala Ser Thr Lys Gly Pro
        115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Ala Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro

```
                     325                 330                 335
Ile Glu Lys Thr Ile Ser Lys Ala Lys Gly Gln Pro Arg Glu Pro Gln
                340                 345                 350

Val Tyr Thr Leu Pro Pro Ser Arg Glu Glu Met Thr Lys Asn Gln Val
                355                 360                 365

Ser Leu Thr Cys Leu Val Lys Gly Phe Tyr Pro Ser Asp Ile Ala Val
                370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly Lys
            450

<210> SEQ ID NO 70
<211> LENGTH: 10
<212> TYPE: PRT
<213> ORGANISM: Artificial Sequence
<220> FEATURE:
<223> OTHER INFORMATION: Synthetic Construct

<400> SEQUENCE: 70

Phe Gly Gly Gly Thr Lys Val Glu Leu Lys
1               5                   10

<210> SEQ ID NO 71
<211> LENGTH: 214
<212> TYPE: PRT
<213> ORGANISM: Artificial Sequence
<220> FEATURE:
<223> OTHER INFORMATION: Synthetic Construct

<400> SEQUENCE: 71

Ile Ile Val Met Thr Gln Ser Pro Lys Ser Met Ser Ile Ser Val Gly
1               5                   10                  15

Asp Arg Val Thr Met Asn Cys Lys Ala Ser Gln Asn Val Gly Asn Asn
                20                  25                  30

Ile Ala Trp Tyr Arg Gln Lys Pro Gly Gln Ser Pro Glu Leu Leu Ile
            35                  40                  45

Tyr Tyr Ala Ser Asn Arg Tyr Thr Gly Val Pro Asp Arg Phe Thr Gly
        50                  55                  60

Gly Gly Tyr Gly Thr Asp Phe Thr Leu Thr Ile Asn Ser Val Gln Ala
65                  70                  75                  80

Glu Asp Ala Ala Phe Tyr Tyr Cys Gln Arg Ile Tyr Asn Ser Pro Pro
                85                  90                  95

Thr Phe Gly Gly Gly Thr Lys Val Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160
```

-continued

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 72
<211> LENGTH: 122
<212> TYPE: PRT
<213> ORGANISM: Artificial Sequence
<220> FEATURE:
<223> OTHER INFORMATION: Synthetic Construct

<400> SEQUENCE: 72

Gln Val Lys Leu Leu Gln Ser Gly Ala Ala Leu Val Lys Pro Gly Ala
1               5                   10                  15

Ser Val Lys Met Ser Cys Ala Thr Ser Gly Phe Ser Phe Thr Asp Tyr
            20                  25                  30

Trp Val Ser Trp Val Lys Gln Ser His Gly Lys Gly Leu Glu Trp Ile
        35                  40                  45

Gly Glu Ile Tyr Pro Asn Ser Gly Ala Asp Asn Phe Asn Glu Asn Phe
    50                  55                  60

Lys Gly Lys Ala Thr Leu Thr Val Asp Lys Ser Thr Ser Thr Ala Tyr
65                  70                  75                  80

Met Glu Leu Ser Arg Leu Thr Ser Glu Asp Ser Ala Ile Tyr Tyr Cys
                85                  90                  95

Thr Arg Gly Pro Tyr Tyr Tyr Ser Thr Gln Ile Ile Phe Ala Tyr Trp
            100                 105                 110

Gly Gln Gly Thr Leu Val Thr Val Ser Ser
        115                 120

<210> SEQ ID NO 73
<211> LENGTH: 10
<212> TYPE: PRT
<213> ORGANISM: Artificial Sequence
<220> FEATURE:
<223> OTHER INFORMATION: Synthetic Construct

<400> SEQUENCE: 73

Gly Phe Ser Phe Thr Asp Tyr Trp Val Ser
1               5                   10

<210> SEQ ID NO 74
<211> LENGTH: 17
<212> TYPE: PRT
<213> ORGANISM: Artificial Sequence
<220> FEATURE:
<223> OTHER INFORMATION: Synthetic Construct

<400> SEQUENCE: 74

Glu Ile Tyr Pro Asn Ser Gly Ala Asp Asn Phe Asn Glu Asn Phe Lys
1               5                   10                  15

Gly

<210> SEQ ID NO 75
<211> LENGTH: 13
<212> TYPE: PRT
<213> ORGANISM: Artificial Sequence

```
<220> FEATURE:
<223> OTHER INFORMATION: Synthetic Construct

<400> SEQUENCE: 75

Gly Pro Tyr Tyr Tyr Ser Thr Gln Ile Ile Phe Ala Tyr
1               5                   10

<210> SEQ ID NO 76
<211> LENGTH: 107
<212> TYPE: PRT
<213> ORGANISM: Artificial Sequence
<220> FEATURE:
<223> OTHER INFORMATION: Synthetic Construct

<400> SEQUENCE: 76

Asn Ile Val Met Thr Gln Ser Pro Lys Ser Met Ser Ile Ser Val Gly
1               5                   10                  15

Asp Arg Val Thr Met Asn Cys Lys Ala Ser Gln Asn Val Gly Asn Asn
            20                  25                  30

Leu Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Gly Gly Tyr Gly Thr Asp Phe Thr Leu Thr Ile Asn Ser Val Gln Ala
65                  70                  75                  80

Glu Asp Ala Ala Phe Tyr Tyr Cys Gln Arg Ile Tyr Asn Ser Pro Pro
                85                  90                  95

Thr Phe Gly Gly Gly Thr Lys Val Glu Leu Arg
            100                 105

<210> SEQ ID NO 77
<211> LENGTH: 11
<212> TYPE: PRT
<213> ORGANISM: Artificial Sequence
<220> FEATURE:
<223> OTHER INFORMATION: Synthetic Construct

<400> SEQUENCE: 77

Lys Ala Ser Gln Asn Val Gly Asn Asn Leu Ala
1               5                   10

<210> SEQ ID NO 78
<211> LENGTH: 452
<212> TYPE: PRT
<213> ORGANISM: Artificial Sequence
<220> FEATURE:
<223> OTHER INFORMATION: Synthetic Construct

<400> SEQUENCE: 78

Gln Val Lys Leu Leu Gln Ser Gly Ala Ala Leu Val Lys Pro Gly Ala
1               5                   10                  15

Ser Val Lys Met Ser Cys Ala Thr Ser Gly Phe Ser Phe Thr Asp Tyr
            20                  25                  30

Trp Val Ser Trp Val Lys Gln Ser His Gly Lys Gly Leu Glu Trp Ile
        35                  40                  45

Gly Glu Ile Tyr Pro Asn Ser Gly Ala Asp Asn Phe Asn Glu Asn Phe
    50                  55                  60

Lys Gly Lys Ala Thr Leu Thr Val Asp Lys Ser Thr Ser Thr Ala Tyr
65                  70                  75                  80

Met Glu Leu Ser Arg Leu Thr Ser Glu Asp Ser Ala Ile Tyr Tyr Cys
                85                  90                  95
```

Thr Arg Gly Pro Tyr Tyr Ser Thr Gln Ile Ile Phe Ala Tyr Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
            210                 215                 220

Cys Asp Lys Thr His Thr Cys Pro Pro Cys Pro Ala Pro Glu Ala Ala
225                 230                 235                 240

Gly Ala Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
        450

<210> SEQ ID NO 79
<211> LENGTH: 10
<212> TYPE: PRT
<213> ORGANISM: Artificial Sequence
<220> FEATURE:
<223> OTHER INFORMATION: Synthetic Construct

<400> SEQUENCE: 79

<210> SEQ ID NO 80
<211> LENGTH: 214
<212> TYPE: PRT
<213> ORGANISM: Artificial Sequence
<220> FEATURE:
<223> OTHER INFORMATION: Synthetic Construct

<400> SEQUENCE: 80

```
Phe Gly Gly Gly Thr Lys Val Glu Leu Arg
1               5                   10

Asn Ile Val Met Thr Gln Ser Pro Lys Ser Met Ser Ile Ser Val Gly
1               5                   10                  15

Asp Arg Val Thr Met Asn Cys Lys Ala Ser Gln Asn Val Gly Asn Asn
            20                  25                  30

Leu Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Gly Gly Tyr Gly Thr Asp Phe Thr Leu Thr Ile Asn Ser Val Gln Ala
65                  70                  75                  80

Glu Asp Ala Ala Phe Tyr Tyr Cys Gln Arg Ile Tyr Asn Ser Pro Pro
                85                  90                  95

Thr Phe Gly Gly Gly Thr Lys Val Glu Leu Arg Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 81
<211> LENGTH: 106
<212> TYPE: PRT
<213> ORGANISM: Artificial Sequence
<220> FEATURE:
<223> OTHER INFORMATION: Synthetic Construct

<400> SEQUENCE: 81

```
Asp Ile Gln Met Thr Gln Ser Pro Ser Val Leu Ser Ala Ser Val Gly
1               5                   10                  15

Asp Arg Val Thr Leu Ser Cys Lys Ala Ser His Asn Ile Asn Lys His
            20                  25                  30

Leu Asp Trp Cys Gln Gln Lys Val Gly Glu Ala Pro Lys Leu Leu Ile
        35                  40                  45

Tyr Phe Thr Asn Asn Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
```

```
                65                  70                  75                  80
Glu Asp Val Ala Thr Tyr Phe Cys Phe Gln Tyr Asn Ser Gly Trp Thr
                    85                  90                  95

Phe Gly Gln Gly Thr Lys Val Glu Ile Lys
            100                 105

<210> SEQ ID NO 82
<211> LENGTH: 10
<212> TYPE: PRT
<213> ORGANISM: Artificial Sequence
<220> FEATURE:
<223> OTHER INFORMATION: Synthetic Construct

<400> SEQUENCE: 82

Phe Gly Gln Gly Thr Lys Val Glu Ile Lys
1               5                   10

<210> SEQ ID NO 83
<211> LENGTH: 213
<212> TYPE: PRT
<213> ORGANISM: Artificial Sequence
<220> FEATURE:
<223> OTHER INFORMATION: Synthetic Construct

<400> SEQUENCE: 83

Asp Ile Gln Met Thr Gln Ser Pro Ser Val Leu Ser Ala Ser Val Gly
1               5                   10                  15

Asp Arg Val Thr Leu Ser Cys Lys Ala Ser His Asn Ile Asn Lys His
                20                  25                  30

Leu Asp Trp Cys Gln Gln Lys Val Gly Glu Ala Pro Lys Leu Leu Ile
            35                  40                  45

Tyr Phe Thr Asn Asn Leu Gln Thr Gly Ile Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Phe Gln Tyr Asn Ser Gly Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 84
<211> LENGTH: 107
<212> TYPE: PRT
<213> ORGANISM: Artificial Sequence
<220> FEATURE:
```

<223> OTHER INFORMATION: Synthetic Construct

<400> SEQUENCE: 84

Asp Ile Gln Leu Thr Gln Ser Pro Ser Thr Leu Pro Ala Ser Leu Gly
1               5                   10                  15

Glu Arg Val Thr Ile Ser Cys Arg Thr Ser Gln Ser Ile Asn Asn Asn
            20                  25                  30

Leu Cys Trp Tyr Gln Gln Lys Pro Asp Gly Thr Val Lys Arg Leu Ile
        35                  40                  45

Tyr Ser Thr Ser Thr Leu Glu Ser Gly Val Pro Ser Arg Phe Ser Gly
    50                  55                  60

Ser Gly Ser Gly Thr Asp Tyr Ser Leu Ser Ile Ser Ser Leu Glu Ser
65                  70                  75                  80

Gln Asp Phe Ala Met Tyr Tyr Cys Leu Gln Tyr Ala Thr Tyr Pro Trp
                85                  90                  95

Thr Phe Gly Gln Gly Thr Lys Val Glu Ile Lys
            100                 105

<210> SEQ ID NO 85
<211> LENGTH: 214
<212> TYPE: PRT
<213> ORGANISM: Artificial Sequence
<220> FEATURE:
<223> OTHER INFORMATION: Synthetic Construct

<400> SEQUENCE: 85

Asp Ile Gln Leu Thr Gln Ser Pro Ser Thr Leu Pro Ala Ser Leu Gly
1               5                   10                  15

Glu Arg Val Thr Ile Ser Cys Arg Thr Ser Gln Ser Ile Asn Asn Asn
            20                  25                  30

Leu Cys Trp Tyr Gln Gln Lys Pro Asp Gly Thr Val Lys Arg Leu Ile
        35                  40                  45

Tyr Ser Thr Ser Thr Leu Glu Ser Gly Val Pro Ser Arg Phe Ser Gly
    50                  55                  60

Ser Gly Ser Gly Thr Asp Tyr Ser Leu Ser Ile Ser Ser Leu Glu Ser
65                  70                  75                  80

Gln Asp Phe Ala Met Tyr Tyr Cys Leu Gln Tyr Ala Thr Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 86

```
<211> LENGTH: 107
<212> TYPE: PRT
<213> ORGANISM: Artificial Sequence
<220> FEATURE:
<223> OTHER INFORMATION: Synthetic Construct

<400> SEQUENCE: 86

Ile Ile Val Met Thr Gln Ser Pro Lys Ser Met Ser Ile Ser Val Gly
1               5                   10                  15

Asp Arg Val Thr Met Asn Cys Lys Ala Ser Gln Asn Val Gly Asn Asn
            20                  25                  30

Ile Ala Trp Tyr Arg Gln Lys Pro Gly Gln Ser Pro Glu Leu Leu Ile
        35                  40                  45

Tyr Tyr Ala Ser Asn Arg Tyr Thr Gly Val Pro Asp Arg Phe Thr Gly
50                  55                  60

Gly Gly Tyr Gly Thr Asp Phe Thr Leu Thr Ile Asn Ser Val Gln Ala
65                  70                  75                  80

Glu Asp Ala Ala Phe Tyr Tyr Cys Gln Arg Ile Tyr Asn Ser Pro Pro
                85                  90                  95

Thr Phe Gly Gly Gly Thr Lys Val Glu Ile Lys
            100                 105

<210> SEQ ID NO 87
<211> LENGTH: 214
<212> TYPE: PRT
<213> ORGANISM: Artificial Sequence
<220> FEATURE:
<223> OTHER INFORMATION: Synthetic Construct

<400> SEQUENCE: 87

Ile Ile Val Met Thr Gln Ser Pro Lys Ser Met Ser Ile Ser Val Gly
1               5                   10                  15

Asp Arg Val Thr Met Asn Cys Lys Ala Ser Gln Asn Val Gly Asn Asn
            20                  25                  30

Ile Ala Trp Tyr Arg Gln Lys Pro Gly Gln Ser Pro Glu Leu Leu Ile
        35                  40                  45

Tyr Tyr Ala Ser Asn Arg Tyr Thr Gly Val Pro Asp Arg Phe Thr Gly
50                  55                  60

Gly Gly Tyr Gly Thr Asp Phe Thr Leu Thr Ile Asn Ser Val Gln Ala
65                  70                  75                  80

Glu Asp Ala Ala Phe Tyr Tyr Cys Gln Arg Ile Tyr Asn Ser Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
```

<210> SEQ ID NO 88
<211> LENGTH: 107
<212> TYPE: PRT
<213> ORGANISM: Artificial Sequence
<220> FEATURE:
<223> OTHER INFORMATION: Synthetic Construct

<400> SEQUENCE: 88

```
Asn Ile Val Met Thr Gln Ser Pro Lys Ser Met Ser Ile Ser Val Gly
1               5                   10                  15

Asp Arg Val Thr Met Asn Cys Lys Ala Ser Gln Asn Val Gly Asn Asn
            20                  25                  30

Leu Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
50                  55                  60

Gly Gly Tyr Gly Thr Asp Phe Thr Leu Thr Ile Asn Ser Val Gln Ala
65                  70                  75                  80

Glu Asp Ala Ala Phe Tyr Tyr Cys Gln Arg Ile Tyr Asn Ser Pro Pro
                85                  90                  95

Thr Phe Gly Gly Gly Thr Lys Val Glu Ile Lys
            100                 105
```

<210> SEQ ID NO 89
<211> LENGTH: 214
<212> TYPE: PRT
<213> ORGANISM: Artificial Sequence
<220> FEATURE:
<223> OTHER INFORMATION: Synthetic Construct

<400> SEQUENCE: 89

```
Asn Ile Val Met Thr Gln Ser Pro Lys Ser Met Ser Ile Ser Val Gly
1               5                   10                  15

Asp Arg Val Thr Met Asn Cys Lys Ala Ser Gln Asn Val Gly Asn Asn
            20                  25                  30

Leu Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
50                  55                  60

Gly Gly Tyr Gly Thr Asp Phe Thr Leu Thr Ile Asn Ser Val Gln Ala
65                  70                  75                  80

Glu Asp Ala Ala Phe Tyr Tyr Cys Gln Arg Ile Tyr Asn Ser Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
            195                 200                 205

Phe Asn Arg Gly Glu Cys
    210

<210> SEQ ID NO 90
<211> LENGTH: 123
<212> TYPE: PRT
<213> ORGANISM: Artificial Sequence
<220> FEATURE:
<223> OTHER INFORMATION: Synthetic Construct

<400> SEQUENCE: 90

His Ser Glu Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Trp Met Tyr Trp Val Arg Gln Ala Pro Gly Lys Gly Leu Glu
        35                  40                  45

Trp Val Ala Ser Ile Thr Pro Asn Gly Gly Asn Thr Tyr Tyr Pro Asp
50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Gly His Tyr Tyr Tyr Thr Ser Tyr Ser Leu Gly Tyr
            100                 105                 110

Trp Gly Gln Gly Thr Leu Val Thr Val Ser Ser
        115                 120

<210> SEQ ID NO 91
<211> LENGTH: 106
<212> TYPE: PRT
<213> ORGANISM: Artificial Sequence
<220> FEATURE:
<223> OTHER INFORMATION: Synthetic Construct

<400> SEQUENCE: 91

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asn Lys His
            20                  25                  30

Leu Asp Trp Tyr Gln Gln Lys Pro Gly Lys Ala Pro Lys Leu Leu Ile
        35                  40                  45

Tyr Phe Thr Asn Asn Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Phe Gln Tyr Asn Asn Gly Trp Thr
                85                  90                  95

Phe Gly Gly Gly Thr Lys Val Glu Ile Lys
            100                 105

<210> SEQ ID NO 92
<211> LENGTH: 453
<212> TYPE: PRT
<213> ORGANISM: Artificial Sequence
<220> FEATURE:
<223> OTHER INFORMATION: Synthetic Construct

<400> SEQUENCE: 92

```
His Ser Glu Val Gln Leu Val Glu Ser Gly Gly Gly Leu Val Gln Pro
 1               5                  10                  15

Gly Gly Ser Leu Arg Leu Ser Cys Ala Ala Ser Gly Phe Thr Phe Ser
            20                  25                  30

Ser Tyr Trp Met Tyr Trp Val Arg Gln Ala Pro Gly Lys Gly Leu Glu
        35                  40                  45

Trp Val Ala Ser Ile Thr Pro Asn Gly Gly Asn Thr Tyr Tyr Pro Asp
    50                  55                  60

Ser Val Lys Gly Arg Phe Thr Ile Ser Arg Asp Asn Ala Lys Asn Ser
 65                  70                  75                  80

Leu Tyr Leu Gln Met Asn Ser Leu Arg Ala Glu Asp Thr Ala Val Tyr
                85                  90                  95

Tyr Cys Ala Arg Gly His Tyr Tyr Thr Ser Tyr Ser Leu Gly Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Ala
225                 230                 235                 240

Ala Gly Ala Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415
```

```
Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 93
<211> LENGTH: 213
<212> TYPE: PRT
<213> ORGANISM: Artificial Sequence
<220> FEATURE:
<223> OTHER INFORMATION: Synthetic Construct

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asn Lys His
            20                  25                  30

Leu Asp Trp Tyr Gln Gln Lys Pro Gly Lys Ala Pro Lys Leu Leu Ile
        35                  40                  45

Tyr Phe Thr Asn Asn Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Phe Gln Tyr Asn Asn Gly Trp Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 94
<211> LENGTH: 121
<212> TYPE: PRT
<213> ORGANISM: Artificial Sequence
<220> FEATURE:
<223> OTHER INFORMATION: Synthetic Construct

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
```

```
            35                  40                  45
Ala Ser Ile Thr Pro Asn Gly Gly Asn Thr Tyr Tyr Pro Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Thr Ser Tyr Ser Leu Gly Tyr Trp Gly
            100                 105                 110

Gln Gly Thr Leu Val Thr Val Ser Ser
            115                 120

<210> SEQ ID NO 95
<211> LENGTH: 451
<212> TYPE: PRT
<213> ORGANISM: Artificial Sequence
<220> FEATURE:
<223> OTHER INFORMATION: Synthetic Construct

<400> SEQUENCE: 95

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
            35                  40                  45

Ala Ser Ile Thr Pro Asn Gly Gly Asn Thr Tyr Tyr Pro Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Thr Ser Tyr Ser Leu Gly Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
```

```
                275                 280                 285
His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
    435                 440                 445

Pro Gly Lys
    450

<210> SEQ ID NO 96
<211> LENGTH: 110
<212> TYPE: PRT
<213> ORGANISM: Artificial Sequence
<220> FEATURE:
<223> OTHER INFORMATION: Synthetic Construct

<400> SEQUENCE: 96

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 97
<211> LENGTH: 121
<212> TYPE: PRT
<213> ORGANISM: Artificial Sequence
<220> FEATURE:
<223> OTHER INFORMATION: Synthetic Construct

<400> SEQUENCE: 97

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Asn Tyr
            20                  25                  30

Trp Met Tyr Trp Val Arg Gln Ala Pro Gly Lys Gly Leu Glu Trp Val
            35                  40                  45

Ala Ser Ile Asn Asn Asp Gly Gly Asn Thr Tyr Tyr Leu Asp Ser Val
 50                      55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly His Tyr Ser Tyr Ser Ser Tyr Ser Phe Tyr Tyr Trp Gly
            100                 105                 110

Gln Gly Thr Leu Val Thr Val Ser Ser
            115                 120

<210> SEQ ID NO 98
<211> LENGTH: 106
<212> TYPE: PRT
<213> ORGANISM: Artificial Sequence
<220> FEATURE:
<223> OTHER INFORMATION: Synthetic Construct

<400> SEQUENCE: 98

Asp Ile Gln Met Thr Gln Ser Pro Ser Ser Leu Ser Ala Ser Val Gly
 1               5                  10                  15

Asp Arg Val Thr Ile Thr Cys Lys Ala Ser His Asn Ile Asn Lys His
            20                  25                  30

Leu Asp Trp Tyr Gln Gln Lys Pro Gly Lys Ala Pro Lys Leu Leu Ile
            35                  40                  45

Tyr Phe Thr Asn Asn Leu Gln Thr Gly Val Pro Ser Arg Phe Ser Gly
 50                      55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Phe Gln Tyr Asn Ser Gly Trp Thr
                 85                  90                  95

Phe Gly Gly Gly Thr Lys Val Glu Ile Lys
            100                 105

<210> SEQ ID NO 99
<211> LENGTH: 451
<212> TYPE: PRT
<213> ORGANISM: Artificial Sequence
<220> FEATURE:
<223> OTHER INFORMATION: Synthetic Construct

<400> SEQUENCE: 99

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Trp Met Tyr Trp Val Arg Gln Ala Pro Gly Lys Gly Leu Glu Trp Val
            35                  40                  45

Ala Ser Ile Asn Asn Asp Gly Gly Asn Thr Tyr Tyr Leu Asp Ser Val
 50                      55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95
```

```
Ala Arg Gly His Tyr Ser Tyr Ser Ser Tyr Ser Phe Ser Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 100
<211> LENGTH: 213
<212> TYPE: PRT
<213> ORGANISM: Artificial Sequence
<220> FEATURE:
<223> OTHER INFORMATION: Synthetic Construct

<400> SEQUENCE: 100
```

Asp Ile Gln Met Thr Gln Ser Pro Ser Ser Leu Ser Ala Ser Val Gly
1               5                   10                  15

Asp Arg Val Thr Ile Thr Cys Lys Ala Ser His Asn Ile Asn Lys His
            20                  25                  30

Leu Asp Trp Tyr Gln Lys Pro Gly Lys Ala Pro Lys Leu Leu Ile
        35                  40                  45

Tyr Phe Thr Asn Asn Leu Gln Thr Gly Val Pro Ser Arg Phe Ser Gly
50                      55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Phe Gln Tyr Asn Ser Gly Trp Thr
                85                  90                  95

Phe Gly Gly Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
        210

<210> SEQ ID NO 101
<211> LENGTH: 121
<212> TYPE: PRT
<213> ORGANISM: Artificial Sequence
<220> FEATURE:
<223> OTHER INFORMATION: Synthetic Construct

<400> SEQUENCE: 101

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Lys Asn Tyr
            20                  25                  30

Trp Met Thr Trp Val Arg Gln Ala Pro Gly Lys Gly Leu Glu Trp Val
        35                  40                  45

Ala Ser Ile Thr Asn Thr Gly Gly Ala Thr Tyr Tyr Pro Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Arg Tyr Asn Ser Gly Ser Pro Phe Ala Tyr Trp Gly
                100                 105                 110

Gln Gly Thr Leu Val Thr Val Ser Ser
            115                 120

<210> SEQ ID NO 102

```
<211> LENGTH: 10
<212> TYPE: PRT
<213> ORGANISM: Artificial Sequence
<220> FEATURE:
<223> OTHER INFORMATION: Synthetic Construct

<400> SEQUENCE: 102

Gly Phe Thr Phe Lys Asn Tyr Trp Met Thr
1               5                   10

<210> SEQ ID NO 103
<211> LENGTH: 107
<212> TYPE: PRT
<213> ORGANISM: Artificial Sequence
<220> FEATURE:
<223> OTHER INFORMATION: Synthetic Construct

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Ser
            20                  25                  30

Leu Ile Trp Tyr Gln Gln Lys Pro Gly Lys Ala Pro Lys Leu Leu Ile
        35                  40                  45

Tyr Ser Ser Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Ala Thr Tyr Pro Trp
                85                  90                  95

Thr Phe Gly Gly Gly Thr Lys Val Glu Ile Lys
            100                 105

<210> SEQ ID NO 104
<211> LENGTH: 451
<212> TYPE: PRT
<213> ORGANISM: Artificial Sequence
<220> FEATURE:
<223> OTHER INFORMATION: Synthetic Construct

<400> SEQUENCE: 104

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Lys Asn Tyr
            20                  25                  30

Trp Met Thr Trp Val Arg Gln Ala Pro Gly Lys Gly Leu Glu Trp Val
        35                  40                  45

Ala Ser Ile Thr Asn Thr Gly Gly Ala Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Arg Tyr Asn Ser Gly Ser Pro Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140
```

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 105
<211> LENGTH: 214
<212> TYPE: PRT
<213> ORGANISM: Artificial Sequence
<220> FEATURE:
<223> OTHER INFORMATION: Synthetic Construct

<400> SEQUENCE: 105

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Ser
            20                  25                  30

Leu Ile Trp Tyr Gln Gln Lys Pro Gly Lys Ala Pro Lys Leu Leu Ile
        35                  40                  45

```
Tyr Ser Ser Ser Thr Leu Glu Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Tyr Ala Thr Tyr Pro Trp
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 106
<211> LENGTH: 122
<212> TYPE: PRT
<213> ORGANISM: Artificial Sequence
<220> FEATURE:
<223> OTHER INFORMATION: Synthetic Construct

<400> SEQUENCE: 106

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
             20                  25                  30

Trp Val Ser Trp Val Arg Gln Ala Pro Gly Lys Gly Leu Glu Trp Val
         35                  40                  45

Ala Glu Ile Tyr Pro Asn Ser Gly Ala Asp Asn Phe Asn Glu Asn Phe
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Pro Tyr Tyr Tyr Ser Thr Gln Ile Ile Phe Ala Tyr Trp
            100                 105                 110

Gly Gln Gly Thr Leu Val Thr Val Ser Ser
        115                 120

<210> SEQ ID NO 107
<211> LENGTH: 10
<212> TYPE: PRT
<213> ORGANISM: Artificial Sequence
<220> FEATURE:
<223> OTHER INFORMATION: Synthetic Construct

<400> SEQUENCE: 107

Gly Phe Thr Phe Thr Asp Tyr Trp Val Ser
 1               5                  10
```

<210> SEQ ID NO 108
<211> LENGTH: 107
<212> TYPE: PRT
<213> ORGANISM: Artificial Sequence
<220> FEATURE:
<223> OTHER INFORMATION: Synthetic Construct

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Asn Asn
            20                  25                  30

Leu Ala Trp Tyr Gln Gln Lys Pro Gly Lys Ala Pro Lys Leu Leu Ile
        35                  40                  45

Tyr Tyr Ala Ser Asn Arg Tyr Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Arg Ile Tyr Asn Ser Pro Pro
                85                  90                  95

Thr Phe Gly Gly Gly Thr Lys Val Glu Ile Lys
            100                 105

<210> SEQ ID NO 109
<211> LENGTH: 452
<212> TYPE: PRT
<213> ORGANISM: Artificial Sequence
<220> FEATURE:
<223> OTHER INFORMATION: Synthetic Construct

<400> SEQUENCE: 109

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Trp Ser Trp Val Arg Gln Ala Pro Gly Lys Gly Leu Glu Trp Val
        35                  40                  45

Ala Glu Ile Tyr Pro Asn Ser Gly Ala Asp Asn Phe Asn Glu Asn Phe
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Tyr Tyr Tyr Ser Thr Gln Ile Ile Phe Ala Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn

```
                195                 200                 205
His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Ala Ala
225                 230                 235                 240

Gly Ala Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 110
<211> LENGTH: 214
<212> TYPE: PRT
<213> ORGANISM: Artificial Sequence
<220> FEATURE:
<223> OTHER INFORMATION: Synthetic Construct

<400> SEQUENCE: 110

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Asn Asn
            20                  25                  30

Leu Ala Trp Tyr Gln Gln Lys Pro Gly Lys Ala Pro Lys Leu Leu Ile
        35                  40                  45

Tyr Tyr Ala Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Arg Ile Tyr Asn Ser Pro Pro
                85                  90                  95

Thr Phe Gly Gly Gly Thr Lys Val Glu Ile Lys Arg Thr Val Ala Ala
```

-continued

```
                100                 105                 110
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 111
<211> LENGTH: 122
<212> TYPE: PRT
<213> ORGANISM: Artificial Sequence
<220> FEATURE:
<223> OTHER INFORMATION: Synthetic Construct

<400> SEQUENCE: 111

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Trp Val Ser Trp Val Arg Gln Ala Pro Gly Lys Gly Leu Glu Trp Val
        35                  40                  45

Ala Glu Ile Tyr Pro Asn Ser Gly Ala Asp Asn Phe Asn Glu Asn Phe
    50                  55                  60

Lys Gly Arg Phe Thr Ile Ser Val Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Tyr Tyr Tyr Ser Thr Gln Ile Ile Phe Ala Tyr Trp
            100                 105                 110

Gly Gln Gly Thr Leu Val Thr Val Ser Ser
        115                 120

<210> SEQ ID NO 112
<211> LENGTH: 452
<212> TYPE: PRT
<213> ORGANISM: Artificial Sequence
<220> FEATURE:
<223> OTHER INFORMATION: Synthetic Construct

<400> SEQUENCE: 112

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Trp Val Ser Trp Val Arg Gln Ala Pro Gly Lys Gly Leu Glu Trp Val
        35                  40                  45

Ala Glu Ile Tyr Pro Asn Ser Gly Ala Asp Asn Phe Asn Glu Asn Phe
    50                  55                  60
```

-continued

```
Lys Gly Arg Phe Thr Ile Ser Val Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Pro Tyr Tyr Tyr Ser Thr Gln Ile Ile Phe Ala Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Ala Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 113
<211> LENGTH: 121
<212> TYPE: PRT
```

<213> ORGANISM: Artificial Sequence
<220> FEATURE:
<223> OTHER INFORMATION: Synthetic Construct

<400> SEQUENCE: 113

```
Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Ser Asn Tyr
            20                  25                  30

Trp Met Tyr Trp Ile Arg Gln Ala Pro Gly Met Gly Leu Glu Trp Val
        35                  40                  45

Ser Ser Ile Asn Asn Asp Gly Gly Asn Thr Tyr Tyr Leu Asp Ser Val
    50                  55                  60

Lys Gly Arg Phe Thr Ile Ser Arg Asn Asn Ala Glu Asn Thr Val Tyr
65                  70                  75                  80

Leu Gln Met Asn Ser Leu Arg Ser Glu Asp Thr Ala Thr Tyr Tyr Cys
                85                  90                  95

Ala Lys Gly His Tyr Tyr Tyr Ser Ser Tyr Ser Leu Gly Tyr Trp Gly
            100                 105                 110

Gln Gly Thr Leu Val Thr Val Ser Ser
        115                 120
```

<210> SEQ ID NO 114
<211> LENGTH: 12
<212> TYPE: PRT
<213> ORGANISM: Artificial Sequence
<220> FEATURE:
<223> OTHER INFORMATION: Synthetic Construct

<400> SEQUENCE: 114

```
Gly His Tyr Tyr Tyr Ser Ser Tyr Ser Leu Gly Tyr
1               5                   10
```

<210> SEQ ID NO 115
<211> LENGTH: 106
<212> TYPE: PRT
<213> ORGANISM: Artificial Sequence
<220> FEATURE:
<223> OTHER INFORMATION: Synthetic Construct

<400> SEQUENCE: 115

```
Asp Ile Gln Met Thr Gln Ser Pro Ser Val Leu Ser Ala Ser Val Gly
1               5                   10                  15

Asp Arg Val Thr Leu Ser Cys Lys Ala Ser His Asn Ile Asn Lys His
            20                  25                  30

Leu Asp Trp Tyr Gln Gln Lys Val Gly Glu Ala Pro Lys Leu Leu Ile
        35                  40                  45

Tyr Phe Thr Asn Asn Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Phe Gln Tyr Asn Ser Gly Trp Thr
                85                  90                  95

Phe Gly Gln Gly Thr Lys Val Glu Ile Lys
            100                 105
```

<210> SEQ ID NO 116
<211> LENGTH: 451
<212> TYPE: PRT
<213> ORGANISM: Artificial Sequence
<220> FEATURE:
<223> OTHER INFORMATION: Synthetic Construct

<400> SEQUENCE: 116

```
Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Ser Asn Tyr
            20                  25                  30

Trp Met Tyr Trp Ile Arg Gln Ala Pro Gly Met Gly Leu Glu Trp Val
        35                  40                  45

Ser Ser Ile Asn Asn Asp Gly Gly Asn Thr Tyr Tyr Leu Asp Ser Val
    50                  55                  60

Lys Gly Arg Phe Thr Ile Ser Arg Asn Asn Ala Glu Asn Thr Val Tyr
65                  70                  75                  80

Leu Gln Met Asn Ser Leu Arg Ser Glu Asp Thr Ala Thr Tyr Tyr Cys
                85                  90                  95

Ala Lys Gly His Tyr Tyr Ser Ser Tyr Ser Leu Gly Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400
```

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
        450

<210> SEQ ID NO 117
<211> LENGTH: 213
<212> TYPE: PRT
<213> ORGANISM: Artificial Sequence
<220> FEATURE:
<223> OTHER INFORMATION: Synthetic Construct

<400> SEQUENCE: 117

Asp Ile Gln Met Thr Gln Ser Pro Ser Val Leu Ser Ala Ser Val Gly
1               5                   10                  15

Asp Arg Val Thr Leu Ser Cys Lys Ala Ser His Asn Ile Asn Lys His
                20                  25                  30

Leu Asp Trp Tyr Gln Gln Lys Val Gly Glu Ala Pro Lys Leu Leu Ile
            35                  40                  45

Tyr Phe Thr Asn Asn Leu Gln Thr Gly Ile Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Phe Gln Tyr Asn Ser Gly Trp Thr
                85                  90                  95

Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
            195                 200                 205

Asn Arg Gly Glu Cys
        210

<210> SEQ ID NO 118
<211> LENGTH: 121
<212> TYPE: PRT
<213> ORGANISM: Artificial Sequence
<220> FEATURE:
<223> OTHER INFORMATION: Synthetic Construct

<400> SEQUENCE: 118

Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Ser Asn Tyr

```
                    20                  25                  30
Trp Met Tyr Trp Ile Arg Gln Ala Pro Gly Met Gly Leu Glu Trp Val
            35                  40                  45

Ser Ser Ile Asn Asn Asp Gly Gly Asn Thr Tyr Tyr Leu Asp Ser Val
    50                  55                  60

Lys Gly Arg Phe Thr Ile Ser Arg Asn Asn Ala Glu Asn Thr Val Tyr
65                  70                  75                  80

Leu Gln Met Asn Ser Leu Arg Ser Glu Asp Thr Ala Thr Tyr Tyr Cys
                85                  90                  95

Ala Lys Gly His Tyr Ser Tyr Ser Ser Tyr Ser Phe Gly Tyr Trp Gly
            100                 105                 110

Gln Gly Thr Leu Val Thr Val Ser Ser
            115                 120

<210> SEQ ID NO 119
<211> LENGTH: 12
<212> TYPE: PRT
<213> ORGANISM: Artificial Sequence
<220> FEATURE:
<223> OTHER INFORMATION: Synthetic Construct

<400> SEQUENCE: 119

Gly His Tyr Ser Tyr Ser Ser Tyr Ser Phe Gly Tyr
1               5                   10

<210> SEQ ID NO 120
<211> LENGTH: 451
<212> TYPE: PRT
<213> ORGANISM: Artificial Sequence
<220> FEATURE:
<223> OTHER INFORMATION: Synthetic Construct

<400> SEQUENCE: 120

Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Ser Asn Tyr
            20                  25                  30

Trp Met Tyr Trp Ile Arg Gln Ala Pro Gly Met Gly Leu Glu Trp Val
            35                  40                  45

Ser Ser Ile Asn Asn Asp Gly Gly Asn Thr Tyr Tyr Leu Asp Ser Val
    50                  55                  60

Lys Gly Arg Phe Thr Ile Ser Arg Asn Asn Ala Glu Asn Thr Val Tyr
65                  70                  75                  80

Leu Gln Met Asn Ser Leu Arg Ser Glu Asp Thr Ala Thr Tyr Tyr Cys
                85                  90                  95

Ala Lys Gly His Tyr Ser Tyr Ser Ser Tyr Ser Phe Gly Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 121
<211> LENGTH: 121
<212> TYPE: PRT
<213> ORGANISM: Artificial Sequence
<220> FEATURE:
<223> OTHER INFORMATION: Synthetic Construct

<400> SEQUENCE: 121

Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Ser Asn Tyr
            20                  25                  30

Trp Met Tyr Trp Ile Arg Gln Ala Pro Gly Met Gly Leu Glu Trp Val
            35                  40                  45

Ser Ser Ile Asn Asn Asp Gly Gly Asn Thr Tyr Tyr Leu Asp Ser Val
        50                  55                  60

Lys Gly Arg Phe Thr Ile Ser Arg Asn Asn Ala Glu Asn Thr Val Tyr
65                  70                  75                  80

Leu Gln Met Asn Ser Leu Arg Ser Glu Asp Thr Ala Thr Tyr Tyr Cys
            85                  90                  95

```
Val Lys Gly His Tyr Ser Tyr Ser Ser Tyr Ser Ile Asp Tyr Trp Gly
            100                 105                 110

Gln Gly Thr Leu Val Thr Val Ser Ser
        115                 120

<210> SEQ ID NO 122
<211> LENGTH: 12
<212> TYPE: PRT
<213> ORGANISM: Artificial Sequence
<220> FEATURE:
<223> OTHER INFORMATION: Synthetic Construct

<400> SEQUENCE: 122

Gly His Tyr Ser Tyr Ser Ser Tyr Ser Ile Asp Tyr
1               5                   10

<210> SEQ ID NO 123
<211> LENGTH: 451
<212> TYPE: PRT
<213> ORGANISM: Artificial Sequence
<220> FEATURE:
<223> OTHER INFORMATION: Synthetic Construct

<400> SEQUENCE: 123

Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Ser Asn Tyr
            20                  25                  30

Trp Met Tyr Trp Ile Arg Gln Ala Pro Gly Met Gly Leu Glu Trp Val
        35                  40                  45

Ser Ser Ile Asn Asn Asp Gly Gly Asn Thr Tyr Tyr Leu Asp Ser Val
    50                  55                  60

Lys Gly Arg Phe Thr Ile Ser Arg Asn Asn Ala Glu Asn Thr Val Tyr
65                  70                  75                  80

Leu Gln Met Asn Ser Leu Arg Ser Glu Asp Thr Ala Thr Tyr Tyr Cys
            85                  90                  95

Val Lys Gly His Tyr Ser Tyr Ser Ser Tyr Ser Ile Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270
```

```
Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
        450

<210> SEQ ID NO 124
<211> LENGTH: 121
<212> TYPE: PRT
<213> ORGANISM: Artificial Sequence
<220> FEATURE:
<223> OTHER INFORMATION: Synthetic Construct

<400> SEQUENCE: 124

Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Ser Asn Tyr
            20                  25                  30

Trp Met Tyr Trp Ile Arg Gln Ala Pro Gly Met Gly Leu Glu Trp Val
        35                  40                  45

Ser Ser Ile Asn Asn Asp Gly Gly Asn Thr Tyr Tyr Leu Asp Ser Val
    50                  55                  60

Lys Gly Arg Phe Thr Ile Ser Arg Asn Asn Ala Glu Asn Thr Val Tyr
65                  70                  75                  80

Leu Gln Met Asn Ser Leu Arg Ser Glu Asp Thr Ala Thr Tyr Tyr Cys
                85                  90                  95

Ala Lys Gly His Tyr Ser Tyr Ser Ser Tyr Ser Ile Asp Tyr Trp Gly
            100                 105                 110

Gln Gly Thr Leu Val Thr Val Ser Ser
        115                 120

<210> SEQ ID NO 125
<211> LENGTH: 451
<212> TYPE: PRT
<213> ORGANISM: Artificial Sequence
<220> FEATURE:
<223> OTHER INFORMATION: Synthetic Construct
```

```
<400> SEQUENCE: 125

Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Ser Asn Tyr
            20                  25                  30

Trp Met Tyr Trp Ile Arg Gln Ala Pro Gly Met Gly Leu Glu Trp Val
        35                  40                  45

Ser Ser Ile Asn Asn Asp Gly Gly Asn Thr Tyr Tyr Leu Asp Ser Val
    50                  55                  60

Lys Gly Arg Phe Thr Ile Ser Arg Asn Ala Glu Asn Thr Val Tyr
65                  70                  75                  80

Leu Gln Met Asn Ser Leu Arg Ser Glu Asp Thr Ala Thr Tyr Tyr Cys
                85                  90                  95

Ala Lys Gly His Tyr Ser Tyr Ser Ser Tyr Ser Ile Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415
```

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
        450

<210> SEQ ID NO 126
<211> LENGTH: 121
<212> TYPE: PRT
<213> ORGANISM: Artificial Sequence
<220> FEATURE:
<223> OTHER INFORMATION: Synthetic Construct

<400> SEQUENCE: 126

Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Ser Asn Tyr
            20                  25                  30

Trp Met Tyr Trp Ile Arg Gln Ala Pro Gly Met Gly Leu Glu Trp Val
        35                  40                  45

Ser Ser Ile Asn Asn Asp Gly Gly Asn Thr Tyr Tyr Leu Asp Ser Val
    50                  55                  60

Lys Gly Arg Phe Thr Ile Ser Arg Asn Asn Ala Glu Asn Thr Val Tyr
65                  70                  75                  80

Leu Gln Met Asn Ser Leu Arg Ser Glu Asp Thr Ala Thr Tyr Tyr Cys
                85                  90                  95

Ala Lys Gly His Tyr Ser Tyr Thr Ser Tyr Ser Phe Gly Tyr Trp Gly
            100                 105                 110

Gln Gly Thr Leu Val Thr Val Ser Ser
        115                 120

<210> SEQ ID NO 127
<211> LENGTH: 12
<212> TYPE: PRT
<213> ORGANISM: Artificial Sequence
<220> FEATURE:
<223> OTHER INFORMATION: Synthetic Construct

<400> SEQUENCE: 127

Gly His Tyr Ser Tyr Thr Ser Tyr Ser Phe Gly Tyr
1               5                   10

<210> SEQ ID NO 128
<211> LENGTH: 451
<212> TYPE: PRT
<213> ORGANISM: Artificial Sequence
<220> FEATURE:
<223> OTHER INFORMATION: Synthetic Construct

<400> SEQUENCE: 128

Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Ser Asn Tyr
            20                  25                  30

Trp Met Tyr Trp Ile Arg Gln Ala Pro Gly Met Gly Leu Glu Trp Val
        35                  40                  45

Ser Ser Ile Asn Asn Asp Gly Gly Asn Thr Tyr Tyr Leu Asp Ser Val
    50                  55                  60

-continued

Lys Gly Arg Phe Thr Ile Ser Arg Asn Asn Ala Glu Asn Thr Val Tyr
 65                  70                  75                  80

Leu Gln Met Asn Ser Leu Arg Ser Glu Asp Thr Ala Thr Tyr Tyr Cys
                 85                  90                  95

Ala Lys Gly His Tyr Ser Tyr Thr Ser Tyr Ser Phe Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 129
<211> LENGTH: 121
<212> TYPE: PRT

<213> ORGANISM: Artificial Sequence
<220> FEATURE:
<223> OTHER INFORMATION: Synthetic Construct

<400> SEQUENCE: 129

```
Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Ser Asn Tyr
            20                  25                  30

Trp Met Tyr Trp Ile Arg Gln Ala Pro Gly Met Gly Leu Glu Trp Val
        35                  40                  45

Ser Ser Ile Asn Asn Asp Gly Gly Asn Thr Tyr Tyr Leu Asp Ser Val
    50                  55                  60

Lys Gly Arg Phe Thr Ile Ser Arg Asn Asn Ala Glu Asn Thr Val Tyr
65                  70                  75                  80

Leu Gln Met Asn Ser Leu Arg Ser Glu Asp Thr Ala Thr Tyr Tyr Cys
                85                  90                  95

Ala Lys Gly Arg Tyr Tyr Tyr Ser Ser Tyr Ser Phe Ala Tyr Trp Gly
            100                 105                 110

Gln Gly Thr Leu Val Thr Val Ser Ser
            115                 120
```

<210> SEQ ID NO 130
<211> LENGTH: 12
<212> TYPE: PRT
<213> ORGANISM: Artificial Sequence
<220> FEATURE:
<223> OTHER INFORMATION: Synthetic Construct

<400> SEQUENCE: 130

```
Gly Arg Tyr Tyr Tyr Ser Ser Tyr Ser Phe Ala Tyr
1               5                   10
```

<210> SEQ ID NO 131
<211> LENGTH: 451
<212> TYPE: PRT
<213> ORGANISM: Artificial Sequence
<220> FEATURE:
<223> OTHER INFORMATION: Synthetic Construct

<400> SEQUENCE: 131

```
Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Ser Asn Tyr
            20                  25                  30

Trp Met Tyr Trp Ile Arg Gln Ala Pro Gly Met Gly Leu Glu Trp Val
        35                  40                  45

Ser Ser Ile Asn Asn Asp Gly Gly Asn Thr Tyr Tyr Leu Asp Ser Val
    50                  55                  60

Lys Gly Arg Phe Thr Ile Ser Arg Asn Asn Ala Glu Asn Thr Val Tyr
65                  70                  75                  80

Leu Gln Met Asn Ser Leu Arg Ser Glu Asp Thr Ala Thr Tyr Tyr Cys
                85                  90                  95

Ala Lys Gly Arg Tyr Tyr Tyr Ser Ser Tyr Ser Phe Ala Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140
```

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 132
<211> LENGTH: 121
<212> TYPE: PRT
<213> ORGANISM: Artificial Sequence
<220> FEATURE:
<223> OTHER INFORMATION: Synthetic Construct

<400> SEQUENCE: 132

Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Ser Asn Tyr
            20                  25                  30

Trp Met Tyr Trp Ile Arg Gln Ala Pro Gly Met Gly Leu Glu Trp Val
        35                  40                  45

```
Ser Ser Ile Asn Asn Asp Gly Gly Asn Thr Tyr Tyr Leu Asp Ser Val
 50                  55                  60

Lys Gly Arg Phe Thr Ile Ser Arg Asn Asn Ala Glu Asn Thr Val Tyr
 65                  70                  75                  80

Leu Gln Met Asn Ser Leu Arg Ser Glu Asp Thr Ala Thr Tyr Tyr Cys
                 85                  90                  95

Ala Arg Gly His Tyr Tyr Tyr Asn Ser Tyr Ser Phe Ala His Trp Gly
                100                 105                 110

Gln Gly Thr Leu Val Thr Val Ser Ser
                115                 120

<210> SEQ ID NO 133
<211> LENGTH: 12
<212> TYPE: PRT
<213> ORGANISM: Artificial Sequence
<220> FEATURE:
<223> OTHER INFORMATION: Synthetic Construct

<400> SEQUENCE: 133

Gly His Tyr Tyr Tyr Asn Ser Tyr Ser Phe Ala His
 1               5                  10

<210> SEQ ID NO 134
<211> LENGTH: 451
<212> TYPE: PRT
<213> ORGANISM: Artificial Sequence
<220> FEATURE:
<223> OTHER INFORMATION: Synthetic Construct

<400> SEQUENCE: 134

Glu Val Gln Leu Val Glu Thr Gly Gly Gly Leu Val Gln Pro Gly Arg
 1               5                  10                  15

Ser Leu Lys Leu Ser Cys Val Ala Ser Gly Phe Thr Phe Ser Asn Tyr
                 20                  25                  30

Trp Met Tyr Trp Ile Arg Gln Ala Pro Gly Met Gly Leu Glu Trp Val
                 35                  40                  45

Ser Ser Ile Asn Asn Asp Gly Gly Asn Thr Tyr Tyr Leu Asp Ser Val
 50                  55                  60

Lys Gly Arg Phe Thr Ile Ser Arg Asn Asn Ala Glu Asn Thr Val Tyr
 65                  70                  75                  80

Leu Gln Met Asn Ser Leu Arg Ser Glu Asp Thr Ala Thr Tyr Tyr Cys
                 85                  90                  95

Ala Arg Gly His Tyr Tyr Tyr Asn Ser Tyr Ser Phe Ala His Trp Gly
                100                 105                 110

Gln Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
```

```
            210                 215                 220
Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
                435                 440                 445

Pro Gly Lys
    450

<210> SEQ ID NO 135
<211> LENGTH: 121
<212> TYPE: PRT
<213> ORGANISM: Artificial Sequence
<220> FEATURE:
<223> OTHER INFORMATION: Synthetic Construct

<400> SEQUENCE: 135

Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Ser Asn Tyr
                20                  25                  30

Trp Met Tyr Trp Ile Arg Gln Ala Pro Gly Met Gly Leu Glu Trp Val
            35                  40                  45

Ser Ser Ile Asn Asn Asp Gly Gly Asn Thr Tyr Tyr Leu Asp Ser Val
        50                  55                  60

Lys Gly Arg Phe Thr Ile Ser Arg Asn Asn Ala Glu Asn Thr Val Tyr
65                  70                  75                  80

Leu Gln Met Asn Ser Leu Arg Ser Glu Asp Thr Ala Thr Tyr Tyr Cys
                85                  90                  95

Ala Lys Gly His Tyr Ser Tyr Ser Ser Tyr Ser Phe Ala Asn Trp Gly
            100                 105                 110

Gln Gly Thr Leu Val Thr Val Ser Ser
```

<210> SEQ ID NO 136
<211> LENGTH: 12
<212> TYPE: PRT
<213> ORGANISM: Artificial Sequence
<220> FEATURE:
<223> OTHER INFORMATION: Synthetic Construct

<400> SEQUENCE: 136

Gly His Tyr Ser Tyr Ser Ser Tyr Ser Phe Ala Asn
1               5                   10

<210> SEQ ID NO 137
<211> LENGTH: 451
<212> TYPE: PRT
<213> ORGANISM: Artificial Sequence
<220> FEATURE:
<223> OTHER INFORMATION: Synthetic Construct

<400> SEQUENCE: 137

Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Ser Asn Tyr
            20                  25                  30

Trp Met Tyr Trp Ile Arg Gln Ala Pro Gly Met Gly Leu Glu Trp Val
        35                  40                  45

Ser Ser Ile Asn Asn Asp Gly Gly Asn Thr Tyr Tyr Leu Asp Ser Val
    50                  55                  60

Lys Gly Arg Phe Thr Ile Ser Arg Asn Asn Ala Glu Asn Thr Val Tyr
65                  70                  75                  80

Leu Gln Met Asn Ser Leu Arg Ser Glu Asp Thr Ala Thr Tyr Tyr Cys
                85                  90                  95

Ala Lys Gly His Tyr Ser Tyr Ser Ser Tyr Ser Phe Ala Asn Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
435                 440                 445

Pro Gly Lys
    450

<210> SEQ ID NO 138
<211> LENGTH: 121
<212> TYPE: PRT
<213> ORGANISM: Artificial Sequence
<220> FEATURE:
<223> OTHER INFORMATION: Synthetic Construct

<400> SEQUENCE: 138

Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Ser Asn Tyr
            20                  25                  30

Trp Met Tyr Trp Ile Arg Gln Ala Pro Gly Met Gly Leu Glu Trp Val
        35                  40                  45

Ser Ser Ile Asn Asn Asp Gly Gly Asn Thr Tyr Tyr Leu Asp Ser Val
50                  55                  60

Lys Gly Arg Phe Thr Ile Ser Arg Asn Asn Ala Glu Asn Thr Val Tyr
65                  70                  75                  80

Leu Gln Met Asn Ser Leu Arg Ser Glu Asp Thr Ala Thr Tyr Tyr Cys
                85                  90                  95

Ala Arg Gly His Tyr Tyr Tyr Ser Ser Tyr Ser Phe Gly Ser Trp Gly
            100                 105                 110

Gln Gly Thr Leu Val Thr Val Ser Ser
        115                 120

<210> SEQ ID NO 139
<211> LENGTH: 12
<212> TYPE: PRT
<213> ORGANISM: Artificial Sequence
<220> FEATURE:
<223> OTHER INFORMATION: Synthetic Construct

<400> SEQUENCE: 139

Gly His Tyr Tyr Tyr Ser Ser Tyr Ser Phe Gly Ser
1               5                   10

```
<210> SEQ ID NO 140
<211> LENGTH: 451
<212> TYPE: PRT
<213> ORGANISM: Artificial Sequence
<220> FEATURE:
<223> OTHER INFORMATION: Synthetic Construct

<400> SEQUENCE: 140
```

| | | | | | | | | | | | | | | | |
|---|---|---|---|---|---|---|---|---|---|---|---|---|---|---|---|
| Glu | Val | Gln | Leu | Val | Glu | Thr | Gly | Gly | Gly | Leu | Val | Gln | Pro | Gly | Arg |
| 1 | | | | 5 | | | | | 10 | | | | | 15 | |
| Ser | Leu | Lys | Leu | Ser | Cys | Val | Ala | Ser | Gly | Phe | Thr | Phe | Ser | Asn | Tyr |
| | | | 20 | | | | | 25 | | | | | 30 | | |
| Trp | Met | Tyr | Trp | Ile | Arg | Gln | Ala | Pro | Gly | Met | Gly | Leu | Glu | Trp | Val |
| | | | 35 | | | | | 40 | | | | | 45 | | |
| Ser | Ser | Ile | Asn | Asn | Asp | Gly | Gly | Asn | Thr | Tyr | Tyr | Leu | Asp | Ser | Val |
| | 50 | | | | | 55 | | | | | 60 | | | | |
| Lys | Gly | Arg | Phe | Thr | Ile | Ser | Arg | Asn | Asn | Ala | Glu | Asn | Thr | Val | Tyr |
| 65 | | | | | 70 | | | | | 75 | | | | | 80 |
| Leu | Gln | Met | Asn | Ser | Leu | Arg | Ser | Glu | Asp | Thr | Ala | Thr | Tyr | Tyr | Cys |
| | | | | 85 | | | | | 90 | | | | | 95 | |
| Ala | Arg | Gly | His | Tyr | Tyr | Ser | Ser | Tyr | Ser | Phe | Gly | Ser | Trp | Gly |
| | | | 100 | | | | | 105 | | | | | 110 | | |
| Gln | Gly | Thr | Leu | Val | Thr | Val | Ser | Ser | Ala | Ser | Thr | Lys | Gly | Pro | Ser |
| | | | 115 | | | | | 120 | | | | | 125 | | |
| Val | Phe | Pro | Leu | Ala | Pro | Ser | Ser | Lys | Ser | Thr | Ser | Gly | Gly | Thr | Ala |
| | 130 | | | | | 135 | | | | | 140 | | | | |
| Ala | Leu | Gly | Cys | Leu | Val | Lys | Asp | Tyr | Phe | Pro | Glu | Pro | Val | Thr | Val |
| 145 | | | | | 150 | | | | | 155 | | | | | 160 |
| Ser | Trp | Asn | Ser | Gly | Ala | Leu | Thr | Ser | Gly | Val | His | Thr | Phe | Pro | Ala |
| | | | | 165 | | | | | 170 | | | | | 175 | |
| Val | Leu | Gln | Ser | Ser | Gly | Leu | Tyr | Ser | Leu | Ser | Ser | Val | Val | Thr | Val |
| | | | 180 | | | | | 185 | | | | | 190 | | |
| Pro | Ser | Ser | Ser | Leu | Gly | Thr | Gln | Thr | Tyr | Ile | Cys | Asn | Val | Asn | His |
| | | | 195 | | | | | 200 | | | | | 205 | | |
| Lys | Pro | Ser | Asn | Thr | Lys | Val | Asp | Lys | Lys | Val | Glu | Pro | Lys | Ser | Cys |
| | 210 | | | | | 215 | | | | | 220 | | | | |
| Asp | Lys | Thr | His | Thr | Cys | Pro | Pro | Cys | Pro | Ala | Pro | Glu | Ala | Ala | Gly |
| 225 | | | | | 230 | | | | | 235 | | | | | 240 |
| Ala | Pro | Ser | Val | Phe | Leu | Phe | Pro | Pro | Lys | Pro | Lys | Asp | Thr | Leu | Met |
| | | | | 245 | | | | | 250 | | | | | 255 | |
| Ile | Ser | Arg | Thr | Pro | Glu | Val | Thr | Cys | Val | Val | Val | Asp | Val | Ser | His |
| | | | 260 | | | | | 265 | | | | | 270 | | |
| Glu | Asp | Pro | Glu | Val | Lys | Phe | Asn | Trp | Tyr | Val | Asp | Gly | Val | Glu | Val |
| | | | | 275 | | | | | 280 | | | | | 285 | |
| His | Asn | Ala | Lys | Thr | Lys | Pro | Arg | Glu | Glu | Gln | Tyr | Asn | Ser | Thr | Tyr |
| | 290 | | | | | 295 | | | | | 300 | | | | |
| Arg | Val | Val | Ser | Val | Leu | Thr | Val | Leu | His | Gln | Asp | Trp | Leu | Asn | Gly |
| 305 | | | | | 310 | | | | | 315 | | | | | 320 |
| Lys | Glu | Tyr | Lys | Cys | Lys | Val | Ser | Asn | Lys | Ala | Leu | Pro | Ala | Pro | Ile |
| | | | | 325 | | | | | 330 | | | | | 335 | |
| Glu | Lys | Thr | Ile | Ser | Lys | Ala | Lys | Gly | Gln | Pro | Arg | Glu | Pro | Gln | Val |
| | | | 340 | | | | | 345 | | | | | 350 | | |
| Tyr | Thr | Leu | Pro | Pro | Ser | Arg | Glu | Glu | Met | Thr | Lys | Asn | Gln | Val | Ser |
| | | | | 355 | | | | | 360 | | | | | 365 | |

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 141
<211> LENGTH: 121
<212> TYPE: PRT
<213> ORGANISM: Artificial Sequence
<220> FEATURE:
<223> OTHER INFORMATION: Synthetic Construct

<400> SEQUENCE: 141

Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Ser Asn Tyr
            20                  25                  30

Trp Met Tyr Trp Ile Arg Gln Ala Pro Gly Met Gly Leu Glu Trp Val
        35                  40                  45

Ser Ser Ile Asn Asn Asp Gly Gly Asn Thr Tyr Tyr Leu Asp Ser Val
    50                  55                  60

Lys Gly Arg Phe Thr Ile Ser Arg Asn Asn Ala Glu Asn Thr Val Tyr
65                  70                  75                  80

Leu Gln Met Asn Ser Leu Arg Ser Glu Asp Thr Ala Thr Tyr Tyr Cys
            85                  90                  95

Ala Lys Gly His Phe Ser Tyr Thr Ser Tyr Ser Phe Ala Tyr Trp Gly
            100                 105                 110

Gln Gly Thr Leu Val Thr Val Ser Ser
        115                 120

<210> SEQ ID NO 142
<211> LENGTH: 12
<212> TYPE: PRT
<213> ORGANISM: Artificial Sequence
<220> FEATURE:
<223> OTHER INFORMATION: Synthetic Construct

<400> SEQUENCE: 142

Gly His Phe Ser Tyr Thr Ser Tyr Ser Phe Ala Tyr
1               5                   10

<210> SEQ ID NO 143
<211> LENGTH: 451
<212> TYPE: PRT
<213> ORGANISM: Artificial Sequence
<220> FEATURE:
<223> OTHER INFORMATION: Synthetic Construct

<400> SEQUENCE: 143

Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Ser Asn Tyr
            20                  25                  30

Trp Met Tyr Trp Ile Arg Gln Ala Pro Gly Met Gly Leu Glu Trp Val
        35                  40                  45

Ser Ser Ile Asn Asn Asp Gly Gly Asn Thr Tyr Tyr Leu Asp Ser Val
    50                  55                  60

Lys Gly Arg Phe Thr Ile Ser Arg Asn Asn Ala Glu Asn Thr Val Tyr
65                  70                  75                  80

Leu Gln Met Asn Ser Leu Arg Ser Glu Asp Thr Ala Thr Tyr Tyr Cys
                85                  90                  95

Ala Lys Gly His Phe Ser Tyr Thr Ser Tyr Ser Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser

```
                435                 440                 445

Pro Gly Lys
    450

<210> SEQ ID NO 144
<211> LENGTH: 121
<212> TYPE: PRT
<213> ORGANISM: Artificial Sequence
<220> FEATURE:
<223> OTHER INFORMATION: Synthetic Construct

<400> SEQUENCE: 144

Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Ser Asn Tyr
            20                  25                  30

Trp Met Tyr Trp Ile Arg Gln Ala Pro Gly Met Gly Leu Glu Trp Val
        35                  40                  45

Ser Ser Ile Asn Asn Asp Gly Asn Thr Tyr Tyr Leu Asp Ser Val
    50                  55                  60

Lys Gly Arg Phe Thr Ile Ser Arg Asn Asn Ala Glu Asn Thr Val Tyr
65                  70                  75                  80

Leu Gln Met Asn Ser Leu Arg Ser Glu Asp Thr Ala Thr Tyr Tyr Cys
                85                  90                  95

Ala Lys Gly His Tyr Tyr Tyr Ser Ser Tyr Ser Phe Ala Phe Trp Gly
            100                 105                 110

Gln Gly Thr Leu Val Thr Val Ser Ser
        115                 120

<210> SEQ ID NO 145
<211> LENGTH: 12
<212> TYPE: PRT
<213> ORGANISM: Artificial Sequence
<220> FEATURE:
<223> OTHER INFORMATION: Synthetic Construct

<400> SEQUENCE: 145

Gly His Tyr Tyr Tyr Ser Ser Tyr Ser Phe Ala Phe
1               5                   10

<210> SEQ ID NO 146
<211> LENGTH: 451
<212> TYPE: PRT
<213> ORGANISM: Artificial Sequence
<220> FEATURE:
<223> OTHER INFORMATION: Synthetic Construct

<400> SEQUENCE: 146

Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Ser Asn Tyr
            20                  25                  30

Trp Met Tyr Trp Ile Arg Gln Ala Pro Gly Met Gly Leu Glu Trp Val
        35                  40                  45

Ser Ser Ile Asn Asn Asp Gly Asn Thr Tyr Tyr Leu Asp Ser Val
    50                  55                  60

Lys Gly Arg Phe Thr Ile Ser Arg Asn Asn Ala Glu Asn Thr Val Tyr
65                  70                  75                  80

Leu Gln Met Asn Ser Leu Arg Ser Glu Asp Thr Ala Thr Tyr Tyr Cys
                85                  90                  95
```

Ala Lys Gly His Tyr Tyr Ser Ser Tyr Ser Phe Ala Phe Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 147
<211> LENGTH: 121
<212> TYPE: PRT
<213> ORGANISM: Artificial Sequence
<220> FEATURE:
<223> OTHER INFORMATION: Synthetic Construct

<400> SEQUENCE: 147

```
Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Ser Asn Tyr
            20                  25                  30

Trp Met Tyr Trp Ile Arg Gln Ala Pro Gly Met Gly Leu Glu Trp Val
            35                  40                  45

Ser Ser Ile Asn Asn Asp Gly Gly Asn Thr Tyr Tyr Leu Asp Ser Val
50                      55                  60

Lys Gly Arg Phe Thr Ile Ser Arg Asn Asn Ala Glu Asn Thr Val Tyr
65                      70                  75                  80

Leu Gln Met Asn Ser Leu Arg Ser Glu Asp Thr Ala Thr Tyr Tyr Cys
                85                  90                  95

Ala Lys Gly His Tyr Tyr Tyr Thr Ser Tyr Ser Phe Ala Tyr Trp Gly
                100                 105                 110

Gln Gly Thr Leu Val Thr Val Ser Ser
            115                 120
```

<210> SEQ ID NO 148
<211> LENGTH: 12
<212> TYPE: PRT
<213> ORGANISM: Artificial Sequence
<220> FEATURE:
<223> OTHER INFORMATION: Synthetic Construct

<400> SEQUENCE: 148

```
Gly His Tyr Tyr Tyr Thr Ser Tyr Ser Phe Ala Tyr
1               5                   10
```

<210> SEQ ID NO 149
<211> LENGTH: 451
<212> TYPE: PRT
<213> ORGANISM: Artificial Sequence
<220> FEATURE:
<223> OTHER INFORMATION: Synthetic Construct

<400> SEQUENCE: 149

```
Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Ser Asn Tyr
            20                  25                  30

Trp Met Tyr Trp Ile Arg Gln Ala Pro Gly Met Gly Leu Glu Trp Val
            35                  40                  45

Ser Ser Ile Asn Asn Asp Gly Gly Asn Thr Tyr Tyr Leu Asp Ser Val
50                      55                  60

Lys Gly Arg Phe Thr Ile Ser Arg Asn Asn Ala Glu Asn Thr Val Tyr
65                      70                  75                  80

Leu Gln Met Asn Ser Leu Arg Ser Glu Asp Thr Ala Thr Tyr Tyr Cys
                85                  90                  95

Ala Lys Gly His Tyr Tyr Tyr Thr Ser Tyr Ser Phe Ala Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
```

```
                    165                 170                 175
Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 150
<211> LENGTH: 121
<212> TYPE: PRT
<213> ORGANISM: Artificial Sequence
<220> FEATURE:
<223> OTHER INFORMATION: Synthetic Construct

<400> SEQUENCE: 150

Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Ser Asn Tyr
            20                  25                  30

Trp Met Tyr Trp Ile Arg Gln Ala Pro Gly Met Gly Leu Glu Trp Val
        35                  40                  45

Ser Ser Ile Asn Asn Asp Gly Gly Asn Thr Tyr Tyr Leu Asp Ser Val
    50                  55                  60

Lys Gly Arg Phe Thr Ile Ser Arg Asn Asn Ala Glu Asn Thr Val Tyr
```

```
            65                  70                  75                  80
Leu Gln Met Asn Ser Leu Arg Ser Glu Asp Thr Ala Thr Tyr Tyr Cys
                85                  90                  95

Ala Arg Gly His Tyr Tyr Tyr Thr Ser Tyr Ser Phe Ala Tyr Trp Gly
            100                 105                 110

Gln Gly Thr Leu Val Thr Val Ser Ser
        115                 120

<210> SEQ ID NO 151
<211> LENGTH: 451
<212> TYPE: PRT
<213> ORGANISM: Artificial Sequence
<220> FEATURE:
<223> OTHER INFORMATION: Synthetic Construct

<400> SEQUENCE: 151

Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Ser Asn Tyr
            20                  25                  30

Trp Met Tyr Trp Ile Arg Gln Ala Pro Gly Met Gly Leu Glu Trp Val
        35                  40                  45

Ser Ser Ile Asn Asn Asp Gly Gly Asn Thr Tyr Tyr Leu Asp Ser Val
    50                  55                  60

Lys Gly Arg Phe Thr Ile Ser Arg Asn Asn Ala Glu Asn Thr Val Tyr
65                  70                  75                  80

Leu Gln Met Asn Ser Leu Arg Ser Glu Asp Thr Ala Thr Tyr Tyr Cys
                85                  90                  95

Ala Arg Gly His Tyr Tyr Tyr Thr Ser Tyr Ser Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
```

```
                305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
                340                 345                 350
Tyr Thr Leu Pro Pro Ser Arg Glu Glu Met Thr Lys Asn Gln Val Ser
                355                 360                 365
Leu Thr Cys Leu Val Lys Gly Phe Tyr Pro Ser Asp Ile Ala Val Glu
                370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
                435                 440                 445
Pro Gly Lys
    450

<210> SEQ ID NO 152
<211> LENGTH: 121
<212> TYPE: PRT
<213> ORGANISM: Artificial Sequence
<220> FEATURE:
<223> OTHER INFORMATION: Synthetic Construct

<400> SEQUENCE: 152

Glu Val Gln Leu Val Glu Thr Gly Gly Gly Leu Val Gln Pro Gly Arg
1               5                   10                  15
Ser Leu Lys Leu Ser Cys Val Ala Ser Gly Phe Thr Phe Ser Asn Tyr
                20                  25                  30
Trp Met Tyr Trp Ile Arg Gln Ala Pro Gly Met Gly Leu Glu Trp Val
                35                  40                  45
Ser Ser Ile Asn Asn Asp Gly Gly Asn Thr Tyr Tyr Leu Asp Ser Val
                50                  55                  60
Lys Gly Arg Phe Thr Ile Ser Arg Asn Asn Ala Glu Asn Thr Val Tyr
65              70                  75                  80
Leu Gln Met Asn Ser Leu Arg Ser Glu Asp Thr Ala Thr Tyr Tyr Cys
                85                  90                  95
Ala Lys Gly His Tyr Tyr Tyr Thr Ser Tyr Ser Phe Gly Tyr Trp Gly
                100                 105                 110
Gln Gly Thr Leu Val Thr Val Ser Ser
        115                 120

<210> SEQ ID NO 153
<211> LENGTH: 12
<212> TYPE: PRT
<213> ORGANISM: Artificial Sequence
<220> FEATURE:
<223> OTHER INFORMATION: Synthetic Construct

<400> SEQUENCE: 153

Gly His Tyr Tyr Tyr Thr Ser Tyr Ser Phe Gly Tyr
1               5                   10

<210> SEQ ID NO 154
<211> LENGTH: 451
```

```
<212> TYPE: PRT
<213> ORGANISM: Artificial Sequence
<220> FEATURE:
<223> OTHER INFORMATION: Synthetic Construct

<400> SEQUENCE: 154

Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Ser Asn Tyr
            20                  25                  30

Trp Met Tyr Trp Ile Arg Gln Ala Pro Gly Met Gly Leu Glu Trp Val
        35                  40                  45

Ser Ser Ile Asn Asn Asp Gly Gly Asn Thr Tyr Tyr Leu Asp Ser Val
    50                  55                  60

Lys Gly Arg Phe Thr Ile Ser Arg Asn Asn Ala Glu Asn Thr Val Tyr
65                  70                  75                  80

Leu Gln Met Asn Ser Leu Arg Ser Glu Asp Thr Ala Thr Tyr Tyr Cys
                85                  90                  95

Ala Lys Gly His Tyr Tyr Thr Ser Tyr Ser Phe Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380
```

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 155
<211> LENGTH: 121
<212> TYPE: PRT
<213> ORGANISM: Artificial Sequence
<220> FEATURE:
<223> OTHER INFORMATION: Synthetic Construct

<400> SEQUENCE: 155

Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Ser Asn Tyr
            20                  25                  30

Trp Met Tyr Trp Ile Arg Gln Ala Pro Gly Met Gly Leu Glu Trp Val
        35                  40                  45

Ser Ser Ile Asn Asn Asp Gly Gly Asn Thr Tyr Tyr Leu Asp Ser Val
    50                  55                  60

Lys Gly Arg Phe Thr Ile Ser Arg Asn Asn Ala Glu Asn Thr Val Tyr
65                  70                  75                  80

Leu Gln Met Asn Ser Leu Arg Ser Glu Asp Thr Ala Thr Tyr Tyr Cys
                85                  90                  95

Ala Lys Gly His Tyr Tyr Tyr Ser Ser Tyr Ser Phe Gly Tyr Trp Gly
            100                 105                 110

Gln Gly Thr Leu Val Thr Val Ser Ser
        115                 120

<210> SEQ ID NO 156
<211> LENGTH: 12
<212> TYPE: PRT
<213> ORGANISM: Artificial Sequence
<220> FEATURE:
<223> OTHER INFORMATION: Synthetic Construct

<400> SEQUENCE: 156

Gly His Tyr Tyr Tyr Ser Ser Tyr Ser Phe Gly Tyr
1               5                   10

<210> SEQ ID NO 157
<211> LENGTH: 451
<212> TYPE: PRT
<213> ORGANISM: Artificial Sequence
<220> FEATURE:
<223> OTHER INFORMATION: Synthetic Construct

<400> SEQUENCE: 157

Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Ser Asn Tyr
            20                  25                  30

Trp Met Tyr Trp Ile Arg Gln Ala Pro Gly Met Gly Leu Glu Trp Val

```
                35                  40                  45
Ser Ser Ile Asn Asn Asp Gly Gly Asn Thr Tyr Tyr Leu Asp Ser Val
 50                  55                  60

Lys Gly Arg Phe Thr Ile Ser Arg Asn Asn Ala Glu Asn Thr Val Tyr
 65                  70                  75                  80

Leu Gln Met Asn Ser Leu Arg Ser Glu Asp Thr Ala Thr Tyr Tyr Cys
                 85                  90                  95

Ala Lys Gly His Tyr Tyr Ser Ser Tyr Ser Phe Gly Tyr Trp Gly
                100                 105                 110

Gln Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
                130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
                290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
450
```

<210> SEQ ID NO 158
<211> LENGTH: 121
<212> TYPE: PRT
<213> ORGANISM: Artificial Sequence
<220> FEATURE:
<223> OTHER INFORMATION: Synthetic Construct

<400> SEQUENCE: 158

Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Ser Asn Tyr
                20                  25                  30

Trp Met Tyr Trp Ile Arg Gln Ala Pro Gly Met Gly Leu Glu Trp Val
            35                  40                  45

Ser Ser Ile Asn Asn Asp Gly Gly Asn Thr Tyr Tyr Leu Asp Ser Val
        50                  55                  60

Lys Gly Arg Phe Thr Ile Ser Arg Asn Asn Ala Glu Asn Thr Val Tyr
65                  70                  75                  80

Leu Gln Met Asn Ser Leu Arg Ser Glu Asp Thr Ala Thr Tyr Tyr Cys
                85                  90                  95

Ala Lys Gly His Tyr Tyr Tyr Ser Ser Tyr Ser Phe Ala Tyr Trp Gly
            100                 105                 110

Gln Gly Thr Leu Val Thr Val Ser Ser
        115                 120

<210> SEQ ID NO 159
<211> LENGTH: 12
<212> TYPE: PRT
<213> ORGANISM: Artificial Sequence
<220> FEATURE:
<223> OTHER INFORMATION: Synthetic Construct

<400> SEQUENCE: 159

Gly His Tyr Tyr Tyr Ser Ser Tyr Ser Phe Ala Tyr
1               5                   10

<210> SEQ ID NO 160
<211> LENGTH: 451
<212> TYPE: PRT
<213> ORGANISM: Artificial Sequence
<220> FEATURE:
<223> OTHER INFORMATION: Synthetic Construct

<400> SEQUENCE: 160

Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Ser Asn Tyr
                20                  25                  30

Trp Met Tyr Trp Ile Arg Gln Ala Pro Gly Met Gly Leu Glu Trp Val
            35                  40                  45

Ser Ser Ile Asn Asn Asp Gly Gly Asn Thr Tyr Tyr Leu Asp Ser Val
        50                  55                  60

Lys Gly Arg Phe Thr Ile Ser Arg Asn Asn Ala Glu Asn Thr Val Tyr
65                  70                  75                  80

Leu Gln Met Asn Ser Leu Arg Ser Glu Asp Thr Ala Thr Tyr Tyr Cys
                85                  90                  95

Ala Lys Gly His Tyr Tyr Tyr Ser Ser Tyr Ser Phe Ala Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 161
<211> LENGTH: 121
<212> TYPE: PRT
<213> ORGANISM: Artificial Sequence
<220> FEATURE:
<223> OTHER INFORMATION: Synthetic Construct

<400> SEQUENCE: 161

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Tyr Trp Val Arg Gln Ala Pro Gly Lys Gly Leu Glu Trp Val
            35                  40                  45

Ala Ser Ile Thr Pro Asn Gly Gly Asn Thr Tyr Tyr Pro Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly His Tyr Tyr Tyr Thr Ser Tyr Ser Leu Gly Tyr Trp Gly
                100                 105                 110

Gln Gly Thr Leu Val Thr Val Ser Ser
            115                 120

<210> SEQ ID NO 162
<211> LENGTH: 451
<212> TYPE: PRT
<213> ORGANISM: Artificial Sequence
<220> FEATURE:
<223> OTHER INFORMATION: Synthetic Construct

<400> SEQUENCE: 162

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Tyr Trp Val Arg Gln Ala Pro Gly Lys Gly Leu Glu Trp Val
            35                  40                  45

Ala Ser Ile Thr Pro Asn Gly Gly Asn Thr Tyr Tyr Pro Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly His Tyr Tyr Tyr Thr Ser Tyr Ser Leu Gly Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

-continued

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 163
<211> LENGTH: 121
<212> TYPE: PRT
<213> ORGANISM: Artificial Sequence
<220> FEATURE:
<223> OTHER INFORMATION: Synthetic Construct

<400> SEQUENCE: 163

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ser Ile Asn Asn Asp Gly Gly Asn Thr Tyr Tyr Leu Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Thr Ser Tyr Ser Leu Gly Tyr Trp Gly
            100                 105                 110

Gln Gly Thr Leu Val Thr Val Ser Ser
        115                 120

<210> SEQ ID NO 164
<211> LENGTH: 451
<212> TYPE: PRT
<213> ORGANISM: Artificial Sequence
<220> FEATURE:

<223> OTHER INFORMATION: Synthetic Construct

<400> SEQUENCE: 164

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ser Ile Asn Asn Asp Gly Gly Asn Thr Tyr Tyr Leu Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Thr Ser Tyr Ser Leu Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400
```

```
Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 165
<211> LENGTH: 121
<212> TYPE: PRT
<213> ORGANISM: Artificial Sequence
<220> FEATURE:
<223> OTHER INFORMATION: Synthetic Construct

<400> SEQUENCE: 165

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ser Ile Thr Pro Asn Gly Gly Asn Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Ser Tyr Ser Tyr Ser Phe Ser Tyr Trp Gly
            100                 105                 110

Gln Gly Thr Leu Val Thr Val Ser Ser
        115                 120

<210> SEQ ID NO 166
<211> LENGTH: 451
<212> TYPE: PRT
<213> ORGANISM: Artificial Sequence
<220> FEATURE:
<223> OTHER INFORMATION: Synthetic Construct

<400> SEQUENCE: 166

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ser Ile Thr Pro Asn Gly Gly Asn Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Ser Tyr Ser Ser Tyr Ser Phe Ser Tyr Trp Gly
            100                 105                 110

Gln Gly Thr Leu Val Thr Val Ser Ser Ala Ser Thr Lys Gly Pro Ser
        115                 120                 125
```

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 167
<211> LENGTH: 121
<212> TYPE: PRT
<213> ORGANISM: Artificial Sequence
<220> FEATURE:
<223> OTHER INFORMATION: Synthetic Construct

<400> SEQUENCE: 167

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

```
Trp Met Tyr Trp Val Arg Gln Ala Pro Gly Lys Gly Leu Glu Trp Val
            35                  40                  45

Ala Ser Ile Thr Pro Asp Gly Gly Asn Thr Tyr Tyr Pro Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly His Tyr Tyr Tyr Thr Ser Tyr Ser Leu Gly Tyr Trp Gly
                100                 105                 110

Gln Gly Thr Leu Val Thr Val Ser Ser
            115                 120

<210> SEQ ID NO 168
<211> LENGTH: 17
<212> TYPE: PRT
<213> ORGANISM: Artificial Sequence
<220> FEATURE:
<223> OTHER INFORMATION: Synthetic Construct

<400> SEQUENCE: 168

Ser Ile Thr Pro Asp Gly Gly Asn Thr Tyr Tyr Pro Asp Ser Val Lys
 1               5                  10                  15

Gly

<210> SEQ ID NO 169
<211> LENGTH: 451
<212> TYPE: PRT
<213> ORGANISM: Artificial Sequence
<220> FEATURE:
<223> OTHER INFORMATION: Synthetic Construct

<400> SEQUENCE: 169

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Trp Met Tyr Trp Val Arg Gln Ala Pro Gly Lys Gly Leu Glu Trp Val
            35                  40                  45

Ala Ser Ile Thr Pro Asp Gly Gly Asn Thr Tyr Tyr Pro Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly His Tyr Tyr Tyr Thr Ser Tyr Ser Leu Gly Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
        435                 440                 445

Pro Gly Lys
    450

<210> SEQ ID NO 170
<211> LENGTH: 121
<212> TYPE: PRT
<213> ORGANISM: Artificial Sequence
<220> FEATURE:
<223> OTHER INFORMATION: Synthetic Construct

<400> SEQUENCE: 170

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ser Ile Thr Pro Asn Gly Asp Thr Tyr Tyr Pro Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

```
Ala Arg Gly His Tyr Tyr Tyr Thr Ser Tyr Ser Leu Gly Tyr Trp Gly
            100                 105                 110

Gln Gly Thr Leu Val Thr Val Ser Ser
        115                 120

<210> SEQ ID NO 171
<211> LENGTH: 17
<212> TYPE: PRT
<213> ORGANISM: Artificial Sequence
<220> FEATURE:
<223> OTHER INFORMATION: Synthetic Construct

<400> SEQUENCE: 171

Ser Ile Thr Pro Asn Gly Gly Asp Thr Tyr Tyr Pro Asp Ser Val Lys
1               5                   10                  15

Gly

<210> SEQ ID NO 172
<211> LENGTH: 451
<212> TYPE: PRT
<213> ORGANISM: Artificial Sequence
<220> FEATURE:
<223> OTHER INFORMATION: Synthetic Construct

<400> SEQUENCE: 172

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ser Ile Thr Pro Asn Gly Gly Asp Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Thr Ser Tyr Ser Leu Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255
```

```
Ile Ser Arg Thr Pro Glu Val Thr Cys Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 173
<211> LENGTH: 121
<212> TYPE: PRT
<213> ORGANISM: Artificial Sequence
<220> FEATURE:
<223> OTHER INFORMATION: Synthetic Construct

<400> SEQUENCE: 173

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ser Ile Thr Pro Asn Gly Gly Glu Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Thr Ser Tyr Ser Leu Gly Tyr Trp Gly
            100                 105                 110

Gln Gly Thr Leu Val Thr Val Ser Ser
        115                 120

<210> SEQ ID NO 174
<211> LENGTH: 17
<212> TYPE: PRT
<213> ORGANISM: Artificial Sequence
```

<220> FEATURE:
<223> OTHER INFORMATION: Synthetic Construct

<400> SEQUENCE: 174

Ser Ile Thr Pro Asn Gly Gly Glu Thr Tyr Tyr Pro Asp Ser Val Lys
1               5                   10                  15

Gly

<210> SEQ ID NO 175
<211> LENGTH: 451
<212> TYPE: PRT
<213> ORGANISM: Artificial Sequence
<220> FEATURE:
<223> OTHER INFORMATION: Synthetic Construct

<400> SEQUENCE: 175

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ser Ile Thr Pro Asn Gly Gly Glu Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Thr Ser Tyr Ser Leu Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

```
Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro Gly Lys
    450
```

<210> SEQ ID NO 176
<211> LENGTH: 121
<212> TYPE: PRT
<213> ORGANISM: Artificial Sequence
<220> FEATURE:
<223> OTHER INFORMATION: Synthetic Construct

<400> SEQUENCE: 176

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ser Ile Thr Pro Asn Gly Gly Asn Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Thr Asp Tyr Ser Leu Gly Tyr Trp Gly
            100                 105                 110

Gln Gly Thr Leu Val Thr Val Ser Ser
        115                 120
```

<210> SEQ ID NO 177
<211> LENGTH: 12
<212> TYPE: PRT
<213> ORGANISM: Artificial Sequence
<220> FEATURE:
<223> OTHER INFORMATION: Synthetic Construct

<400> SEQUENCE: 177

```
Gly His Tyr Tyr Tyr Thr Asp Tyr Ser Leu Gly Tyr
1               5                   10
```

<210> SEQ ID NO 178
<211> LENGTH: 451
<212> TYPE: PRT

<213> ORGANISM: Artificial Sequence
<220> FEATURE:
<223> OTHER INFORMATION: Synthetic Construct

<400> SEQUENCE: 178

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ser Ile Thr Pro Asn Gly Gly Asn Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Thr Asp Tyr Ser Leu Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
```

```
                385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
        450

<210> SEQ ID NO 179
<211> LENGTH: 121
<212> TYPE: PRT
<213> ORGANISM: Artificial Sequence
<220> FEATURE:
<223> OTHER INFORMATION: Synthetic Construct

<400> SEQUENCE: 179

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ser Ile Thr Pro Leu Gly Gly Asn Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Thr Ser Tyr Ser Leu Gly Tyr Trp Gly
            100                 105                 110

Gln Gly Thr Leu Val Thr Val Ser Ser
        115                 120

<210> SEQ ID NO 180
<211> LENGTH: 17
<212> TYPE: PRT
<213> ORGANISM: Artificial Sequence
<220> FEATURE:
<223> OTHER INFORMATION: Synthetic Construct

<400> SEQUENCE: 180

Ser Ile Thr Pro Leu Gly Gly Asn Thr Tyr Tyr Pro Asp Ser Val Lys
1               5                   10                  15

Gly

<210> SEQ ID NO 181
<211> LENGTH: 451
<212> TYPE: PRT
<213> ORGANISM: Artificial Sequence
<220> FEATURE:
<223> OTHER INFORMATION: Synthetic Construct

<400> SEQUENCE: 181

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

-continued

```
Trp Met Tyr Trp Val Arg Gln Ala Pro Gly Lys Gly Leu Glu Trp Val
         35                  40                  45
Ala Ser Ile Thr Pro Leu Gly Gly Asn Thr Tyr Tyr Pro Asp Ser Val
 50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg Gly His Tyr Tyr Tyr Thr Ser Tyr Ser Leu Gly Tyr Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
```

450

<210> SEQ ID NO 182
<211> LENGTH: 121
<212> TYPE: PRT
<213> ORGANISM: Artificial Sequence
<220> FEATURE:
<223> OTHER INFORMATION: Synthetic Construct

<400> SEQUENCE: 182

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ser Ile Thr Pro Asn Gly Gly Glu Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Thr Asp Tyr Ser Leu Gly Tyr Trp Gly
            100                 105                 110

Gln Gly Thr Leu Val Thr Val Ser Ser
            115                 120

<210> SEQ ID NO 183
<211> LENGTH: 451
<212> TYPE: PRT
<213> ORGANISM: Artificial Sequence
<220> FEATURE:
<223> OTHER INFORMATION: Synthetic Construct

<400> SEQUENCE: 183

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ser Ile Thr Pro Asn Gly Gly Glu Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Thr Asp Tyr Ser Leu Gly Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 184
<211> LENGTH: 121
<212> TYPE: PRT
<213> ORGANISM: Artificial Sequence
<220> FEATURE:
<223> OTHER INFORMATION: Synthetic Construct

<400> SEQUENCE: 184

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ser Ile Thr Pro Asn Gly Gly Asp Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Thr Asp Tyr Ser Leu Gly Tyr Trp Gly
            100                 105                 110

Gln Gly Thr Leu Val Thr Val Ser Ser
        115                 120

<210> SEQ ID NO 185
<211> LENGTH: 451
<212> TYPE: PRT
<213> ORGANISM: Artificial Sequence
<220> FEATURE:
<223> OTHER INFORMATION: Synthetic Construct

<400> SEQUENCE: 185

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ser Ile Thr Pro Asn Gly Gly Asp Thr Tyr Tyr Pro Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Thr Asp Tyr Ser Leu Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

```
Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 186
<211> LENGTH: 121
<212> TYPE: PRT
<213> ORGANISM: Artificial Sequence
<220> FEATURE:
<223> OTHER INFORMATION: Synthetic Construct

<400> SEQUENCE: 186

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ser Ile Thr Pro Asn Gly Gly Asn Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Thr Ala Tyr Ser Leu Gly Tyr Trp Gly
            100                 105                 110

Gln Gly Thr Leu Val Thr Val Ser Ser
        115                 120

<210> SEQ ID NO 187
<211> LENGTH: 12
<212> TYPE: PRT
<213> ORGANISM: Artificial Sequence
<220> FEATURE:
<223> OTHER INFORMATION: Synthetic Construct

<400> SEQUENCE: 187

Gly His Tyr Tyr Tyr Thr Ala Tyr Ser Leu Gly Tyr
1               5                   10

<210> SEQ ID NO 188
<211> LENGTH: 451
<212> TYPE: PRT
<213> ORGANISM: Artificial Sequence
```

<220> FEATURE:
<223> OTHER INFORMATION: Synthetic Construct

<400> SEQUENCE: 188

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ser Ile Thr Pro Asn Gly Gly Asn Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Thr Ala Tyr Ser Leu Gly Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400
```

```
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 189
<211> LENGTH: 106
<212> TYPE: PRT
<213> ORGANISM: Artificial Sequence
<220> FEATURE:
<223> OTHER INFORMATION: Synthetic Construct

<400> SEQUENCE: 189

Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Asn Ile Asn Asp His
            20                  25                  30
Leu Asp Trp Tyr Gln Gln Lys Pro Gly Lys Ala Pro Lys Leu Leu Ile
        35                  40                  45
Tyr Phe Thr Asn Asn Leu Gln Thr Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Phe Gln Tyr Asn Asn Gly Trp Thr
                85                  90                  95
Phe Gly Gly Gly Thr Lys Val Glu Ile Lys
            100                 105

<210> SEQ ID NO 190
<211> LENGTH: 11
<212> TYPE: PRT
<213> ORGANISM: Artificial Sequence
<220> FEATURE:
<223> OTHER INFORMATION: Synthetic Construct

<400> SEQUENCE: 190

Lys Ala Ser Gln Asn Ile Asn Asp His Leu Asp
1               5                   10

<210> SEQ ID NO 191
<211> LENGTH: 213
<212> TYPE: PRT
<213> ORGANISM: Artificial Sequence
<220> FEATURE:
<223> OTHER INFORMATION: Synthetic Construct

<400> SEQUENCE: 191

Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Asn Ile Asn Asp His
            20                  25                  30
Leu Asp Trp Tyr Gln Gln Lys Pro Gly Lys Ala Pro Lys Leu Leu Ile
        35                  40                  45
Tyr Phe Thr Asn Asn Leu Gln Thr Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Phe Gln Tyr Asn Asn Gly Trp Thr
                 85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 192
<211> LENGTH: 106
<212> TYPE: PRT
<213> ORGANISM: Artificial Sequence
<220> FEATURE:
<223> OTHER INFORMATION: Synthetic Construct

<400> SEQUENCE: 192

Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Asn Ile Asp Lys His
                 20                  25                  30

Leu Asp Trp Tyr Gln Gln Lys Pro Gly Lys Ala Pro Lys Leu Leu Ile
             35                  40                  45

Tyr Phe Thr Asn Asn Leu Gln Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Phe Gln Tyr Asn Asn Gly Trp Thr
                 85                  90                  95

Phe Gly Gly Gly Thr Lys Val Glu Ile Lys
            100                 105

<210> SEQ ID NO 193
<211> LENGTH: 11
<212> TYPE: PRT
<213> ORGANISM: Artificial Sequence
<220> FEATURE:
<223> OTHER INFORMATION: Synthetic Construct

<400> SEQUENCE: 193

Lys Ala Ser Gln Asn Ile Asp Lys His Leu Asp
  1               5                  10

<210> SEQ ID NO 194
<211> LENGTH: 213
<212> TYPE: PRT
<213> ORGANISM: Artificial Sequence
```

<220> FEATURE:
<223> OTHER INFORMATION: Synthetic Construct

<400> SEQUENCE: 194

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Lys His
            20                  25                  30

Leu Asp Trp Tyr Gln Gln Lys Pro Gly Lys Ala Pro Lys Leu Leu Ile
        35                  40                  45

Tyr Phe Thr Asn Asn Leu Gln Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Phe Gln Tyr Asn Asn Gly Trp Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 195
<211> LENGTH: 106
<212> TYPE: PRT
<213> ORGANISM: Artificial Sequence
<220> FEATURE:
<223> OTHER INFORMATION: Synthetic Construct

<400> SEQUENCE: 195

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asn Lys His
            20                  25                  30

Leu Asp Trp Tyr Gln Gln Lys Pro Gly Lys Ala Pro Lys Leu Leu Ile
        35                  40                  45

Tyr Phe Thr Asn Asn Leu Gln Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Phe Gln Tyr Asn Asn Gly Trp Thr
                85                  90                  95

Phe Gly Gly Gly Thr Lys Val Glu Ile Lys
            100                 105

```
<210> SEQ ID NO 196
<211> LENGTH: 7
<212> TYPE: PRT
<213> ORGANISM: Artificial Sequence
<220> FEATURE:
<223> OTHER INFORMATION: Synthetic Construct

<400> SEQUENCE: 196

Phe Thr Asn Asn Leu Gln Asp
1               5

<210> SEQ ID NO 197
<211> LENGTH: 213
<212> TYPE: PRT
<213> ORGANISM: Artificial Sequence
<220> FEATURE:
<223> OTHER INFORMATION: Synthetic Construct

<400> SEQUENCE: 197

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asn Lys His
            20                  25                  30

Leu Asp Trp Tyr Gln Gln Lys Pro Gly Lys Ala Pro Lys Leu Leu Ile
        35                  40                  45

Tyr Phe Thr Asn Asn Leu Gln Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Phe Gln Tyr Asn Asn Gly Trp Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 198
<211> LENGTH: 106
<212> TYPE: PRT
<213> ORGANISM: Artificial Sequence
<220> FEATURE:
<223> OTHER INFORMATION: Synthetic Construct

<400> SEQUENCE: 198

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asn Lys His
            20                  25                  30
```

```
Leu Asp Trp Tyr Gln Gln Lys Pro Gly Lys Ala Pro Lys Leu Leu Ile
        35                  40                  45

Tyr Phe Thr Asn Asn Leu Gln Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Phe Gln Tyr Asn Asn Gly Trp Thr
                85                  90                  95

Phe Gly Gly Gly Thr Lys Val Glu Ile Lys
            100                 105

<210> SEQ ID NO 199
<211> LENGTH: 7
<212> TYPE: PRT
<213> ORGANISM: Artificial Sequence
<220> FEATURE:
<223> OTHER INFORMATION: Synthetic Construct

<400> SEQUENCE: 199

Phe Thr Asn Asn Leu Gln Glu
1               5

<210> SEQ ID NO 200
<211> LENGTH: 213
<212> TYPE: PRT
<213> ORGANISM: Artificial Sequence
<220> FEATURE:
<223> OTHER INFORMATION: Synthetic Construct

<400> SEQUENCE: 200

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asn Lys His
            20                  25                  30

Leu Asp Trp Tyr Gln Gln Lys Pro Gly Lys Ala Pro Lys Leu Leu Ile
        35                  40                  45

Tyr Phe Thr Asn Asn Leu Gln Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Phe Gln Tyr Asn Asn Gly Trp Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
```

<210> SEQ ID NO 201
<211> LENGTH: 121
<212> TYPE: PRT
<213> ORGANISM: Artificial Sequence
<220> FEATURE:
<223> OTHER INFORMATION: Synthetic Construct

<400> SEQUENCE: 201

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ala Ile Thr Pro Asn Gly Gly Glu Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Thr Ser Tyr Ser Leu Gly Tyr Trp Gly
            100                 105                 110

Gln Gly Thr Leu Val Thr Val Ser Ser
        115                 120

<210> SEQ ID NO 202
<211> LENGTH: 17
<212> TYPE: PRT
<213> ORGANISM: Artificial Sequence
<220> FEATURE:
<223> OTHER INFORMATION: Synthetic Construct

<400> SEQUENCE: 202

Ala Ile Thr Pro Asn Gly Gly Glu Thr Tyr Tyr Pro Asp Ser Val Lys
1               5                   10                  15

Gly

<210> SEQ ID NO 203
<211> LENGTH: 451
<212> TYPE: PRT
<213> ORGANISM: Artificial Sequence
<220> FEATURE:
<223> OTHER INFORMATION: Synthetic Construct

<400> SEQUENCE: 203

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ala Ile Thr Pro Asn Gly Gly Glu Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

```
Ala Arg Gly His Tyr Tyr Tyr Thr Ser Tyr Ser Leu Gly Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 204
<211> LENGTH: 121
<212> TYPE: PRT
<213> ORGANISM: Artificial Sequence
<220> FEATURE:
<223> OTHER INFORMATION: Synthetic Construct

<400> SEQUENCE: 204
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ser Ile Thr Pro Asn Gly Gly Glu Asp Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Thr Ser Tyr Ser Leu Gly Tyr Trp Gly
            100                 105                 110

Gln Gly Thr Leu Val Thr Val Ser Ser
            115                 120

<210> SEQ ID NO 205
<211> LENGTH: 17
<212> TYPE: PRT
<213> ORGANISM: Artificial Sequence
<220> FEATURE:
<223> OTHER INFORMATION: Synthetic Construct

<400> SEQUENCE: 205

Ser Ile Thr Pro Asn Gly Gly Glu Asp Tyr Tyr Pro Asp Ser Val Lys
1               5                   10                  15

Gly

<210> SEQ ID NO 206
<211> LENGTH: 451
<212> TYPE: PRT
<213> ORGANISM: Artificial Sequence
<220> FEATURE:
<223> OTHER INFORMATION: Synthetic Construct

<400> SEQUENCE: 206

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ser Ile Thr Pro Asn Gly Gly Glu Asp Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Thr Ser Tyr Ser Leu Gly Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

-continued

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 207
<211> LENGTH: 106
<212> TYPE: PRT
<213> ORGANISM: Artificial Sequence
<220> FEATURE:
<223> OTHER INFORMATION: Synthetic Construct

<400> SEQUENCE: 207

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asn Lys His
            20                  25                  30

Leu Asp Trp Tyr Gln Gln Lys Pro Gly Lys Ala Pro Lys Leu Leu Ile
        35                  40                  45

Tyr Phe Thr Asn Asn Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Phe Gln Tyr Asn Gln Gly Trp Thr
                85                  90                  95

Phe Gly Gly Gly Thr Lys Val Glu Ile Lys
            100                 105

<210> SEQ ID NO 208
<211> LENGTH: 8
<212> TYPE: PRT
<213> ORGANISM: Artificial Sequence
<220> FEATURE:
<223> OTHER INFORMATION: Synthetic Construct

<400> SEQUENCE: 208

Phe Gln Tyr Asn Gln Gly Trp Thr
1               5

<210> SEQ ID NO 209
<211> LENGTH: 213
<212> TYPE: PRT
<213> ORGANISM: Artificial Sequence
<220> FEATURE:
<223> OTHER INFORMATION: Synthetic Construct

<400> SEQUENCE: 209

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asn Lys His
            20                  25                  30

Leu Asp Trp Tyr Gln Gln Lys Pro Gly Lys Ala Pro Lys Leu Leu Ile
        35                  40                  45

Tyr Phe Thr Asn Asn Leu Gln Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Phe Gln Tyr Asn Gln Gly Trp Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 210
<211> LENGTH: 121
<212> TYPE: PRT
<213> ORGANISM: Artificial Sequence

```
<220> FEATURE:
<223> OTHER INFORMATION: Synthetic Construct

<400> SEQUENCE: 210

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ser Ile Thr Pro Asn Ala Gly Glu Asp Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Thr Ser Tyr Ser Leu Gly Tyr Trp Gly
            100                 105                 110

Gln Gly Thr Leu Val Thr Val Ser Ser
        115                 120

<210> SEQ ID NO 211
<211> LENGTH: 17
<212> TYPE: PRT
<213> ORGANISM: Artificial Sequence
<220> FEATURE:
<223> OTHER INFORMATION: Synthetic Construct

<400> SEQUENCE: 211

Ser Ile Thr Pro Asn Ala Gly Glu Asp Tyr Tyr Pro Asp Ser Val Lys
1               5                   10                  15

Gly

<210> SEQ ID NO 212
<211> LENGTH: 451
<212> TYPE: PRT
<213> ORGANISM: Artificial Sequence
<220> FEATURE:
<223> OTHER INFORMATION: Synthetic Construct

<400> SEQUENCE: 212

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ser Ile Thr Pro Asn Ala Gly Glu Asp Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Thr Ser Tyr Ser Leu Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
```

```
                130                 135                 140
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 213
<211> LENGTH: 121
<212> TYPE: PRT
<213> ORGANISM: Artificial Sequence
<220> FEATURE:
<223> OTHER INFORMATION: Synthetic Construct

<400> SEQUENCE: 213

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
```

```
                35                  40                  45
Ala Ser Ile Thr Pro Asn Ala Gly Glu Asp Tyr Tyr Pro Glu Ser Val
        50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Gly His Tyr Tyr Tyr Thr Ser Tyr Ser Leu Gly Tyr Trp Gly
            100                 105                 110
Gln Gly Thr Leu Val Thr Val Ser Ser
            115                 120

<210> SEQ ID NO 214
<211> LENGTH: 17
<212> TYPE: PRT
<213> ORGANISM: Artificial Sequence
<220> FEATURE:
<223> OTHER INFORMATION: Synthetic Construct

<400> SEQUENCE: 214

Ser Ile Thr Pro Asn Ala Gly Glu Asp Tyr Tyr Pro Glu Ser Val Lys
1               5                   10                  15
Gly

<210> SEQ ID NO 215
<211> LENGTH: 451
<212> TYPE: PRT
<213> ORGANISM: Artificial Sequence
<220> FEATURE:
<223> OTHER INFORMATION: Synthetic Construct

<400> SEQUENCE: 215

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Trp Met Tyr Trp Val Arg Gln Ala Pro Gly Lys Gly Leu Glu Trp Val
        35                  40                  45
Ala Ser Ile Thr Pro Asn Ala Gly Glu Asp Tyr Tyr Pro Glu Ser Val
        50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Gly His Tyr Tyr Tyr Thr Ser Tyr Ser Leu Gly Tyr Trp Gly
            100                 105                 110
Gln Gly Thr Leu Val Thr Val Ser Ser Ala Ser Thr Lys Gly Pro Ser
            115                 120                 125
Val Phe Pro Leu Ala Pro Ser Ser Lys Ser Thr Ser Gly Gly Thr Ala
        130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
```

```
                195                 200                 205
Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 216
<211> LENGTH: 121
<212> TYPE: PRT
<213> ORGANISM: Artificial Sequence
<220> FEATURE:
<223> OTHER INFORMATION: Synthetic Construct

<400> SEQUENCE: 216

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ala Ile Thr Pro Asn Gly Gly Glu Asp Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Thr Ser Tyr Ser Leu Gly Tyr Trp Gly
```

```
                    100                 105                 110

Gln Gly Thr Leu Val Thr Val Ser Ser
        115                 120

<210> SEQ ID NO 217
<211> LENGTH: 17
<212> TYPE: PRT
<213> ORGANISM: Artificial Sequence
<220> FEATURE:
<223> OTHER INFORMATION: Synthetic Construct

<400> SEQUENCE: 217

Ala Ile Thr Pro Asn Gly Gly Glu Asp Tyr Tyr Pro Asp Ser Val Lys
1               5                   10                  15

Gly

<210> SEQ ID NO 218
<211> LENGTH: 451
<212> TYPE: PRT
<213> ORGANISM: Artificial Sequence
<220> FEATURE:
<223> OTHER INFORMATION: Synthetic Construct

<400> SEQUENCE: 218

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ala Ile Thr Pro Asn Gly Gly Glu Asp Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Thr Ser Tyr Ser Leu Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
```

```
                 260                 265                 270
Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 219
<211> LENGTH: 121
<212> TYPE: PRT
<213> ORGANISM: Artificial Sequence
<220> FEATURE:
<223> OTHER INFORMATION: Synthetic Construct

<400> SEQUENCE: 219

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ala Ile Thr Pro Asn Gly Gly Glu Asp Tyr Tyr Pro Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Ser Tyr Ser Leu Gly Tyr Trp Gly
            100                 105                 110

Gln Gly Thr Leu Val Thr Val Ser Ser
        115                 120

<210> SEQ ID NO 220
<211> LENGTH: 17
<212> TYPE: PRT
<213> ORGANISM: Artificial Sequence
<220> FEATURE:
<223> OTHER INFORMATION: Synthetic Construct
```

```
<400> SEQUENCE: 220

Ala Ile Thr Pro Asn Gly Gly Glu Asp Tyr Tyr Pro Glu Ser Val Lys
1               5                   10                  15

Gly

<210> SEQ ID NO 221
<211> LENGTH: 451
<212> TYPE: PRT
<213> ORGANISM: Artificial Sequence
<220> FEATURE:
<223> OTHER INFORMATION: Synthetic Construct

<400> SEQUENCE: 221

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ala Ile Thr Pro Asn Gly Gly Glu Asp Tyr Tyr Pro Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Thr Ser Tyr Ser Leu Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
```

```
                  325                 330                 335
Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
        450

<210> SEQ ID NO 222
<211> LENGTH: 121
<212> TYPE: PRT
<213> ORGANISM: Artificial Sequence
<220> FEATURE:
<223> OTHER INFORMATION: Synthetic Construct

<400> SEQUENCE: 222

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ala Ile Thr Pro Asn Ala Gly Glu Asp Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Thr Ser Tyr Ser Leu Gly Tyr Trp Gly
            100                 105                 110

Gln Gly Thr Leu Val Thr Val Ser Ser
        115                 120

<210> SEQ ID NO 223
<211> LENGTH: 17
<212> TYPE: PRT
<213> ORGANISM: Artificial Sequence
<220> FEATURE:
<223> OTHER INFORMATION: Synthetic Construct

<400> SEQUENCE: 223

Ala Ile Thr Pro Asn Ala Gly Glu Asp Tyr Tyr Pro Asp Ser Val Lys
1               5                   10                  15

Gly

<210> SEQ ID NO 224
<211> LENGTH: 451
<212> TYPE: PRT
```

<213> ORGANISM: Artificial Sequence
<220> FEATURE:
<223> OTHER INFORMATION: Synthetic Construct

<400> SEQUENCE: 224

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ala Ile Thr Pro Asn Ala Gly Glu Asp Tyr Tyr Pro Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Thr Ser Tyr Ser Leu Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
```

```
                385                 390                 395                 400
Val Leu Asp Ser Asp Gly Ser Phe Phe Leu Tyr Ser Lys Leu Thr Val
                    405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
        450

<210> SEQ ID NO 225
<211> LENGTH: 121
<212> TYPE: PRT
<213> ORGANISM: Artificial Sequence
<220> FEATURE:
<223> OTHER INFORMATION: Synthetic Construct

<400> SEQUENCE: 225

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ala Ile Thr Pro Asn Ala Gly Glu Asp Tyr Tyr Pro Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Thr Ser Tyr Ser Leu Gly Tyr Trp Gly
            100                 105                 110

Gln Gly Thr Leu Val Thr Val Ser Ser
        115                 120

<210> SEQ ID NO 226
<211> LENGTH: 17
<212> TYPE: PRT
<213> ORGANISM: Artificial Sequence
<220> FEATURE:
<223> OTHER INFORMATION: Synthetic Construct

<400> SEQUENCE: 226

Ala Ile Thr Pro Asn Ala Gly Glu Asp Tyr Tyr Pro Glu Ser Val Lys
1               5                   10                  15

Gly

<210> SEQ ID NO 227
<211> LENGTH: 451
<212> TYPE: PRT
<213> ORGANISM: Artificial Sequence
<220> FEATURE:
<223> OTHER INFORMATION: Synthetic Construct

<400> SEQUENCE: 227

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Trp Met Tyr Trp Val Arg Gln Ala Pro Gly Lys Gly Leu Glu Trp Val
             35                  40                  45
Ala Ala Ile Thr Pro Asn Ala Gly Glu Asp Tyr Tyr Pro Glu Ser Val
 50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg Gly His Tyr Tyr Thr Ser Tyr Ser Leu Gly Tyr Trp Gly
                100                 105                 110
Gln Gly Thr Leu Val Thr Val Ser Ser Ala Ser Thr Lys Gly Pro Ser
            115                 120                 125
Val Phe Pro Leu Ala Pro Ser Ser Lys Ser Thr Ser Gly Gly Thr Ala
130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Val Glu Pro Lys Ser Cys
    210                 215                 220
Asp Lys Thr His Thr Cys Pro Pro Cys Pro Ala Pro Glu Ala Ala Gly
225                 230                 235                 240
Ala Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
```

<210> SEQ ID NO 228
<211> LENGTH: 121
<212> TYPE: PRT
<213> ORGANISM: Artificial Sequence
<220> FEATURE:
<223> OTHER INFORMATION: Synthetic Construct

<400> SEQUENCE: 228

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ala Ile Thr Pro Asn Ala Gly Glu Thr Tyr Tyr Pro Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Thr Ser Tyr Ser Leu Gly Tyr Trp Gly
            100                 105                 110

Gln Gly Thr Leu Val Thr Val Ser Ser
        115                 120
```

<210> SEQ ID NO 229
<211> LENGTH: 17
<212> TYPE: PRT
<213> ORGANISM: Artificial Sequence
<220> FEATURE:
<223> OTHER INFORMATION: Synthetic Construct

<400> SEQUENCE: 229

```
Ala Ile Thr Pro Asn Ala Gly Glu Thr Tyr Tyr Pro Glu Ser Val Lys
1               5                   10                  15

Gly
```

<210> SEQ ID NO 230
<211> LENGTH: 451
<212> TYPE: PRT
<213> ORGANISM: Artificial Sequence
<220> FEATURE:
<223> OTHER INFORMATION: Synthetic Construct

<400> SEQUENCE: 230

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ala Ile Thr Pro Asn Ala Gly Glu Thr Tyr Tyr Pro Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

-continued

Ala Arg Gly His Tyr Tyr Thr Ser Tyr Ser Leu Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 231
<211> LENGTH: 121
<212> TYPE: PRT
<213> ORGANISM: Artificial Sequence
<220> FEATURE:
<223> OTHER INFORMATION: Synthetic Construct

<400> SEQUENCE: 231

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ala Ile Thr Pro Asn Gly Gly Glu Thr Tyr Tyr Pro Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Thr Ser Tyr Ser Leu Gly Tyr Trp Gly
            100                 105                 110

Gln Gly Thr Leu Val Thr Val Ser Ser
            115                 120
```

<210> SEQ ID NO 232
<211> LENGTH: 17
<212> TYPE: PRT
<213> ORGANISM: Artificial Sequence
<220> FEATURE:
<223> OTHER INFORMATION: Synthetic Construct

<400> SEQUENCE: 232

```
Ala Ile Thr Pro Asn Gly Gly Glu Thr Tyr Tyr Pro Glu Ser Val Lys
1               5                   10                  15

Gly
```

<210> SEQ ID NO 233
<211> LENGTH: 451
<212> TYPE: PRT
<213> ORGANISM: Artificial Sequence
<220> FEATURE:
<223> OTHER INFORMATION: Synthetic Construct

<400> SEQUENCE: 233

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ala Ile Thr Pro Asn Gly Gly Glu Thr Tyr Tyr Pro Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Thr Ser Tyr Ser Leu Gly Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160
```

```
Ser Trp Asn Ser Gly Ala Leu Thr Ser Gly Val His Thr Phe Pro Ala
            165                 170                 175
Val Leu Gln Ser Ser Gly Leu Tyr Ser Leu Ser Ser Val Val Thr Val
        180                 185                 190
Pro Ser Ser Ser Leu Gly Thr Gln Thr Tyr Ile Cys Asn Val Asn His
    195                 200                 205
Lys Pro Ser Asn Thr Lys Val Asp Lys Lys Val Glu Pro Lys Ser Cys
210                 215                 220
Asp Lys Thr His Thr Cys Pro Pro Cys Pro Ala Pro Glu Ala Ala Gly
225                 230                 235                 240
Ala Pro Ser Val Phe Leu Phe Pro Pro Lys Pro Lys Asp Thr Leu Met
            245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
            325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
            405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 234
<211> LENGTH: 121
<212> TYPE: PRT
<213> ORGANISM: Artificial Sequence
<220> FEATURE:
<223> OTHER INFORMATION: Synthetic Construct

<400> SEQUENCE: 234

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Trp Met Tyr Trp Val Arg Gln Ala Pro Gly Lys Gly Leu Glu Trp Val
        35                  40                  45
Ala Ala Ile Thr Pro Asn Ala Gly Glu Thr Tyr Tyr Pro Asp Ser Val
    50                  55                  60
```

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly His Tyr Tyr Tyr Thr Ser Tyr Ser Leu Gly Tyr Trp Gly
                100                 105                 110

Gln Gly Thr Leu Val Thr Val Ser Ser
            115                 120
```

<210> SEQ ID NO 235
<211> LENGTH: 17
<212> TYPE: PRT
<213> ORGANISM: Artificial Sequence
<220> FEATURE:
<223> OTHER INFORMATION: Synthetic Construct

<400> SEQUENCE: 235

```
Ala Ile Thr Pro Asn Ala Gly Glu Thr Tyr Tyr Pro Asp Ser Val Lys
 1               5                  10                  15

Gly
```

<210> SEQ ID NO 236
<211> LENGTH: 451
<212> TYPE: PRT
<213> ORGANISM: Artificial Sequence
<220> FEATURE:
<223> OTHER INFORMATION: Synthetic Construct

<400> SEQUENCE: 236

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Trp Met Tyr Trp Val Arg Gln Ala Pro Gly Lys Gly Leu Glu Trp Val
         35                  40                  45

Ala Ala Ile Thr Pro Asn Ala Gly Glu Thr Tyr Tyr Pro Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly His Tyr Tyr Tyr Thr Ser Tyr Ser Leu Gly Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

```
Asp Lys Thr His Thr Cys Pro Pro Cys Pro Ala Glu Ala Ala Gly
225                 230                 235                 240

Ala Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
        450

<210> SEQ ID NO 237
<211> LENGTH: 329
<212> TYPE: PRT
<213> ORGANISM: Artificial Sequence
<220> FEATURE:
<223> OTHER INFORMATION: Synthetic Construct

<400> SEQUENCE: 237

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125
```

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 238
<211> LENGTH: 329
<212> TYPE: PRT
<213> ORGANISM: Artificial Sequence
<220> FEATURE:
<223> OTHER INFORMATION: Synthetic Construct

<400> SEQUENCE: 238

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

```
Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Leu His Glu Ala Leu His Ser His Tyr Thr
305                 310                 315                 320

Gln Lys Ser Leu Ser Leu Ser Pro Gly
                325

<210> SEQ ID NO 239
<211> LENGTH: 19
<212> TYPE: PRT
<213> ORGANISM: Artificial Sequence
<220> FEATURE:
<223> OTHER INFORMATION: Synthetic Construct

<400> SEQUENCE: 239

Met Gly Trp Ser Cys Ile Ile Leu Phe Leu Val Ala Thr Ala Thr Gly
1               5                   10                  15

Val His Ser

<210> SEQ ID NO 240
<211> LENGTH: 106
<212> TYPE: PRT
<213> ORGANISM: Artificial Sequence
<220> FEATURE:
<223> OTHER INFORMATION: Synthetic Construct

<400> SEQUENCE: 240

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
                100                 105
```

```
<210> SEQ ID NO 241
<211> LENGTH: 450
<212> TYPE: PRT
<213> ORGANISM: Artificial Sequence
<220> FEATURE:
<223> OTHER INFORMATION: Synthetic Construct

<400> SEQUENCE: 241

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ala Ile Thr Pro Asn Ala Gly Glu Asp Tyr Tyr Pro Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Thr Ser Tyr Ser Leu Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365
```

```
Leu Thr Cys Leu Val Lys Gly Phe Tyr Pro Ser Asp Ile Ala Val Glu
    370                 375                 380

Trp Glu Ser Asn Gly Gln Pro Glu Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly
    450

<210> SEQ ID NO 242
<211> LENGTH: 450
<212> TYPE: PRT
<213> ORGANISM: Artificial Sequence
<220> FEATURE:
<223> OTHER INFORMATION: Synthetic Construct

<400> SEQUENCE: 242

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ser Ile Thr Pro Asn Ala Gly Glu Asp Tyr Tyr Pro Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Thr Ser Tyr Ser Leu Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270
```

```
Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly
    450

<210> SEQ ID NO 243
<211> LENGTH: 106
<212> TYPE: PRT
<213> ORGANISM: Artificial Sequence
<220> FEATURE:
<223> OTHER INFORMATION: Synthetic Construct

<400> SEQUENCE: 243

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Leu His Glu Ala Leu His Ser His Tyr
                85                  90                  95

Thr Gln Lys Ser Leu Ser Leu Ser Pro Gly
            100                 105

<210> SEQ ID NO 244
<211> LENGTH: 450
<212> TYPE: PRT
<213> ORGANISM: Artificial Sequence
<220> FEATURE:
<223> OTHER INFORMATION: Synthetic Construct

<400> SEQUENCE: 244

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30
Trp Met Tyr Trp Val Arg Gln Ala Pro Gly Lys Gly Leu Glu Trp Val
        35                  40                  45
Ala Ala Ile Thr Pro Asn Ala Gly Glu Asp Tyr Tyr Pro Glu Ser Val
50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Gly His Tyr Tyr Thr Ser Tyr Ser Leu Gly Tyr Trp Gly
                100                 105                 110
Gln Gly Thr Leu Val Thr Val Ser Ser Ala Ser Thr Lys Gly Pro Ser
            115                 120                 125
Val Phe Pro Leu Ala Pro Ser Ser Lys Ser Thr Ser Gly Gly Thr Ala
130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
                195                 200                 205
Lys Pro Ser Asn Thr Lys Val Asp Lys Lys Val Glu Pro Lys Ser Cys
            210                 215                 220
Asp Lys Thr His Thr Cys Pro Pro Cys Pro Ala Pro Glu Ala Ala Gly
225                 230                 235                 240
Ala Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
                275                 280                 285
His Asn Ala Lys Thr Lys Pro Arg Glu Glu Gln Tyr Asn Ser Thr Tyr
290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
                355                 360                 365
Leu Thr Cys Leu Val Lys Gly Phe Tyr Pro Ser Asp Ile Ala Val Glu
            370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Leu
            420                 425                 430
```

His Glu Ala Leu His Ser His Tyr Thr Gln Lys Ser Leu Ser Leu Ser
            435                 440                 445

Pro Gly
    450

<210> SEQ ID NO 245
<211> LENGTH: 450
<212> TYPE: PRT
<213> ORGANISM: Artificial Sequence
<220> FEATURE:
<223> OTHER INFORMATION: Synthetic Construct

<400> SEQUENCE: 245

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Ser Ile Thr Pro Asn Ala Gly Glu Asp Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Thr Ser Tyr Ser Leu Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

```
Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                    405                 410                 415

Asp Lys Ser Arg Trp Gln Gln Gly Asn Val Phe Ser Cys Ser Val Leu
            420                 425                 430

His Glu Ala Leu His Ser His Tyr Thr Gln Lys Ser Leu Ser Leu Ser
            435                 440                 445

Pro Gly
    450
```

```
<210> SEQ ID NO 246
<211> LENGTH: 117
<212> TYPE: PRT
<213> ORGANISM: Artificial Sequence
<220> FEATURE:
<223> OTHER INFORMATION: Synthetic Construct

<400> SEQUENCE: 246

Gln Val Leu Leu Val Gln Ser Gly Ala Glu Val Lys Lys Pro Gly Ala
1               5                   10                  15

Thr Val Lys Val Ser Cys Lys Ala Ser Gly Ser Thr Phe Thr Gly Tyr
            20                  25                  30

Tyr Met His Trp Val Arg Gln Ala Pro Gly Gln Gly Leu Glu Trp Met
            35                  40                  45

Gly Trp Ile Asn Pro Asn Asn Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Leu Arg Tyr Asn Trp Lys Ser Trp Gly Gln Gly Thr Leu
            100                 105                 110

Val Thr Val Ser Ser
        115
```

```
<210> SEQ ID NO 247
<211> LENGTH: 10
<212> TYPE: PRT
<213> ORGANISM: Artificial Sequence
<220> FEATURE:
<223> OTHER INFORMATION: Synthetic Construct

<400> SEQUENCE: 247

Gly Ser Thr Phe Thr Gly Tyr Tyr Met His
1               5                   10
```

```
<210> SEQ ID NO 248
<211> LENGTH: 17
<212> TYPE: PRT
<213> ORGANISM: Artificial Sequence
<220> FEATURE:
<223> OTHER INFORMATION: Synthetic Construct
```

<400> SEQUENCE: 248

Trp Ile Asn Pro Asn Asn Gly Gly Thr Asn Tyr Ala Gln Lys Phe Gln
1               5                   10                  15

Gly

<210> SEQ ID NO 249
<211> LENGTH: 8
<212> TYPE: PRT
<213> ORGANISM: Artificial Sequence
<220> FEATURE:
<223> OTHER INFORMATION: Synthetic Construct

<400> SEQUENCE: 249

Glu Leu Arg Tyr Asn Trp Lys Ser
1               5

<210> SEQ ID NO 250
<211> LENGTH: 108
<212> TYPE: PRT
<213> ORGANISM: Artificial Sequence
<220> FEATURE:
<223> OTHER INFORMATION: Synthetic Construct

<400> SEQUENCE: 250

Glu Ile Val Leu Thr Gln Ser Pro Gly Thr Leu Ser Leu Ser Pro Gly
1               5                   10                  15

Glu Arg Val Thr Leu Ser Cys Arg Ala Ser Gln Ser Val Gly Arg Pro
            20                  25                  30

Tyr Leu Ala Trp Tyr Gln Gln Ile Pro Gly Gln Ala Pro Arg Leu Leu
        35                  40                  45

Ile Tyr Gly Ala Ser Ser Arg Ala Thr Asp Ile Pro Asp Arg Phe Ser
    50                  55                  60

Gly Asn Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Asn Ser Pro
                85                  90                  95

Tyr Thr Phe Gly Gln Gly Thr Arg Leu Glu Ile Lys
            100                 105

<210> SEQ ID NO 251
<211> LENGTH: 12
<212> TYPE: PRT
<213> ORGANISM: Artificial Sequence
<220> FEATURE:
<223> OTHER INFORMATION: Synthetic Construct

<400> SEQUENCE: 251

Arg Ala Ser Gln Ser Val Gly Arg Pro Tyr Leu Ala
1               5                   10

<210> SEQ ID NO 252
<211> LENGTH: 7
<212> TYPE: PRT
<213> ORGANISM: Artificial Sequence
<220> FEATURE:
<223> OTHER INFORMATION: Synthetic Construct

<400> SEQUENCE: 252

Gly Ala Ser Ser Arg Ala Thr
1               5

<210> SEQ ID NO 253

```
<211> LENGTH: 9
<212> TYPE: PRT
<213> ORGANISM: Artificial Sequence
<220> FEATURE:
<223> OTHER INFORMATION: Synthetic Construct

<400> SEQUENCE: 253

Gln Gln Tyr Asp Asn Ser Pro Tyr Thr
1               5

<210> SEQ ID NO 254
<211> LENGTH: 447
<212> TYPE: PRT
<213> ORGANISM: Artificial Sequence
<220> FEATURE:
<223> OTHER INFORMATION: Synthetic Construct

<400> SEQUENCE: 254

Gln Val Leu Leu Val Gln Ser Gly Ala Glu Val Lys Lys Pro Gly Ala
1               5                   10                  15

Thr Val Lys Val Ser Cys Lys Ala Ser Gly Ser Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Asn Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Leu Arg Tyr Asn Trp Lys Ser Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
```

```
                305                 310                 315                 320
Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445
```

<210> SEQ ID NO 255
<211> LENGTH: 10
<212> TYPE: PRT
<213> ORGANISM: Artificial Sequence
<220> FEATURE:
<223> OTHER INFORMATION: Synthetic Construct

<400> SEQUENCE: 255

```
Phe Gly Gln Gly Thr Arg Leu Glu Ile Lys
1               5                   10
```

<210> SEQ ID NO 256
<211> LENGTH: 215
<212> TYPE: PRT
<213> ORGANISM: Artificial Sequence
<220> FEATURE:
<223> OTHER INFORMATION: Synthetic Construct

<400> SEQUENCE: 256

```
Glu Ile Val Leu Thr Gln Ser Pro Gly Thr Leu Ser Leu Ser Pro Gly
1               5                   10                  15

Glu Arg Val Thr Leu Ser Cys Arg Ala Ser Gln Ser Val Gly Arg Pro
                20                  25                  30

Tyr Leu Ala Trp Tyr Gln Gln Ile Pro Gly Gln Ala Pro Arg Leu Leu
            35                  40                  45

Ile Tyr Gly Ala Ser Ser Arg Ala Thr Asp Ile Pro Asp Arg Phe Ser
        50                  55                  60

Gly Asn Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Asn Ser Pro
                85                  90                  95

Tyr Thr Phe Gly Gln Gly Thr Arg Leu Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160
```

-continued

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
        180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 257
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa can be K, S, H, T, Q, W, Y, F or R
<220> FEATURE:
<221> NAME/KEY: MISC_FEATURE
<222> LOCATION: (2)..(2)
<223> OTHER INFORMATION: Xaa can be A, S or G
<220> FEATURE:
<221> NAME/KEY: MISC_FEATURE
<222> LOCATION: (3)..(3)
<223> OTHER INFORMATION: Xaa can be S, A or D
<220> FEATURE:
<221> NAME/KEY: MISC_FEATURE
<222> LOCATION: (4)..(4)
<223> OTHER INFORMATION: Xaa can be Q, H, S, E, D, or T
<220> FEATURE:
<221> NAME/KEY: MISC_FEATURE
<222> LOCATION: (5)..(5)
<223> OTHER INFORMATION: Xaa can be N, S, D, R, K, Y, E or G
<220> FEATURE:
<221> NAME/KEY: MISC_FEATURE
<222> LOCATION: (6)..(6)
<223> OTHER INFORMATION: Xaa can be I or V
<220> FEATURE:
<221> NAME/KEY: MISC_FEATURE
<222> LOCATION: (7)..(7)
<223> OTHER INFORMATION: Xaa can be N, F, K, H, R, L, M, I, E or S
<220> FEATURE:
<221> NAME/KEY: MISC_FEATURE
<222> LOCATION: (8)..(8)
<223> OTHER INFORMATION: Xaa can be K, Q, E, R, W, F, Y, N, A, S or H
<220> FEATURE:
<221> NAME/KEY: MISC_FEATURE
<222> LOCATION: (9)..(9)
<223> OTHER INFORMATION: Xaa can be H, F, R or W
<220> FEATURE:
<221> NAME/KEY: MISC_FEATURE
<222> LOCATION: (10)..(10)
<223> OTHER INFORMATION: Xaa can be L, I, V or A
<220> FEATURE:
<221> NAME/KEY: MISC_FEATURE
<222> LOCATION: (11)..(11)
<223> OTHER INFORMATION: Xaa can be D, S or A

<400> SEQUENCE: 257

Xaa Xaa Xaa Xaa Xaa Xaa Xaa Xaa Xaa Xaa Xaa
1               5                   10

<210> SEQ ID NO 258
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)

```
<223> OTHER INFORMATION: Xaa can be K or R
<220> FEATURE:
<221> NAME/KEY: MISC_FEATURE
<222> LOCATION: (4)..(4)
<223> OTHER INFORMATION: Xaa can be Q or H
<220> FEATURE:
<221> NAME/KEY: MISC_FEATURE
<222> LOCATION: (5)..(5)
<223> OTHER INFORMATION: Xaa can be N or S
<220> FEATURE:
<221> NAME/KEY: MISC_FEATURE
<222> LOCATION: (6)..(6)
<223> OTHER INFORMATION: Xaa can be I or V
<220> FEATURE:
<221> NAME/KEY: MISC_FEATURE
<222> LOCATION: (7)..(7)
<223> OTHER INFORMATION: Xaa can be N or S
<220> FEATURE:
<221> NAME/KEY: MISC_FEATURE
<222> LOCATION: (8)..(8)
<223> OTHER INFORMATION: Xaa can be K, S or N

<400> SEQUENCE: 258

Xaa Ala Ser Xaa Xaa Xaa Xaa Xaa His Leu Asp
1               5                   10

<210> SEQ ID NO 259
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa can be K or R
<220> FEATURE:
<221> NAME/KEY: MISC_FEATURE
<222> LOCATION: (4)..(4)
<223> OTHER INFORMATION: Xaa can be Q or H
<220> FEATURE:
<221> NAME/KEY: MISC_FEATURE
<222> LOCATION: (5)..(5)
<223> OTHER INFORMATION: Xaa can be N or S
<220> FEATURE:
<221> NAME/KEY: MISC_FEATURE
<222> LOCATION: (7)..(7)
<223> OTHER INFORMATION: Xaa can be N or S
<220> FEATURE:
<221> NAME/KEY: MISC_FEATURE
<222> LOCATION: (8)..(8)
<223> OTHER INFORMATION: Xaa can be K or S

<400> SEQUENCE: 259

Xaa Ala Ser Xaa Xaa Ile Xaa Xaa His Leu Asp
1               5                   10

<210> SEQ ID NO 260
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa can be K or R
<220> FEATURE:
<221> NAME/KEY: MISC_FEATURE
<222> LOCATION: (5)..(5)
<223> OTHER INFORMATION: Xaa can be N or S
<220> FEATURE:
<221> NAME/KEY: MISC_FEATURE
<222> LOCATION: (7)..(7)
<223> OTHER INFORMATION: Xaa can be N or S
```

```
<220> FEATURE:
<221> NAME/KEY: MISC_FEATURE
<222> LOCATION: (8)..(8)
<223> OTHER INFORMATION: Xaa can be K or S

<400> SEQUENCE: 260

Xaa Ala Ser Gln Xaa Ile Xaa Xaa His Leu Asp
1               5                   10

<210> SEQ ID NO 261
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa can be F, W, Y, D, E, G or S
<220> FEATURE:
<221> NAME/KEY: MISC_FEATURE
<222> LOCATION: (2)..(2)
<223> OTHER INFORMATION: Xaa can be T, G, R, A, N or V
<220> FEATURE:
<221> NAME/KEY: MISC_FEATURE
<222> LOCATION: (3)..(3)
<223> OTHER INFORMATION: Xaa can be N, W, Y, R, F, K,Q, E, D, H or S
<220> FEATURE:
<221> NAME/KEY: MISC_FEATURE
<222> LOCATION: (4)..(4)
<223> OTHER INFORMATION: Xaa can be N, F, Y, I, M, Q, L, A, R, G, P or S
<220> FEATURE:
<221> NAME/KEY: MISC_FEATURE
<222> LOCATION: (5)..(5)
<223> OTHER INFORMATION: Xaa can be L, I, V or R
<220> FEATURE:
<221> NAME/KEY: MISC_FEATURE
<222> LOCATION: (6)..(6)
<223> OTHER INFORMATION: Xaa can be Q, R, K, F, H, L, W, Y, A or E
<220> FEATURE:
<221> NAME/KEY: MISC_FEATURE
<222> LOCATION: (7)..(7)
<223> OTHER INFORMATION: Xaa can be T, S, N or Y

<400> SEQUENCE: 261

Xaa Xaa Xaa Xaa Xaa Xaa Xaa
1               5

<210> SEQ ID NO 262
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa can be F or Y
<220> FEATURE:
<221> NAME/KEY: MISC_FEATURE
<222> LOCATION: (2)..(2)
<223> OTHER INFORMATION: Xaa can be A or T
<220> FEATURE:
<221> NAME/KEY: MISC_FEATURE
<222> LOCATION: (3)..(3)
<223> OTHER INFORMATION: Xaa can be N or S
<220> FEATURE:
<221> NAME/KEY: MISC_FEATURE
<222> LOCATION: (4)..(4)
<223> OTHER INFORMATION: Xaa can be N or S
<220> FEATURE:
<221> NAME/KEY: MISC_FEATURE
<222> LOCATION: (6)..(6)
<223> OTHER INFORMATION: Xaa can be Q or E
<220> FEATURE:
```

```
<221> NAME/KEY: MISC_FEATURE
<222> LOCATION: (7)..(7)
<223> OTHER INFORMATION: Xaa can be T or S

<400> SEQUENCE: 262

Xaa Xaa Xaa Xaa Leu Xaa Xaa
1               5

<210> SEQ ID NO 263
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa cn be T or A
<220> FEATURE:
<221> NAME/KEY: MISC_FEATURE
<222> LOCATION: (3)..(3)
<223> OTHER INFORMATION: Xaa cn be N or S
<220> FEATURE:
<221> NAME/KEY: MISC_FEATURE
<222> LOCATION: (4)..(4)
<223> OTHER INFORMATION: Xaa cn be N or S
<220> FEATURE:
<221> NAME/KEY: MISC_FEATURE
<222> LOCATION: (7)..(7)
<223> OTHER INFORMATION: Xaa cn be T or S

<400> SEQUENCE: 263

Phe Xaa Xaa Xaa Leu Gln Xaa
1               5

<210> SEQ ID NO 264
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa can be A or T
<220> FEATURE:
<221> NAME/KEY: MISC_FEATURE
<222> LOCATION: (3)..(3)
<223> OTHER INFORMATION: Xaa can be N or S
<220> FEATURE:
<221> NAME/KEY: MISC_FEATURE
<222> LOCATION: (7)..(7)
<223> OTHER INFORMATION: Xaa can be T or S

<400> SEQUENCE: 264

Phe Xaa Xaa Asn Leu Gln Xaa
1               5

<210> SEQ ID NO 265
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa can be F, Q, W, H or A
<220> FEATURE:
<221> NAME/KEY: MISC_FEATURE
<222> LOCATION: (2)..(2)
<223> OTHER INFORMATION: Xaa can be Q, S, T or A
<220> FEATURE:
```

```
<221> NAME/KEY: MISC_FEATURE
<222> LOCATION: (3)..(3)
<223> OTHER INFORMATION: Xaa can be Y, H or F
<220> FEATURE:
<221> NAME/KEY: MISC_FEATURE
<222> LOCATION: (4)..(4)
<223> OTHER INFORMATION: Xaa can be N, W, F, Y, R, K, H or D
<220> FEATURE:
<221> NAME/KEY: MISC_FEATURE
<222> LOCATION: (5)..(5)
<223> OTHER INFORMATION: Xaa can be N, S,Q, W, K, R, H, Y, D, G, T or V
<220> FEATURE:
<221> NAME/KEY: MISC_FEATURE
<222> LOCATION: (6)..(6)
<223> OTHER INFORMATION: Xaa can be G, R, P, K, W, F, I, N or Q
<220> FEATURE:
<221> NAME/KEY: MISC_FEATURE
<222> LOCATION: (7)..(7)
<223> OTHER INFORMATION: Xaa can be W or H
<220> FEATURE:
<221> NAME/KEY: MISC_FEATURE
<222> LOCATION: (8)..(8)
<223> OTHER INFORMATION: Xaa can be T, S or Q

<400> SEQUENCE: 265

Xaa Xaa Xaa Xaa Xaa Xaa Xaa Xaa
1               5

<210> SEQ ID NO 266
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa can be F or Q
<220> FEATURE:
<221> NAME/KEY: MISC_FEATURE
<222> LOCATION: (3)..(3)
<223> OTHER INFORMATION: Xaa can be Y or F
<220> FEATURE:
<221> NAME/KEY: MISC_FEATURE
<222> LOCATION: (4)..(4)
<223> OTHER INFORMATION: Xaa can be N or Y
<220> FEATURE:
<221> NAME/KEY: MISC_FEATURE
<222> LOCATION: (5)..(5)
<223> OTHER INFORMATION: Xaa can be N, S, Q, R or Y

<400> SEQUENCE: 266

Xaa Gln Xaa Xaa Xaa Gly Trp Thr
1               5

<210> SEQ ID NO 267
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa can be F or Q
<220> FEATURE:
<221> NAME/KEY: MISC_FEATURE
<222> LOCATION: (4)..(4)
<223> OTHER INFORMATION: Xaa can be N or Y
<220> FEATURE:
<221> NAME/KEY: MISC_FEATURE
<222> LOCATION: (5)..(5)
<223> OTHER INFORMATION: Xaa can be N, S, Q or R

<400> SEQUENCE: 267
```

```
Xaa Gln Tyr Xaa Xaa Gly Trp Thr
1               5

<210> SEQ ID NO 268
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa can be F or Q
<220> FEATURE:
<221> NAME/KEY: MISC_FEATURE
<222> LOCATION: (4)..(4)
<223> OTHER INFORMATION: Xaa can be N or Y
<220> FEATURE:
<221> NAME/KEY: MISC_FEATURE
<222> LOCATION: (5)..(5)
<223> OTHER INFORMATION: Xaa can be N, S or Q

<400> SEQUENCE: 268

Xaa Gln Tyr Xaa Xaa Gly Trp Thr
1               5

<210> SEQ ID NO 269
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa can be F, Y or H
<220> FEATURE:
<221> NAME/KEY: MISC_FEATURE
<222> LOCATION: (3)..(3)
<223> OTHER INFORMATION: Xaa can be T, Q, N, S, E, D, R or Y
<220> FEATURE:
<221> NAME/KEY: MISC_FEATURE
<222> LOCATION: (4)..(4)
<223> OTHER INFORMATION: Xaa can be F, Y or H
<220> FEATURE:
<221> NAME/KEY: MISC_FEATURE
<222> LOCATION: (5)..(5)
<223> OTHER INFORMATION: Xaa can be S, E, D, T or W
<220> FEATURE:
<221> NAME/KEY: MISC_FEATURE
<222> LOCATION: (6)..(6)
<223> OTHER INFORMATION: Xaa can be N, S, T, E, D, H, L, I, Y, R, K or G
<220> FEATURE:
<221> NAME/KEY: MISC_FEATURE
<222> LOCATION: (7)..(7)
<223> OTHER INFORMATION: Xaa can be Y, F or H
<220> FEATURE:
<221> NAME/KEY: MISC_FEATURE
<222> LOCATION: (8)..(8)
<223> OTHER INFORMATION: Xaa can be W, H, Y, A or G
<220> FEATURE:
<221> NAME/KEY: MISC_FEATURE
<222> LOCATION: (9)..(9)
<223> OTHER INFORMATION: Xaa can be M, E, Q or I
<220> FEATURE:
<221> NAME/KEY: MISC_FEATURE
<222> LOCATION: (10)..(10)
<223> OTHER INFORMATION: Xaa can be Y, F, H or N

<400> SEQUENCE: 269

Gly Xaa Xaa Xaa Xaa Xaa Xaa Xaa Xaa Xaa
1               5                   10
```

```
<210> SEQ ID NO 270
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa can be T or E
<220> FEATURE:
<221> NAME/KEY: MISC_FEATURE
<222> LOCATION: (5)..(5)
<223> OTHER INFORMATION: Xaa can be S or E
<220> FEATURE:
<221> NAME/KEY: MISC_FEATURE
<222> LOCATION: (6)..(6)
<223> OTHER INFORMATION: Xaa can be N or S

<400> SEQUENCE: 270

Gly Phe Xaa Phe Xaa Xaa Tyr Trp Met Tyr
1               5                   10

<210> SEQ ID NO 271
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa can be N or S

<400> SEQUENCE: 271

Gly Phe Thr Phe Ser Xaa Tyr Trp Met Tyr
1               5                   10

<210> SEQ ID NO 272
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa can be S, A or T
<220> FEATURE:
<221> NAME/KEY: MISC_FEATURE
<222> LOCATION: (2)..(2)
<223> OTHER INFORMATION: Xaa can be I or V
<220> FEATURE:
<221> NAME/KEY: MISC_FEATURE
<222> LOCATION: (3)..(3)
<223> OTHER INFORMATION: Xaa can be T, H, N or S
<220> FEATURE:
<221> NAME/KEY: MISC_FEATURE
<222> LOCATION: (4)..(4)
<223> OTHER INFORMATION: Xaa can be P, N, F or M
<220> FEATURE:
<221> NAME/KEY: MISC_FEATURE
<222> LOCATION: (5)..(5)
<223> OTHER INFORMATION: Xaa can be N, I, D, Y or W
<220> FEATURE:
<221> NAME/KEY: MISC_FEATURE
<222> LOCATION: (6)..(6)
<223> OTHER INFORMATION: Xaa can be G or A
<220> FEATURE:
<221> NAME/KEY: MISC_FEATURE
<222> LOCATION: (7)..(7)
<223> OTHER INFORMATION: Xaa can be G, H, D, E, R, K, Y or S
<220> FEATURE:
<221> NAME/KEY: MISC_FEATURE
<222> LOCATION: (8)..(8)
```

<223> OTHER INFORMATION: Xaa can be N, Y, D, E, Q or H
<220> FEATURE:
<221> NAME/KEY: MISC_FEATURE
<222> LOCATION: (9)..(9)
<223> OTHER INFORMATION: Xaa can be T, K, E, S, I, A or D
<220> FEATURE:
<221> NAME/KEY: MISC_FEATURE
<222> LOCATION: (10)..(10)
<223> OTHER INFORMATION: Xaa can be Y, H or W
<220> FEATURE:
<221> NAME/KEY: MISC_FEATURE
<222> LOCATION: (11)..(11)
<223> OTHER INFORMATION: Xaa can be Y, F or H
<220> FEATURE:
<221> NAME/KEY: MISC_FEATURE
<222> LOCATION: (12)..(12)
<223> OTHER INFORMATION: Xaa can be P, V, L, D or S
<220> FEATURE:
<221> NAME/KEY: MISC_FEATURE
<222> LOCATION: (13)..(13)
<223> OTHER INFORMATION: Xaa can be D, E, Q or A
<220> FEATURE:
<221> NAME/KEY: MISC_FEATURE
<222> LOCATION: (14)..(14)
<223> OTHER INFORMATION: Xaa can be S, A, N or D
<220> FEATURE:
<221> NAME/KEY: MISC_FEATURE
<222> LOCATION: (15)..(15)
<223> OTHER INFORMATION: Xaa can be V, D or T
<220> FEATURE:
<221> NAME/KEY: MISC_FEATURE
<222> LOCATION: (16)..(16)
<223> OTHER INFORMATION: Xaa can be K, N, D, S, E or Q

<400> SEQUENCE: 272

Xaa Xaa Xaa Xaa Xaa Xaa Xaa Xaa Xaa Xaa Xaa Xaa Xaa Xaa Xaa Xaa
1               5                   10                  15

Gly

<210> SEQ ID NO 273
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa can be S or A
<220> FEATURE:
<221> NAME/KEY: MISC_FEATURE
<222> LOCATION: (3)..(3)
<223> OTHER INFORMATION: Xaa can be T or N
<220> FEATURE:
<221> NAME/KEY: MISC_FEATURE
<222> LOCATION: (4)..(4)
<223> OTHER INFORMATION: Xaa can be P or N
<220> FEATURE:
<221> NAME/KEY: MISC_FEATURE
<222> LOCATION: (5)..(5)
<223> OTHER INFORMATION: Xaa can be N or D
<220> FEATURE:
<221> NAME/KEY: MISC_FEATURE
<222> LOCATION: (6)..(6)
<223> OTHER INFORMATION: Xaa can be G or A
<220> FEATURE:
<221> NAME/KEY: MISC_FEATURE
<222> LOCATION: (7)..(7)
<223> OTHER INFORMATION: Xaa can be G, S or H
<220> FEATURE:
<221> NAME/KEY: MISC_FEATURE
<222> LOCATION: (8)..(8)
<223> OTHER INFORMATION: Xaa can be N, D or E
<220> FEATURE:
<221> NAME/KEY: MISC_FEATURE
<222> LOCATION: (9)..(9)

<223> OTHER INFORMATION: Xaa can be T, K, D or E
<220> FEATURE:
<221> NAME/KEY: MISC_FEATURE
<222> LOCATION: (12)..(12)
<223> OTHER INFORMATION: Xaa can be P, V or L
<220> FEATURE:
<221> NAME/KEY: MISC_FEATURE
<222> LOCATION: (13)..(13)
<223> OTHER INFORMATION: Xaa can be D or E
<220> FEATURE:
<221> NAME/KEY: MISC_FEATURE
<222> LOCATION: (16)..(16)
<223> OTHER INFORMATION: Xaa can be K or Q

<400> SEQUENCE: 273

Xaa Ile Xaa Xaa Xaa Xaa Xaa Xaa Xaa Tyr Tyr Xaa Xaa Ser Val Xaa
1               5                   10                  15

Gly

<210> SEQ ID NO 274
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa can be S or A
<220> FEATURE:
<221> NAME/KEY: MISC_FEATURE
<222> LOCATION: (3)..(3)
<223> OTHER INFORMATION: Xaa can be T or N
<220> FEATURE:
<221> NAME/KEY: MISC_FEATURE
<222> LOCATION: (4)..(4)
<223> OTHER INFORMATION: Xaa can be P or N
<220> FEATURE:
<221> NAME/KEY: MISC_FEATURE
<222> LOCATION: (5)..(5)
<223> OTHER INFORMATION: Xaa can be N or D
<220> FEATURE:
<221> NAME/KEY: MISC_FEATURE
<222> LOCATION: (6)..(6)
<223> OTHER INFORMATION: Xaa can be G or A
<220> FEATURE:
<221> NAME/KEY: MISC_FEATURE
<222> LOCATION: (7)..(7)
<223> OTHER INFORMATION: Xaa can be G or S
<220> FEATURE:
<221> NAME/KEY: MISC_FEATURE
<222> LOCATION: (8)..(8)
<223> OTHER INFORMATION: Xaa can be N or E
<220> FEATURE:
<221> NAME/KEY: MISC_FEATURE
<222> LOCATION: (9)..(9)
<223> OTHER INFORMATION: Xaa can be T, K or D
<220> FEATURE:
<221> NAME/KEY: MISC_FEATURE
<222> LOCATION: (12)..(12)
<223> OTHER INFORMATION: Xaa can be P, V or L
<220> FEATURE:
<221> NAME/KEY: MISC_FEATURE
<222> LOCATION: (13)..(13)
<223> OTHER INFORMATION: Xaa can be D or E

<400> SEQUENCE: 274

Xaa Ile Xaa Xaa Xaa Xaa Xaa Xaa Xaa Tyr Tyr Xaa Xaa Ser Val Lys
1               5                   10                  15

Gly

<210> SEQ ID NO 275
<211> LENGTH: 17

```
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa can be S or A
<220> FEATURE:
<221> NAME/KEY: MISC_FEATURE
<222> LOCATION: (5)..(5)
<223> OTHER INFORMATION: Xaa can be N or D
<220> FEATURE:
<221> NAME/KEY: MISC_FEATURE
<222> LOCATION: (6)..(6)
<223> OTHER INFORMATION: Xaa can be G or A
<220> FEATURE:
<221> NAME/KEY: MISC_FEATURE
<222> LOCATION: (7)..(7)
<223> OTHER INFORMATION: Xaa can be G or S
<220> FEATURE:
<221> NAME/KEY: MISC_FEATURE
<222> LOCATION: (8)..(8)
<223> OTHER INFORMATION: Xaa can be N or E
<220> FEATURE:
<221> NAME/KEY: MISC_FEATURE
<222> LOCATION: (9)..(9)
<223> OTHER INFORMATION: Xaa can be T, K or D
<220> FEATURE:
<221> NAME/KEY: MISC_FEATURE
<222> LOCATION: (12)..(12)
<223> OTHER INFORMATION: Xaa can be P or V
<220> FEATURE:
<221> NAME/KEY: MISC_FEATURE
<222> LOCATION: (13)..(13)
<223> OTHER INFORMATION: Xaa can be D or E

<400> SEQUENCE: 275

Xaa Ile Thr Pro Xaa Xaa Xaa Xaa Xaa Tyr Tyr Xaa Xaa Ser Val Lys
1               5                   10                  15

Gly

<210> SEQ ID NO 276
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa can be G, S, A, T or D
<220> FEATURE:
<221> NAME/KEY: MISC_FEATURE
<222> LOCATION: (2)..(2)
<223> OTHER INFORMATION: Xaa can be H, K, R or Y
<220> FEATURE:
<221> NAME/KEY: MISC_FEATURE
<222> LOCATION: (3)..(3)
<223> OTHER INFORMATION: Xaa can be Y, H, F or S
<220> FEATURE:
<221> NAME/KEY: MISC_FEATURE
<222> LOCATION: (4)..(4)
<223> OTHER INFORMATION: Xaa can be Y, H, R or S
<220> FEATURE:
<221> NAME/KEY: MISC_FEATURE
<222> LOCATION: (5)..(5)
<223> OTHER INFORMATION: Xaa can be Y, H, W, F, R or S
<220> FEATURE:
<221> NAME/KEY: MISC_FEATURE
<222> LOCATION: (6)..(6)
<223> OTHER INFORMATION: Xaa can be T, N, V, I, S, A, G or Y
<220> FEATURE:
<221> NAME/KEY: MISC_FEATURE
<222> LOCATION: (7)..(7)
<223> OTHER INFORMATION: Xaa can be S, N, A, Q, D, G, R or Y
```

```
<220> FEATURE:
<221> NAME/KEY: MISC_FEATURE
<222> LOCATION: (8)..(8)
<223> OTHER INFORMATION: Xaa can be Y, W,H, F, G, D or N
<220> FEATURE:
<221> NAME/KEY: MISC_FEATURE
<222> LOCATION: (9)..(9)
<223> OTHER INFORMATION: Xaa can be S, A or G
<220> FEATURE:
<221> NAME/KEY: MISC_FEATURE
<222> LOCATION: (10)..(10)
<223> OTHER INFORMATION: Xaa can be L, M, F or I
<220> FEATURE:
<221> NAME/KEY: MISC_FEATURE
<222> LOCATION: (11)..(11)
<223> OTHER INFORMATION: Xaa can be G, A, Y, S or D
<220> FEATURE:
<221> NAME/KEY: MISC_FEATURE
<222> LOCATION: (12)..(12)
<223> OTHER INFORMATION: Xaa can be Y, N, S, F, E, D, H, I or V

<400> SEQUENCE: 276

Xaa Xaa Xaa Xaa Xaa Xaa Xaa Xaa Xaa Xaa Xaa Xaa
1               5                   10

<210> SEQ ID NO 277
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa can be H, R or Y
<220> FEATURE:
<221> NAME/KEY: MISC_FEATURE
<222> LOCATION: (3)..(3)
<223> OTHER INFORMATION: Xaa can be Y or F
<220> FEATURE:
<221> NAME/KEY: MISC_FEATURE
<222> LOCATION: (4)..(4)
<223> OTHER INFORMATION: Xaa can be Y or S
<220> FEATURE:
<221> NAME/KEY: MISC_FEATURE
<222> LOCATION: (5)..(5)
<223> OTHER INFORMATION: Xaa can be Y or H
<220> FEATURE:
<221> NAME/KEY: MISC_FEATURE
<222> LOCATION: (6)..(6)
<223> OTHER INFORMATION: Xaa can be T, S or N
<220> FEATURE:
<221> NAME/KEY: MISC_FEATURE
<222> LOCATION: (7)..(7)
<223> OTHER INFORMATION: Xaa can be S or A
<220> FEATURE:
<221> NAME/KEY: MISC_FEATURE
<222> LOCATION: (10)..(10)
<223> OTHER INFORMATION: Xaa can be L, F or I
<220> FEATURE:
<221> NAME/KEY: MISC_FEATURE
<222> LOCATION: (11)..(11)
<223> OTHER INFORMATION: Xaa can be G, S or A
<220> FEATURE:
<221> NAME/KEY: MISC_FEATURE
<222> LOCATION: (12)..(12)
<223> OTHER INFORMATION: Xaa can be Y, H, N, S or F

<400> SEQUENCE: 277

Gly Xaa Xaa Xaa Xaa Xaa Xaa Tyr Ser Xaa Xaa Xaa
1               5                   10

<210> SEQ ID NO 278
<211> LENGTH: 12
<212> TYPE: PRT
```

```
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa can be H or Y
<220> FEATURE:
<221> NAME/KEY: MISC_FEATURE
<222> LOCATION: (4)..(4)
<223> OTHER INFORMATION: Xaa can be Y or S
<220> FEATURE:
<221> NAME/KEY: MISC_FEATURE
<222> LOCATION: (5)..(5)
<223> OTHER INFORMATION: Xaa can be Y or H
<220> FEATURE:
<221> NAME/KEY: MISC_FEATURE
<222> LOCATION: (6)..(6)
<223> OTHER INFORMATION: Xaa can be T, S or N
<220> FEATURE:
<221> NAME/KEY: MISC_FEATURE
<222> LOCATION: (7)..(7)
<223> OTHER INFORMATION: Xaa can be S or A
<220> FEATURE:
<221> NAME/KEY: MISC_FEATURE
<222> LOCATION: (10)..(10)
<223> OTHER INFORMATION: Xaa can be L or F
<220> FEATURE:
<221> NAME/KEY: MISC_FEATURE
<222> LOCATION: (11)..(11)
<223> OTHER INFORMATION: Xaa can be G or S

<400> SEQUENCE: 278

Gly Xaa Tyr Xaa Xaa Xaa Xaa Tyr Ser Xaa Xaa Tyr
1               5                   10

<210> SEQ ID NO 279
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa can be Y or S
<220> FEATURE:
<221> NAME/KEY: MISC_FEATURE
<222> LOCATION: (6)..(6)
<223> OTHER INFORMATION: Xaa can be T or S
<220> FEATURE:
<221> NAME/KEY: MISC_FEATURE
<222> LOCATION: (10)..(10)
<223> OTHER INFORMATION: Xaa can be L or F
<220> FEATURE:
<221> NAME/KEY: MISC_FEATURE
<222> LOCATION: (11)..(11)
<223> OTHER INFORMATION: Xaa can be G or S

<400> SEQUENCE: 279

Gly His Tyr Xaa Tyr Xaa Ser Tyr Ser Xaa Xaa Tyr
1               5                   10

<210> SEQ ID NO 280
<211> LENGTH: 11
<212> TYPE: PRT
<213> ORGANISM: Artificial Sequence
<220> FEATURE:
<223> OTHER INFORMATION: Synthetic Construct

<400> SEQUENCE: 280

Arg Ala Ser Gln Ser Ile Ser Ser Tyr Leu Asn
1               5                   10
```

```
<210> SEQ ID NO 281
<211> LENGTH: 7
<212> TYPE: PRT
<213> ORGANISM: Artificial Sequence
<220> FEATURE:
<223> OTHER INFORMATION: Synthetic Construct

<400> SEQUENCE: 281

Ala Ala Ser Ser Leu Gln Ser
1               5

<210> SEQ ID NO 282
<211> LENGTH: 7
<212> TYPE: PRT
<213> ORGANISM: Artificial Sequence
<220> FEATURE:
<223> OTHER INFORMATION: Synthetic Construct

<400> SEQUENCE: 282

Gln Gln Ser Tyr Ser Thr Pro
1               5

<210> SEQ ID NO 283
<211> LENGTH: 16
<212> TYPE: PRT
<213> ORGANISM: Artificial Sequence
<220> FEATURE:
<223> OTHER INFORMATION: Synthetic Construct

<400> SEQUENCE: 283

Lys Ser Ser Gln Ser Leu Leu His Ser Asp Gly Lys Thr Tyr Leu Tyr
1               5                   10                  15

<210> SEQ ID NO 284
<211> LENGTH: 7
<212> TYPE: PRT
<213> ORGANISM: Artificial Sequence
<220> FEATURE:
<223> OTHER INFORMATION: Synthetic Construct

<400> SEQUENCE: 284

Glu Val Ser Asn Arg Phe Ser
1               5

<210> SEQ ID NO 285
<211> LENGTH: 7
<212> TYPE: PRT
<213> ORGANISM: Artificial Sequence
<220> FEATURE:
<223> OTHER INFORMATION: Synthetic Construct

<400> SEQUENCE: 285

Met Gln Ser Ile Gln Leu Pro
1               5

<210> SEQ ID NO 286
<211> LENGTH: 16
<212> TYPE: PRT
<213> ORGANISM: Artificial Sequence
<220> FEATURE:
<223> OTHER INFORMATION: Synthetic Construct

<400> SEQUENCE: 286

Arg Ser Ser Gln Ser Leu Val Tyr Ser Asp Gly Asn Thr Tyr Leu Asn
1               5                   10                  15
```

```
<210> SEQ ID NO 287
<211> LENGTH: 7
<212> TYPE: PRT
<213> ORGANISM: Artificial Sequence
<220> FEATURE:
<223> OTHER INFORMATION: Synthetic Construct

<400> SEQUENCE: 287

Lys Val Ser Asn Arg Asp Ser
1               5

<210> SEQ ID NO 288
<211> LENGTH: 7
<212> TYPE: PRT
<213> ORGANISM: Artificial Sequence
<220> FEATURE:
<223> OTHER INFORMATION: Synthetic Construct

<400> SEQUENCE: 288

Met Gln Gly Thr His Trp Pro
1               5

<210> SEQ ID NO 289
<211> LENGTH: 17
<212> TYPE: PRT
<213> ORGANISM: Artificial Sequence
<220> FEATURE:
<223> OTHER INFORMATION: Synthetic Construct

<400> SEQUENCE: 289

Lys Ser Ser Gln Ser Val Leu Tyr Ser Ser Asn Asn Lys Asn Tyr Leu
1               5                   10                  15

Ala

<210> SEQ ID NO 290
<211> LENGTH: 7
<212> TYPE: PRT
<213> ORGANISM: Artificial Sequence
<220> FEATURE:
<223> OTHER INFORMATION: Synthetic Construct

<400> SEQUENCE: 290

Trp Ala Ser Thr Arg Glu Ser
1               5

<210> SEQ ID NO 291
<211> LENGTH: 7
<212> TYPE: PRT
<213> ORGANISM: Artificial Sequence
<220> FEATURE:
<223> OTHER INFORMATION: Synthetic Construct

<400> SEQUENCE: 291

Gln Gln Tyr Tyr Ser Thr Pro
1               5

<210> SEQ ID NO 292
<211> LENGTH: 11
<212> TYPE: PRT
<213> ORGANISM: Artificial Sequence
<220> FEATURE:
<223> OTHER INFORMATION: Synthetic Construct

<400> SEQUENCE: 292

Arg Ala Ser Gln Ser Ile Ser Ser Trp Leu Ala
1               5                   10
```

<210> SEQ ID NO 293
<211> LENGTH: 7
<212> TYPE: PRT
<213> ORGANISM: Artificial Sequence
<220> FEATURE:
<223> OTHER INFORMATION: Synthetic Construct

<400> SEQUENCE: 293

Asp Ala Ser Ser Leu Glu Ser
1               5

<210> SEQ ID NO 294
<211> LENGTH: 7
<212> TYPE: PRT
<213> ORGANISM: Artificial Sequence
<220> FEATURE:
<223> OTHER INFORMATION: Synthetic Construct

<400> SEQUENCE: 294

Gln Gln Tyr Asn Ser Tyr Ser
1               5

<210> SEQ ID NO 295
<211> LENGTH: 11
<212> TYPE: PRT
<213> ORGANISM: Artificial Sequence
<220> FEATURE:
<223> OTHER INFORMATION: Synthetic Construct

<400> SEQUENCE: 295

Gln Ala Ser Gln Asp Ile Ser Asn Tyr Leu Asn
1               5                   10

<210> SEQ ID NO 296
<211> LENGTH: 7
<212> TYPE: PRT
<213> ORGANISM: Artificial Sequence
<220> FEATURE:
<223> OTHER INFORMATION: Synthetic Construct

<400> SEQUENCE: 296

Asp Ala Ser Asn Leu Glu Thr
1               5

<210> SEQ ID NO 297
<211> LENGTH: 7
<212> TYPE: PRT
<213> ORGANISM: Artificial Sequence
<220> FEATURE:
<223> OTHER INFORMATION: Synthetic Construct

<400> SEQUENCE: 297

Gln Gln Tyr Asp Asn Leu Pro
1               5

<210> SEQ ID NO 298
<211> LENGTH: 11
<212> TYPE: PRT
<213> ORGANISM: Artificial Sequence
<220> FEATURE:
<223> OTHER INFORMATION: Synthetic Construct

<400> SEQUENCE: 298

Arg Ala Ser Gln Gly Ile Ser Ser Tyr Leu Ala
1               5                   10

```
<210> SEQ ID NO 299
<211> LENGTH: 7
<212> TYPE: PRT
<213> ORGANISM: Artificial Sequence
<220> FEATURE:
<223> OTHER INFORMATION: Synthetic Construct

<400> SEQUENCE: 299

Ala Ala Ser Thr Leu Gln Ser
1               5

<210> SEQ ID NO 300
<211> LENGTH: 7
<212> TYPE: PRT
<213> ORGANISM: Artificial Sequence
<220> FEATURE:
<223> OTHER INFORMATION: Synthetic Construct

<400> SEQUENCE: 300

Gln Gln Leu Asn Ser Tyr Pro
1               5

<210> SEQ ID NO 301
<211> LENGTH: 11
<212> TYPE: PRT
<213> ORGANISM: Artificial Sequence
<220> FEATURE:
<223> OTHER INFORMATION: Synthetic Construct

<400> SEQUENCE: 301

Arg Ala Ser Gln Ser Val Ser Ser Asn Leu Ala
1               5                   10

<210> SEQ ID NO 302
<211> LENGTH: 7
<212> TYPE: PRT
<213> ORGANISM: Artificial Sequence
<220> FEATURE:
<223> OTHER INFORMATION: Synthetic Construct

<400> SEQUENCE: 302

Gly Ala Ser Thr Arg Ala Thr
1               5

<210> SEQ ID NO 303
<211> LENGTH: 7
<212> TYPE: PRT
<213> ORGANISM: Artificial Sequence
<220> FEATURE:
<223> OTHER INFORMATION: Synthetic Construct

<400> SEQUENCE: 303

Gln Gln Tyr Asn Asn Trp Pro
1               5

<210> SEQ ID NO 304
<211> LENGTH: 11
<212> TYPE: PRT
<213> ORGANISM: Artificial Sequence
<220> FEATURE:
<223> OTHER INFORMATION: Synthetic Construct

<400> SEQUENCE: 304

Arg Ala Ser Gln Ser Val Ser Ser Tyr Leu Ala
1               5                   10

<210> SEQ ID NO 305
```

```
<211> LENGTH: 7
<212> TYPE: PRT
<213> ORGANISM: Artificial Sequence
<220> FEATURE:
<223> OTHER INFORMATION: Synthetic Construct

<400> SEQUENCE: 305

Asp Ala Ser Asn Arg Ala Thr
1               5

<210> SEQ ID NO 306
<211> LENGTH: 7
<212> TYPE: PRT
<213> ORGANISM: Artificial Sequence
<220> FEATURE:
<223> OTHER INFORMATION: Synthetic Construct

<400> SEQUENCE: 306

Gln Gln Arg Ser Asn Trp Pro
1               5

<210> SEQ ID NO 307
<211> LENGTH: 12
<212> TYPE: PRT
<213> ORGANISM: Artificial Sequence
<220> FEATURE:
<223> OTHER INFORMATION: Synthetic Construct

<400> SEQUENCE: 307

Arg Ala Ser Gln Ser Val Ser Ser Ser Tyr Leu Ala
1               5                   10

<210> SEQ ID NO 308
<211> LENGTH: 7
<212> TYPE: PRT
<213> ORGANISM: Artificial Sequence
<220> FEATURE:
<223> OTHER INFORMATION: Synthetic Construct

<400> SEQUENCE: 308

Gly Ala Ser Ser Arg Ala Thr
1               5

<210> SEQ ID NO 309
<211> LENGTH: 7
<212> TYPE: PRT
<213> ORGANISM: Artificial Sequence
<220> FEATURE:
<223> OTHER INFORMATION: Synthetic Construct

<400> SEQUENCE: 309

Gln Gln Tyr Gly Ser Ser Pro
1               5

<210> SEQ ID NO 310
<211> LENGTH: 16
<212> TYPE: PRT
<213> ORGANISM: Artificial Sequence
<220> FEATURE:
<223> OTHER INFORMATION: Synthetic Construct

<400> SEQUENCE: 310

Arg Ser Ser Gln Ser Leu Leu His Ser Asn Gly Tyr Asn Tyr Leu Asp
1               5                   10                  15

<210> SEQ ID NO 311
<211> LENGTH: 7
```

```
<212> TYPE: PRT
<213> ORGANISM: Artificial Sequence
<220> FEATURE:
<223> OTHER INFORMATION: Synthetic Construct

<400> SEQUENCE: 311

Leu Gly Ser Asn Arg Ala Ser
1               5

<210> SEQ ID NO 312
<211> LENGTH: 7
<212> TYPE: PRT
<213> ORGANISM: Artificial Sequence
<220> FEATURE:
<223> OTHER INFORMATION: Synthetic Construct

<400> SEQUENCE: 312

Met Gln Ala Leu Gln Thr Pro
1               5

<210> SEQ ID NO 313
<211> LENGTH: 11
<212> TYPE: PRT
<213> ORGANISM: Artificial Sequence
<220> FEATURE:
<223> OTHER INFORMATION: Synthetic Construct

<400> SEQUENCE: 313

Gln Gly Asp Ser Leu Arg Ser Tyr Tyr Ala Ser
1               5                   10

<210> SEQ ID NO 314
<211> LENGTH: 7
<212> TYPE: PRT
<213> ORGANISM: Artificial Sequence
<220> FEATURE:
<223> OTHER INFORMATION: Synthetic Construct

<400> SEQUENCE: 314

Gly Lys Asn Asn Arg Pro Ser
1               5

<210> SEQ ID NO 315
<211> LENGTH: 9
<212> TYPE: PRT
<213> ORGANISM: Artificial Sequence
<220> FEATURE:
<223> OTHER INFORMATION: Synthetic Construct

<400> SEQUENCE: 315

Asn Ser Arg Asp Ser Ser Gly Asn His
1               5

<210> SEQ ID NO 316
<211> LENGTH: 14
<212> TYPE: PRT
<213> ORGANISM: Artificial Sequence
<220> FEATURE:
<223> OTHER INFORMATION: Synthetic Construct

<400> SEQUENCE: 316

Thr Gly Ser Ser Ser Asn Ile Gly Ala Gly Tyr Asp Val His
1               5                   10

<210> SEQ ID NO 317
<211> LENGTH: 7
<212> TYPE: PRT
```

```
<213> ORGANISM: Artificial Sequence
<220> FEATURE:
<223> OTHER INFORMATION: Synthetic Construct

<400> SEQUENCE: 317

Gly Asn Ser Asn Arg Pro Ser
1               5

<210> SEQ ID NO 318
<211> LENGTH: 9
<212> TYPE: PRT
<213> ORGANISM: Artificial Sequence
<220> FEATURE:
<223> OTHER INFORMATION: Synthetic Construct

<400> SEQUENCE: 318

Gln Ser Tyr Asp Ser Ser Leu Ser Gly
1               5

<210> SEQ ID NO 319
<211> LENGTH: 13
<212> TYPE: PRT
<213> ORGANISM: Artificial Sequence
<220> FEATURE:
<223> OTHER INFORMATION: Synthetic Construct

<400> SEQUENCE: 319

Thr Arg Ser Ser Gly Ser Ile Ala Ser Asn Tyr Val Gln
1               5                   10

<210> SEQ ID NO 320
<211> LENGTH: 7
<212> TYPE: PRT
<213> ORGANISM: Artificial Sequence
<220> FEATURE:
<223> OTHER INFORMATION: Synthetic Construct

<400> SEQUENCE: 320

Glu Asp Asn Gln Arg Pro Ser
1               5

<210> SEQ ID NO 321
<211> LENGTH: 7
<212> TYPE: PRT
<213> ORGANISM: Artificial Sequence
<220> FEATURE:
<223> OTHER INFORMATION: Synthetic Construct

<400> SEQUENCE: 321

Gln Ser Tyr Asp Ser Ser Asn
1               5

<210> SEQ ID NO 322
<211> LENGTH: 12
<212> TYPE: PRT
<213> ORGANISM: Artificial Sequence
<220> FEATURE:
<223> OTHER INFORMATION: Synthetic Construct

<400> SEQUENCE: 322

Thr Gly Ser Ser Ser Gly Gly Ser Tyr Tyr Val Ser
1               5                   10

<210> SEQ ID NO 323
<211> LENGTH: 14
<212> TYPE: PRT
<213> ORGANISM: Artificial Sequence
```

```
<220> FEATURE:
<223> OTHER INFORMATION: Synthetic Construct

<400> SEQUENCE: 323

Thr Gly Ser Ser Ser Asp Val Gly Gly Ser Tyr Tyr Val Ser
1               5                   10

<210> SEQ ID NO 324
<211> LENGTH: 8
<212> TYPE: PRT
<213> ORGANISM: Artificial Sequence
<220> FEATURE:
<223> OTHER INFORMATION: Synthetic Construct

<400> SEQUENCE: 324

Glu Asn Asp Ser Asn Arg Pro Ser
1               5

<210> SEQ ID NO 325
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa can be S or D
<220> FEATURE:
<221> NAME/KEY: MISC_FEATURE
<222> LOCATION: (8)..(8)
<223> OTHER INFORMATION: Xaa can be Q or G

<400> SEQUENCE: 325

Glu Asp Ser Asn Arg Xaa Lys Xaa Gln Lys Pro Ser
1               5                   10

<210> SEQ ID NO 326
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa can be N or T

<400> SEQUENCE: 326

Gln Ser Trp Asp Ser Ser Ala Xaa
1               5

<210> SEQ ID NO 327
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa can be N or T
<220> FEATURE:
<221> NAME/KEY: MISC_FEATURE
<222> LOCATION: (10)..(10)
<223> OTHER INFORMATION: Xaa can be F or V
<220> FEATURE:
<221> NAME/KEY: MISC_FEATURE
<222> LOCATION: (11)..(11)
<223> OTHER INFORMATION: Xaa can be G or V
```

<400> SEQUENCE: 327

Gln Ser Trp Asp Ser Ser Ala Xaa Phe Xaa Xaa
1               5                   10

<210> SEQ ID NO 328
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (11)..(11)
<223> OTHER INFORMATION: Xaa can be A or Y
<220> FEATURE:
<221> NAME/KEY: MISC_FEATURE
<222> LOCATION: (13)..(13)
<223> OTHER INFORMATION: Xaa can be N, H or S

<400> SEQUENCE: 328

Ser Gly Ser Ser Ser Asn Ile Gly Asn Asn Xaa Val Xaa
1               5                   10

<210> SEQ ID NO 329
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (12)..(12)
<223> OTHER INFORMATION: Xaa can be A or Y
<220> FEATURE:
<221> NAME/KEY: MISC_FEATURE
<222> LOCATION: (14)..(14)
<223> OTHER INFORMATION: Xaa can be N, H or S

<400> SEQUENCE: 329

Ser Gly Ser Ser Ser Asn Ile Ile Gly Asn Asn Xaa Val Xaa
1               5                   10

<210> SEQ ID NO 330
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa can be K, N or Q

<400> SEQUENCE: 330

Gly Asn Asn Xaa Arg Pro Ser
1               5

<210> SEQ ID NO 331
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa can be N or S

<400> SEQUENCE: 331

Ala Ala Trp Asp Asp Ser Leu Xaa Gly

```
<210> SEQ ID NO 332
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa can be A or V
<220> FEATURE:
<221> NAME/KEY: MISC_FEATURE
<222> LOCATION: (8)..(8)
<223> OTHER INFORMATION: Xaa can be K or S

<400> SEQUENCE: 332

Cys Ser Gly Asp Xaa Leu Gly Xaa Lys Tyr Ala His
1               5                   10

<210> SEQ ID NO 333
<211> LENGTH: 7
<212> TYPE: PRT
<213> ORGANISM: Artificial Sequence
<220> FEATURE:
<223> OTHER INFORMATION: Synthetic Construct

<400> SEQUENCE: 333

Lys Asp Ser Glu Arg Pro Ser
1               5

<210> SEQ ID NO 334
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa can be N, D, T or A

<400> SEQUENCE: 334

Gln Ser Trp Asp Ser Ser Gly Xaa
1               5

<210> SEQ ID NO 335
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa can be N, D, T, or A

<400> SEQUENCE: 335

Gln Ser Trp Asp Ser Ser Gly Xaa His
1               5

<210> SEQ ID NO 336
<211> LENGTH: 17
<212> TYPE: PRT
<213> ORGANISM: Artificial Sequence
<220> FEATURE:
<223> OTHER INFORMATION: Synthetic Construct

<400> SEQUENCE: 336
```

Arg Ala Ser Gln Ser Leu Leu His Ser Asp Gly Ile Ser Ser Tyr Leu
1               5                   10                  15
Ala

<210> SEQ ID NO 337
<211> LENGTH: 11
<212> TYPE: PRT
<213> ORGANISM: Artificial Sequence
<220> FEATURE:
<223> OTHER INFORMATION: Synthetic Construct

<400> SEQUENCE: 337

Arg Ala Ser Gln Gly Ile Ser Ser Tyr Leu Ala
1               5                   10

<210> SEQ ID NO 338
<211> LENGTH: 7
<212> TYPE: PRT
<213> ORGANISM: Artificial Sequence
<220> FEATURE:
<223> OTHER INFORMATION: Synthetic Construct

<400> SEQUENCE: 338

Ala Ala Ser Ser Arg Ala Ser
1               5

<210> SEQ ID NO 339
<211> LENGTH: 7
<212> TYPE: PRT
<213> ORGANISM: Artificial Sequence
<220> FEATURE:
<223> OTHER INFORMATION: Synthetic Construct

<400> SEQUENCE: 339

Gln Gln Tyr Asn Ser Tyr Pro
1               5

<210> SEQ ID NO 340
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa can be N or S

<400> SEQUENCE: 340

Arg Ala Ser Gln Gly Ile Ser Xaa Tyr Leu Ala
1               5                   10

<210> SEQ ID NO 341
<211> LENGTH: 7
<212> TYPE: PRT
<213> ORGANISM: Artificial Sequence
<220> FEATURE:
<223> OTHER INFORMATION: Synthetic Construct

<400> SEQUENCE: 341

Ala Ala Ser Ser Leu Gln Ser
1               5

<210> SEQ ID NO 342
<211> LENGTH: 7
<212> TYPE: PRT

<213> ORGANISM: Artificial Sequence
<220> FEATURE:
<223> OTHER INFORMATION: Synthetic Construct

<400> SEQUENCE: 342

Gln Gln Tyr Asn Ser Tyr Pro
1               5

<210> SEQ ID NO 343
<211> LENGTH: 16
<212> TYPE: PRT
<213> ORGANISM: Artificial Sequence
<220> FEATURE:
<223> OTHER INFORMATION: Synthetic Construct

<400> SEQUENCE: 343

Arg Ser Ser Gln Ser Leu Leu His Ser Asp Gly Asn Thr Tyr Leu Asp
1               5                   10                  15

<210> SEQ ID NO 344
<211> LENGTH: 17
<212> TYPE: PRT
<213> ORGANISM: Artificial Sequence
<220> FEATURE:
<223> OTHER INFORMATION: Synthetic Construct

<400> SEQUENCE: 344

Arg Ser Ser Gln Ser Leu Leu His Ser Asp Asp Gly Asn Thr Tyr Leu
1               5                   10                  15

Asp

<210> SEQ ID NO 345
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa can be K or T
<220> FEATURE:
<221> NAME/KEY: MISC_FEATURE
<222> LOCATION: (2)..(2)
<223> OTHER INFORMATION: Xaa can be V or I
<220> FEATURE:
<221> NAME/KEY: MISC_FEATURE
<222> LOCATION: (6)..(6)
<223> OTHER INFORMATION: Xaa can be A or F

<400> SEQUENCE: 345

Xaa Xaa Ser Asn Arg Xaa Ser
1               5

<210> SEQ ID NO 346
<211> LENGTH: 7
<212> TYPE: PRT
<213> ORGANISM: Artificial Sequence
<220> FEATURE:
<223> OTHER INFORMATION: Synthetic Construct

<400> SEQUENCE: 346

Met Gln Ala Thr Gln Phe Pro
1               5

<210> SEQ ID NO 347
<211> LENGTH: 12
<212> TYPE: PRT

```
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa can be S or V
<220> FEATURE:
<221> NAME/KEY: MISC_FEATURE
<222> LOCATION: (7)..(7)
<223> OTHER INFORMATION: Xaa can be S or V

<400> SEQUENCE: 347

Arg Ala Ser Gln Ser Xaa Xaa Ser Ser Tyr Leu Ala
1               5                   10

<210> SEQ ID NO 348
<211> LENGTH: 7
<212> TYPE: PRT
<213> ORGANISM: Artificial Sequence
<220> FEATURE:
<223> OTHER INFORMATION: Synthetic Construct

<400> SEQUENCE: 348

Gly Ala Ser Thr Arg Ala Thr
1               5

<210> SEQ ID NO 349
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa can be S, N, G or H

<400> SEQUENCE: 349

Gln Gln Tyr Xaa Asn Trp Pro
1               5

<210> SEQ ID NO 350
<211> LENGTH: 11
<212> TYPE: PRT
<213> ORGANISM: Artificial Sequence
<220> FEATURE:
<223> OTHER INFORMATION: Synthetic Construct

<400> SEQUENCE: 350

Arg Ala Ser Gln Gly Ile Arg Asn Asp Leu Gly
1               5                   10

<210> SEQ ID NO 351
<211> LENGTH: 7
<212> TYPE: PRT
<213> ORGANISM: Artificial Sequence
<220> FEATURE:
<223> OTHER INFORMATION: Synthetic Construct

<400> SEQUENCE: 351

Ala Ala Ser Ser Leu Gln Ser
1               5

<210> SEQ ID NO 352
<211> LENGTH: 9
<212> TYPE: PRT
<213> ORGANISM: Artificial Sequence
<220> FEATURE:
```

<223> OTHER INFORMATION: Synthetic Construct

<400> SEQUENCE: 352

Leu Gln Asp Tyr Asn Tyr Pro Leu Thr
1               5

<210> SEQ ID NO 353
<211> LENGTH: 10
<212> TYPE: PRT
<213> ORGANISM: Artificial Sequence
<220> FEATURE:
<223> OTHER INFORMATION: Synthetic Construct

<400> SEQUENCE: 353

Gly Phe Thr Phe Ser Ser Tyr Trp Met Ser
1               5                   10

<210> SEQ ID NO 354
<211> LENGTH: 18
<212> TYPE: PRT
<213> ORGANISM: Artificial Sequence
<220> FEATURE:
<223> OTHER INFORMATION: Synthetic Construct

<400> SEQUENCE: 354

Ala Asn Ile Lys Gln Asp Gly Ser Glu Lys Tyr Tyr Val Asp Ser Val
1               5                   10                  15

Lys Gly

<210> SEQ ID NO 355
<211> LENGTH: 10
<212> TYPE: PRT
<213> ORGANISM: Artificial Sequence
<220> FEATURE:
<223> OTHER INFORMATION: Synthetic Construct

<400> SEQUENCE: 355

Gly Phe Thr Phe Ser Ser Tyr Ala Met Ser
1               5                   10

<210> SEQ ID NO 356
<211> LENGTH: 17
<212> TYPE: PRT
<213> ORGANISM: Artificial Sequence
<220> FEATURE:
<223> OTHER INFORMATION: Synthetic Construct

<400> SEQUENCE: 356

Ala Ile Ser Gly Ser Gly Gly Ser Thr Tyr Tyr Ala Asp Ser Val Lys
1               5                   10                  15

Gly

<210> SEQ ID NO 357
<211> LENGTH: 10
<212> TYPE: PRT
<213> ORGANISM: Artificial Sequence
<220> FEATURE:
<223> OTHER INFORMATION: Synthetic Construct

<400> SEQUENCE: 357

Gly Gly Ser Ile Ser Ser Tyr Tyr Trp Ser
1               5                   10

<210> SEQ ID NO 358
<211> LENGTH: 17

```
<212> TYPE: PRT
<213> ORGANISM: Artificial Sequence
<220> FEATURE:
<223> OTHER INFORMATION: Synthetic Construct

<400> SEQUENCE: 358

Gly Tyr Ile Tyr Tyr Ser Gly Ser Thr Asn Tyr Asn Pro Ser Leu Lys
1               5                   10                  15

Ser

<210> SEQ ID NO 359
<211> LENGTH: 10
<212> TYPE: PRT
<213> ORGANISM: Artificial Sequence
<220> FEATURE:
<223> OTHER INFORMATION: Synthetic Construct

<400> SEQUENCE: 359

Gly Tyr Thr Phe Thr Gly Tyr Tyr Met His
1               5                   10

<210> SEQ ID NO 360
<211> LENGTH: 18
<212> TYPE: PRT
<213> ORGANISM: Artificial Sequence
<220> FEATURE:
<223> OTHER INFORMATION: Synthetic Construct

<400> SEQUENCE: 360

Gly Trp Ile Asn Pro Asn Ser Gly Gly Thr Asn Tyr Ala Gln Lys Phe
1               5                   10                  15

Gln Gly

<210> SEQ ID NO 361
<211> LENGTH: 10
<212> TYPE: PRT
<213> ORGANISM: Artificial Sequence
<220> FEATURE:
<223> OTHER INFORMATION: Synthetic Construct

<400> SEQUENCE: 361

Gly Gly Thr Phe Ser Ser Tyr Ala Ile Ser
1               5                   10

<210> SEQ ID NO 362
<211> LENGTH: 18
<212> TYPE: PRT
<213> ORGANISM: Artificial Sequence
<220> FEATURE:
<223> OTHER INFORMATION: Synthetic Construct

<400> SEQUENCE: 362

Gly Gly Ile Ile Pro Ile Phe Gly Thr Ala Asn Tyr Ala Gln Lys Phe
1               5                   10                  15

Gln Gly

<210> SEQ ID NO 363
<211> LENGTH: 10
<212> TYPE: PRT
<213> ORGANISM: Artificial Sequence
<220> FEATURE:
<223> OTHER INFORMATION: Synthetic Construct

<400> SEQUENCE: 363

Gly Tyr Thr Gly Thr Ser Tyr Tyr Met His
```

```
<210> SEQ ID NO 364
<211> LENGTH: 18
<212> TYPE: PRT
<213> ORGANISM: Artificial Sequence
<220> FEATURE:
<223> OTHER INFORMATION: Synthetic Construct

<400> SEQUENCE: 364

Gly Ile Ile Asn Pro Ser Gly Gly Ser Thr Ser Tyr Ala Gln Lys Phe
1               5                   10                  15

Gln Gly

<210> SEQ ID NO 365
<211> LENGTH: 10
<212> TYPE: PRT
<213> ORGANISM: Artificial Sequence
<220> FEATURE:
<223> OTHER INFORMATION: Synthetic Construct

<400> SEQUENCE: 365

Gly Phe Thr Phe Ser Ser Tyr Gly Met His
1               5                   10

<210> SEQ ID NO 366
<211> LENGTH: 18
<212> TYPE: PRT
<213> ORGANISM: Artificial Sequence
<220> FEATURE:
<223> OTHER INFORMATION: Synthetic Construct

<400> SEQUENCE: 366

Ala Val Ile Ser Tyr Asp Gly Ser Asn Lys Tyr Tyr Ala Asp Ser Val
1               5                   10                  15

Lys Gly

<210> SEQ ID NO 367
<211> LENGTH: 10
<212> TYPE: PRT
<213> ORGANISM: Artificial Sequence
<220> FEATURE:
<223> OTHER INFORMATION: Synthetic Construct

<400> SEQUENCE: 367

Gly Phe Thr Phe Ser Ser Tyr Ser Met Asn
1               5                   10

<210> SEQ ID NO 368
<211> LENGTH: 18
<212> TYPE: PRT
<213> ORGANISM: Artificial Sequence
<220> FEATURE:
<223> OTHER INFORMATION: Synthetic Construct

<400> SEQUENCE: 368

Ser Tyr Ile Ser Ser Ser Ser Ser Thr Ile Tyr Tyr Ala Asp Ser Val
1               5                   10                  15

Lys Gly

<210> SEQ ID NO 369
<211> LENGTH: 10
<212> TYPE: PRT
<213> ORGANISM: Artificial Sequence
<220> FEATURE:
```

```
<223> OTHER INFORMATION: Synthetic Construct

<400> SEQUENCE: 369

Gly Phe Thr Phe Ser Asn Ala Trp Met Ser
1               5                   10

<210> SEQ ID NO 370
<211> LENGTH: 20
<212> TYPE: PRT
<213> ORGANISM: Artificial Sequence
<220> FEATURE:
<223> OTHER INFORMATION: Synthetic Construct

<400> SEQUENCE: 370

Gly Arg Ile Lys Ser Lys Thr Asp Gly Gly Thr Thr Asp Tyr Ala Ala
1               5                   10                  15

Pro Val Lys Gly
            20

<210> SEQ ID NO 371
<211> LENGTH: 12
<212> TYPE: PRT
<213> ORGANISM: Artificial Sequence
<220> FEATURE:
<223> OTHER INFORMATION: Synthetic Construct

<400> SEQUENCE: 371

Gly Gly Ser Ile Ser Ser Ser Ser Tyr Tyr Trp Gly
1               5                   10

<210> SEQ ID NO 372
<211> LENGTH: 17
<212> TYPE: PRT
<213> ORGANISM: Artificial Sequence
<220> FEATURE:
<223> OTHER INFORMATION: Synthetic Construct

<400> SEQUENCE: 372

Gly Ser Ile Tyr Tyr Ser Gly Ser Thr Tyr Tyr Asn Pro Ser Leu Lys
1               5                   10                  15

Ser

<210> SEQ ID NO 373
<211> LENGTH: 12
<212> TYPE: PRT
<213> ORGANISM: Artificial Sequence
<220> FEATURE:
<223> OTHER INFORMATION: Synthetic Construct

<400> SEQUENCE: 373

Gly Gly Ser Ile Ser Ser Gly Asp Tyr Tyr Trp Ser
1               5                   10

<210> SEQ ID NO 374
<211> LENGTH: 17
<212> TYPE: PRT
<213> ORGANISM: Artificial Sequence
<220> FEATURE:
<223> OTHER INFORMATION: Synthetic Construct

<400> SEQUENCE: 374

Gly Tyr Ile Tyr Tyr Ser Gly Ser Thr Tyr Tyr Asn Pro Ser Leu Lys
1               5                   10                  15

Ser
```

```
<210> SEQ ID NO 375
<211> LENGTH: 10
<212> TYPE: PRT
<213> ORGANISM: Artificial Sequence
<220> FEATURE:
<223> OTHER INFORMATION: Synthetic Construct

<400> SEQUENCE: 375

Gly Tyr Ser Phe Thr Ser Tyr Trp Ile Gly
1               5                   10

<210> SEQ ID NO 376
<211> LENGTH: 18
<212> TYPE: PRT
<213> ORGANISM: Artificial Sequence
<220> FEATURE:
<223> OTHER INFORMATION: Synthetic Construct

<400> SEQUENCE: 376

Gly Ile Ile Tyr Pro Gly Asp Ser Asp Thr Arg Tyr Ser Pro Ser Phe
1               5                   10                  15

Gln Gly

<210> SEQ ID NO 377
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (10)..(10)
<223> OTHER INFORMATION: Xaa can be H or S

<400> SEQUENCE: 377

Gly Phe Thr Phe Ser Ser Tyr Ala Met Xaa
1               5                   10

<210> SEQ ID NO 378
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (10)..(10)
<223> OTHER INFORMATION: Xaa can be H or S

<400> SEQUENCE: 378

Gly Phe Thr Phe Ser Ser Tyr Ala Met Xaa Trp Ser
1               5                   10

<210> SEQ ID NO 379
<211> LENGTH: 18
<212> TYPE: PRT
<213> ORGANISM: Artificial Sequence
<220> FEATURE:
<223> OTHER INFORMATION: Synthetic Construct

<400> SEQUENCE: 379

Gly Trp Ile Ser Pro Asn Gly Gly Ser Thr Tyr Tyr Ala Asp Ser Val
1               5                   10                  15

Lys Gly

<210> SEQ ID NO 380
```

```
<211> LENGTH: 20
<212> TYPE: PRT
<213> ORGANISM: Artificial Sequence
<220> FEATURE:
<223> OTHER INFORMATION: Synthetic Construct

<400> SEQUENCE: 380

Gly Trp Ile Ser Pro Lys Ala Asn Gly Gly Ser Thr Tyr Tyr Ala Asp
1               5                   10                  15

Ser Val Lys Gly
            20

<210> SEQ ID NO 381
<211> LENGTH: 10
<212> TYPE: PRT
<213> ORGANISM: Artificial Sequence
<220> FEATURE:
<223> OTHER INFORMATION: Synthetic Construct

<400> SEQUENCE: 381

Gly Phe Thr Phe Ser Ser Tyr Ala Met Ser
1               5                   10

<210> SEQ ID NO 382
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa can be G or S

<400> SEQUENCE: 382

Ser Val Ile Ser Ser Asp Gly Xaa Ser Thr Tyr Tyr Ala Asp Ser Val
1               5                   10                  15

Lys Gly

<210> SEQ ID NO 383
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (10)..(10)
<223> OTHER INFORMATION: Xaa can be G or S

<400> SEQUENCE: 383

Ser Val Ile Ser Ser Lys Ala Asp Gly Xaa Ser Thr Tyr Tyr Ala Asp
1               5                   10                  15

Ser Val Lys Gly
            20

<210> SEQ ID NO 384
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (10)..(10)
<223> OTHER INFORMATION: Xaa can be S, G or H

<400> SEQUENCE: 384
```

```
Gly Tyr Ser Phe Thr Ser Tyr Trp Ile Xaa
1               5                   10

<210> SEQ ID NO 385
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa can be R, I or S

<400> SEQUENCE: 385

Gly Xaa Ile Tyr Pro Gly Asp Ser Asp Thr Arg Tyr Ser Pro Ser Phe
1               5                   10                  15

Gln Gly

<210> SEQ ID NO 386
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa can be A or Y
<220> FEATURE:
<221> NAME/KEY: MISC_FEATURE
<222> LOCATION: (9)..(9)
<223> OTHER INFORMATION: Xaa can be I or M

<400> SEQUENCE: 386

Gly Tyr Thr Phe Thr Ser Tyr Xaa Xaa His
1               5                   10

<210> SEQ ID NO 387
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa can be G or Y

<400> SEQUENCE: 387

Gly Trp Ile Asn Pro Xaa Asn Gly Asn Thr Asn Tyr Ala Gln Lys Phe
1               5                   10                  15

Gln

<210> SEQ ID NO 388
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa can be N or Y

<400> SEQUENCE: 388

Gly Gly Ser Ile Ser Ser Gly Xaa Tyr Tyr Trp Ser
1               5                   10
```

<210> SEQ ID NO 389
<211> LENGTH: 17
<212> TYPE: PRT
<213> ORGANISM: Artificial Sequence
<220> FEATURE:
<223> OTHER INFORMATION: Synthetic Construct

<400> SEQUENCE: 389

Gly Tyr Ile Tyr Tyr Ser Gly Ser Thr Tyr Tyr Asn Pro Ser Leu Lys
1               5                   10                  15

Ser

<210> SEQ ID NO 390
<211> LENGTH: 10
<212> TYPE: PRT
<213> ORGANISM: Artificial Sequence
<220> FEATURE:
<223> OTHER INFORMATION: Synthetic Construct

<400> SEQUENCE: 390

Gly Phe Thr Phe Ser Ser Tyr Gly Met His
1               5                   10

<210> SEQ ID NO 391
<211> LENGTH: 17
<212> TYPE: PRT
<213> ORGANISM: Artificial Sequence
<220> FEATURE:
<223> OTHER INFORMATION: Synthetic Construct

<400> SEQUENCE: 391

Val Ile Trp Tyr Asp Gly Ser Asn Lys Tyr Tyr Ala Asp Ser Ala Lys
1               5                   10                  15

Gly

<210> SEQ ID NO 392
<211> LENGTH: 10
<212> TYPE: PRT
<213> ORGANISM: Artificial Sequence
<220> FEATURE:
<223> OTHER INFORMATION: Synthetic Construct

<400> SEQUENCE: 392

Gly Phe Thr Phe Ser Ser Tyr Ala Met His
1               5                   10

<210> SEQ ID NO 393
<211> LENGTH: 17
<212> TYPE: PRT
<213> ORGANISM: Artificial Sequence
<220> FEATURE:
<223> OTHER INFORMATION: Synthetic Construct

<400> SEQUENCE: 393

Val Ile Ser Tyr Asp Gly Ser Asn Lys Tyr Tyr Ala Asp Ser Val Lys
1               5                   10                  15

Gly

<210> SEQ ID NO 394
<211> LENGTH: 10
<212> TYPE: PRT
<213> ORGANISM: Artificial Sequence
<220> FEATURE:
<223> OTHER INFORMATION: Synthetic Construct

<400> SEQUENCE: 394

Gly Phe Thr Phe Asp Asp Tyr Ala Met His
1               5                   10

<210> SEQ ID NO 395
<211> LENGTH: 17
<212> TYPE: PRT
<213> ORGANISM: Artificial Sequence
<220> FEATURE:
<223> OTHER INFORMATION: Synthetic Construct

<400> SEQUENCE: 395

Gly Ile Ser Trp Asn Ser Gly Ser Ile Gly Tyr Ala Asp Ser Val Lys
1               5                   10                  15

Gly

<210> SEQ ID NO 396
<211> LENGTH: 270
<212> TYPE: PRT
<213> ORGANISM: Artificial Sequence
<220> FEATURE:
<223> OTHER INFORMATION: Synthetic Construct

<400> SEQUENCE: 396

Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Lys Ser
                20                  25                  30

Gln Gln Lys Ala Lys Glu Val Cys Pro Met Tyr Phe Met Lys Leu Arg
            35                  40                  45

Ser Gly Leu Met Ile Lys Lys Glu Ala Cys Tyr Phe Arg Arg Glu Thr
        50                  55                  60

Thr Lys Arg Pro Ser Leu Lys Thr Gly Arg Lys His Lys Arg His Leu
65                  70                  75                  80

Val Leu Ala Ala Cys Gln Gln Gln Ser Thr Val Glu Cys Phe Ala Phe
                85                  90                  95

Gly Ile Ser Gly Val Gln Lys Tyr Thr Arg Ala Leu His Asp Ser Ser
            100                 105                 110

Ile Thr Gly Ile Ser Pro Ile Thr Glu Tyr Leu Ala Ser Leu Ser Thr
        115                 120                 125

Tyr Asn Asp Gln Ser Ile Thr Phe Ala Leu Glu Asp Glu Ser Tyr Glu
    130                 135                 140

Ile Tyr Val Glu Asp Leu Lys Lys Asp Lys Lys Asp Lys Val Leu
145                 150                 155                 160

Leu Ser Tyr Tyr Glu Ser Gln His Pro Ser Asn Glu Ser Gly Asp Gly
                165                 170                 175

Val Asp Gly Lys Met Leu Met Val Thr Leu Ser Pro Thr Lys Asp Phe
            180                 185                 190

Trp Leu His Ala Asn Asn Lys Glu His Ser Val Glu Leu His Lys Cys
        195                 200                 205

Glu Lys Pro Leu Pro Asp Gln Ala Phe Phe Val Leu His Asn Met His
    210                 215                 220

Ser Asn Cys Val Ser Phe Glu Cys Lys Thr Asp Pro Gly Val Phe Ile
225                 230                 235                 240

Gly Val Lys Asp Asn His Leu Ala Leu Ile Lys Val Asp Ser Ser Glu
                245                 250                 255

Asn Leu Cys Thr Glu Asn Ile Leu Phe Lys Leu Ser Glu Thr
             260                 265                 270

<210> SEQ ID NO 397
<211> LENGTH: 165
<212> TYPE: PRT
<213> ORGANISM: Artificial Sequence
<220> FEATURE:
<223> OTHER INFORMATION: Synthetic Construct

<400> SEQUENCE: 397

Ser Ile Thr Gly Ile Ser Pro Ile Thr Glu Ser Leu Ala Ser Leu Ser
1               5                   10                  15

Thr Tyr Asn Asp Gln Ser Ile Thr Phe Ala Leu Glu Asp Ser Tyr
            20                  25                  30

Glu Ile Tyr Val Glu Asp Leu Lys Lys Asp Lys Lys Asp Lys Val
        35                  40                  45

Leu Leu Ser Tyr Tyr Glu Ser Gln His Pro Ser Ser Glu Ser Gly Asp
50                  55                  60

Gly Val Asp Gly Lys Met Leu Met Val Thr Leu Ser Pro Thr Lys Asp
65                  70                  75                  80

Phe Trp Leu Gln Ala Asn Asn Lys Glu His Ser Val Glu Leu His Lys
                85                  90                  95

Cys Glu Lys Pro Leu Pro Asp Gln Ala Phe Phe Val Leu His Asn Arg
            100                 105                 110

Ser Phe Asn Cys Val Ser Phe Glu Cys Lys Thr Asp Pro Gly Val Phe
        115                 120                 125

Ile Gly Val Lys Asp Asn His Leu Ala Leu Ile Lys Val Asp Tyr Ser
    130                 135                 140

Glu Asn Leu Gly Ser Glu Asn Ile Leu Phe Lys Leu Ser Glu Ile His
145                 150                 155                 160

His His His His His
            165

<210> SEQ ID NO 398
<211> LENGTH: 639
<212> TYPE: DNA
<213> ORGANISM: Artificial Sequence
<220> FEATURE:
<223> OTHER INFORMATION: Synthetic Construct

<400> SEQUENCE: 398
gacatccaga tgacccagtc cccctcttct ctgtctgcct ctgtgggcga cagagtgacc    60
atcacctgta aagcaagtca gaatattaat aaacacttag actggtatca gcagaagcct   120
ggcaaggctc ccaagctgct gatctacttt acaaacaatt tacaaactgg cgtgccttcc   180
agattctccg gctctggctc tggcaccgat ttcaccctga ccatctcctc cctccagcct   240
gaggatttcg ccacctacta ctgctttcag tataaccagg gtggaccttt ggcggcgga    300
acaaaggtgg agatcaagcg tacggtggct gcaccatctg tcttcatctt cccgccatct   360
gatgagcagt tgaaatctgg aactgcctct gttgtgtgcc tgctgaataa cttctatccc   420
agagaggcca agtacagtg gaaggtggat aacgccctcc aatcgggtaa ctcccaggag   480
agtgtcacag agcaggacag caaggacagc acctacagcc tcagcagcac cctgacgctg   540
agcaaagcag actacgagaa acacaaagtc tacgcctgcg aagtcaccca tcagggcctg   600
agctcgcccg tcacaaagag cttcaacagg ggagagtgt                          639

```
<210> SEQ ID NO 399
<211> LENGTH: 1350
<212> TYPE: DNA
<213> ORGANISM: Artificial Sequence
<220> FEATURE:
<223> OTHER INFORMATION: Synthetic Construct

<400> SEQUENCE: 399
```

| | | | | | |
|---|---|---|---|---|---|
| gaggtgcagc | tggtggagtc | tggcggcgga | ctggtgcagc | ctggcggctc | tctgagactg | 60 |
| tcttgtgccg | cctccggctt | caccttcagt | tcctactgga | tgtactgggt | gaggcaggcc | 120 |
| cctggcaagg | gcctggagtg | ggtggccgcc | attactccta | tgccggtga | ggactactat | 180 |
| ccagagtctg | tgaaaggccg | gttcaccatc | tccaggaca | acgccaagaa | ctccctgtac | 240 |
| ctccagatga | actccctgag | ggccgaggat | accgccgtgt | actactgtgc | cagaggccat | 300 |
| tattactata | ccagctattc | gcttggatac | tggggccagg | gcaccctggt | gaccgtgtcc | 360 |
| tctgcgtcga | ccaagggccc | atcggtcttc | cccctggcac | cctcctccaa | gagcacctct | 420 |
| gggggcacag | cggccctggg | ctgcctggtc | aaggactact | tccccgaacc | ggtgacggtg | 480 |
| tcgtggaact | caggcgccct | gaccagcggc | gtgcacacct | tcccggctgt | cctacagtcc | 540 |
| tcaggactct | actccctcag | cagcgtggtg | accgtgccct | ccagcagctt | gggcacccag | 600 |
| acctacatct | gcaacgtgaa | tcacaagccc | agcaacacca | aggtggacaa | gaaagttgag | 660 |
| cccaaatctt | gtgacaaaac | tcacacatgc | ccaccgtgcc | cagcacctga | agccgctggg | 720 |
| gcaccgtcag | tcttcctctt | ccccccaaaa | cccaaggaca | ccctcatgat | ctcccggacc | 780 |
| cctgaggtca | catgcgtggt | ggtggacgtg | agccacgaag | accctgaggt | caagttcaac | 840 |
| tggtacgtgg | acggcgtgga | ggtgcataat | gccaagacaa | agccgcggga | ggagcagtac | 900 |
| aacagcacgt | accgtgtggt | cagcgtcctc | accgtcctgc | accaggactg | gctgaatggc | 960 |
| aaggagtaca | agtgcaaggt | ctccaacaaa | gccctcccag | cccccatcga | gaaaaccatc | 1020 |
| tccaaagcca | aagggcagcc | ccgagaacca | caggtgtaca | ccctgccccc | atcccgggag | 1080 |
| gagatgacca | agaaccaggt | cagcctgacc | tgcctggtca | aaggcttcta | tcccagcgac | 1140 |
| atcgccgtgg | agtgggagag | caatgggcag | ccggagaaca | actacaagac | cacgcctccc | 1200 |
| gtgctggact | ccgacggctc | cttcttcctc | tatagcaagc | tcaccgtgga | caagagcagg | 1260 |
| tggcagcagg | ggaacgtctt | ctcatgctcc | gtgttgcatg | aggctctgca | ctcccactac | 1320 |
| acgcagaaga | gcctctccct | gtccccggga | | | | 1350 |

```
<210> SEQ ID NO 400
<211> LENGTH: 639
<212> TYPE: DNA
<213> ORGANISM: Artificial Sequence
<220> FEATURE:
<223> OTHER INFORMATION: Synthetic Construct

<400> SEQUENCE: 400
```

| | | | | | |
|---|---|---|---|---|---|
| gacatccaga | tgacccagtc | cccctcttct | ctgtctgcct | ctgtgggcga | cagagtgacc | 60 |
| atcacctgta | aagcaagtca | gaatattaat | aaacacttag | actggtatca | gcagaagcct | 120 |
| ggcaaggctc | ccaagctgct | gatctacttt | acaaacaatt | tacaaactgg | cgtgccttcc | 180 |
| agattctccg | gctctggctc | tggcaccgat | ttcaccctga | ccatctcctc | cctccagcct | 240 |
| gaggatttcg | ccacctacta | ctgctttcag | tataacaatg | gtggaccctt | ggcggcgga | 300 |
| acaaaggtgg | agatcaagcg | tacggtggct | gcaccatctg | tcttcatctt | cccgccatct | 360 |
| gatgagcagt | tgaaatctgg | aactgcctct | gttgtgtgcc | tgctgaataa | cttctatccc | 420 |

| | |
|---|---|
| agagaggcca aagtacagtg aaggtggat aacgccctcc aatcgggtaa ctcccaggag | 480 |
| agtgtcacag agcaggacag caaggacagc acctacagcc tcagcagcac cctgacgctg | 540 |
| agcaaagcag actacgagaa acacaaagtc tacgcctgcg aagtcaccca tcagggcctg | 600 |
| agctcgcccg tcacaaagag cttcaacagg ggagagtgt | 639 |

<210> SEQ ID NO 401
<211> LENGTH: 1350
<212> TYPE: DNA
<213> ORGANISM: Artificial Sequence
<220> FEATURE:
<223> OTHER INFORMATION: Synthetic Construct

<400> SEQUENCE: 401

| | |
|---|---|
| gaggtgcagc tggtggagtc tggcggcgga ctggtgcagc ctggcggctc tctgagactg | 60 |
| tcttgtgccg cctccggctt caccttcagt tcctactgga tgtactgggt gaggcaggcc | 120 |
| cctggcaagg gcctggagtg ggtggcctcc attactccta tgccggtga ggactactat | 180 |
| ccagactctg tgaaaggccg gttcaccatc tccaggaca cgccaagaa ctccctgtac | 240 |
| ctccagatga actccctgag ggccgaggat accgccgtgt actactgtgc cagaggccat | 300 |
| tattactata ccagctattc gcttggatac tggggccagg gcaccctggt gaccgtgtcc | 360 |
| tctgcgtcga ccaagggccc atcggtcttc cccctggcac cctcctccaa gagcacctct | 420 |
| gggggcacag cggccctggg ctgcctggtc aaggactact cccccgaacc ggtgacggtg | 480 |
| tcgtggaact caggcgccct gaccagcggc gtgcacacct tcccggctgt cctacagtcc | 540 |
| tcaggactct actccctcag cagcgtggtg accgtgccct ccagcagctt gggcacccag | 600 |
| acctacatct gcaacgtgaa tcacaagccc agcaacacca aggtggacaa gaaagttgag | 660 |
| cccaaatctt gtgacaaaac tcacacatgc ccaccgtgcc cagcacctga gccgctggg | 720 |
| gcaccgtcag tcttcctctt ccccccaaaa cccaaggaca cctcatgat ctcccggacc | 780 |
| cctgaggtca catgcgtggt ggtggacgtg agccacgaag accctgaggt caagttcaac | 840 |
| tggtacgtgg acggcgtgga ggtgcataat gccaagacaa agccgcggga ggagcagtac | 900 |
| aacagcacgt accgtgtggt cagcgtcctc accgtcctgc accaggactg gctgaatggc | 960 |
| aaggagtaca agtgcaaggt ctccaacaaa gccctcccag cccccatcga gaaaaccatc | 1020 |
| tccaaagcca aagggcagcc ccgagaacca caggtgtaca ccctgccccc atcccgggag | 1080 |
| gagatgacca agaaccaggt cagcctgacc tgcctggtca aaggcttcta tcccagcgac | 1140 |
| atcgccgtgg agtgggagag caatgggcag ccggagaaca actacaagac cacgcctccc | 1200 |
| gtgctggact ccgacggctc cttcttcctc tatagcaagc tcaccgtgga caagagcagg | 1260 |
| tggcagcagg ggaacgtctt ctcatgctcc gtgttgcatg aggctctgca ctcccactac | 1320 |
| acgcagaaga gcctctccct gtccccggga | 1350 |

<210> SEQ ID NO 402
<211> LENGTH: 19
<212> TYPE: PRT
<213> ORGANISM: Artificial Sequence
<220> FEATURE:
<223> OTHER INFORMATION: Synthetic Construct

<400> SEQUENCE: 402

Met Gly Trp Ser Cys Ile Ile Leu Phe Leu Val Ala Thr Ala Thr Gly
1               5                   10                  15

Ala His Ser

```
<210> SEQ ID NO 403
<211> LENGTH: 452
<212> TYPE: PRT
<213> ORGANISM: Artificial Sequence
<220> FEATURE:
<223> OTHER INFORMATION: Synthetic Construct

<400> SEQUENCE: 403
```

| | | | | | | | | | | | | | | |
|---|---|---|---|---|---|---|---|---|---|---|---|---|---|---|
| Glu | Val | Gln | Leu | Val | Glu | Ser | Gly | Gly | Asn | Leu | Glu | Gln | Pro | Gly | Gly |
| 1 | | | | 5 | | | | | 10 | | | | | 15 | |
| Ser | Leu | Arg | Leu | Ser | Cys | Thr | Ala | Ser | Gly | Phe | Thr | Phe | Ser | Arg | Ser |
| | | | 20 | | | | | 25 | | | | | 30 | | |
| Ala | Met | Asn | Trp | Val | Arg | Arg | Ala | Pro | Gly | Lys | Gly | Leu | Glu | Trp | Val |
| | | 35 | | | | | 40 | | | | | 45 | | | |
| Ser | Gly | Ile | Ser | Gly | Ser | Gly | Gly | Arg | Thr | Tyr | Tyr | Ala | Asp | Ser | Val |
| 50 | | | | | 55 | | | | | 60 | | | | | |
| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Ser | Ala | Glu | Asp | Thr | Ala | Ala | Tyr | Tyr | Cys |
| | | | | 85 | | | | | 90 | | | | | 95 | |
| Ala | Lys | Asp | Ser | Tyr | Thr | Thr | Ser | Trp | Tyr | Gly | Gly | Met | Asp | Val | Trp |
| | | | 100 | | | | | 105 | | | | | 110 | | |
| Gly | His | Gly | Thr | Thr | Val | Thr | Val | Ser | Ser | Ala | Ser | Thr | Lys | Gly | Pro |
| | | 115 | | | | | 120 | | | | | 125 | | | |
| Ser | Val | Phe | Pro | Leu | Ala | Pro | Ser | Ser | Lys | Ser | Thr | Ser | Gly | Gly | Thr |
| 130 | | | | | 135 | | | | | 140 | | | | | |
| Ala | Ala | Leu | Gly | Cys | Leu | Val | Lys | Asp | Tyr | Phe | Pro | Glu | Pro | Val | Thr |
| 145 | | | | | 150 | | | | | 155 | | | | | 160 |
| Val | Ser | Trp | Asn | Ser | Gly | Ala | Leu | Thr | Ser | Gly | Val | His | Thr | Phe | Pro |
| | | | | 165 | | | | | 170 | | | | | 175 | |
| Ala | Val | Leu | Gln | Ser | Ser | Gly | Leu | Tyr | Ser | Leu | Ser | Ser | Val | Val | Thr |
| | | | 180 | | | | | 185 | | | | | 190 | | |
| Val | Pro | Ser | Ser | Ser | Leu | Gly | Thr | Gln | Thr | Tyr | Ile | Cys | Asn | Val | Asn |
| | | 195 | | | | | 200 | | | | | 205 | | | |
| His | Lys | Pro | Ser | Asn | Thr | Lys | Val | Asp | Lys | Lys | Val | Glu | Pro | Lys | Ser |
| 210 | | | | | 215 | | | | | 220 | | | | | |
| Cys | Asp | Lys | Thr | His | Thr | Cys | Pro | Pro | Cys | Pro | Ala | Pro | Glu | Ala | Ala |
| 225 | | | | | 230 | | | | | 235 | | | | | 240 |
| Gly | Ala | Pro | Ser | Val | Phe | Leu | Phe | Pro | Pro | Lys | Pro | Lys | Asp | Thr | Leu |
| | | | | 245 | | | | | 250 | | | | | 255 | |
| Met | Ile | Ser | Arg | Thr | Pro | Glu | Val | Thr | Cys | Val | Val | Val | Asp | Val | Ser |
| | | | 260 | | | | | 265 | | | | | 270 | | |
| His | Glu | Asp | Pro | Glu | Val | Lys | Phe | Asn | Trp | Tyr | Val | Asp | Gly | Val | Glu |
| | | 275 | | | | | 280 | | | | | 285 | | | |
| Val | His | Asn | Ala | Lys | Thr | Lys | Pro | Arg | Glu | Glu | Gln | Tyr | Asn | Ser | Thr |
| 290 | | | | | 295 | | | | | 300 | | | | | |
| Tyr | Arg | Val | Val | Ser | Val | Leu | Thr | Val | Leu | His | Gln | Asp | Trp | Leu | Asn |
| 305 | | | | | 310 | | | | | 315 | | | | | 320 |
| Gly | Lys | Glu | Tyr | Lys | Cys | Lys | Val | Ser | Asn | Lys | Ala | Leu | Pro | Ala | Pro |
| | | | | 325 | | | | | 330 | | | | | 335 | |
| Ile | Glu | Lys | Thr | Ile | Ser | Lys | Ala | Lys | Gly | Gln | Pro | Arg | Glu | Pro | Gln |
| | | | 340 | | | | | 345 | | | | | 350 | | |
| Val | Tyr | Thr | Leu | Pro | Pro | Ser | Arg | Glu | Glu | Met | Thr | Lys | Asn | Gln | Val |
| | | 355 | | | | | 360 | | | | | 365 | | | |

```
Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 404
<211> LENGTH: 214
<212> TYPE: PRT
<213> ORGANISM: Artificial Sequence
<220> FEATURE:
<223> OTHER INFORMATION: Synthetic Construct

<400> SEQUENCE: 404

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Phe Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Gln Gln Ala Asn Ser Val Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 405
<211> LENGTH: 445
<212> TYPE: PRT
<213> ORGANISM: Artificial Sequence
<220> FEATURE:
<223> OTHER INFORMATION: Synthetic Construct

<400> SEQUENCE: 405
```

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Phe
             20                  25                  30

Ser Met Ser Trp Val Arg Gln Ala Pro Gly Lys Gly Leu Glu Trp Val
         35                  40                  45

Ala Thr Ile Ser Gly Gly Lys Thr Phe Thr Asp Tyr Val Asp Ser Val
     50                  55                  60

Lys Gly Arg Phe Thr Ile Ser Arg Asp Asp Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Arg Ala Asn Tyr Gly Asn Trp Phe Phe Glu Val Trp Gly Gln Gly
             100                 105                 110

Thr Leu Val Thr Val Ser Ser Ala Ser Thr Lys Gly Pro Ser Val Phe
         115                 120                 125

Pro Leu Ala Pro Cys Ser Arg Ser Thr Ser Glu Ser Thr Ala Ala Leu
     130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
             165                 170                 175

Gln Ser Ser Gly Leu Tyr Ser Leu Ser Ser Val Val Thr Val Pro Ser
         180                 185                 190

Ser Ser Leu Gly Thr Lys Thr Tyr Thr Cys Asn Val Asp His Lys Pro
         195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
             245                 250                 255

Glu Val Thr Cys Val Val Val Asp Val Ser Gln Glu Asp Pro Glu Val
         260                 265                 270

Gln Phe Asn Trp Tyr Val Asp Gly Val Glu Val His Asn Ala Lys Thr
         275                 280                 285

Lys Pro Arg Glu Glu Gln Phe Asn Ser Thr Tyr Arg Val Val Ser Val
     290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
             325                 330                 335

Lys Ala Lys Gly Gln Pro Arg Glu Pro Gln Val Tyr Thr Leu Pro Pro
             340                 345                 350

Ser Gln Glu Glu Met Thr Lys Asn Gln Val Ser Leu Ser Cys Ala Val
         355                 360                 365

Lys Gly Phe Tyr Pro Ser Asp Ile Ala Val Glu Trp Glu Ser Asn Gly
     370                 375                 380

Gln Pro Glu Asn Asn Tyr Lys Thr Thr Pro Pro Val Leu Asp Ser Asp
385                 390                 395                 400

Gly Ser Phe Phe Leu Val Ser Arg Leu Thr Val Asp Lys Ser Arg Trp
             405                 410                 415
```

```
Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
            435                 440                 445

<210> SEQ ID NO 406
<211> LENGTH: 218
<212> TYPE: PRT
<213> ORGANISM: Artificial Sequence
<220> FEATURE:
<223> OTHER INFORMATION: Synthetic Construct

<400> SEQUENCE: 406

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Ala Lys Tyr
            20                  25                  30

Gly Leu Ser Leu Leu Asn Trp Phe Gln Gln Lys Pro Gly Gln Pro Pro
        35                  40                  45

Arg Leu Leu Ile Phe Ala Ala Ser Asn Arg Gly Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Lys
                85                  90                  95

Glu Val Pro Phe Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 407
<211> LENGTH: 456
<212> TYPE: PRT
<213> ORGANISM: Artificial Sequence
<220> FEATURE:
<223> OTHER INFORMATION: Synthetic Construct

<400> SEQUENCE: 407

Glu Val Gln Leu Leu Glu Ser Gly Gly Gly Leu Val Gln Pro Gly Gly
1               5                   10                  15

Ser Leu Arg Leu Ser Cys Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Ala Ile Asp Gln Ser Thr Tyr Tyr Ala Asp Ser Val
    50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Gln Lys Phe Met Gln Leu Trp Gly Gly Leu Arg Tyr Pro
        100                 105                 110

Phe Gly Tyr Trp Gly Gln Gly Thr Met Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
210                 215                 220

Glu Pro Lys Ser Cys Asp Lys Thr His Thr Cys Pro Pro Cys Pro Ala
225                 230                 235                 240

Pro Glu Phe Glu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Ser Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 408
<211> LENGTH: 212

<212> TYPE: PRT
<213> ORGANISM: Artificial Sequence
<220> FEATURE:
<223> OTHER INFORMATION: Synthetic Construct

<400> SEQUENCE: 408

Ser Tyr Val Leu Thr Gln Pro Pro Ser Val Ser Val Ser Pro Gly Gln
1               5                   10                  15

Thr Ala Ser Ile Thr Cys Ser Gly Glu Gly Met Gly Asp Lys Tyr Ala
            20                  25                  30

Ala Trp Tyr Gln Gln Lys Pro Gly Gln Ser Pro Val Leu Val Ile Tyr
        35                  40                  45

Arg Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gly Val Ile Gln Asp Asn Thr Gly Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210

<210> SEQ ID NO 409
<211> LENGTH: 456
<212> TYPE: PRT
<213> ORGANISM: Artificial Sequence
<220> FEATURE:
<223> OTHER INFORMATION: Synthetic Construct

<400> SEQUENCE: 409

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ala Asp Asp Phe Thr Ser Thr Tyr Tyr Ala Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Trp Met Met Asn Tyr Ala Gly Gly Leu Arg Tyr Pro
            100                 105                 110

Phe Gly Tyr Trp Gly Gln Gly Thr Met Val Thr Val Ser Ser Ala Ser
            115                 120                 125

Thr Lys Gly Pro Ser Val Phe Pro Leu Ala Pro Ser Ser Lys Ser Thr
        130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
210                 215                 220

Glu Pro Lys Ser Cys Asp Lys Thr His Thr Cys Pro Pro Cys Pro Ala
225                 230                 235                 240

Pro Glu Phe Glu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Ser Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
450                 455

<210> SEQ ID NO 410
<211> LENGTH: 212
<212> TYPE: PRT
<213> ORGANISM: Artificial Sequence
<220> FEATURE:
<223> OTHER INFORMATION: Synthetic Construct

<400> SEQUENCE: 410

Ser Tyr Val Leu Thr Gln Pro Pro Ser Val Ser Val Pro Gly Gln
1               5                   10                  15

-continued

```
Thr Ala Ser Ile Thr Cys Ser Gly Glu Arg Met Gly Asp Lys Tyr Ala
            20              25                  30

Ala Trp Tyr Gln Gln Lys Pro Gly Gln Ser Pro Val Leu Val Ile Tyr
        35              40                  45

Arg Asp Thr Lys Arg Pro Ser Gly Ile Pro Glu Arg Phe Ser Gly Ser
    50              55                  60

Asn Ser Gly Asn Thr Ala Thr Leu Thr Ile Ser Gly Thr Gln Ala Met
65              70              75                  80

Asp Glu Ala Asp Tyr Tyr Cys Gly Val Leu Lys Gln Asp Thr Gly Val
                85              90                  95

Phe Gly Gly Gly Thr Lys Leu Thr Val Leu Gly Gln Pro Lys Ala Ala
            100             105                 110

Pro Ser Val Thr Leu Phe Pro Pro Ser Ser Glu Glu Leu Gln Ala Asn
        115             120                 125

Lys Ala Thr Leu Val Cys Leu Ile Ser Asp Phe Tyr Pro Gly Ala Val
        130             135             140

Thr Val Ala Trp Lys Ala Asp Ser Ser Pro Val Lys Ala Gly Val Glu
145             150             155                 160

Thr Thr Thr Pro Ser Lys Gln Ser Asn Asn Lys Tyr Ala Ala Ser Ser
                165             170             175

Tyr Leu Ser Leu Thr Pro Glu Gln Trp Lys Ser His Arg Ser Tyr Ser
            180             185                 190

Cys Gln Val Thr His Glu Gly Ser Thr Val Glu Lys Thr Val Ala Pro
        195             200             205

Thr Glu Cys Ser
        210
```

ANTI-IL-33 ANTIBODIES, COMPOSITIONS, METHODS AND USES THEREOF

CROSS-REFERENCE TO RELATED APPLICATIONS

This application claims the benefit of U.S. provisional application 62/328,294, filed Apr. 27, 2016; and U.S. provisional application 62/483,781, filed Apr. 10, 2017. The complete content of all of the above-referenced patent applications are hereby incorporated by reference for all purposes.

REFERENCE TO SEQUENCE LISTING

This application contains a Sequence Listing which has been submitted electronically in ASCII format and is hereby incorporated by reference in its entirety. Said ASCII copy, created on Mar. 29, 2017, is named PC72256A_Seq_Listing_ST25.txt and is 473,842 bytes in size.

FIELD

The present invention relates to antibodies, and antigen-binding fragments thereof, that specifically bind interleukin-33, and compositions, methods and uses thereof.

BACKGROUND

IL-33 is a critical IL-1 family member that amplifies the responses of many cell types that are involved in asthma and atopic inflammation. IL-33 binds to Interleukin-1 Receptor-Like 1 (IL1RL1; also known as suppression of tumorigenicity 2 [ST2]), with high affinity and forms a ternary complex with IL1RAcP to form the signaling complex. This signaling complex leads to a series of events that is dependent on the Myddosome, with MyD88 and IRAK family members. This signaling ultimately leads to NFKb activation and other pathways in a cellular and cytokine environment specific context. When cells such as mast cells or basophils are stimulated by IL-33, type 2 cytokines such as IL-4, 5, and 13 are produced.

IL-33 has been shown to play a critical role in a number of preclinical models of asthma and allergic disease when its activity is blocked by either pharmacologic or genetic approaches. Blockade of the pathway has been accomplished by neutralizing antibodies to IL-33 or the receptor IL1RL1, genetic deletion of IL-33 or IL1RL1, or soluble forms of the receptor IL1RL1 coupled as a fusion protein to an Fc (Coyle et al., 1999, J. Exper. Med 190(7):895-902). In most model systems where physiologic allergens are used that contain a proteolytic allergen, such as in dust mite, cock roach or the fungus alternaria, IL-33 plays an important role in driving the inflammation and other aspects of airway remodeling (Chu et al., 2013, J. Allergy Clin. Immunol. 131:187-200). In pharmacologic models that rely on adjuvants for sensitization such as aluminum hydroxide (alum), or monosodium urate crystals, IL-33 plays an important role in the sensitization phase of the model and induction of type 2 cytokines such as IL-5 and IL13 (Hara et al., 2014, J. Immunol. 192(9):4032-4042). IL-33 has also been found to play an important role in the inflammatory response associated with viral infections in the airways. Damage of the airway epithelium by viral infections can trigger the release of IL-33 and modify the type of immune response.

Diseases such as chronic rhinosinusitis with nasal polyps (CRSwNP), atopic dermatitis (AD), and asthma are diseases where multiple cytokines are likely involved in the pathogenesis. The IL-33 receptor, ST2, is expressed on many of the cell types associated with type 2 inflammation, including mast cells, basophils, Th2-T cells, innate lymphoid cells type 2 and others (Cayrol & Girard, 2014, Current Opinion in Immunology 31:31-37; Molofsky et al. 2015, Immunity 42(6):1005-1019). The primary response of these cell types to IL-33 is the production of inflammatory cytokines, and in particular those associated with type 2 inflammation, including IL-5, IL-13, IL-4, IL-31 and IL-9 (Molofsky et al., 2015, Immunity 42(6):1005-1019; Rivellese et al, 2014, Eur. J. Immunol. 44(10):3045-3055; Suzukawa et al., 2008, J. Immunology 181(9):5981-5989; Vocca et al. Immunobiology 220(8):954-963; Maier et al., 2014, J. Immunology 193(2):645-654). Other cytokines as well as chemokines are also produced which are important in driving the recruitment of additional inflammatory cell types to the tissue site (Cayrol & Girard, 2014; Molofsky et al., 2015). The initial release of IL-33 is triggered by damage to the epithelium at the body or mucosal surfaces. Disease relevant triggers include allergens with proteolytic activity, physical damage to the epithelium, viruses as well as fungi and bacteria that are common at the body surfaces. In diseases where the tissue is rich with eosinophils and mast cells, damage to the epithelium sets off a cascade whereby IL-33 is released, acts on local target cells, and drives the production of multiple cytokines that are central to a Type 2 inflammatory response.

SUMMARY OF THE INVENTION

The invention provides antibodies (and antigen-binding fragments thereof) that specifically bind to IL-33, as well as uses, and associated methods thereof. Those skilled in the art will recognize, or be able to ascertain using no more than routine experimentation, many equivalents to the specific embodiments of the invention described herein. Such equivalents are intended to be encompassed by the following embodiments (E).

E1. An isolated antibody or antigen-binding fragment thereof that specifically binds to human IL-33.

E2. The antibody, or antigen-binding fragment thereof, of E1, comprising the CDR-H1, CDR-H2, and CDR-H3 sequences of one of the group consisting of SEQ ID NO:14, 32, 90, 94, 97, 113, 118, 121, 124, 126, 129, 132, 135, 138, 141, 144, 147, 150, 152, 155, 158, 161, 163, 165, 167, 170, 173, 176, 179, 182, 184, 186, 201, 204, 210, 213, 216, 219, 222, 225, 228, 231, and 234.

E3. The antibody, or antigen-binding fragment thereof, of any one of E1-E2, comprising the CDR-L1, CDR-L2, and CDR-L3 sequences of one of the group consisting of SEQ ID NO:19, 36, 81, 91, 98, 115, 189, 192, 195, 198, and 207.

E4. The antibody, or antigen binding fragment thereof, as in any one of E1-E3 comprising one or more of (i)-(vi)
  (i) a CDR-L1 selected from the group consisting of SEQ ID NO:20, 37, 190, 193, 257, 258, 259, and 260,
  (ii) a CDR-L2 selected from the group consisting of SEQ ID NO:21, 196, 199, 261, 262, 263, and 264,
  (iii) a CDR-L3 selected from the group consisting of SEQ ID NO:22, 38, 208, 265, 26, 267, and 268,
  (iv) a CDR-H1 selected from the group consisting of SEQ ID NO:16, 33, 269, 270, and 271,
  (v) a CDR-H2 selected from the group consisting of SEQ ID NO:17, 34, 168, 171, 174, 180, 202, 205, 211, 214, 217, 220, 223, 226, 229, 232, 235, 272, 273, 274, and 275, (vi) a CDR-H3 selected from the group consisting of SEQ ID NO:18, 35, 114, 119, 122, 127, 130, 133, 136, 139, 142, 145, 148, 153, 156, 159, 177, 187, 276, 277, 278 and 279.

E5. The antibody, or antigen binding fragment thereof, as in any one of E1-E4 comprising
  (i) a CDR-L1 selected from the group consisting of SEQ ID NO:257, 258, 259, and 260,
  (ii) a CDR-L2 selected from the group consisting of SEQ ID NO:261, 262, 263, and 264,
  (iii) a CDR-L3 selected from the group consisting of SEQ ID NO:265, 266, 267, and 268,
  (iv) a CDR-H1 selected from the group consisting of SEQ ID NO:269, 270, and 271,
  (v) a CDR-H2 selected from the group consisting of SEQ ID NO:272, 273, 274, and 275,
  (vi) a CDR-H3 selected from the group consisting of SEQ ID NO: 276, 277, 278, and 279.

E6. The antibody, or antigen binding fragment thereof, as in any one of E1-E5 comprising
  (i) a CDR-L1 comprising SEQ ID NO:257,
  (ii) a CDR-L2 comprising SEQ ID NO:261,
  (iii) a CDR-L3 comprising SEQ ID NO:265,
  (iv) a CDR-H1 comprising SEQ ID NO:269,
  (v) a CDR-H2 comprising SEQ ID NO:272,
  (vi) a CDR-H3 comprising SEQ ID NO: 276.

E7. The antibody, or antigen binding fragment thereof, as in any one of E1-E6 comprising
  (i) a CDR-L1 comprising SEQ ID NO:258,
  (ii) a CDR-L2 comprising SEQ ID NO:262,
  (iii) a CDR-L3 comprising SEQ ID NO:266,
  (iv) a CDR-H1 comprising SEQ ID NO:270,
  (v) a CDR-H2 comprising SEQ ID NO:273,
  (vi) a CDR-H3 comprising SEQ ID NO: 277.

E8. The antibody, or antigen binding fragment thereof, as in any one of E1-E7 comprising
  (i) a CDR-L1 comprising SEQ ID NO:259,
  (ii) a CDR-L2 comprising SEQ ID NO:263,
  (iii) a CDR-L3 comprising SEQ ID NO:267,
  (iv) a CDR-H1 comprising SEQ ID NO:271,
  (v) a CDR-H2 comprising SEQ ID NO:274,
  (vi) a CDR-H3 comprising SEQ ID NO: 278.

E9. The antibody, or antigen binding fragment thereof, as in any one of E1-E8 comprising
  (i) a CDR-L1 comprising SEQ ID NO:260,
  (ii) a CDR-L2 comprising SEQ ID NO:264,
  (iii) a CDR-L3 comprising SEQ ID NO:268,
  (iv) a CDR-H1 comprising SEQ ID NO:271,
  (v) a CDR-H2 comprising SEQ ID NO:275,
  (vi) a CDR-H3 comprising SEQ ID NO: 278.

E10. The antibody, or antigen binding fragment thereof, as in any one of E1-E9 comprising
  (i) a CDR-L1 comprising SEQ ID NO:20,
  (ii) a CDR-L2 comprising SEQ ID NO:21,
  (iii) a CDR-L3 comprising SEQ ID NO:208,
  (iv) a CDR-H1 comprising SEQ ID NO:16,
  (v) a CDR-H2 comprising SEQ ID NO:226,
  (vi) a CDR-H3 comprising SEQ ID NO: 18.

E11. The antibody, or antigen-binding fragment thereof, of any one of E1-E10, comprising the CDR-H1, CDR-H2, and CDR-H3 sequences of SEQ ID NO:225.

E12. The antibody, or antigen-binding fragment thereof, of any one of E1-E11, comprising the CDR-L1, CDR-L2, and CDR-L3 sequences of SEQ ID NO:207.

E13. The antibody, or antigen-binding fragment thereof, of any one of E1-E12, comprising one or more of the following substitutions:

(i) 1, 2, 3, 4, 5, or 6 substitutions in CDR L1 to the corresponding residue of a human germline VL sequence,
  (ii) 1, 2, 3, 4, or 5 substitutions in CDR L2 to the corresponding residue of a human VL germline sequence,
  (iii) 1, 2, 3, 4, 5, or 6 substitutions in CDR L3 to the corresponding residue of a human germline VL sequence,
  (iv) 1 substitution in CDR H1 to the corresponding residue of a human germline VH sequence,
  (v) 1, 2, 3, 4, 5, 6, 7, or 8 substitutions in CDR H2 to the corresponding residue of a human germline VH sequence,
  wherein the human germline VL sequence is selected from the group consisting of DPK9, DPK12, DPK18, DPK24, HK102_V1, DPK1, DPK8, DPK3, DPK21, Vg_38K, DPK22, DPK15, DPL16, DPL8, V1-22, Vλ consensus, Vλ1 consensus, Vλ3 consensus, Vκ consensus, Vκ1 consensus, Vκ2 consensus, and Vκ3, and the human germline VH is selected from the group consisting of DP54, DP47, DP50, DP31, DP46, DP71, DP75, DP10, DP7, DP49, DP51, DP38, DP79, DP78, DP73, VH3, VH5, VH1, and VH4.

E14. The antibody, or antigen-binding fragment thereof, of any one of E1-E13, comprising a VH framework sequence derived from a human germline VH sequence selected from the group consisting of DP54, DP47, DP50, DP31, DP46, DP71, DP75, DP10, DP7, DP49, DP51, DP38, DP79, DP78, DP73, VH3, VH5, VH1, and VH4.

E15. The antibody, or antigen-binding fragment thereof, of any one of E1-E14, comprising a framework VH sequence derived from a human VH3 germline sequence.

E16. The antibody, or antigen-binding fragment thereof, of any one of E1-E15, comprising a framework VH sequence derived from a human germline VH sequence selected from the group consisting of DP54, DP47, DP50, DP31, DP46, DP49, and DP51.

E17. The antibody, or antigen-binding fragment thereof, of any one of E1-E16, comprising a framework VH sequence derived from a human germline VH sequence selected from the group consisting of DP54, DP47, DP50, and DP31.

E18. The antibody, or antigen-binding fragment thereof, of any one of E1-E17, comprising a VH framework sequence derived from a human germline DP54 sequence.

E19. The antibody, or antigen-binding fragment thereof, of any one of E1-E18, comprising a VL framework sequence derived from a human germline VL sequence selected from the group consisting of DPK9, DPK12, DPK18, DPK24, HK102_V1, DPK1, DPK8, DPK3, DPK21, Vg_38K, DPK22, DPK15, DPL16, DPL8, V1-22, Vλ consensus, Vλ1 consensus, Vλ3 consensus, Vκ consensus, Vκ1 consensus, Vκ2 consensus, and Vκ3.

E20. The antibody, or antigen-binding fragment thereof, of any one of E1-E19, comprising a VL framework sequence derived from a human germline VL sequence selected from the group consisting of DPK9, DPK12, DPK18, DPK24, HK102_V1, DPK1, DPK8, DPK3, DPK21, Vg_38K, DPK22, DPK15, Vκ consensus, Vκ1 consensus, Vκ2 consensus, and Vκ3.

E21. The antibody, or antigen-binding fragment thereof, of any one of E1-E20, comprising a VL framework sequence derived from a human germline Vκ1 sequence.

E22. The antibody, or antigen-binding fragment thereof, of any one of E1-E21, comprising a VL framework sequence derived from a human germline VL sequence selected from the group consisting of DPK9, HK102_V1, DPK1, and DPK8.

E23. The antibody, or antigen-binding fragment thereof, of any one of E1-E22, comprising a VL framework sequence derived from a human germline DPK9 sequence.

E24. The antibody, or antigen-binding fragment thereof, of any one of E1-E23, comprising a VL framework sequence and a VH framework sequence, and wherein one or both of the VL framework sequence or VH framework sequence is at least 90% identical to the human germline sequence from which it was derived.

E25. The antibody, or antigen-binding fragment thereof, of any one of E1-E24, comprising a VL framework sequence and a VH framework sequence, and wherein one or both of the VL framework sequence or VH framework sequence is at least 66%, 76%, 80%, 90%, 91%, 92%, 93%, 94%, 95%, 96%, 97%, 98%, or 99% identical to the human germline sequence from which it was derived.

E26. The antibody, or antigen-binding fragment thereof, of any one of E1-E25, comprising a VL framework sequence and a VH framework sequence, and wherein one or both of the VL framework sequence or VH framework sequence is identical to the human germline sequence from which it was derived.

E27. The antibody, or antigen-binding fragment thereof, of any one of E1-E26, comprising a VH comprising an amino acid sequence at least 90% identical to SEQ ID NO:225.

E28. The antibody, or antigen-binding fragment thereof, of any one of E1-E27, comprising a VH comprising an amino acid sequence at least 92% identical to SEQ ID NO:225.

E29. The antibody, or antigen-binding fragment thereof, of any one of E1-E28, comprising a VH comprising the amino acid sequence of SEQ ID NO:225.

E30. The antibody, or antigen-binding fragment thereof, of any one of E1-E29, comprising a VL comprising an amino acid sequence at least 66% identical to SEQ ID NO:207.

E31. The antibody, or antigen-binding fragment thereof, of any one of E1-E30, comprising a VL comprising an amino acid sequence at least 66%, 76%, 80%, 91%, 92%, 93%, 94%, 95%, 96%, 97%, 98%, or 99%, identical to SEQ ID NO:207.

E32. The antibody, or antigen-binding fragment thereof, of any one of E1-E31, comprising a VL comprising the amino acid sequence of SEQ ID NO:207.

E33. The antibody, or antigen-binding fragment thereof, of any one of E1-E32, comprising an Fc domain.

E34. The antibody, or antigen-binding fragment thereof, of E33, wherein the Fc domain is the Fc domain of an IgA (for example IgA$_1$ or IgA$_2$), IgD, IgE, IgM, or IgG (for example IgG$_1$, IgG$_2$, IgG$_3$, or IgG$_4$).

E35. The antibody, or antigen-binding fragment thereof, of E34 wherein the Fc domain is the Fc domain of an IgG.

E36. The antibody, or antigen-binding fragment thereof, of E35, wherein the IgG is selected from the group consisting of IgG$_1$, IgG$_2$, IgG$_3$, or IgG$_4$.

E37. The antibody, or antigen-binding fragment thereof, of E36, wherein the IgG is IgG$_1$.

E38. The antibody, or antigen-binding fragment thereof, of any one of E1-E37, comprising a heavy chain comprising an amino acid sequence at least 90% identical to SEQ ID NO:244.

E39. The antibody, or antigen-binding fragment thereof, of any one of E1-E38, comprising a heavy chain comprising an amino acid sequence at least 91%, 92%, 93%, 94%, 95%, 96%, 97%, 98%, or 99%, identical to SEQ ID NO:244

E40. The antibody, or antigen-binding fragment thereof, of any one of E1-E39, comprising a heavy chain comprising the amino acid sequence of SEQ ID NO:244.

E41. The antibody, or antigen-binding fragment thereof, of any one of E1-E40, comprising a LC comprising an amino acid sequence at least 90% identical to SEQ ID NO:209.

E42. The antibody, or antigen-binding fragment thereof, of any one of E1-E41, comprising a LC comprising an amino acid sequence at least 91%, 92%, 93%, 94%, 95%, 96%, 97%, 98%, or 99%, identical to SEQ ID NO:209.

E43. The antibody, or antigen-binding fragment thereof, of any one of E1-E42, comprising a LC comprising the amino acid sequence of SEQ ID NO:209.

E44. The antibody, or antigen-binding fragment thereof, of any one of E1-E43, comprising the VH sequence encoded by the plasmid deposited at the ATCC and having ATCC Accession No. PTA-122724.

E45. The antibody, or antigen-binding fragment thereof, of any one of E1-E44, comprising the VL sequence encoded by the plasmid deposited at the ATCC and having ATCC Accession No. PTA-122725.

E46. An antibody, or antigen-binding fragment thereof, that competes for binding to human IL-33 with an antibody or antigen-binding fragment thereof of any one of E1-E45.

E47. An antibody, or antigen-binding fragment thereof, that competes for binding to human IL-33 with one or more of 7E8_chimera, 9B3_chimera, 9B3_chimera_huJseg, 7E8 CDR graft, IL33-10, 9B3 CDR graft, 9B3_1, 9B3_2A, 9B3_2B, 9B3_3, 9B3_5, 9B3_79B3_13, 9B3_15, 9B3_17, 9B3_22, 9B3_31V2, 9B3_36, 9B3_79, 9B3_124, 9B3_162, 7E8H/9B3K, 9B3_563, IL33-11, IL33-12, IL33-13, IL33-45, IL33-55, IL33-56, IL33-57, IL33-58, IL33-61, IL33-62, IL33-68, IL33-74, IL33-75, IL33-80, IL33-81, IL33-103, IL33-117, IL33-136, IL33-153, IL33-154, IL33-155, IL33-156, IL33-157, IL33-158, IL33-167, IL33-168, IL33-169, IL33-170, IL33-171, IL33-172, IL33-175, IL33-186, IL33-187, IL33-188, IL33-158-152, IL33-167-153, IL33-158LS, and IL33-167LS.

E48. An antibody, or antigen-binding fragment thereof, that competes for binding to human IL-33 with IL33-158LS, or an antigen-binding fragment of IL33-158LS.

E49. The antibody, or antigen-binding fragment thereof, of any one of E1-E48, wherein the antibody or antigen-binding fragment is an Fc fusion protein, a monobody, a maxibody, a bifunctional antibody, an scFab, an scFv, a peptibody.

E50. The antibody, or antigen-binding fragment thereof, of E1-E49, wherein the antibody, or antigen binding fragment thereof, binds human IL-33 with a $K_D$ about or less than a value selected from the group consisting of about 10 nM, 5 nM, 2 nM, 1 nM, 900 pM, 800 pM, 700 pM, 600 pM, 500 pM, 400 pM, 300 pM, 250 pM, 200 pM, 150 pM, 100 pM, 50 pM, 40 pM, 30 pM, 25 pM, 20 pM, 15 pM, 10 pM, 5 pM, and 1 pM.

E51. The antibody, or antigen-binding fragment thereof, of E1-E50, wherein the antibody, or antigen binding fragment thereof, binds cynomologus monkey IL-33 with a $K_D$ about or less than a value selected from the group consisting of about 10 nM, 5 nM, 2 nM, 1 nM, 900 pM, 800 pM, 700 pM, 600 pM, 500 pM, 400 pM, 300 pM, 250 pM, 200 pM, 150 pM, 100 pM, 50 pM, 40 pM, 30 pM, 25 pM, 20 pM, 15 pM, 13 pM, 10 pM, 5 pM, and 1 pM.

E52. The antibody, or antigen-binding fragment thereof, of E1-E51, wherein the binding $K_D$ of the antibody or antigen binding fragment to cynomologous IL-33 is within 1 order of magnitude of the binding $K_D$ of the antibody, or antigen binding fragment thereof, to human IL-33.

E53. The antibody, or antigen-binding fragment thereof, of E1-E52, wherein the ratio of binding $K_D$ of the antibody or antigen binding fragment to human IL-33 compared with the binding to cynomologous IL-33 is between 5:1 and 1:5.

E54. The antibody, or antigen-binding fragment thereof, of E1-E53, wherein the ratio of binding $K_D$ of the antibody or antigen binding fragment to human IL-33 compared with the binding to cynomologous IL-33 is between 2:1 and 1:2.

E55. The antibody, or antigen-binding fragment thereof, of E1-E54, wherein the antibody, or antigen binding fragment thereof, binds active IL-33 with a lower $K_D$ than the $K_D$ with which it binds inactive IL-33.

E56. The antibody, or antigen-binding fragment thereof, of E1-E55, wherein the $K_D$ of the antibody, or antigen binding fragment thereof, binding to active IL-33 is at least 10, times lesser than the $K_D$ of the antibody, or antigen binding fragment thereof, binding to inactive IL-33.

E57. The antibody, or antigen-binding fragment thereof, of E1-E56, wherein the $K_D$ of the antibody, or antigen binding fragment thereof, binding to active IL-33 is at least 10, 100, $1\times10^3$, $1\times10^4$, $1\times10^5$, $1\times10^6$, $1\times10^7$ times lesser than the $K_D$ of the antibody, or antigen binding fragment thereof, binding to an inactive form of IL-33.

E58. The antibody, or antigen-binding fragment thereof, of E1-E57, wherein the antibody, or antigen binding fragment thereof, binds active IL-33, but does not bind inactive IL-33.

E59. The antibody, or antigen-binding fragment thereof, of E55-E58, wherein the measurement of $K_D$ of active IL-33 is made using an IL-33 variant, wherein cysteine amino acid residue at position 208 (C208), according to the numbering of SEQ ID NO:396, is substituted with a non-cysteine amino acid residue.

E60. The antibody, or antigen-binding fragment thereof, of E55-E59, wherein the measurement of $K_D$ of active IL-33 is made using an IL-33 variant, wherein C208 and C232, according to the numbering of SEQ ID NO:396, are substituted with a non-cysteine amino acid residue.

E61. The antibody, or antigen-binding fragment thereof, of E55-E60, wherein the measurement of $K_D$ of active IL-33 is made using a reduced form of wild-type IL-33.

E62. The antibody, or antigen-binding fragment thereof, of E55-E61, wherein the measurement of $K_D$ of inactive IL-33 is made using a non-reduced form of wild-type IL-33.

E63. The antibody, or antigen-binding fragment thereof, of E55-E62, wherein the IL-33 is human IL-33.

E64. The antibody, or antigen-binding fragment thereof, of E55-E62, wherein the IL-33 is cynomologus monkey IL-33.

E65. The antibody, or antigen-binding fragment thereof, of E1-E64, wherein the ratio of binding $K_D$ of the antibody or antigen binding fragment to cynomologous IL-33 compared with the binding to human IL-33 is within a range whose lower value is selected from the group consisting of 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, and 6.2, and whose upper value is selected from the group consisting of 1.4, 1.5, 1.6, 1.7, 1.8, 1.9, 2.0, 2.1, 2.2, 2.3, 2.4, 2.5, 2.6, 2.7, 2.8, 2.9, 3.0 3.1, 3.2, 3.3, 3.4, 3.5, 3.6, 3.7, 3.8, 3.9, 4.0, 4.1, 4.2, 4.3, 4.4, 4.5, 6.2, 9, 9.2, and 10.

E66. The antibody, or antigen-binding fragment thereof, of E1-E55, wherein the ratio of binding $K_D$ of the antibody or antigen binding fragment to cynomologous IL-33 compared with the binding to human IL-33 is between about 0.5 and about 3.0.

E67. The antibody, or antigen-binding fragment thereof, of E1-E56, wherein the ratio of binding $K_D$ of the antibody or antigen binding fragment to cynomologous IL-33 compared with the binding to human IL-33 is between about 1.2 and about 2.4.

E68. The antibody, or antigen-binding fragment thereof, of E1-E57, wherein the ratio of binding $K_D$ of the antibody or antigen binding fragment to cynomologous IL-33 compared with the binding to human IL-33 is between about 1 and about 2.

E69. The antibody, or antigen-binding fragment thereof, of E1-58 wherein the ratio of binding $K_D$ of the antibody or antigen binding fragment to cynomologous IL-33 compared with the binding to human IL-33 is between about 1.3 and about 2.3.

E70. The antibody, or antigen-binding fragment thereof, of E1-E59, wherein the ratio of binding $K_D$ of the antibody or antigen binding fragment to cynomologous IL-33 compared with the binding to human IL-33 is between about 1.3 and about 1.8.

E71. The antibody, or antigen-binding fragment thereof, of E1-E70, wherein the ratio of binding $K_D$ of the antibody or antigen binding fragment to cynomologous IL-33 of SEQ ID NO:5 compared with the binding to human IL-33 of SEQ ID NO:3 is between about 1.0 and about 2.3.

E72. The antibody, or antigen-binding fragment thereof, of E1-E71, wherein the ratio of binding $K_D$ of the antibody or antigen binding fragment to cynomologous IL-33 of SEQ ID NO:5 compared with the binding to human IL-33 of SEQ ID NO:3 is between about 1.0 and about 2.0.

E73. The antibody, or antigen-binding fragment thereof, of E1-E72, wherein the ratio of binding $K_D$ of the antibody or antigen binding fragment to cynomologous IL-33 of SEQ ID NO:5 compared with the binding to human IL-33 of SEQ ID NO:3 is between about 1.3 and about 1.8.

E74. The antibody, or antigen-binding fragment thereof, of E1-E73, wherein the ratio of binding $K_D$ of the antibody or antigen binding fragment to cynomologous IL-33 of SEQ ID NO:5 compared with the binding to human IL-33 of SEQ ID NO:3 is measured by comparing the results of a HEK293 ST2 NFκB reporter assay for neutralization of cynomologous and human IL-33.

E75. The antibody, or antigen-binding fragment thereof, of E1-74, wherein the ratio of binding $K_D$ of the antibody or antigen binding fragment to cynomologous IL-33 of SEQ ID NO:397 compared with the binding to human IL-33 of SEQ ID NO:1 is between about 4 and about 10.

E76. The antibody, or antigen-binding fragment thereof, of E1-E75, wherein the ratio of binding $K_D$ of the antibody or antigen binding fragment to cynomologous IL-33 of SEQ ID NO:397 compared with the binding to human IL-33 of SEQ ID NO:1 is between about 4.2 and about 9.2.

E77. The antibody, or antigen-binding fragment thereof, of E1-E76, wherein the ratio of binding $K_D$ of the antibody or antigen binding fragment to cynomologous IL-33 of SEQ ID NO:397 compared with the binding to human IL-33 of SEQ ID NO:1 is about 4.2.

E78. The antibody, or antigen-binding fragment thereof, of E1-E77, wherein the ratio of binding $K_D$ of the antibody or antigen binding fragment to cynomologous IL-33 of SEQ ID NO:397 compared with the binding to human IL-33 of SEQ ID NO:1 is about 6.2.

E79. The antibody, or antigen-binding fragment thereof, of E1-E78, wherein the ratio of binding $K_D$ of the antibody or antigen binding fragment to cynomologous IL-33 of SEQ ID NO:397 compared with the binding to human IL-33 of SEQ ID NO:1 is about 9.2.

E80. The antibody, or antigen-binding fragment thereof, of E1-E79, wherein the ratio of binding $K_D$ of the antibody or antigen binding fragment to cynomologous IL-33 of SEQ ID NO:397 compared with the binding to human IL-33 of SEQ ID NO:1 is measured by comparing the results of a HEK293 ST2 NFκB reporter assay for neutralization of cynomologous and human IL-33.

E81. The antibody, or antigen-binding fragment thereof, of any one of E50-E80, wherein the $K_D$ value is measured by surface plasmon resonance (SPR).

E82. The antibody, or antigen-binding fragment thereof, of any one of E50-E81, wherein the $K_D$ value is measured by surface plasmon resonance (SPR), and the IL-33 is immobilized.

E83. The antibody, or antigen-binding fragment thereof, of any one of E1-E82, wherein the terminal half life in cynomologous monkeys is at least about 15 days.

E84. The antibody, or antigen-binding fragment thereof, of any one of E1-E83, wherein the terminal half life in cynomologous monkeys is at least about 16 days.

E85. The antibody, or antigen-binding fragment thereof, of any one of E1-E84, wherein the terminal half life in cynomologous monkeys is at least about 18 days.

E86. The antibody, or antigen-binding fragment thereof, of any one of E1-E85, wherein the terminal half life in humans is at least about 30 days.

E87. The antibody, or antigen-binding fragment thereof, of any one of E1-E86, wherein the terminal half life in humans is at least about 50 days.

E88. The antibody, or antigen-binding fragment thereof, of any one of E1-E87, wherein the terminal half life in humans is at least about 55 days.

E89. The antibody, or antigen-binding fragment thereof, of any one of E1-E88, wherein the terminal half life in humans is at least about 60 days E90. The antibody, or antigen-binding fragment thereof, of any one of E1-E89, wherein the terminal half life in humans is at least about 65 days.

E91. The antibody, or antigen-binding fragment thereof, of any one of E1-E90, wherein the terminal half life in humans is at least about 70 days.

E92. The antibody, or antigen-binding fragment thereof, of any one of E1-E91, wherein the terminal half life in humans is at least about 75 days.

E93. The antibody, or antigen-binding fragment thereof, of any one of E1-E92, wherein the terminal half life in humans is at least about 80 days.

E94. The antibody, or antigen-binding fragment thereof, of any one of E1-E93, wherein the terminal half life in humans is at least about 85 days.

E95. The antibody, or antigen-binding fragment thereof, of any one of E1-E94, wherein the terminal half life in humans is at least about 90 days.

E96. The antibody, or antigen-binding fragment thereof, of any one of E1-E95, wherein the antibody has a wavelength of maximum absorbance relative to blank of less than 15 nm in an affinity-capture self-interaction nanoparticle spectroscopy assay.

E97. The antibody, or antigen-binding fragment thereof, of any one of E1-E96, wherein the antibody has a wavelength of maximum absorbance relative to blank of less than 10 nm in an affinity-capture self-interaction nanoparticle spectroscopy assay.

E98. The antibody, or antigen-binding fragment thereof, of any one of E1-E97, wherein the antibody has a wavelength of maximum absorbance relative to blank of less than 5 nm in an affinity-capture self-interaction nanoparticle spectroscopy assay.

E99. The antibody, or antigen-binding fragment thereof, of any one of E1-E98, wherein the antibody has a wavelength of maximum absorbance relative to blank of less than 1 nm in an affinity-capture self-interaction nanoparticle spectroscopy assay.

E100. The antibody, or antigen-binding fragment thereof, of any one of E1-E99, wherein the antibody has a DNA binding score normalized to blank of less than 19.

E101. The antibody, or antigen-binding fragment thereof, of any one of E1-E100, wherein the antibody has a DNA binding score normalized to blank of less than 15.

E102. The antibody, or antigen-binding fragment thereof, of any one of E1-E101, wherein the antibody has a DNA binding score normalized to blank of less than 10.

E103. The antibody, or antigen-binding fragment thereof, of any one of E1-E102, wherein the antibody has a DNA binding score normalized to blank of less than 7.55.

E104. An antibody, or antigen binding fragment thereof, that competes for binding with the antibody, or antigen-binding fragment thereof, of any one of E1-E103

E105. An antibody, or antigen binding fragment thereof, that binds the same epitope as The antibody, or antigen-binding fragment thereof, of any one of E1-E104.

E106. An antibody, or antigen binding fragment thereof, comprising the CDRs of an antibody selected from the group consisting of 7E8_chimera, 9B3_chimera, 9B3_chimera_huJseg, 7E8 CDR graft, IL33-10, 9B3 CDR graft, 9B3_1, 9B3_2A, 9B3_2B, 9B3_3, 9B3_5, 9B3_79B3_13, 9B3_15, 9B3_17, 9B3_22, 9B3_31V2, 9B3_36, 9B3_79, 9B3_124, 9B3_162, 7E8H/9B3K, 9B3_563, IL33-11, IL33-12, IL33-13, IL33-45, IL33-55, IL33-56, IL33-57, IL33-58, IL33-61, IL33-62, IL33-68, IL33-74, IL33-75, IL33-80, IL33-81, IL33-103, IL33-117, IL33-136, IL33-153, IL33-154, IL33-155, IL33-156, IL33-157, IL33-158, IL33-167, IL33-168, IL33-169, IL33-170, IL33-171, IL33-172, IL33-175, IL33-186, IL33-187, IL33-188, IL33-158-152, IL33-167-153, IL33-158LS, and IL33-167LS.

E107. An antibody, or antigen binding fragment thereof, comprising the VL and VH of an antibody selected from the group consisting of 7E8_chimera, 9B3_chimera, 9B3_chimera_huJseg, 7E8 CDR graft, IL33-10, 9B3 CDR graft, 9B3_1, 9B3_2A, 9B3_2B, 9B3_3, 9B3_5, 9B3_79B3_13, 9B3_15, 9B3_17, 9B3_22, 9B3_31V2, 9B3_36, 9B3_79, 9B3_124, 9B3_162, 7E8H/9B3K, 9B3_563, IL33-11, IL33-12, IL33-13, IL33-45, IL33-55, IL33-56, IL33-57, IL33-58, IL33-61, IL33-62, IL33-68, IL33-74, IL33-75, IL33-80, IL33-81, IL33-103, IL33-117, IL33-136, IL33-153, IL33-154, IL33-155, IL33-156, IL33-157, IL33-158, IL33-167, IL33-168, IL33-169, IL33-170, IL33-171, IL33-172, IL33-175, IL33-186, IL33-187, IL33-188, IL33-158-152, IL33-167-153, IL33-158LS, and IL33-167LS.

E108. An antibody, or antigen binding fragment thereof, selected from the group consisting of 7E8_chimera, 9B3_chimera, 9B3_chimera_huJseg, 7E8 CDR graft, IL33-10, 9B3 CDR graft, 9B3_1, 9B3_2A, 9B3_2B, 9B3_3, 9B3_5, 9B3_79B3_13, 9B3_15, 9B3_17, 9B3_22, 9B3_31V2, 9B3_36, 9B3_79, 9B3_124, 9B3_162, 7E8H/9B3K, 9B3_563, IL33-11, IL33-12, IL33-13, IL33-45, IL33-55, IL33-56, IL33-57, IL33-58, IL33-61, IL33-62, IL33-68, IL33-74, IL33-75, IL33-80, IL33-81, IL33-103, IL33-117, IL33-136, IL33-153, IL33-154, IL33-155, IL33-156, IL33-157, IL33-158, IL33-167, IL33-168, IL33-169, IL33-170, IL33-171, IL33-172, IL33-175, IL33-186, IL33-187, IL33-188, IL33-158-152, IL33-167-153, IL33-158LS, and IL33-167LS.

E109. An isolated nucleic acid molecule, comprising one or more nucleotide sequences encoding the antibody, or antigen-binding fragment thereof, of any one of E1-E108.

E110. An isolated nucleic acid molecule comprising the nucleic acid sequence as set forth as one or more of SEQ ID NOs: 398, 399, 400, and 401.

E111. An isolated nucleic acid molecule comprising the nucleic acid sequence as set forth as SEQ ID NO:398.

E112. An isolated nucleic acid molecule comprising the nucleic acid sequence isolated nucleic acid molecule comprising the nucleic acid sequence as set forth as one or more of SEQ ID NOs: 398, 399, 400, and 401. as set forth as SEQ ID NO:399.

E113. An isolated nucleic acid molecule comprising the nucleic acid sequence as set forth as SEQ ID NO:400.

E114. An isolated nucleic acid molecule comprising the nucleic acid sequence as set forth as SEQ ID NO:401.

E115. An isolated nucleic acid molecule comprising the coding sequence of the nucleic acid molecule deposited with the ATCC and having Accession No. PTA-122724.

E116. An isolated nucleic acid molecule comprising the coding sequence of the nucleic acid molecule deposited with the ATCC and having Accession No. PTA-122725.

E117. A vector comprising the nucleic acid molecule of any one of E109-E116.

E118. A host cell comprising the nucleic acid molecule of any one of E109-E116, or the vector of E117.

E119. The host cell of E118, wherein said cell is a mammalian cell.

E120. The host cell of E119, wherein said host cell is a CHO cell, a HEK-293 cell, or an Sp2.0 cell.

E121. A method of making an antibody or antigen-binding fragment thereof, comprising culturing the host cell of any one of E119-E120, under a condition wherein said antibody or antigen-binding fragment is expressed by said host cell.

E122. The method of E121, further comprising isolating said antibody or antigen-binding fragment thereof.

E123. A pharmaceutical composition comprising an antibody or antigen-binding fragment thereof of any one of E1-E108, and a pharmaceutically acceptable carrier or excipient.

E124. A method of reducing the activity of IL-33, comprising administering to a subject in need thereof a therapeutically effective amount of the antibody, or antigen-binding fragment thereof, of any one of embodiments E1-E108, or the pharmaceutical composition of E123.

E125. A method of treating an inflammatory disease, comprising administering to a subject in need thereof a therapeutically effective amount of the antibody, or antigen-binding fragment thereof, of any one of E1-E108, or the pharmaceutical composition of E123.

E126. A method of treating atopic dermatitis, comprising administering to a subject in need thereof a therapeutically effective amount of the antibody, or antigen-binding fragment thereof, of any one of E1-E108, or the pharmaceutical composition of E123.

E127. A method of treating inflammatory bowel disease, comprising administering to a subject in need thereof a therapeutically effective amount of the antibody, or antigen-binding fragment thereof, of any one of any one of E1-E108, or the pharmaceutical composition of E123.

E128. The method of any one of E121-E127, wherein said subject is a human.

E129. The method of any one of E121-E128, comprising administering said antibody or antigen-binding fragment thereof, or pharmaceutical composition, intravenously.

E130. The method of any one of E121-E128, comprising administering said antibody or antigen-binding fragment thereof, or pharmaceutical composition, subcutaneously.

E131. The method of any one of E121-E130, wherein said antibody or antigen-binding fragment thereof, or pharmaceutical composition, is administered about twice a week, once a week, once every two weeks, once every three weeks, once every four weeks, once every five weeks, once every six weeks, once every seven weeks, once every eight weeks, once every nine weeks, once every ten weeks, twice a month, once a month, once every two months, once every three months, or once every four months.

E132. The antibody, or antigen-binding fragment thereof, of any one of E1-E108, or the pharmaceutical composition of E123, for use as a medicament.

E133. The antibody, or antigen-binding fragment thereof, of any one of E1-108, or the pharmaceutical composition of E123, for use in reducing the activity of IL-33 in a subject.

E134. The antibody, or antigen-binding fragment thereof, of any one of E1-E108, or the pharmaceutical composition of E123, for use in treating an inflammatory disease in a subject.

E135. The antibody, or antigen-binding fragment thereof, of any one of E1-E108, or the pharmaceutical composition of E123, for use in treating atopic dermatitis in a subject.

E136. A method of treating a medical condition, comprising administering to a subject in need thereof a therapeutically effective amount of the antibody, or antigen-binding fragment thereof, of any one of E1-E108, or the pharmaceutical composition of E123.

E137. The method of E136, wherein the condition is selected from the group consisting of inflammatory bowel disease, allergies, allergic rhinitis, allergic conjunctivitis, vernal keratoconjunctivitis, a seasonal allergy, pet allergy, asthma, food allergy, peanut allergy, atopic dermatitis, chronic rhinosinusitis with nasal polyps (CRSwNP), allergic rhinitis, bronchitis, chronic obstructive pulmonary disease (COPD), viral exacerbations of respiratory disease, viral infection in children and adults, (respiratory syncytial virus (RSV), rhinovirus, influenza), urticarias, eosinophilic esophagitis, chronic fibrosis, liver fibrosis, non-alcoholic steatohepatitis (NASH), chronic kidney disease, idiopathic pulmonary fibrosis (IPF), scleroderma, systemic sclerosis, acute kidney injury, sepsis, pancreatitis, type 1 diabetes, graft-versus-host disease (GVHD), tissue transplant, Alzheimer's, rheumatoid arthritis, irritable bowel syndrome (IBS), Crohns disease, ulcerative colitis, multiple sclerosis, psoriasis, celiac disease and Raynaud's disease or phenomenon.

BRIEF DESCRIPTION OF THE DRAWINGS

FIG. 1A shows binding of rat 7E8 Fab to immobilized human IL-33 (mm2). FIG. 1B shows binding of rat 7E8 Fab to immobilized human IL-33 (WT) in the absence of reducing agent. FIG. 1C shows binding of rat 7E8 Fab to immobilized human IL-33 (WT) in the presence of reducing agent (DTT).

FIGS. 2A-2B are panels showing sequence alignment of anti-IL-33 optimized variable regions to human DP-54/DPK9 germlines. FIG. 2A. shows alignment of VH (SEQ ID NO:225) and VL (SEQ ID NO:207) of IL33-158-152/IL33-158LS with human germline sequences DP-54/JH4 (SEQ ID NO:7) and DPK9/JK4 (SEQ ID NO:11). FIG. 2B shows alignment of VH (SEQ ID NO:210) and VL (SEQ ID NO:91) of IL33-167-153/IL33-167LS with human germline sequences DP-54/JH4 (SEQ ID NO:7) and DPK9/JK4 (SEQ ID NO:11)

FIG. 3A shows binding of cytokines to immobilized IL33-158LS Fab. FIG. 3B shows binding of cytokines to immobilized 7E8 Fab.

DETAILED DESCRIPTION OF THE INVENTION

Antibodies

Figure 1A:
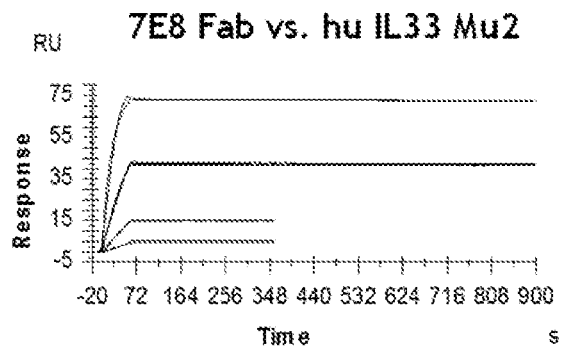
FIGS. 1A-1C are panels showing surface plasmon resonance traces of IL-33 binding to captured rat 7E8 Fab.

An "antigen-binding fragment" of an antibody refers to a fragment of a full-length antibody that retains the ability to specifically bind to an antigen (preferably with substantially the same binding affinity). Examples of an antigen-binding fragment includes (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., 1989 Nature 341:544-546), which consists of a VH domain; and (vi) an isolated complementarity determining region (CDR), disulfide-linked Fvs (dsFv), and anti-idiotypic (anti-Id) antibodies and intrabodies. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)); see e.g., Bird et al. Science 242:423-426 (1988) and Huston et al., 1988, Proc. Natl. Acad. Sci. USA 85:5879-5883. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen-binding sites (see e.g., Holliger et al, 1993, Proc. Natl. Acad. Sci. USA 90:6444-6448; Poljak et al., 1994, Structure 2:1121-1123).

An antibody "variable domain" refers to the variable region of the antibody light chain (VL) or the variable region of the antibody heavy chain (VH), either alone or in combination. As known in the art, the variable regions of the heavy and light chains each consist of four framework regions (FR) connected by three complementarity determining regions (CDRs), and contribute to the formation of the antigen-binding site of antibodies.

"Complementarity Determining Regions" (CDRs) can be identified according to the definitions of the Kabat, Chothia, the accumulation of both Kabat and Chothia, AbM, contact, North, and/or conformational definitions or any method of CDR determination well known in the art. See, e.g., Kabat et al., 1991, Sequences of Proteins of Immunological Interest, 5th ed. (hypervariable regions); Chothia et al., 1989, Nature 342:877-883 (structural loop structures). The identity of the amino acid residues in a particular antibody that make up a CDR can be determined using methods well known in the art. AbM definition of CDRs is a compromise between Kabat and Chothia and uses Oxford Molecular's AbM antibody modeling software (Accelrys®). The "contact" definition of CDRs is based on observed antigen contacts, set forth in MacCallum et al., 1996, J. Mol. Biol., 262:732-745. The "conformational" definition of CDRs is based on residues that make enthalpic contributions to antigen binding (see, e.g., Makabe et al., 2008, J. Biol. Chem., 283:1156-1166). North has identified canonical CDR conformations using a different preferred set of CDR definitions (North et al., 2011, J. Mol. Biol. 406: 228-256). In another approach, referred to herein as the "conformational definition" of CDRs, the positions of the CDRs may be identified as the residues that make enthalpic contributions to antigen binding (Makabe et al., 2008, J Biol. Chem. 283:1156-1166). Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs (or other residue of the antibody) may be defined in accordance with any of Kabat, Chothia, North, extended, AbM, contact, and/or conformational definitions.

Residues in a variable domain are numbered according Kabat, which is a numbering system used for heavy chain variable domains or light chain variable domains of the compilation of antibodies. See, Kabat et al., 1991, Sequences of Proteins of Immunological Interest, 5th Ed. Public Health Service, National Institutes of Health, Bethesda, Md. Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, according to Kabat) after heavy chain FR residue 82. The Kabat numbering of residues may be determined for a given antibody by alignment at regions of homology of the sequence of the antibody with a "standard" Kabat numbered sequence. Various algorithms for assigning Kabat numbering are available. The algorithm implemented in the version 2.3.3 release of Abysis (www.abysis.org) is used herein to assign Kabat numbering to variable regions CDR-L1, CDR-L2, CDR-L3, CDR-H2, and CDR-H3. AbM definition is used for CDR-H1.

Specific amino acid residue positions in an antibody may also be numbered according to Kabat.

"Framework" (FR) residues are antibody variable domain residues other than the CDR residues. A VH or VL domain framework comprises four framework sub-regions, FR1, FR2, FR3 and FR4, interspersed with CDRs in the following structure: FR1-CDR1-FR2-CDR2-FR3-CDR3-FR4.

An "epitope" refers to the area or region of an antigen to which an antibody specifically binds, e.g., an area or region comprising residues that interacts with the antibody. Epitopes can be linear or conformational.

An antibody that "preferentially binds" or "specifically binds" (used interchangeably herein) to an epitope is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a IL-33 epitope is an antibody that binds this epitope with greater affinity, avidity, more readily, and/or with greater duration than it binds to other IL-33 epitopes or non-IL-33 epitopes. It is also understood by reading this definition that, for example, an antibody (or moiety or epitope) which specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding. "Specific binding" or "preferential binding" includes a compound, e.g., a protein, a nucleic acid, an antibody, and the like, which recognizes and binds to a specific molecule, but does not substantially recognize or bind other molecules in a sample. For instance, an antibody or a peptide receptor which recognizes and binds to a cognate ligand or binding partner (e.g., an anti-human tumor antigen antibody that binds a tumor antigen) in a sample, but does not substantially recognize or bind other molecules in the sample, specifically binds to that cognate ligand or binding partner. Thus, under designated assay conditions, the specified binding moiety (e.g., an antibody or an antigen-binding portion thereof or a receptor or a ligand binding portion thereof) binds preferentially to a particular target molecule and does not bind in a significant amount to other components present in a test sample.

A variety of assay formats may be used to select an antibody or peptide that specifically binds a molecule of interest. For example, solid-phase ELISA immunoassay, immunoprecipitation, BIAcore™ (GE Healthcare, Piscataway, N.J.), fluorescence-activated cell sorting (FACS), Octet™ (FortéBio, Inc., Menlo Park, Calif.) and Western blot analysis are among many assays that may be used to identify an antibody that specifically reacts with an antigen or a receptor, or ligand binding portion thereof, that specifically binds with a cognate ligand or binding partner. Typically, a specific or selective reaction will be at least twice background signal or noise and more typically more than 10 times background, even more specifically, an antibody is said to "specifically bind" an antigen when the equilibrium dissociation constant ($K_D$) is ≤1 µM, preferably ≤100 nM, more preferably ≤10 nM, even more preferably, ≤100 pM, yet more preferably, ≤10 pM, and even more preferably, ≤1 pM.

The term "compete", as used herein with regard to an antibody, means that binding of a first antibody, or an antigen-binding portion thereof, to an antigen reduces the subsequent binding of the same antigen by a second antibody or an antigen-binding portion thereof. In general, the binding a first antibody creates steric hindrance, conformational change, or binding to a common epitope (or portion thereof), such that the binding of the second antibody to the same antigen is reduced. Standard competition assays may be used to determine whether two antibodies compete with each other. One suitable assay for antibody competition involves the use of the Biacore technology, which can measure the extent of interactions using surface plasmon resonance (SPR) technology, typically using a biosensor system (such as a BIACORE® system). For example, SPR can be used in an in vitro competitive binding inhibition assay to determine the ability of one antibody to inhibit the binding of a second antibody. Another assay for measuring antibody competition uses an ELISA-based approach.

Furthermore, a high throughput process for "binning" antibodies based upon their competition is described in International Patent Application No. WO2003/48731. Competition is present if one antibody (or fragment) reduces the binding of another antibody (or fragment) to IL-33. For example, a sequential binding competition assay may be used, with different antibodies being added sequentially. The first antibody may be added to reach binding that is close to saturation. Then, the second antibody is added. If the binding of second antibody to IL-33 is not detected, or is significantly reduced (e.g., at least about 10%, at least about 20%, at least about 30%, at least about 40%, at least about 50%, at least about 60%, at least about 70%, at least about 80%, or at least about 90% reduction) as compared to a parallel assay in the absence of the first antibody (which value can be set as 100%), the two antibodies are considered as competing with each other. An exemplary antibody competition assay (and overlapping epitope analysis) by SPR is provided in Example 4.

An "Fc fusion" protein is a protein wherein one or more polypeptides are operably linked to an Fc polypeptide. An Fc fusion combines the Fc region of an immunoglobulin with a fusion partner.

The term "treatment" includes prophylactic and/or therapeutic treatments. If it is administered prior to clinical manifestation of a condition, the treatment is considered prophylactic. Therapeutic treatment includes, e.g., ameliorating or reducing the severity of a disease, or shortening the length of the disease.

Binding Affinity

The binding affinity of an antibody can be expressed as $K_D$ value, which refers to the dissociation rate of a particular antigen-antibody interaction. $K_D$ is the ratio of the rate of dissociation, also called the "off-rate ($k_{off}$)", to the association rate, or "on-rate ($k_{on}$)". Thus, $K_D$ equals $k_{off}/k_{on}$ and is expressed as a molar concentration (M), and the smaller the $K_D$, the stronger the affinity of binding. $K_D$ values for antibodies can be determined using methods well established in the art. One exemplary method for measuring Kd is surface plasmon resonance (SPR), typically using a biosensor system such as a BIACORE® system. BIAcore kinetic analysis comprises analyzing the binding and dissociation of an antigen from chips with immobilized molecules (e.g. molecules comprising epitope binding domains), on their surface. Another method for determining the Kd of an antibody is by using Bio-Layer Interferometry, typically using OCTET® technology (Octet QKe system, ForteBio). Alternatively or in addition, a KinExA® (Kinetic Exclusion Assay) assay, available from Sapidyne Instruments (Boise, Id.) can also be used.

In some aspects, the $K_D$ value is measured by surface plasmon resonance (SPR). The IL-33 may be immobilized. The IL-33 may be immobilized to a solid surface. The IL-33 may be immobilized to a chip, for example by covalent coupling (such as amine coupling). The chip may be a CM5 sensor chip.

As the analyte binds to the ligand the accumulation of protein on the sensor surface causes an increase in refractive index. This refractive index change is measured in real time (sampling in a kinetic analysis experiment is taken every 0.1 s), and the result plotted as response units (RU) versus time (termed a sensorgram). Importantly, a response (background response) will also be generated if there is a difference in the refractive indices of the running and sample buffers. This background response must be subtracted from the sensorgram to obtain the actual binding response. The background response is recorded by injecting the analyte through a control or reference flow cell, which has no ligand or an irrelevant ligand immobilized to the sensor surface. The real time measurement of association and dissociation of a binding interaction allows for the calculation of association and dissociation rate constants and the corresponding affinity constants. One RU represents the binding of 1 pg of protein per square mm. More than 50 pg per square mm of analyte binding is generally needed in practice to generate good reproducible responses. Between 85 and 370 RU of IL-33 may be immobilized. Between 85 and 225 RU of IL-33 may be immobilized.

Dissociation of the antibody from the IL-33 may be monitored for about 3600 seconds. The SPR analysis may be conducted, and the data collected at between about 15° C. and about 37° C. The SPR analysis may be conducted, and the data collected at between about 25° C. and 37° C. The SPR analysis may be conducted, and the data collected at about 37° C. The SPR analysis may be conducted, and the data collected at 37° C. The $K_D$ value may be measured by SPR using a BIAcore T200 instrument. The SPR rates and affinities may be determined by fitting resulting sensorgram data to a 1:1 model in BIAcore T200 Evaluation software version 1.0. The collection rate may be about 1 Hz.

The term "IL-33 molecule" refers to molecules that demonstrate a greater sequence identity to wild type IL-33 than to another member of the IL-1 family of cytokines, (such comparisons being made within the same species). The term IL-33 molecule includes mutants, variants, truncations, fragments, splice variants, species variants, and IL-33 like portions of fusion proteins.

IL-33 is produced as precursor with an N-terminal domain that is responsible for translocation to the nucleus and binding to chromatin, and a C-terminal 12-stranded beta-trefoil domain that interacts with the ST2 receptor and is responsible for the biological activity of IL-33. The full length form of human IL-33 as represented by UniProtKB/Swiss-Prot accession number O95760.1 is herein provided as SEQ ID NO:396.

Upon release of IL-33 from cells, the N-terminal domain is cleaved, leading to the release of a C-terminal domain with greater activity than that of the full-length protein. A number of different proteases, both endogenous to the cellular source of IL-33, such as calpains, as well as exogenous proteases derived from inflammatory cells, such as mast cells and neutrophils, can cleave the IL-33 precursor molecule. The precise cleavage site of IL-33 will vary depending on the proteases that are present. A recombinant form of IL-33 C terminal domain from amino acids 112-270 of SEQ ID NO:396 is representative of the active C-terminal forms of IL-33, and is given as SEQ ID NO:1.

The structure of IL-33 suggests it is a β-trefoil protein with four free cysteine residues (C208, C232, C227 and C259, according to the numbering of SEQ ID NO:396). Evidence suggest that IL-33 exists in an active form, with these four cysteines reduced, and an inactive form, with disulfide bonds between pairs of cysteine residues, (including disulfide bonds between the pairs C208-C259 and C227-C232), which likely coincide with a substantial conformational change, including disruption to the high-affinity ST2 binding site, thus providing a potential structural explanation for the loss of ST2 binding (Cohen et al., 2015, Nature Communications 6:8327; doi: 10.1038/ncomms9327). Mutational evidence further suggests that cysteine residues C208 and C232 may also form a disulfide bond that leads to inactivation of IL-33 (Cohen et al., 2015).

A constitutively active form of IL-33 may be generated by mutating one or more of the cysteine residues to a non-cysteine residue. Residue C208 has been found to be particularly important for the inactivation process, with mutation of residue C232 also appearing to confer resistance to inactivation. Evidence also suggests that possible disulfide bonds between C208-C259 and C227-C232 are not the entire source of inactivation, as mutations in C227 and C259 do not confer similar levels of resistance to inactivity; thus there may be several patterns of disulfide bond formation for IL-33. (Cohen_2015).

"Active IL-33" may be defined as an IL-33 molecule able to bind ST2. Active IL-33 may be defined as an IL-33 molecule lacking one or two intramolecular covalent bonds between pairs of residues at positions 208, 227, 232, and 259 (according to the numbering of SEQ ID NO:396). Active IL-33 may be defined as an IL-33 molecule lacking two intramolecular covalent bonds between pairs of residues at positions 208, 227, 232, and 259 (according to the numbering of SEQ ID NO:396). In some aspects, active IL-33 is an IL-33 molecule lacking a covalent bond between residues 208 and 259. In some aspects, active IL-33 is an IL-33 molecule lacking a covalent bond between residues 227 and 232. In some aspects, active IL-33 is an IL-33 molecule lacking a covalent bond between residues 208 and 227. In some aspects, active IL-33 is an IL-33 molecule lacking a covalent bond between residues 208 and 232. In some aspects, active IL-33 is an IL-33 molecule lacking a covalent bond between residue pairs 208/259 and 227/232, or between residue pairs 208/232 and 227/259. Active IL-33 therefore includes reduced forms of wild type IL-33, and mutant forms of IL-33, wherein at least one, two, three or four residues at position numbers 208, 227, 232, and 259, are not cysteine. In some aspects, at least one of residue 208 and 232 is not cysteine. In some aspects, at least residue 208 is not cysteine. In some aspects, at least residues 208 and 232 are not cysteine. In some aspects, each of residues 208, 227, 232 and 259 are not cysteine. In some aspects, one or more of residues 208, 227, 232 and 259 are serine. The covalent bond may be a disulfide bond. The foregoing residue numbering is according to the numbering of SEQ ID NO:1. In some aspects, active IL-33 comprises a fully reduced molecule comprising SEQ ID NO:1. In some aspects, active IL-33 comprises a fully reduced molecule comprising SEQ ID NO:4. In some aspects, active IL-33 comprises a molecule comprising SEQ ID NO:3. In some aspects, active IL-33 comprises a molecule comprising SEQ ID NO:5.

Inactive IL-33 may be defined as an IL-33 molecule that binds ST2 with an affinity at least 10-fold lower than active IL-33. In some aspects, inactive IL-33 binds ST2 with an affinity at least 100-fold lower than active IL-33. In some aspects, inactive IL-33 binds ST2 with an affinity at least 1000-fold lower than active IL-33. In some aspects, inactive IL-33 binds ST2 with an affinity at least 4 orders of magnitude lower than active IL-33. In some aspects, inactive IL-33 binds ST2 with an affinity at least 5 orders of magnitude lower than active IL-33. In some aspects, inactive IL-33 comprises a covalent bond between one or both of residue pairs 208/259 and 227/232. In some aspects, inactive IL-33 comprises a covalent bond between one or both of residue pairs 208/232 and 227/259. In some aspects, inactive IL-33 comprises a covalent bond between residues 208 and 232. In some aspects, inactive IL-33 comprises a covalent bond between residues 208 and 259. In some aspects, inactive IL-33 comprises a covalent bond between residues 227 and 232. In some aspects, inactive IL-33 comprises a covalent bond between both of residue pairs 208/259 and 227/232. One or more of the residues may be cysteines. One or both of the covalent bonds may be a disulfide bond. The foregoing residue numbering is according to the numbering of SEQ ID NO:396.

In some aspects, the IL-33 is human IL-33. In some aspects, the sequence of wild type IL-33 is SEQ ID NO:1. In some aspects, the IL-33 is rat IL-33. In some aspects, the IL-33 is mouse IL-33. In some aspects, the IL-33 is primate IL-33. In some aspects, the IL-33 is ape IL-33. In some aspects, the IL-33 is monkey IL-33. In some aspects, the IL-33 is cynomolgus monkey IL-33.

The measurement of $K_D$ of active IL-33 may be made using an IL-33 variant, wherein at least C208 is substituted with another amino acid residue. In some aspects, the measurement of $K_D$ of active IL-33 is made using an IL-33 variant, wherein at least C232 is substituted with another residue. In some aspects, the measurement of $K_D$ of active IL-33 is made using an IL-33 variant, wherein at least C208 and C232 are substituted. In some aspects, the measurement of $K_D$ of active IL-33 is made using an IL-33 variant, wherein C208, C227, C232, and C259 are substituted. In some aspects, one or more of the cysteine residues are substituted with serine.

Antibodies to IL-33

In some aspects, the invention provides antagonistic IL-33 antibodies. A high affinity antagonist of the IL-33 pathway may be effective on multiple cell types, and multiple tissue compartments where IL-33 is thought to act on its target cells. In some aspects, antibodies of the invention may access sites where IL-33 is released from cells, particularly epithelial and endothelial cells. In some aspects, the invention provides an IL-33 antibody that can partition to the extracellular spaces within the lung and other tissues, can effectively compete with binding of IL-33 to the cell surface receptor and has a relatively long half-life so as to allow for infrequent dosing. Antibodies of the invention have the potential to modify an important pathway that drives the development and inflammation associated with asthma.

A neutralizing or "blocking" antibody, refers to an antibody whose binding to IL-33: (i) interferes with, limits, or inhibits the interaction between IL-33 or an IL-33 fragment and an IL-33 receptor component (for example, ST2, IL-1 RAcP, etc.); and/or (ii) results in inhibition of at least one biological function of IL-33. Assays to determine the neutralization by an antibody of the invention are described elsewhere herein and are well-known in the art.

The present invention provides antibodies that specifically bind to IL-33. In some aspects, the invention provides an antibody, or antigen binding fragment thereof, that neutralizes IL-33 by at least 50%. In some aspects, the invention provides an antibody, or antigen binding fragment thereof, that neutralizes IL-33 by at least 60%. In some aspects, the invention provides an antibody, or antigen binding fragment thereof, that neutralizes IL-33 by at least 70%. In some aspects, the invention provides an antibody, or antigen binding fragment thereof, that neutralizes IL-33 by at least 80%. In some aspects, the invention provides an antibody, or antigen binding fragment thereof, that neutralizes IL-33 by at least 90%. In some aspects, the invention provides an antibody, or antigen binding fragment thereof, that neutralizes IL-33 by at least 95%. In some aspects, the invention provides an antibody, or antigen binding fragment thereof, that neutralizes IL-33 by at least 96%. In some aspects, the invention provides an antibody, or antigen binding fragment thereof, that neutralizes IL-33 by at least 97%. In some aspects, the invention provides an antibody, or antigen binding fragment thereof, that neutralizes IL-33 by at least 98%. In some aspects, the invention provides an antibody, or antigen binding fragment thereof, that neutralizes IL-33 by at least 99%.

The antibody, or an antigen binding fragment thereof, may be selected from the group consisting of 7E8_chimera, 9B3_chimera, 9B3_chimera_huJseg, 7E8 CDR graft, IL33-10, 9B3 CDR graft, 9B3_1, 9B3_2A, 9B3_2B, 9B3_3, 9B3_5, 9B3_7, 9B3_13, 9B3_15, 9B3_17, 9B3_22, 9B3_31V2, 9B3_36, 9B3_79, 9B3_124, 9B3_162, 7E8H/9B3K, 9B3_563, IL33-11, IL33-12, IL33-13, IL33-45, IL33-55, IL33-56, IL33-57, IL33-58, IL33-61, IL33-62, IL33-68, IL33-74, IL33-75, IL33-80, IL33-81, IL33-103, IL33-117, IL33-136, IL33-153, IL33-154, IL33-155, IL33-156, IL33-157, IL33-158, IL33-167, IL33-168, IL33-169, IL33-170, IL33-171, IL33-172, IL33-175, IL33-186, IL33-187, IL33-188, IL33-158-152, IL33-167-153, IL33-158LS, and IL33-167LS, antigen binding fragments thereof, and mutants, variants, derivatives and substantially similar versions thereof.

CDR Consensus Sequences

In some aspects, the CDRs comprise SEQ ID NOs: 257, 261, 265, 269, 272, and 276. These CDR sequences incorporate the consensus based on all available data (ABS plus mutations plus rat repertoire), tested VH germlines, and mutations that were based on modeling to either retain/improve binding to IL-33 or reduce polyreactivity or sequence liabilities without disrupting binding.

CDR H1:

The broad consensus sequence for CDR H1 is SEQ ID NO:269, based on the totality of information available. A further refined subset of consensus sequences for CDR H1 is SEQ ID NO:270, including the results from optimization of parental rat antibodies 7E8 and 9B3 and augmented binary substitution (ABS). The consensus CDR H1 sequence for optimized 7E8 is $^{26}$GF(T/E)F(S/E)(N/S)YWMY$^{32}$ (SEQ ID NO:270). Substitution of the CDR H1 from 9B3, which introduced a S31N mutation, or introduction of the mutations T28E or S30E, allowed retention of full activity. Augmented binary substitution mutagenesis showed a strong preference for Y at position 35 instead of the DP54 germline residue S. The consensus CDR H1 sequence for optimized 7E8 addressing the 9B3 sequence at position 31 and the ABS preferences at position 35 is SEQ ID NO:271.

CDR H2:

The broad consensus sequence for CDR H2 is SEQ ID NO:272, based on the totality of information available. A further refined subset of consensus sequences for CDR H2 is SEQ ID NO:273, including the results from optimization of 7E8 and 9B3 and augmented binary substitution (ABS). The consensus CDR H2 sequence for optimized 7E8 is $^{50}$(S/A)I(T/N)(P/N)(N/D)(G/A)(G/S/H)(N/D/E)(T/K/D/E)YY(P/V/L)(D/E) SV(K/Q)G$^{66}$ (SEQ ID NO:273). Introduction of the mutations S50A, G55A, G56H, N57D, N57E, T58D, T58E, D62E, or K65Q allowed retention of human IL-33 neutralization potency without substantial increases in non-specific binding. N54I, N54L, N54V, N54Y, and N54W allowed retention of human IL-33 neutralization potency but introduced increased non-specific binding. Substitution of the CDR H2 from 9B3 into 7E8, which introduced four changes (T52N, P53N, N54D, and P61L), allowed retention of potent neutralization of human IL-33 but led to a reduction in potency of cynomolgus monkey IL-33 neutralization. Augmented binary substitution mutagenesis showed a strong preference for S, T and P at positions 50, 52 and 53 instead of the DP54 germline residues N, K and Q, but incorporation of the DP54 germline mutations N54D, G56S, N57E, T58K, and P61V was tolerated. The consensus CDR H2 sequence for optimized 7E8 addressing the ABS preferences at positions 52 and 53 and the 9B3 sequences tolerated for neutralization of human IL-33 is SEQ ID NO:274. The consensus CDR H2 sequence for optimized 7E8 addressing the ABS preferences at positions 52 and 53 is SEQ ID NO:275.

CDR H3:

The broad consensus sequence for CDR H3 is SEQ ID NO:276, based on the totality of information available. A further refined subset of consensus sequences for CDR H3 is SEQ ID NO:277, including the results from optimization of 7E8 and 9B3 and analysis of sequence from the antibody repertoire of a rat immunized with human IL-33. The consensus CDR H3 sequence for optimized 7E8 is $^{99}$G(H/Y)Y(Y/S)(Y/H)(T/S/N)(S/A)YS(L/F)(G/S)Y$^{110}$ (SEQ ID NO:278). Introduction of the mutations H100Y, Y103H, T104N, T104S, or S105A allowed retention of human IL-33 neutralization potency without substantial increases in non-specific binding. The mutations S105D and S105N led to loss of human IL-33 neutralization potency. Substitution of the CDR H3 from 9B3 into 7E8, which introduced the mutations Y102S, T104S, L108F, and G109S, allowed retention of potent neutralization of human IL-33 but led to a reduction in potency of cynomolgus monkey IL-33 neutralization. Incorporation of 7E8-related CDR H3 sequences identified from the antibody repertoire of a rat immunized with human IL-33 showed that the following amino acids are compatible with high human IL-33 neutralization potency: R100, F101, N104, I108, A109, H110, N110, S110, and F110. The consensus CDR H3 sequence for optimized 7E8 addressing the 9B3 sequences tolerated for neutralization of human IL-33 is SEQ ID NO:279.

CDR L1:

The broad consensus sequence for CDR L1 is SEQ ID NO:257, based on the totality of information available. A further refined subset of consensus sequences for CDR L1 is SEQ ID NO:258, including the results from optimization of 7E8 and 9B3 and augmented binary substitution (ABS). The consensus CDR L1 sequence for optimized 7E8 is $^{24}$(K/R)AS(Q/H)(N/S)I(N/S)(K/S)HLD$^{34}$ (SEQ ID NO:259). Augmented binary substitution mutagenesis showed a strong preference for H and D at positions 32 and 34 instead of the DPK9 germline residues Y$^{32}$ and N$^{34}$ but incorporation of the DPK9 germline mutations K24R, N28S, N30S, and K31S was tolerated. Substitution of the 9B3 light chain for the 7E8 light chain (which includes the light chain sequence variation Q27H) allowed retention of IL-33 neutralization potency without introducing non-specific binding. Introduction of the mutations N30H, K31R, and H32Y allowed retention of human IL-33 neutralization but increased non-specific binding, while the mutations N30Y, N30D, N30W, K31E, and K31D reduced potency and/or introduced higher nonspecific binding. The consensus CDR L1 sequence for optimized 7E8 addressing the ABS preferences at positions 32 and 34 without allowing for the light chain sequence variation at position 27 is SEQ ID NO:260.

CDR L2:

The broad consensus sequence for CDR L2 is SEQ ID NO:261, based on the totality of information available. A further refined subset of consensus sequences for CDR L2 is SEQ ID NO:262, including the results from optimization of 7E8 and 9B3 and augmented binary substitution (ABS). The consensus CDR L2 sequence for optimized 7E8 is $^{50}$F(T/A)(N/S)(N/S)LQ(T/S)$^{56}$ (SEQ ID NO:263). Augmented binary substitution mutagenesis showed a strong preference for F at position 50 instead of the DPK9 germline residue A, but incorporation of the DPK9 germline mutations T51A, N52S, N53S, and T56S was tolerated. Introduction of the mutations N52Y or N53R allowed retention of human IL-33 neutralization but increased nonspecific binding, while the mutations F50H, T56D, T56E, and T56Q reduced potency and/or introduced higher nonspecific binding. The consensus CDR L2 sequence for optimized 7E8 without allowing for variation at position 53 is SEQ ID NO:264.

CDR L3:

The broad consensus sequence for CDR L3 is SEQ ID NO:265, based on the totality of information available. A further refined subset of consensus sequences for CDR L3 is SEQ ID NO:266, including the results from optimization of 7E8 and 9B3 and augmented binary substitution (ABS). The consensus CDR L3 sequence for optimized 7E8 is $^{89}$(F/Q)QY(N/Y)(N/S/Q/R)GWT$^{96}$ (SEQ ID NO:267). Introduction of the mutation N93Q allowed retention of human IL-33 neutralization potency without a substantial increase in non-specific binding, while the mutation N93R allowed retention of human IL-33 neutralization potency with minor increases in non-specific binding. The mutations N92R and G94R allowed retention of human IL-33 neutralization potency but led to increases in nonspecific binding. Substitution of the 9B3 light chain for the 7E8 light chain (which includes the light chain sequence variation N93S) allowed retention of IL-33 neutralization potency without introducing non-specific binding. Augmented binary substitution mutagenesis showed a strong preference for Y and G at positions 91 and 94 instead of the DPK9 germline residues S and T, but incorporation of the DPK9 germline mutations F89Q, N92Y, and N93S was tolerated. Retention of the rat J segment residue W95 was strongly favored over substitution of the human JK4 residue W95L. The consensus CDR L3 sequence for optimized 7E8 addressing the ABS preferences at positions 91 and 94 without allowing for incorporation of R at position 93 is SEQ ID NO:268.

In some aspects, the antibody, or antigen binding fragment thereof, comprises a CDR-L1 comprising SEQ ID NO:257, a CDR-L2 comprising SEQ ID NO:261, a CDR-L3 comprising SEQ ID NO:265, a CDR-H1 comprising SEQ ID NO:269, a CDR-H2 comprising SEQ ID NO:272, and a CDR-H3 comprising SEQ ID NO: 276

In some aspects, the antibody, or antigen binding fragment thereof, comprises a CDR-L1 comprising SEQ ID NO:258, a CDR-L2 comprising SEQ ID NO:262, a CDR-L3 comprising SEQ ID NO:266, a CDR-H1 comprising SEQ ID NO:270, a CDR-H2 comprising SEQ ID NO:273, and a CDR-H3 comprising SEQ ID NO: 277.

In some aspects, the antibody, or antigen binding fragment thereof, comprises a CDR-L1 comprising SEQ ID NO:259, a CDR-L2 comprising SEQ ID NO:263, a CDR-L3 comprising SEQ ID NO:267, a CDR-H1 comprising SEQ ID NO:271, a CDR-H2 comprising SEQ ID NO:274, and a CDR-H3 comprising SEQ ID NO: 278.

In some aspects, the antibody, or antigen binding fragment thereof, comprises a CDR-L1 comprising SEQ ID NO:260, a CDR-L2 comprising SEQ ID NO:264, a CDR-L3 comprising SEQ ID NO:268, a CDR-H1 comprising SEQ ID NO:271, a CDR-H2 comprising SEQ ID NO:275, and a CDR-H3 comprising SEQ ID NO: 279.

In some aspects, the antibody, or antigen binding fragment thereof, comprises a CDR-L1 comprising SEQ ID NO:20, a CDR-L2 comprising SEQ ID NO:21, a CDR-L3 comprising SEQ ID NO:208, a CDR-H1 comprising SEQ ID NO:16, a CDR-H2 comprising SEQ ID NO:226, and a CDR-H3 comprising SEQ ID NO: 18.

In some aspects, the antibody, or antigen binding fragment thereof, comprises the CDR-H1, CDR-H2, and CDR-H3 sequences of SEQ ID NO:225.

In some aspects, the antibody, or antigen binding fragment thereof, comprises a CDR-L1, CDR-L2, and CDR-L3 sequences of SEQ ID NO:207.

The antibody or antigen-binding fragment may comprise a VH comprising an amino acid sequence at least 90% identical to SEQ ID NO:225. The VH may comprise an amino acid sequence at least 91%, 92%, 93%, 94%, 95%, 96%, 97%, 98%, or 99%, identical to SEQ ID N0:225. The VH may comprise the amino acid sequence of SEQ ID NO:225.

The antibody or antigen-binding fragment may comprise a VL comprising an amino acid sequence at least 90% identical to SEQ ID NO:207. The VL may comprise an amino acid sequence at least 91%, 92%, 93%, 94%, 95%, 96%, 97%, 98%, or 99%, identical to SEQ ID N0:207. The VL may comprise the amino acid sequence of SEQ ID NO:207.

The antibody or antigen-binding fragment may comprise a HC comprising an amino acid sequence at least 90%, 91%, 92%, 93%, 94%, 95%, 96%, 97%, 98%, or 99%, identical to SEQ ID NO:244. The HC may comprise the amino acid sequence of SEQ ID NO:244.

The antibody or antigen-binding fragment may comprise a LC comprising an amino acid sequence at least 90%, 91%, 92%, 93%, 94%, 95%, 96%, 97%, 98%, or 99%, identical to SEQ ID NO:209. The LC may comprise the amino acid sequence of SEQ ID NO:209.

In some aspects, the antibody, or antigen binding fragment thereof, comprises a CDR-L1 comprising SEQ ID NO:20, a CDR-L2 comprising SEQ ID NO:21, a CDR-L3 comprising SEQ ID NO:22, a CDR-H1 comprising SEQ ID NO:16, a CDR-H2 comprising SEQ ID NO:211, and a CDR-H3 comprising SEQ ID NO: 18.

In some aspects, the antibody, or antigen binding fragment thereof, comprises the CDR-H1, CDR-H2, and CDR-H3 sequences of SEQ ID NO:210.

In some aspects, the antibody, or antigen binding fragment thereof, comprises a CDR-L1, CDR-L2, and CDR-L3 sequences of SEQ ID NO:91.

The antibody or antigen-binding fragment may comprise a VH comprising an amino acid sequence at least 90% identical to SEQ ID NO:210. The VH may comprise an amino acid sequence at least 91%, 92%, 93%, 94%, 95%, 96%, 97%, 98%, or 99%, identical to SEQ ID NO:210. The VH may comprise the amino acid sequence of SEQ ID NO:210.

The antibody or antigen-binding fragment may comprise a VL comprising an amino acid sequence at least 90% identical to SEQ ID NO:91. The VL may comprise an amino acid sequence at least 91%, 92%, 93%, 94%, 95%, 96%, 97%, 98%, or 99%, identical to SEQ ID NO:91. The VL may comprise the amino acid sequence of SEQ ID NO:91.

The antibody or antigen-binding fragment may comprise a HC comprising an amino acid sequence at least 90%, 91%, 92%, 93%, 94%, 95%, 96%, 97%, 98%, or 99%, identical to SEQ ID NO:245. The HC may comprise the amino acid sequence of SEQ ID NO:245.

The antibody or antigen-binding fragment may comprise a LC comprising an amino acid sequence at least 90%, 91%, 92%, 93%, 94%, 95%, 96%, 97%, 98%, or 99%, identical to SEQ ID NO:93. The LC may comprise the amino acid sequence of SEQ ID NO:93.

Germline Substitutions

In certain embodiments, The antibody, or antigen-binding fragment thereof, comprises the following heavy chain CDR sequences: (i) CDR-H1 comprising SEQ ID NO:16, CDR-H2 comprising SEQ ID NO:226, and CDR-H3 comprising SEQ ID NO:18; and/or (ii) the following light chain CDR sequences: CDR-L1 comprising SEQ ID NO:20, CDR-L2 comprising SEQ ID NO:21, and CDR-L3 comprising SEQ ID NO:208.

In certain embodiments, no more than 11, or no more than one 10, no more than 9, no more than 8, no more than 7, no more than 6, no more than 5, no more than 4, no more than 3, no more than 2, or no more than 1 substitution is made in CDR-L1, relative to SEQ ID NO:20. In certain embodiments, no more than 6, no more than 5, no more than 4, no more than 3, no more than 3, no more than 2, or no more than one substitution is made in CDR-L2, relative to SEQ ID NO:21. In certain embodiments, no more than 8, no more than 7, no more than 6, no more than 5, no more than 4, no more than 3, no more than 3, no more than 2, or no more than one substitution is made in CDR-L3, relative to SEQ ID NO:208. In some embodiments, no more than one 10, no more than 9, no more than 8, no more than 7, no more than 6, no more than 5, no more than 4, no more than 3, no more than 2, or no more than 1 substitution is made in CDR-H1, relative to SEQ ID NO:16. In some embodiments, no more than no more than 17, no more than 16, no more than 15, no more than 14, no more than 13, no more than 12, no more than 11, or no more than one 10, no more than 9, no more than 8, no more than 7, no more than 6, no more than 5, no more than 4, no more than 3, no more than 2, or no more than 1 substitution is made in CDR-H2, relative to SEQ ID NO:211. In some embodiments, no more than 12, no more than 11, or no more than one 10, no more than 9, no more than 8, no more than 7, no more than 6, no more than 5, no more than 4, no more than 3, no more than 2, or no more than 1 substitution is made in CDR-H3, relative to SEQ ID NO:18. In certain embodiments, the substitution(s) do not change binding affinity ($K_D$) value by more than 1000-fold, more than 100-fold, or 10-fold. In certain embodiments, the substitution is a conservative substation according to Table 1.

TABLE 1

Conservative Substitutions

| Residue | Conservative substitution |
|---------|---------------------------|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln |
| Met | Leu, Ile |
| Phe | Met, Leu, Tyr |
| Ser | Thr; Gly |
| Thr | Ser, Val |
| Trp | Tyr |
| Tyr | Trp, Phe |
| Val | Ile, Leu |
| Pro | — |

In certain embodiments, the substitution is human germline substitution in which a CDR residue is replaced with the corresponding human germline residue, to increase the human amino acid content and potentially reduce immunogenicity of the antibody. For example, if human germline DPK9 framework is used and the exemplary antibody IL-33-158LS, then the alignment of the CDR-L1 of IL33-158LS antibody (SEQ ID NO:20) and human germline DPK9 is as follows:

| Position | 24 | 25 | 26 | 27 | 28 | 29 | 30 | 31 | 32 | 33 | 34 |
|---|---|---|---|---|---|---|---|---|---|---|---|
| Human Germline DPK9 | R | A | S | Q | S | I | S | S | Y | L | N |
| IL33-158LS (SEQ ID NO: 20) | K | A | S | Q | N | I | N | K | H | L | D |

For positions 25 26, 27, 29, 33, and 34, the human germline residue and the corresponding IL33-158LS residue are the same, and a germline substitution is not possible. For positions 24, 28, 30, 31, and 32 (bold and underlined), the human germline residue and the corresponding IL33-158LS residue are different. Residues of IL33-158LS at these positions may be replaced with the corresponding human germline DPK9 residue to further increase the human residue content.

Methods and libraries for introducing human germline residues in antibody CDRs are described in detail in U.S. provisional application 62/162,905, and (Townsend et al., 2015, Proc. Natl. Acad. Sci. USA. 112(50):15354-15359), and both are herein incorporated by reference in their entirety.

The antibody, or antigen-binding fragment thereof, may comprise a VH framework comprising a human germline VH framework sequence. The VH framework sequence can be from a human VH3 germline, a VH1 germline, a VH5 germline, or a VH4 germline. Preferred human germline heavy chain frameworks are frameworks derived from VH1, VH3, or VH5 germlines. For example, VH frameworks from the following germlines may be used: IGHV3-23, IGHV3-7, or IGHV1-69 (germline names are based on IMGT germline definition). Preferred human germline light chain frameworks are frameworks derived from VK or Vλ germlines. For example, VL frameworks from the following germlines may be used: IGKV1-39 or IGKV3-20 (germline names are based on IMGT germline definition). Alternatively or in addition, the framework sequence may be a human germline consensus framework sequence, such as the framework of human Vλ1 consensus sequence, Vκ1 consensus sequence, Vκ2 consensus sequence, Vκ3 consensus sequence, VH3 germline consensus sequence, VH1 germline consensus sequence, VH5 germline consensus sequence, or VH4 germline consensus sequence. Sequences of human germline frameworks are available from various public databases, such as V-base, IMGT, NCBI, or Abysis.

The antibody, or antigen-binding fragment thereof, may comprise a VL framework comprising a human germline VL framework sequence. The VL framework may comprise one or more amino acid substitutions, additions, or deletions while still retaining functional and structural similarity with the germline from which it was derived. In some aspects, the VL framework is at least 90%, at least 91%, at least 92%, at least 93%, at least 94%, at least 95%, at least 96%, at least 97%, at least 98%, at least 99%, or 100% identical to a human germline VL framework sequence. In some aspects, the antibody, or antigen binding fragment thereof, comprises a VL framework comprising 1, 2, 3, 4, 5, 6, 7, 8, 9, 10 amino acid substitutions, additions or deletions relative to the human germline VL framework sequence. In some aspects, the 1, 2, 3, 4, 5, 6, 7, 8, 9, or 10 amino acid substitutions, additions or deletions are only in the framework regions. In some aspects, the % identity is based on similarity with VL excluding those portions herein defined as CDRs.

The human germline VL framework may be the framework of DPK9 (IMGT name: IGKV1-39). The human germline VL framework may be the framework of DPK12 (IMGT name: IGKV2D-29). The human germline VL framework may be the framework of DPK18 (IMGT name: IGKV2-30). The human germline VL framework may be the framework of DPK24 (IMGT name: IGKV4-1). The human germline VL framework may be the framework of HK102_V1 (IMGT name: IGKV1-5). The human germline VL framework may be the framework of DPK1 (IMGT name: IGKV1-33). The human germline VL framework may be the framework of DPK8 (IMGT name: IGKV1-9). The human germline VL framework may be the framework of DPK3 (IMGT name: IGKV1-6). The human germline VL framework may be the framework of DPK21 (IMGT name: IGKV3-15). The human germline VL framework may be the framework of Vg_38K (IMGT name: IGKV3-11). The human germline VL framework may be the framework of DPK22 (IMGT name: IGKV3-20). The human germline VL framework may be the framework of DPK15 (IMGT name: IGKV2-28). The human germline VL framework may be the framework of DPL16 (IMGT name: IGLV3-19). The human germline VL framework may be the framework of DPL8 (IMGT name: IGLV1-40). The human germline VL framework may be the framework of V1-22 (IMGT name: IGLV6-57). The human germline VL framework may be the framework of human Vλ consensus sequence. The human germline VL framework may be the framework of human Vλ1 consensus sequence. The human germline VL framework may be the framework of human Vλ3 consensus sequence. The human germline VL framework may be the framework of human VK consensus sequence. The human germline VL framework may be the framework of human Vκ1 consensus sequence. The human germline VL framework may be the framework of human Vκ2 consensus sequence. The human germline VL framework may be the framework of human Vκ3 consensus sequence.

In some aspects, the VL framework is DPK9. Other similar framework regions are also predicted to deliver advantageous antibodies of the invention comprising CDRs of SEQ ID NOs: 257, 261, an 265; or SEQ ID NOs: 258, 262, and 266; or SEQ ID NOs: 259, 263, and 267; or SEQ ID NOs: 260, 264, an 268; or SEQ ID NOs: 20, 21, and 208; including DPK5, DPK4, DPK1, IGKV1-5*01, DPK24, DPK21, DPK15, IGKV1-13*02, IGKV1-17*01, DPK8, IGKV3-11*01, and DPK22 which comprise 99, 97, 97, 96, 80, 76, 66, 97, 97, 96, 76, and 74% identity respectively to the FW region of DPK-9 and one or fewer amino acid differences in common structural features (Kabat Numbering) (A) residues directly underneath CDR (Vernier Zone), L2, L4, L35, L36, L46, L47, L48, L49, L64, L66, L68, L69, L71, (B) VH/VL Chain packing Residues: L36, L38, L44, L46, L87 and (C) canonical CDR Structural support residues L2, L48, L64, L71 (see Lo, "Antibody Humanization by CDR Grafting", (2004) Antibody Engineering, Vol. 248, Methods in Molecular Biology pp 135-159 and O'Brien and Jones, "Humanization of Monoclonal Antibodies by CDR Grafting", (2003) Recombinant Antibodies for Cancer Therapy, Vol. 207, Methods in Molecular Biology pp 81-100). Particularly preferred are framework regions of DPK5, DPK4, DPK1, IGKV1-5*01, DPK24, DPK21, DPK15 sharing 99, 97, 97, 96, 80, 76, 66% identity to DPK9 respectively and have no amino acid differences in these common structural features. In some aspects, the % identity is based on similarity with VL excluding those portions herein defined as CDRs.

Residues in CDR-L1, CDR-L2, and CDR-L3 of the antibodies (and fragments) of the invention may be substituted with the corresponding germline residues as shown in Table 2.

TABLE 1

| SEQ ID | | Light CHain |
|---|---|---|
| 280 | DPK9 CDR-L1 | RASQSISSYLN |
| 281 | DPK9 CDR-L2 | AASSLQS |
| 282 | DPK9 CDR-L3 | QQSYSTP |
| 283 | DPK12 CDR-L1 | KSSQSLLHSDGKTYLY |
| 284 | DPK12 CDR-L2 | EVSNRFS |
| 285 | DPK12 CDR-L3 | MQSIQLP |
| 286 | DPK18 CDR-L1 | RSSQSLVYSDGNTYLN |
| 287 | DPK18 CDR-L2 | KVSNRDS |
| 288 | DPK18 CDR-L3 | MQGTHWP |
| 289 | DPK24 CDR-L1 | KSSQSVLYSSNNKNYLA |
| 290 | DPK24 CDR-L2 | WASTRES |
| 291 | DPK24 CDR-L3 | QQYYSTP |
| 292 | HK102_V1 CDR-L1 | RASQSISSWLA |
| 293 | HK102_V1 CDR-L2 | DASSLES |
| 294 | HK102_V1 CDR-L3 | QQYNSYS |
| 295 | DPK1 CDR-L1 | QASQDISNYLN |
| 296 | DPK1 CDR-L2 | DASNLET |
| 297 | DPK1 CDR-L3 | QQYDNLP |
| 298 | DPK8 CDR-L1 | RASQGISSYLA |
| 299 | DPK8 CDR-L2 | AASTLQS |
| 300 | DPK8 CDR-L3 | QQLNSYP |
| 301 | DPK21 CDR-L1 | RASQSVSSNLA |
| 302 | DPK21 CDR-L2 | GASTRAT |
| 303 | DPK21 CDR-L3 | QQYNNWP |
| 304 | Vg_38K CDR-L1 | RASQSVSSYLA |
| 305 | Vg_38K CDR-L2 | DASNRAT |
| 306 | Vg_38K CDR-L3 | QQRSNWP |
| 307 | DPK22 CDR-L1 | RASQSVSSSYLA |
| 308 | DPK22 CDR-L2 | GASSRAT |
| 309 | DPK22 CDR-L3 | QQYGSSP |
| 310 | DPK15 CDR-L1 | RSSQSLLHSNGYNYLD |
| 311 | DPK15 CDR-L2 | LGSNRAS |

TABLE 1 -continued

| SEQ ID | | Light CHain |
|---|---|---|
| 312 | DPK15 CDR-L3 | MQALQTP |
| 313 | DPL16 CDR-L1 | QGDSLRSYYAS |
| 314 | DPL16 CDR-L2 | GKNNRPS |
| 315 | DPL16 CDR-L3 | NSRDSSGNH |
| 316 | DPL8 CDR-L1 | TGSSSNIGAGYDVH |
| 317 | DPL8 CDR-L2 | GNSNRPS |
| 318 | DPL8 CDR-L3 | QSYDSSLSG |
| 319 | V1-22 CDR-L1 | TRSSGSIASNYVQ |
| 320 | V1-22 CDR-L2 | EDNQRPS |
| 321 | V1-22 CDR-L3 | QSYDSSN |
| 322 323 | Vλ CDR-L1 | TGSSSGGSYYVS or TGSSSDVGGSYYVS |
| 324 325 | Vλ CDR-L2 | ENDSNRPS or EDSNR(S/D)K(Q/G)QKPS |
| 326 327 | Vλ CDR-L3 | QSWDSSA(N/T) or QSWDSSA(N/T)F(F/V)(G/V) |
| 328 329 | Vλ1 CDR-L1 | SGSSSNIGNN(A/Y)V(N/H/S) or SGSSSNIIGNN(A/Y)V(N/H/S) |
| 330 | Vλ1 CDR-L2 | GNN(K/N/Q)RPS |
| 331 | Vλ1 CDR-L3 | AAWDDSL(N/S)G |
| 332 | Vλ3 CDR-L1 | CSGD(A/V)LG(K/S)KYAH |
| 333 | Vλ3 CDR-L2 | KDSERPS |
| 334 335 | Vλ3 CDR-L3 | QSWDSSG(N/D/T/A) or QSWDSSG(N/D/T/A)H |
| 336 337 | VK CDR-L1 | RASQSLLHSDGISSYLA or RASQGISSYLA |
| 338 | VK CDR-L2 | AASSRAS |
| 339 | VK CDR-L3 | QQYNSYP |
| 340 | VK1 CDR-L1 | RASQGIS(N/S)YLA |
| 341 | VK1 CDR-L2 | AASSLQS |
| 342 | VK1 CDR-L3 | QQYNSYP |
| 343 344 | VK2 CDR-L1 | RSSQSLLHSDGNTYLD or RSSQSLLHSDDGNTYLD |
| 345 | VK2 CDR-L2 | (K/T)(V/I)SNR(A/F)S |
| 346 | VK2 CDR-L3 | MQATQ FP |
| 347 | VK3 CDR-L1 | RASQS(S/V)(S/V)SSYLA |
| 348 | VK3 CDR-L2 | GASTRAT |
| 349 | VK3 CDR-L3 | QQY(S/N/G/H)NWP |
| 350 | DPK3 CDR-L1 | RASQGIRNDLG |

TABLE 1-continued

| SEQ ID | | Light CHain |
|---|---|---|
| 351 | DPK3 CDR-L2 | AASSLQS |
| 352 | DPK3 CDR-L3 | LQDYNYPLT |

Alternative sequences are provided for the consensus sequence with and without gaps. At positions where there is no consensus, residues in( )are those that are tied for the most frequent residues.

The antibody, or antigen-binding fragment thereof, may comprise a VH framework comprising a human germline VH framework sequence. The VH framework may comprise one or more amino acid substitutions, additions, or deletions, while still retaining functional and structural similarity with the germline from which it was derived. In some aspects, the VH framework is at least 90%, at least 91%, at least 92%, at least 93%, at least 94%, at least 95%, at least 96%, at least 97%, at least 98%, at least 99%, or 100% identical to a human germline VH framework sequence. In some aspects, the antibody, or antigen binding fragment thereof, comprises a VH framework comprising 1, 2, 3, 4, 5, 6, 7, 8, 9, 10 amino acid substitutions, additions or deletions relative to the human germline VH framework sequence. In some aspects, the 1, 2, 3, 4, 5, 6, 7, 8, 9, or 10 amino acid substitutions, additions or deletions are only in the framework regions. In some aspects, the % identity is based on similarity with VH excluding those portions herein defined as CDRs.

The human germline VH framework may be the framework of DP54 or IGHV3-7. The human germline VH framework may be the framework of DP47 or IGHV3-23. The human germline VH framework may be the framework of DP71 or IGHV4-59. The human germline VH framework may be the framework of DP75 or IGHV1-2_02. The human germline VH framework may be the framework of DP10 or IGHV1-69. The human germline VH framework may be the framework of DP7 or IGHV1-46. The human germline VH framework may be the framework of DP49 or IGHV3-30. The human germline VH framework may be the framework of DP51 or IGHV3-48. The human germline VH framework may be the framework of DP38 or IGHV3-15. The human germline VH framework may be the framework of DP79 or IGHV4-39. The human germline VH framework may be the framework of DP78 or IGHV4-30-4. The human germline VH framework may be the framework of DP73 or IGHV5-51. The human germline VH framework may be the framework of DP50 or IGHV3-33. The human germline VH framework may be the framework of DP46 or IGHV3-30-3. The human germline VH framework may be the framework of DP31 or IGHV3-9. The human germline VH framework may be the framework of human VH germline consensus sequence. The human germline VH framework may be the framework of human VH3 germline consensus sequence. The human germline VH framework may be the framework of human VH5 germline consensus sequence. The human germline VH framework may be the framework of human VH1 germline consensus sequence. The human germline VH framework may be the framework of human VH4 germline consensus sequence.

In some aspects, the VH framework is DP-54. Other similar framework regions are also predicted to deliver advantageous antibodies of the invention comprising CDRs of SEQ ID NOs: 269, 272, and 276; or SEQ ID NOs: 270, 273, and 277; or SEQ ID NOs: 271, 274, and 278; or SEQ ID NOs: 271, 275, and 278; or SEQ ID NOs: 16, 226, and 18; including DP-50, IGHV3-30*09, IGHV3-30*15, IGHV3-48*01, DP-77, DP-51, IGHV3-66*01, DP-53, DP-48, IGHV3-53*01, IGHV3-30*02, and DP-49 which comprise 93, 92, 92, 99, 97, 97, 96, 96, 94, 94, 93, 92% identity respectively to the FW region of DP-54 and one or fewer amino acid differences in common structural features (Kabat Numbering) (A) residues directly underneath CDR (Vernier Zone), H2, H47, H48, and H49, H67, H69, H71, H73, H93, H94, (B) VH/VL Chain packing Residues: H37, H39, H45, H47, H91, H93 and (C) canonical CDR Structural support residues H24, H71, H94 (see Lo 2004, and O'Brien and Jones 2003). Particularly preferred are framework regions of DP-50, IGHV3-30*09, IGHV3-30*15 sharing 93, 92 and 92% identity to DP-54 respectively and have no amino acid differences in these common structural features. In some aspects, the % identity is based on similarity with VH excluding those portions herein defined as CDRs.

Residues in CDR-H1, CDR-H2, and CDR-H3 of the antibodies (and fragments) of the invention may be substituted with the corresponding germline residues as shown in Table 3.

TABLE 3

| SEQ ID | | Heavy Chain |
|---|---|---|
| 353 | DP54 CDR-H1 | GFTFSSYWMS |
| 354 | DP54 CDR-H2 | ANIKQDGSEKYYVDSVKG |
| 355 | DP47 CDR-H1 | GFTFSSYAMS |
| 356 | DP47 CDR-H2 | AISGSGGSTYYADSVKG |
| 357 | DP71 CDR-H1 | GGSISSYYWS |
| 358 | DP71 CDR-H2 | GYIYYSGSTNYNPSLKS |
| 359 | DP75 CDR-H1 | GYTFTGYYMH |
| 360 | DP75 CDR-H2 | GWINPNSGGTNYAQKFQG |
| 361 | DP10 CDR-H1 | GGTFSSYAIS |
| 362 | DP10 CDR-H2 | GGIIPIFGTANYAQKFQG |
| 363 | DP7 CDR-H1 | GYTGTSYYMH |
| 364 | DP7 CDR-H2 | GIINPSGGSTSYAQKFQG |
| 365 | DP49 CDR-H1 | GFTFSSYGMH |
| 366 | DP49 CDR-H2 | AVISYDGSNKYYADSVKG |
| 367 | DP51 CDR-H1 | GFTFSSYSMN |
| 368 | DP51 CDR-H2 | SYISSSSSTIYYADSVKG |
| 369 | DP38 CDR-H1 | GFTFSNAWMS |
| 370 | DP38 CDR-H2 | GRIKSKTDGGTTDYAAPVKG |
| 371 | DP79 CDR-H1 | GGSISSSSYYWG |
| 372 | DP79 CDR-H2 | GSIYYSGSTYYNPSLKS |
| 373 | DP78 CDR-H1 | GGSISSGDYYWS |
| 374 | DP78 CDR-H2 | GYIYYSGSTYYNPSLKS |
| 375 | DP73 CDR-H1 | GYSFTSYWIG |
| 376 | DP73 CDR-H2 | GIIYPGDSDTRYSPSFQG |

TABLE 3 -continued

| SEQ ID | | Heavy Chain |
|---|---|---|
| 377 | VH consensus | GFTFSSYAM(H/S)or |
| 378 | CDR-H1 | GFTFSSYAM(H/S)WS |
| 379 | VH consensus | GWISPNGGSTYYADSVKG or |
| 380 | CDR-H2 | GWISPKANGGSTYYADSVKG |
| 381 | VH3 consensus CDR-H1 | GFTFSSYAMS |
| 382 | VH3 consensus | SVISSDG(G/S)STYYADSVKG or |
| 383 | CDR-H2 | SVISSKADG(G/S)STYYADSVKG |
| 384 | VH5 consensus CDR-H1 | GYSFTSYWI(S/G/H) |
| 385 | VH5 consensus CDR-H2 | G(R/I/S)IYPGDSDTRYSPSFQG |
| 386 | VH1 consensus CDR-H1 | GYTFTSY(A/Y)(I/M)H |
| 387 | VH1 consensus CDR-H2 | GWINP(G/Y)NGNTNYAQKFQ |
| 388 | VH4 consensus CDR-H1 | GGSISSG(N/Y)YYWS |
| 389 | VH4 consensus CDR-H2 | GYIYYSGSTYYNPSLKS |
| 390 | DPK50 CDR-L1 | GFTFSSYGMH |
| 391 | DPK50 CDR-L2 | VIWYDGSNKYYADSAKG |
| 392 | DPK46 CDR-L1 | GFTFSSYAMH |
| 393 | DPK46 CDR-L2 | VISYDGSNKYYADSVKG |
| 394 | DPK31 CDR-L1 | GFTFDDYAMH |
| 395 | DPK31 CDR-L2 | GISWNSGSIGYADSVKG |

Alternative sequences are provided for the consensus sequence with and without gaps. At positions where there is no consensus, residues in( )are those that are tied for the most frequent residues.

In certain embodiments, the antibody, or antigen-binding fragment thereof, described herein comprises (i) a VH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:225, and/or (ii) a VL comprising an amino acid sequence that is at least 50%, at least 60%, at least 66%, at least 70%, at least 75%, at least 76%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:207. Any combination of these VL and VH sequences is also encompassed by the invention.

In certain embodiments, the antibody, or antigen-binding fragment thereof, described herein comprises (i) a HC comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:244; and/or (ii) a LC comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:209. Any combination of these HC and LC sequences is also encompassed by the invention.

In certain embodiments, the antibody, or antigen-binding fragment thereof, described herein comprises an Fc domain. The Fc domain can be derived from IgA (e.g., $IgA_1$ or $IgA_2$), IgG, IgE, or IgG (e.g., $IgG_1$, $IgG_2$, $IgG_3$, or $IgG_4$).

In some embodiments, the antibody, or antigen-binding fragment thereof, described herein comprises (i) a VH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to one of the group consisting of SEQ ID NOs: 14, 32, 43, 54, 61, 72, 90, 94, 97, 101, 106, 111, 113, 118, 121, 124, 126, 129, 132, 135, 138, 141, 144, 147, 150, 152, 155, 158, 161, 163, 165, 167, 170, 173, 176, 179, 182, 184, 186, 201, 204, 210, 213, 216, 219, 222, 225, 228, 231, and 234, and/or (ii) a VL comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to any of SEQ ID NOs:19, 36, 47, 56, 65, 76, 81, 84, 86, 88, 91, 98, 103, 108, 115, 189, 192, 195, 198, and 207. Any combination of these VL and VH sequences is also encompassed by the invention. In some aspects, the VH is not one or more selected from the group consisting of SEQ ID NOs:43, 54, and 101. In some aspects, the VL is not one or more selected from the group consisting of SEQ ID NOs:47, 56, and 103.

Also provided by the invention is an antibody, or antigen-binding fragment thereof, that competes for binding to human IL-33 with any of the antibody, or antigen-binding fragment thereof, described herein, such as any one of the antibodies provided herein (or antigen-binding fragment thereof). For example, if the binding of an antibody, or an antigen-binding portion thereof, to human IL-33 hinders the subsequent binding to human IL-33 by IL33-158LS, the antibody or an antigen-binding portion thereof competes with IL33-158LS for human IL-33 binding.

Also provided by the invention is an antibody, or antigen-binding fragment thereof, that binds to the same human IL-33 epitope as any of the antibody, or antigen-binding fragment thereof, described herein, such as any one of the antibodies provided herein or antigen-binding fragment thereof. For example, antibody competition assay (and overlapping epitope analysis) can be assessed by SPR, as described in detail herein.

The antibodies and antigen-binding fragments provided by the invention include monoclonal antibodies, polyclonal antibodies, antibody fragments (e.g., Fab, Fab', F(ab')$_2$, Fv, Fc, etc.), chimeric antibodies, bispecific antibodies, heteroconjugate antibodies, single chain (ScFv), mutants thereof, fusion proteins comprising an antibody portion, domain antibodies (dAbs), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies and antigen-binding fragments may be murine, rat, human, or any other origin (including chimeric or humanized antibodies). In some embodiments, the antibody is a monoclonal antibody. In some embodiments, the antibody is a chimeric, humanized or human antibody. In certain embodiments, the antibody is a human antibody. In certain embodiments, the antibody is a humanized antibody.

Biological Deposit

Representative materials of the present invention were deposited in the American Type Culture Collection, 10801 University Boulevard, Manassas, Va. 20110-2209, USA, on 23 Dec. 2015. Vector VH-IL33-158LS having ATCC Accession No. PTA-122724 comprises a DNA insert encoding the heavy chain variable region of antibody IL33-158LS, and vector VL-IL33-158LS having ATCC Accession No. PTA-122725 comprises a DNA insert encoding the light chain variable region of antibody IL33-158LS. The deposits were made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, and subject to an agreement between Pfizer Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. Section 122 and the Commissioner's rules pursuant thereto (including 37 C.F.R. Section 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

Nucleic Acids

The invention also provides polynucleotides encoding any of the antibodies, including antibody portions and modified antibodies described herein. The invention also provides a method of making any of the polynucleotides described herein. Polynucleotides can be made and expressed by procedures known in the art.

The sequence of a desired antibody, defined antibody fragment, or antigen-binding fragment thereof, and nucleic acid encoding such antibody, or fragment thereof, can be determined using standard sequencing techniques. A nucleic acid sequence encoding a desired antibody, defined antibody fragment, or antigen-binding fragment thereof, may be inserted into various vectors (such as cloning and expression vectors) for recombinant production and characterization. A nucleic acid encoding the heavy chain, defined antibody fragment, or an antigen-binding fragment of the heavy chain, and a nucleic acid encoding the light chain, defined antibody fragment, or an antigen-binding fragment of the light chain, can be cloned into the same vector, or different vectors.

In one aspect, the invention provides polynucleotides encoding the amino acid sequences of any of the following IL-33 antibodies and antigen-binding portions thereof: 7E8_chimera, 9B3_chimera, 9B3_chimera_huJseg, 7E8 CDR graft, IL33-10, 9B3 CDR graft, 9B3_1, 9B3_2A, 9B3_2B, 9B3_3, 9B3_5, 9B3_79B3_13, 9B3_15, 9B3_17, 9B3_22, 9B3_31V2, 9B3_36, 9B3_79, 9B3_124, 9B3_162, 7E8H/9B3K, 9B3_563, IL33-11, IL33-12, IL33-13, IL33-45, IL33-55, IL33-56, IL33-57, IL33-58, IL33-61, IL33-62, IL33-68, IL33-74, IL33-75, IL33-80, IL33-81, IL33-103, IL33-117, IL33-136, IL33-153, IL33-154, IL33-155, IL33-156, IL33-157, IL33-158, IL33-167, IL33-168, IL33-169, IL33-170, IL33-171, IL33-172, IL33-175, IL33-186, IL33-187, IL33-188, IL33-158-152, IL33-167-153, IL33-158LS, and IL33-167LS.

The invention provides polynucleotides encoding the amino acid sequences an antibody, or antigen-binding fragment thereof, that binds substantial the same epitope as an antibody selected from the group consisting of: 7E8_chimera, 9B3_chimera, 9B3_chimera_huJseg, 7E8 CDR graft, IL33-10, 9B3 CDR graft, 9B3_1, 9B3_2A, 9B3_2B, 9B3_3, 9B3_5, 9B3_79B3_13, 9B3_15, 9B3_17, 9B3_22, 9B3_31V2, 9B3_36, 9B3_79, 9B3_124, 9B3_162, 7E8H/9B3K, 9B3_563, IL33-11, IL33-12, IL33-13, IL33-45, IL33-55, IL33-56, IL33-57, IL33-58, IL33-61, IL33-62, IL33-68, IL33-74, IL33-75, IL33-80, IL33-81, IL33-103, IL33-117, IL33-136, IL33-153, IL33-154, IL33-155, IL33-156, IL33-157, IL33-158, IL33-167, IL33-168, IL33-169, IL33-170, IL33-171, IL33-172, IL33-175, IL33-186, IL33-187, IL33-188, IL33-158-152, IL33-167-153, IL33-158LS, and IL33-167LS.

The invention provides polynucleotides encoding the amino acid sequences of an antibody, or antigen-binding fragment thereof, that competes for binding to IL-33 with an antibody selected from the group consisting of: 7E8_chimera, 9B3_chimera, 9B3_chimera_huJseg, 7E8 CDR graft, IL33-10, 9B3 CDR graft, 9B3_1, 9B3_2A, 9B3_2B, 9B3_3, 9B3_5, 9B3_79B3_13, 9B3_15, 9B3_17, 9B3_22, 9B3_31V2, 9B3_36, 9B3_79, 9B3_124, 9B3_162, 7E8H/9B3K, 9B3_563, IL33-11, IL33-12, IL33-13, IL33-45, IL33-55, IL33-56, IL33-57, IL33-58, IL33-61, IL33-62, IL33-68, IL33-74, IL33-75, IL33-80, IL33-81, IL33-103, IL33-117, IL33-136, IL33-153, IL33-154, IL33-155, IL33-156, IL33-157, IL33-158, IL33-167, IL33-168, IL33-169, IL33-170, IL33-171, IL33-172, IL33-175, IL33-186, IL33-187, IL33-188, IL33-158-152, IL33-167-153, IL33-158LS, and IL33-167LS.

The invention provides polynucleotides encoding one or more proteins comprising the amino acid sequence selected from the group consisting of: (i) SEQ ID NOs:1-279.

The invention provides polynucleotides comprising the nucleic acid sequence as set forth as one or more of SEQ ID NOs: 398, 399, 400, and 401. The invention provides a polynucleotide comprising the nucleic acid sequence as set forth as SEQ ID NO:398. The invention provides a polynucleotide comprising the nucleic acid sequence as set forth as SEQ ID NO:399. The invention provides a polynucleotide comprising the nucleic acid sequence as set forth as SEQ ID NO:400. The invention provides a polynucleotide comprising the nucleic acid sequence as set forth as SEQ ID NO:401.

The invention provides a polynucleotide comprising one or both of the coding sequence of the DNA insert of the nucleic acid molecule deposited with the ATCC and having Accession No. PTA-122724, and Accession No. PTA-122725. The invention provides a polynucleotide comprising the nucleic acid molecule deposited with the ATCC and having Accession No. PTA-122724. The invention provides a polynucleotide comprising the nucleic acid molecule deposited with the ATCC and having Accession No. PTA-122725.

The invention provides cells comprising one or more nucleic acid molecules as set forth in one or more of SEQ ID NOs: 398, 399, 400, and 401. The invention provides cells comprising one or more nucleic acid molecules as set forth in SEQ ID NOs:398 and 399. The invention provides cells comprising one or more nucleic acid molecules as set forth in SEQ ID NOs:400 and 401.

In another aspect, the invention provides polynucleotides and variants thereof encoding an anti-IL-33 antibody, wherein such variant polynucleotides share at least 70%, at least 75%, at least 80%, at least 85%, at least 87%, at least 89%, at least 90%, at least 91%, at least 92%, at least 93%, at least 94%, at least 95%, at least 96%, at least 97%, at least 98%, or at least 99% sequence identity to any of the specific nucleic acid sequences disclosed herein. These amounts are not meant to be limiting, and increments between the recited percentages are specifically envisioned as part of the disclosure.

The invention provides polypeptides encoded by the nucleic acid molecules described herein.

In one embodiment, the VH and VL domains, or antigen-binding portion thereof, or full length HC or LC, are encoded by separate polynucleotides. Alternatively, both VH and VL, or antigen-binding portion thereof, or HC and LC, are encoded by a single polynucleotide.

Polynucleotides complementary to any such sequences are also encompassed by the present disclosure. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present disclosure, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. In some embodiments, variants exhibit at least about 70% identity, in some embodiments, at least about 80% identity, in some embodiments, at least about 90% identity, and in some embodiments, at least about 95% identity to a polynucleotide sequence that encodes a native antibody or a portion thereof. These amounts are not meant to be limiting, and increments between the recited percentages are specifically envisioned as part of the disclosure.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the MegAlign® program in the Lasergene® suite of bioinformatics software (DNASTAR®, Inc., Madison, Wis.), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645 Methods in Enzymology vol. 183, Academic Press, Inc., San Diego, Calif.; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, Calif.; Wilbur, W. J. and Lipman, D. J., 1983, Proc. Natl. Acad. Sci. USA 80:726-730.

In some embodiments, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include pre-washing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/mL), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present disclosure. Further, alleles of the genes comprising the polynucleotide sequences provided herein are within the scope of the present disclosure. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this disclosure can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, for example.

Suitable cloning and expression vectors can include a variety of components, such as promoter, enhancer, and other transcriptional regulatory sequences. The vector may also be constructed to allow for subsequent cloning of an antibody variable domain into different vectors. Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratagene, and Invitrogen. Expression vectors are further provided. Expression vectors generally are replicable polynucleotide constructs that contain a polynucleotide according to the disclosure. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest and/or the polynucleotides themselves, can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The antibody, or antigen-binding fragment thereof, may be made recombinantly using a suitable host cell. A nucleic acid encoding the antibody or antigen-binding fragment thereof can be cloned into an expression vector, which can then be introduced into a host cell, such as E. coli cell, a yeast cell, an insect cell, a simian COS cell, a Chinese hamster ovary (CHO) cell, or a myeloma cell where the cell does not otherwise produce an immunoglobulin protein, to obtain the synthesis of an antibody in the recombinant host cell. Preferred host cells include a CHO cell, a Human embryonic kidney (HEK) 293 cell, or an Sp2.0 cell, among many cells well-known in the art. An antibody fragment can be produced by proteolytic or other degradation of a full-length antibody, by recombinant methods, or by chemical synthesis. A polypeptide fragment of an antibody, especially shorter polypeptides up to about 50 amino acids, can be conveniently made by chemical synthesis. Methods of chemical synthesis for proteins and peptides are known in the art and are commercially available.

The antibody, or antigen-binding fragment thereof, of the invention may be affinity matured. For example, an affinity matured antibody can be produced by procedures known in the art (Marks et al., 1992, Bio/Technology, 10:779-783; Barbas et al., 1994, Proc Nat. Acad. Sci, USA 91:3809-3813; Schier et al., 1995, Gene, 169:147-155; Yelton et al., 1995, J. Immunol., 155:1994-2004; Jackson et al., 1995, J. Immunol., 154(7):3310-9; Hawkins et al., 1992, J. Mol. Biol., 226:889-896; and WO2004/058184).

Uses and Medical Therapies

In some aspects, the invention provides for therapeutic methods for inhibiting IL-33 activity using an anti-IL-33 antibody or antigen-binding fragment thereof, wherein the therapeutic methods comprise administering a therapeutically effective amount of a pharmaceutical composition comprising an antibody or antigen-binding fragment thereof. The disorder treated is any disease or condition which is improved, ameliorated, inhibited or prevented by removal, inhibition or reduction of IL-33 activity or signaling.

In some aspects, the disorder is an inflammatory disease or disorder, or a condition with at least one symptom associated with the inflammatory disease or disorder. The inflammatory disease or disorder or symptom may be alleviated, or reduced in severity, duration or frequency of occurrence.

Allergic as well as other diseases at mucosal or body surfaces where antibodies and antigen binding fragments thereof of the invention may be effective include: allergies, allergic rhinitis, allergic conjunctivitis, vernal keratoconjunctivitis, seasonal allergies, pet allergy, asthma, food allergies, peanut allergy, atopic dermatitis, chronic rhinosinusitis with nasal polyps (CRSwNP), allergic rhinitis, bronchitis, chronic obstructive pulmonary disease (COPD), viral exacerbations of respiratory disease, viral infections in children and adults, (respiratory syncytial virus (RSV), rhinovirus, influenza), urticarias, and eosinophilic esophagitis. Diseases involving chronic fibrosis may also be treated by antibodies and antigen binding fragments thereof of the invention. These include: liver fibrosis, non-alcoholic steatohepatitis (NASH), chronic kidney disease, idiopathic pulmonary fibrosis (IPF), scleroderma, systemic sclerosis. Disease involving acute tissue injury may also be treated by antibodies and antigen binding fragments thereof of the invention, including: Acute kidney injury, sepsis, pancreatitis, type 1 Diabetes, graft-versus-host disease (GVHD), tissue transplant. Other chronic degenerative or chronic inflammatory diseases that may be treated with antibodies and antigen binding fragments thereof of the invention, include: Alzheimer's, rheumatoid arthritis, inflammatory bowel diseases: irritable bowel syndrome (IBS), Crohn's disease, ulcerative colitis. Further diseases that may be treated with antibodies and antigen binding fragments thereof of the invention include multiple sclerosis, psoriasis, celiac disease and Raynaud's disease.

The antibodies and antibody fragments thereof may be administered in combination with one or more additional therapeutically active compounds. The additional therapeutically active compounds include antagonists to one or more of IL-la, IL-1b, IL-2, IL-3, IL-4, IL-5, IL-6, IL-8, IL-9, IL-10, IL-12, IL-13, IL-17, IL-18, IL-21, IL-23, IL-25, IL-26, IL-31, IL36 IFNα, IFNγ, or antagonists of their respective receptors, NSAIDs, steroids, and corticosteroids.

The anti-IL-33 antibodies of the present invention may also be used to detect and/or measure IL-33, or IL-33-expressing cells in a sample, e.g., for diagnostic purposes. For example, an anti-IL-33 antibody, or fragment thereof, may be used to diagnose a condition or disease characterized by aberrant expression (e.g., over-expression, under-expression, lack of expression, etc.) of IL-33. Exemplary diagnostic assays for IL-33 may comprise, e.g., contacting a sample, obtained from a patient, with an anti-IL-33 antibody of the invention, wherein the anti-IL-33 antibody is labeled with a detectable label or reporter molecule.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy, 20th Ed., Mack Publishing, 2000).

Compositions

The antibody, or antigen-binding fragment thereof, of the invention can be formulated as a pharmaceutical composition. The pharmaceutical composition may further comprise a pharmaceutically acceptable carrier, excipient, and/or stabilizer (Remington: The Science and practice of Pharmacy 20th Ed., 2000, Lippincott Williams and Wilkins, Ed. K. E. Hoover), in the form of lyophilized formulation or aqueous solution. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Pharmaceutically acceptable excipients are further described herein.

Dosage

As used herein, an "effective dosage", "effective amount", or "therapeutically effective amount" of drug, compound, or pharmaceutical composition is an amount sufficient to effect any one or more beneficial or desired results. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing inflammation or one or more symptoms resulting from high expression of active IL-33, decreasing the dose of other medications required to treat the disease, enhancing the effect of another medication, and/or delaying the progression of the disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably, a human. Mammals also include, but are not limited to, farm animals, sport animals, pets, primates, horses, dogs, cats, mice and rats.

In some embodiments, the method or use comprises administering an initial dose of about 0.025 mg/kg to about 20 mg/kg of an antibody, or antigen binding fragment thereof, or a pharmaceutical composition of the invention. The initial dose may be followed by one or more subsequent doses. In some embodiments, one or more subsequent dose may be administered at least any of weekly, every other week, every three weeks, every four weeks, every five weeks, every six weeks, every seven weeks, every eight weeks, every nine weeks, every ten weeks, every eleven weeks, or every twelve weeks.

In some embodiments, the method or use comprises administering a fixed dose of about 0.25 mg to about 2000 mg of an antibody, or antigen binding fragment thereof, of the invention. In some embodiments, the antibody, or antigen binding fragment thereof, is administered weekly, every other week, every three weeks, every four weeks, every five weeks, every six weeks, every seven weeks, every eight weeks, every nine weeks, every ten weeks, every eleven weeks, or every twelve weeks.

Kits

The invention also provides kits or an article of manufacture comprising an antibody, or antigen binding fragment thereof, of the invention, and instructions for use. Accordingly, in some embodiments, provided is a kit or an article of manufacture, comprising a container, a composition within the container comprising an anti-IL-33 antagonist antibody, and a package insert containing instructions to administer a therapeutically effective amount of the anti-IL-33 antagonist antibody for treatment of a patient in need thereof.

In certain embodiments, the kit can contain both a first container having a dried protein and a second container having an aqueous formulation. In certain embodiments, kits containing single and multi-chambered pre-filled syringes (e.g., liquid syringes and lyosyringes) are included.

The instructions relating to the use of antibodies or antigen binding fragments thereof of the invention generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). The container may further comprise a second pharmaceutically active agent.

Kits may optionally provide additional components such as buffers and interpretive information. Normally, the kit comprises a container and a label or package insert(s) on or associated with the container.

Definitions

"About" or "approximately," when used in connection with a measurable numerical variable, refers to the indicated value of the variable and to all values of the variable that are within the experimental error of the indicated value (e.g. within the 95% confidence interval for the mean) or within 10 percent of the indicated value, whichever is greater. Numeric ranges are inclusive of the numbers defining the range.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The term "identity," as known in the art, refers to a relationship between the sequences of two or more polypeptide molecules or two or more nucleic acid molecules, as determined by comparing the sequences. In the art, "identity" also means the degree of sequence relatedness between polypeptide or nucleic acid molecule sequences, as the case may be, as determined by the match between strings of nucleotide or amino acid sequences. "Identity" measures the percent of identical matches between two or more sequences with gap alignments addressed by a particular mathematical model of computer programs (i. e. "algorithms").

The term "similarity" is a related concept, but in contrast to "identity", refers to a measure of similarity which includes both identical matches and conservative substitution matches. Since conservative substitutions apply to polypeptides and not nucleic acid molecules, similarity only deals with polypeptide sequence comparisons. If two polypeptide sequences have, for example, 10 out of 20 identical amino acids, and the remainder are all nonconservative substitutions, then the percent identity and similarity would both be 50%. If in the same example, there are 5 more positions where there are conservative substitutions, then the percent identity remains 50%, but the percent similarity would be 75% (15 out of 20). Therefore, in cases where there are conservative substitutions, the degree of similarity between two polypeptide sequences will be higher than the percent identity between those two sequences.

EXAMPLES

Exemplary methods and materials are described herein, although methods and materials similar or equivalent to those described herein can also be used in the practice or testing of the present invention. The materials, methods, and examples are illustrative only and not intended to be limiting.

Example 1 Isolation of Rat Monoclonal Antibodies that Bind to Human IL-33

Sprague-Dawley rats were immunized with multiple subcutaneous injections with recombinant human IL-33 (SEQ ID NO:1), amino acids S112-T270, R&D Systems, Minneapolis, Minn.; Cat. No. 3625-IL/CF) in alum adjuvant. Sera that showed binding activity to biotinylated human IL-33 immobilized on a streptavidin-coated ELISA plate were also screened for blockade of the binding of 10 ng/ml biotinylated human IL-33 to human ST2-Fc (SEQ ID NO:2) that had been captured by anti-human Fc immobilized on an ELISA plate. For assays, cytokine activity was maintained by reduction of wild-type IL-33 with dithiothreitol (DTT) or by using a human IL-33 variant, mm2 (SEQ ID NO:3), in which all four cysteine residues were mutated to serine.

From the rat with the highest titer, hybridomas and cultured B cells enriched on IL-33-coated beads were screened for antibodies with human IL-33 binding, blockade of human IL-33/ST2-Fc binding, and neutralization of human IL-33 activity on HEK-293 cells stably expressing ST2 and a plasmid expressing secreted alkaline phosphatase under an NFkB-responsive promoter. Two-hundred twenty-seven IL-33 binding antibodies were identified, of which 6 antibodies (30A1, 30B11, 7E8, 9B3, 12F9, and 14D8) also neutralized IL33-ST2 binding and reporter cell activity and were chosen for molecular cloning and subsequent analysis.

Example 2 Cloning of Rat Anti-IL-33 Antibody Heavy and Light Chain Variable Regions Heavy chain and light chain variable regions of the neutralizing anti-IL-33 antibodies were cloned using the SMART® cDNA synthesis system (Clontech Laboratories Inc. of Mountain View, Calif.) followed by PCR amplification. The cDNA was synthesized from 1 μg total RNA isolated from approximately 500,000 cloned B cells (14D8, 12F9) or 7E8, 9B3, 30A1, 30B11 hybridoma cells, using the RNEasy kit (Qiagen) and the SMART® IIA oligo (Clontech Laboratories Inc.) with SuperscriptII™ reverse transcriptase (Clontech Laboratories Inc.). The cDNA was then amplified by PCR using a primer that anneals to the SMART® IIA oligo sequence and rat constant region specific primer (rat Kappa for the light chain and rat IgG1 for the heavy chain) with GoTaq Green polymerase master mix (Promega). Heavy and light chain PCR products were subcloned into the pCR4-TOPO vector (Invitrogen) and the nucleic acid sequence was determined. This method was advantageous in that no prior knowledge of the DNA sequence is required. In addition, the resultant DNA sequence is not altered by use of degenerate PCR primers.

The variable heavy regions were then cloned into the pSMED2 mammalian expression vector containing the human IgG1 constant region (SEQ ID NO:9) that was mutated to abolish effector function (Leu234Ala, Leu235Ala and Gly237Ala, EU numbering; U.S. Pat. No. 5,624,821), producing chimeric heavy chains. Variable light regions were cloned into the pSMEN3 mammalian expression vectors containing the constant region of human kappa (SEQ ID NO:30) to produce chimeric light chains. In the cases of antibodies 9B3, 14D8, 30A1, and 30B11, the closest human kappa chain J segments (SEQ ID NOs:12, 82) were also used to replace the rat kappa chain J segments in order to improve expression of the chimeric antibodies.

Example 3 IL-33 Neutralization by Anti-Human IL-33 Antibodies

The six chimeric antibodies were shown to bind human IL-33 and to neutralize its activity in the HEK293 ST2 NFkB cell-based reporter assay described in Example 1, as shown in Table 4.

TABLE 4

Inhibition of IL-33 (mm2) activity in the HEK293 ST2 NFkB reporter cell assay by parental rat anti-IL-33 antibodies and rat/human chimeras thereof

| Antibody | HC SEQ NO | LC SEQ NO | HEK293 ST2 NFkB human IL-33(mm2) IC$_{50}$ (nM) | replicates |
|---|---|---|---|---|
| 7E8 hybridoma | | | 0.018 | 3 |
| 9B3 hybridoma | | | 0.076 | 3 |
| 30A1 hybridoma | | | 0.665 | 3 |
| 30B11 hybridoma | | | 0.056 | 3 |
| 7E8 chimera | 28 | 31 | 0.049 | 3 |
| 9B3 chimera/hu J | 40 | 83 | 0.056 | 3 |
| 30A1 chimera | 69 | 71 | 0.270 | 3 |
| 30B11 chimera/hu J | 78 | 89 | 0.028 | 3 |
| 12F9 chimera | 51 | 53 | 2.71 | 3 |
| 14D8 chimera/hu J | 59 | 85 | 2.03 | 3 |
| Enzo ALX-804-728 mAb (IL33026B) | | | 32.8% @ 952 nM | 3 |
| Enzo ALX-804-840 Nessy1 mAb | | | 238.74 | 3 |
| Abcam ab-72844 clone [4E9] mAb | | | 10.6% @ 952 nM | 3 |

The chimeric antibodies were also tested to determine their capacity to neutralize cynomolgus monkey IL33, using the HEK293 ST2 NFkB assay with a variant of cynomolgus monkey IL-33 in which its three cysteine residues were mutated to serine (SEQ ID NO:5). 7E8, 30A1, and 30B11 were able to neutralize cynomolgus monkey IL-33 at 0.21, 2.95, and 0.20 nM IC$_{50}$, respectively, while 12F8 and 14B8 were not, and 9B3 showed only weak neutralization (Table 5).

TABLE 5

Inhibition of cynomolgus monkey IL-33 activity in the ST2-NFkB reporter cell assay by anti-IL-33 antibodies. Antibodies were titrated against 0.1 ng/ml cynomolgus monkey IL33.

| Antibody | HC SEQ NO | LC SEQ NO | HEK293 ST2 NFkB cynomolgus monkey IL-33 IC$_{50}$ (nM) | replicates |
|---|---|---|---|---|
| Rat 7E8 | | | 0.21 | 3 |
| Rat 9B3 | | | 23%@20 nM | 3 |
| Rat 30A1 | | | 2.95 | 3 |
| Rat 30B11 | | | 0.20 | 3 |
| 9B3_chimera | 40 | 42 | 35%@20 nM | 3 |
| 12F9_chimera | 51 | 53 | 3.6%@20 nM | 3 |
| 30B11 chimera/hu J | 78 | 89 | 0.11 | 3 |
| 14D8 chimera/hu J | 59 | 85 | 11%@20 nM | 3 |
| human ST2-Fc | | 2 | 0.045 | 3 |

Example 4 Epitope Grouping of Anti-IL-33 Antibodies

The six neutralizing antibodies were grouped into epitope bins based on a competition assay using an Octet biosensor. Streptavidin-coated Octet tips were loaded with 10 ug/ml biotin-hIL-33 (mm2) for 150 sec., transferred to blocking buffer (1% BSA in PBS) for 50 sec, then transferred to a well containing one of the six antibodies for 290 sec to allow the first antibody to bind to IL-33. Tips were then transferred to a second well containing a second antibody for 290 sec. Antibodies were scored as non-competing if the second antibody showed an increase in the biosensor signal above that produced by the first antibody, and they were scored as competing if the second antibody did not produce an additional increase in signal (Table 6). Based on these competition data, antibodies 7E8, 9B3, 30A1, and 30B11 defined one epitope group, and 12F9 and 14D8 defined a second, non-overlapping epitope.

TABLE 6

Epitope grouping of anti-IL-33 antibodies by Octet biosensor

| 1st Ab (rows), 2nd Ab (columns) | 7E8 | 9B3 | 30A1 | 30B11 | 12F9 | 14D8 |
|---|---|---|---|---|---|---|
| 7E8 | − | − | − | − | + | + |
| 9B3 | − | − | − | − | + | + |
| 30A1 | − | − | − | − | + | + |
| 30B11 | − | − | − | − | + | + |
| 12F9 | + | + | + | + | − | − |
| 14D8 | + | + | + | + | − | − |

Table 6. Antibodies were bound sequentially to IL-33-saturated Octet tips. A "+" indicates that the second antibody (indicated by the column heading) bound in the presence of the first antibody (indicated by row headings). A "−" indicates that no increase in signal was observed upon addition of the second antibody.

Example 5 Humanization of Rat Anti-IL-33 Antibodies

Humanized versions of neutralizing rat antibodies 7E8, 9B3, 12F9, and 30B11 were generated by complementarity determining region (CDR) grafting (referred to hereafter as "CDR-grafted"). Heavy chain CDRs were grafted onto a human DP-54 framework region (VH3 sub-group; SEQ ID NO:7) with a JH4 segment (SEQ ID NO:8), while light chain CDRs were grafted onto a human DPK9 framework (VKI sub-group; SEQ ID NO:11) with a JK4 segment (SEQ ID NO:12). The humanized $V_H$ regions were joined to the effector-function mutated human IgG1 constant region (SEQ ID NO:9) and then sub-cloned into a proprietary expression vector to generate the CDR-grafted heavy chains SEQ ID NO:92 (7E8 CDR graft), 99 (9B3 CDR graft), 104 (12F9 CDR graft), and 109 (30B11 CDR graft). A second version of CDR-grafted 30B11 incorporated the rat residue (valine) at position 71 in the heavy chain instead of the germline arginine residue, with the resulting heavy chain designated SEQ ID NO:112. The humanized $V_L$ regions were fused to the human kappa constant region (SEQ ID NO:13) and then sub-cloned into a proprietary expression vector to create the CDR-grafted light chains SEQ ID NO:93 (7E8 CDR graft), 100 (9B3 CDR graft), 105 (12F8 CDR graft), and 110 (30B11 CDR graft). 7E8 was also grafted onto other VH3 germline frameworks (DP47, accession CAA78217.1; DP31, accession CAA78203.1; DP50, accession CAA78220.1) and had similar cell-based activity and non-specific binding to that of CDR-grafted 7E8 (SEQ ID NO:92, 93).

Example 6 Neutralization of Recombinant and Native Human IL-33 and Recombinant Cynomolgus Monkey IL-33 by Humanized IL-33 Antibodies CDR-grafted 7E8, 9B3, 12F9, and 30B11 were shown to neutralize the activity of human IL-33 in the HEK293 ST2 NFkB reporter assay described in Example 1. In particular, CDR-grafted 7E8 exhibited an $IC_{50}$ of 0.019 nM, nearly identical to the 0.024 nM $IC_{50}$ exhibited by the 7E8 hybridoma (Table 7). CDR-grafted 12F9 showed only partial inhibition at high concentration (Table 7) rather than the full inhibition with a 2.71 nM $IC_{50}$ observed for chimeric 12F9 (Table 4). CDR-grafted 9B3 and 30B11 had $IC_{50}$ values of 0.520 and 0.368 nM, respectively (Table 7), approximately 10-fold reduced activity relative to the chimeric versions of these antibodies (Table 4). A second version of CDR-grafted 30B11 containing the heavy-chain framework back-mutation R71V showed a similar reduction in potency compared with the chimera, 0.278 nM vs 0.028 nM $IC_{50}$ (Table 7, Table 4).

TABLE 7

Neutralization of human IL-33 (mm2) activity by CDR-grafted IL-33 antibodies in HEK293 ST2 NFkB reporter assay

| Antibody | HC SEQ NO | LC SEQ NO | $IC_{50}$ (nM) | replicates |
|---|---|---|---|---|
| 7E8 CDR-grafted | 92 | 93 | 0.019 | 3 |
| 9B3 CDR-grafted | 99 | 100 | 0.520 | 3 |
| 12F9 CDR-grafted | 104 | 105 | 34% @ 125 nM | 3 |
| 30B11 CDR-grafted | 109 | 110 | 0.368 | 3 |
| 30B11 CDR-grafted R71V | 112 | 110 | 0.278 | 3 |
| human ST2-Fc | | 2 | 0.043 | 3 |
| Rat 7E8 | | | 0.024 | 3 |

CDR-grafted 7E8 and the 7E8 hybridoma were further shown to have similar neutralizing potency in the ST2-NFkB reporter assay with cynomolgus monkey IL-33 (0.069 nM and 0.032 nM, respectively; Table 8), similar to their activity in the ST2-NFkB reporter assay with human IL-33 (mm2) (0.043 nM $IC_{50}$ for both CDR-grafted 7E8 and 7E8 hybridoma; Table 8). CDR-grafted 7E8 and the soluble human IL-33 receptor ST2-Fc showed similar neutralizing potency on human IL-33 (mm2) (0.043 nM and 0.056 nM, respectively) and on human IL-33 that retained the wild-type cysteine residues (3.21 nM and 1.89 nM, respectively; Table 8).

TABLE 8

Inhibition of IL-33 neutralization in the HEK293 ST2 NFkB assay by hybridoma-derived antibodies and CDR-grafted 7E8.

| Antibody | HC SEQ NO | LC SEQ NO | $IC_{50}$ HEK293 ST2 NFkB human IL-33 (mm2)(nM) | $IC_{50}$ HEK293 ST2 NFkB cyno IL-33 (nM) | $IC_{50}$ HEK293 ST2 NFkB human IL-33 (R&D)(nM) |
|---|---|---|---|---|---|
| 7E8 | | | 0.043 | 0.032 | ND |
| 9B3 | | | 0.17 | 2.72 | ND |
| 30A1 | | | 0.47 | 0.14 | ND |
| 30B11 | | | 0.038 | 0.084 | ND |

TABLE 8-continued

Inhibition of IL-33 neutralization in the HEK293 ST2 NFkB assay by hybridoma-derived antibodies and CDR-grafted 7E8.

| Antibody | HC SEQ NO | LC SEQ NO | $IC_{50}$ HEK293 ST2 NFkB human IL-33 (mm2)(nM) | $IC_{50}$ HEK293 ST2 NFkB cyno IL-33 (nM) | $IC_{50}$ HEK293 ST2 NFkB human IL-33 (R&D)(nM) |
|---|---|---|---|---|---|
| 7E8 CDR-grafted | 92 | 93 | 0.043 | 0.069 | 3.21 |
| human ST2-Fc | | 2 | 0.056 | 0.005 | 1.89 |

Table 8: Inhibition of IL-33 neutralization in the HEK293 ST2 NFkB assay by rat parental hybridoma-derived antibodies and humanized CDR-grafted 7E8. Dilution series of antibodies were tested against 0.1 ng/ml IL-33 (mm2), 0.1 ng/ml cynomolgus monkey IL-33, and 2 ng/ml human IL-33 (R&D). Assays were run in triplicate with a dose range of 0.0018-30 nM IL-33 (R&D). ND, not determined.

Example 7 Neutralization of the Activity of Native IL-33 from Human Cell Extracts by IL-33 Antibodies CDR-grafted 7E8 was further shown to neutralize the activity of native human IL-33 produced by cultured human lung fibroblasts. Early passages of the human lung fibroblast line HFL-1 (ATCC) were grown in DMEM+10% heat-inactivated fetal bovine serum (FBS)+L-glutamine/penicillin/streptomycin+1/100 HEPES. When cells reached 95-100% confluence, the medium was removed and replaced with the same medium without serum and incubated for 24 hr. Medium was then removed, replaced with 20 ng/ml TNF-α, and incubated for an additional 14 hr. Cells were harvested by trypsinization, pelleted, and frozen in serum-free medium. Lysates were prepared by five freeze-thaw cycles at −20° C., brought to 10 mM DTT, and samples were centrifuged and diluted for assessment of IL-33 activity. HFL-1 cell lysates were shown to activate the NFkB reporter gene in the HEK293 ST2 NFkB reporter assay, and this activity could be partially blocked by soluble human ST2-Fc (SEQ ID NO:2) and a polyclonal anti-IL-33 neutralizing antibody. Activity was fully blocked by rat antibodies 7E8, 9B3, 30A11, and 30B11 and chimeras and by chimeric 14D8, indicating that these antibodies can recognize and neutralize endogenous IL-33 produced in human primary cells.

Example 8 Anti-IL-33 Antibodies Neutralize IL-33 with High Potency

In order to measure the affinity for the binding of the antibody to IL-33 in an assay that is not affected by the concentration of ligand, experiments were designed with the HEK293 ST2 NFkB reporter assay system in which a Schild analysis could be performed to calculate an assay- and ligand concentration-independent measure of the affinity of 7E8 for IL-33 (Arunlakshana and Schild, 1959). The $EC_{50}$ of IL-33 was determined at multiple concentrations of 7E8 CDR graft (SEQ ID NOs:92, 93) in the NFkB ST2 reporter assay, and a kB of 6.01 pM was calculated (Table 10) for IL-33 (mm2) and 83.45 pM for wild-type IL-33 (R&D).

IL-33 is also a potent costimulator of IFNγ production from natural killer cells in the blood, when the costimulus is IL-12. Human peripheral blood mononuclear cells (PBMCs) were purified from fresh heparinized human blood by Ficoll and then treated with IL-12 for 2 hr., followed by treatment with a mixture of IL-33 at 5 pM and a dose titration of anti-IL-33 antibodies. The culture supernatant was collected 20 hrs after the addition of IL-33, and the levels of IFNγ measured by a MSD plate reader (Meso Scale Diagnostics, Rockville, Md.). In human PBMCs, similar to the observations made in the HEK293 ST2 NFkB reporter assay, 7E8 inhibition of IL-33 (mm2) produced a calculated kB of 1.04 and 6.64 pM in two donors. Thus, the apparent affinity of

TABLE 9

Inhibition of native human IL-33 from human lung fibroblast lysate by anti-IL-33 antibodies

| Antibody | HC SEQ NO | LC SEQ NO | % inhibition 10 nM Ab | % inhibition 1 nM Ab | % inhibition 0.1 nM Ab | replicates |
|---|---|---|---|---|---|---|
| 7E8 | | | 112.9 | 110.5 | 112.1 | 3 |
| 9B3 | | | 107.7 | 99.2 | 55.1 | 3 |
| 30A1 | | | 107.9 | 77.3 | 35.4 | 3 |
| 30B11 | | | 112.7 | 108.4 | 93.5 | 3 |
| 9B3 chimera | 40 | 42 | 111.3 | 96.0 | 52.5 | 3 |
| 12F9 chimera | 51 | 53 | 104.0 | 82.6 | 44.3 | 3 |
| 30A1 chimera/hu J | 69 | 87 | 107.2 | 98.5 | 63.8 | 3 |
| 30B11 chimera/huJ | 78 | 89 | 109.8 | 109.3 | 101.7 | 3 |
| 14D8 chimera/huJ | 59 | 60 | 107.2 | 99.6 | 61.1 | 3 |
| Human ST2-Fc | | 2 | 53.9 | 43.4 | 30.6 | 3 |
| R&D polyclonal anti-IL-33 Ab (AF3625) | | | 84.6 | −2.4 | −0.9 | 3 |
| Rat IgG1 isotype control | | | −8.2 | 2.5 | 1.9 | 3 |
| Human Fc control | | | −11.3 | −6.9 | −3.5 | 3 |

Table 9. Human lung fibroblast (HFL-1) lysate at a 64-fold dilution was incubated with 0.1, 1, or 10 nM antibodies in the HEK293 ST2 NFkB assay. Lysate alone produced a 3.9-fold increase of signal over medium alone. Percent inhibition is calculated as 100 × (1 − (test sample − medium alone)/(lysate alone − medium alone)).

7E8 CDR graft for IL-33 (mm2) is very high, in the single-digit picomolar range, and below 100 pM for wild-type IL-33.

TABLE 10

Figure 1B:
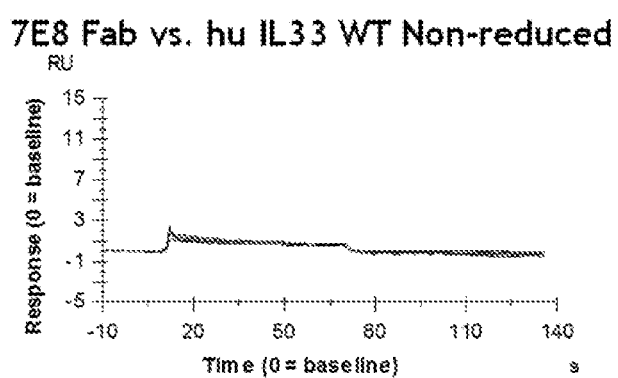
Figure 1C:
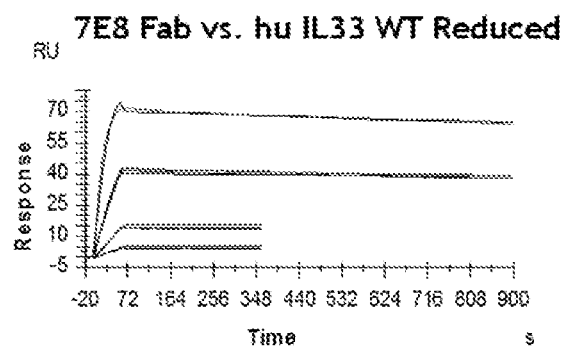

Schild analysis of 7E8 CDR graft inhibition of IL-33 activity in HEK293 ST2 NFkB reporter cells and human PBMCs

| treatment | IL-33 (mm2) HEK293 ST2 NFkB reporter cells $EC_{50}$ (pM) | IL-33 (R&D Systems) HEK293 ST2 NFkB reporter cells $EC_{50}$ (pM) | IL-33 (mm2) human PBMC $EC_{50}$ (pM) donor 149 | donor 172 |
|---|---|---|---|---|
| IL-33 alone | 1.0 | 8.4 | 1.0 | 19.7 |
| IL-33 + 20 nM 7E8 | 2826.5 | 653.4 | ND | ND |
| IL-33 + 2 nM 7E8 | 262.4 | 102.7 | 2826.5 | 1216.1 |
| IL-33 + 200 pM 7E8 | 29.1 | 25.8 | 262.4 | 399.6 |
| IL-33 + 20 pM 7E8 | 2.6 | 10.2 | 29.1 | 154.4 |
| IL-33 + 2 pM 7E8 | ND | 8.0 | 2.6 | 23.2 |
| IL-33 + 0.2 pM 7E8 | ND | ND | 0.9 | 15.1 |
| Calculated $K_{B\ (pM)}$ | 6.01 | 83.45 | 1.04 | 6.64 |

Table 10: 0.028 pM – 55.5 nM (n = 3 replicates). ND, not determined. Schild analysis of 7E8-CDR graft neutralization of IL-33 (mm2) or wild-type IL-33 (R&D Systems) at specified concentrations on HEK293 ST2 NFkB reporter cells or human PBMCs. A plot of log([A']/[A] − 1) vs −log[B], where A' is the $EC_{50}$ of IL-33 in the presence of antibody, A is the $EC_{50}$ of IL-33 in the absence of antibody, and B is the concentration of antibody, produces an X intercept equal to kB, an approximation of the equilibrium constant for antibody binding to IL-33.

Example 9 Binding Affinity of IL-33 Antibodies to Human and Cynomolgus Monkey IL-33

Binding to human and cynomolgus monkey IL-33 was measured by surface plasmon resonance using a BIAcore T200 instrument. An anti-human Fc antibody was immobilized on a CM5 chip, and anti-IL-33 antibodies were captured. Human IL-33 (mm2) or cynomolgus monkey IL-33 was flowed over the chip at 50 μl/min for 45 sec. over the concentration range 3.9-125 nM and allowed to dissociate for 240-1500 sec. Affinity values were determined as shown in Table 11 below. All antibodies bound to human IL-33, with affinity ranging from 171-540 pM. Captured chimeric 12F9 and chimeric 14D8 did not bind to 125 nM cynomolgus monkey IL-33 in solution, while CDR-grafted 7E8, chimeric 9B3, chimeric 30A1, and chimeric 30B11 bound to solution-phase human and cynomolgus monkey IL-33.

TABLE 11

Affinity of anti-IL-33 IgG binding to human and cynomolgus monkey IL-33 measured by surface plasmon resonance in IgG capture format

| Antibody | HC SEQ NO | LC SEQ NO | human IL-33 (mm2) KD (pM) | cynomolgus monkey IL-33 KD (pM) |
|---|---|---|---|---|
| 7E8 CDR graft | 92 | 93 | 171 ± 21.8 | 142.4 ± 4.6 |
| 9B3 chimera | 40 | 42 | 456.96 ± 56.75 | 835.9 ± 42.3 |
| 12F9 chimera | 51 | 53 | 408.15 ± 46.75 | no binding (125 nM IL-33) |
| 14D8 huJseg | 59 | 85 | 394.45 ± 30.45 | no binding (125 nM IL-33) |
| 30A1 hu Jseg | 69 | 87 | 540.3 ± 52.2 | 196.5 ± 7.8 |
| 30B11 hu Jseg | 78 | 89 | 366.7 ± 5 | 148.25 ± 15.95 |

Example 10 Kinetic Evaluation of 7E8 Using Surface Plasmon Resonance and KinExA™ Methodologies Because the apparent affinity of antibodies measured as captured IgG was significantly lower than their potency in IL-33 neutralization in solution phase (Example 11), two alternative approaches to affinity determination were undertaken. To remove the influence of bivalent presentation of the two binding arms of the IgG molecule, monovalent anti-IL-33 antibody Fab fragments were prepared by papain cleavage of CDR-grafted 7E8 (SEQ ID NO:92, 93). Fab fragment affinity was measured by two methods, surface plasmon resonance using a BIAcore instrument, with either Fab or IL-33 captured on the chip, and solution equilibrium affinity measurements using a KinExA instrument, with both Fab and IL-33 in solution.

Surface plasmon resonance experiments were conducted in two formats. When 7E8 Fab was captured by an anti-human Fab capture kit (GE Healthcare Cat. No. 28958325), affinity (Table 12) was measured at 249.5 pM for IL-33 (mm2) and 290 pM for IL-33 (R&D), similar to the results obtained with IgG captured in a similar format (Table 11). However, when biotinylated hIL-33 (mm2) was captured on a streptavidin-coated BIAcore biosensor and a titration series of 7E8 Fab was injected over the sensor surface, the affinity of 7E8 Fab to IL-33 (mm2) was measured to be 3.06 pM (Table 12). Without wishing to be bound by any particular theory, the difference in results between the two formats may arise from matrix effects, e.g., at pH 7.4, attraction of the positively-charged Fab (pI 8.52) in solution to the negatively-charged CM5 sensor chip is expected, as is repulsion of the negatively-charged IL-33 in solution (pI 5.2 for IL-33 mm2, 4.45 for IL-33 WT, and 5.48 for biotinylated IL-33 mm2) to the negatively-charged CM5 sensor chip (Drake et al. 2012, Anal. Biochem. 429(1):58-69). An orthogonal approach to affinity measurement is described in Example 10 below.

In order to assess the binding of 7E8 to wild-type IL33, recombinant IL-33 protein with wild-type cysteine residues (SEQ ID NO:4) was covalently coupled to a CM5 sensor chip (catalogue number BR100530, GE Healthcare) using an amine coupling kit (catalogue number BR100050, GE Healthcare) according to the manufacturer's protocol. Parallel studies were performed with non-reduced IL-33 and with IL-33 samples that had been reduced with 3 mM DTT for 3 hr. at room temperature prior to immobilization. Similar levels of IL-33 were immobilized (293 and 370 resonance units, respectively, for non-reduced and reduced IL-33). Flow cell 1 was activated and blocked for use as a reference flow cell. A titration series of the parental rat Fab 7E8 was performed, using 10 mM HEPES pH 7.4, 0.15M NaCl, 3 mM EDTA, 0.05% P-20 (HBS-EP+) as running and sample buffer, with a flow rate of 50 ul per min. Dissociation was monitored for 3600 seconds. Biacore kinetic assays were conducted at 37° C. at a collection rate of 1 Hz on a Biacore T200 instrument (GE Healthcare). Rate constants and affinities were determined by fitting the resulting sensorgram data to a 1:1 model in Biacore T200 Evaluation software version 1.0 (GE Healthcare). The affinity of rat 7E8 Fab to wild-type human IL-33 that had been pre-treated with DTT was measured to be 44.23 pM (Table 12), while 7E8 Fab did not bind to non-reduced IL-33 (FIG. 1). This observation indicates that 7E8 selectively binds active IL-33 and not IL-33 that has been inactivated by oxidation and suggests that in a therapeutic setting, the presence of inactivated IL-33 would not interfere with the ability of a 7E8-derived antibody to bind active IL-33.

TABLE 12

Affinity of 7E8 Fab binding to human IL-33 measured by surface plasmon resonance in Fab capture format and with immobilized IL-33

| | Captured Fab, IL-33 in solution | | | Immobilized IL-33; Fab in solution | | |
|---|---|---|---|---|---|---|
| Ligand | ka (1/Ms) ± SEM | kd (1/s) ± SEM | KD (pM) ± SEM (n) | ka (1/Ms) | kd (1/s) | KD (pM) ± SEM (n) |
| Hu IL-33 mm2 | 1.38E+06 ± 7.00E+05 | 3.01E−04 ± 6.50E−06 | 249.5 ± 120.5 (2) | 5.47E+06 ± 7.95E+05 | 1.68E−05 ± 3.20E−06 | 3.06 ± 0.14 (2) |
| Hu IL-33 WT Reduced | 2.06E+06 ± 1.12E+06 | 3.77E−04 ± 3.20E−05 | 290 ± 143 (2) | 2.55E+06 ± 2.22E+05 | 1.16E−04 ± 1.18E−05 | 44.23 ± 5.25 (3) |
| Hu IL-33 WT Non-reduced | | ND | | | no binding | |

Table 12. Binding affinity of 7E8 Fab to human IL33 measured by surface plasmon resonance. Solution phase Fab was tested at 0.78-12.5 nM, and solution-phase IL-33 was tested at 0.78-25 nM.

In order to address the format-dependent differences in affinity measured by surface plasmon resonance in different reagent orientations, an orthogonal method was used to assess the affinity of 7E8 Fab for IL-33, with both binding partners in solution. A Kinetics Exclusion Assay (KinExA) instrument (model 3200, Sapidyne) was used to determine the binding affinity of 7E8 Fab to huIL-33 (mm2) (SEQ ID NO:3) and huIL33 wt (SEQ ID NO:4). HuIL33 wt was reduced in 3 mM DTT for a minimum of two hrs prior to use. Affinity determinations were made at room temperature using the fixed antigen assay format. Equilibrium binding was achieved by incubation at 25° C. for 72 hrs. Data analysis was performed with the KinExA Pro software version 3.6.5 (Sapidyne). The "affinity standard" model was used to analyze the data and determine the apparent KDs and apparent active concentrations of huIL33 mm2 and reduced huIL33 wt. The "drift correction" was used when appropriate. Multiple curves were obtained, both receptor and KD controlled, in independent experiments and analyzed using the "n-curve analysis" tool to obtain global best fit values for the KD and active concentration. The software reports each best fit value along with a 95% confidence interval. KinExA analysis showed that 7E8 Fab binds human IL-33 with very high affinity, with KD measured at 0.35 pM for the mm2 form of hIL-33 and 4.04 pM for the reduced WT form (Table 13). These results are consistent with the results of cell-based assays analyzed by Schild analysis (Example 8), which showed that under solution equilibrium conditions, 7E8 CDR graft binds with low picomolar affinity to IL-33 in solution.

TABLE 13

Affinity of 7E8 Fab to human IL-33 (mm2) and human IL-33 (WT) measured by KinExA

| IL-33 form | kD (pM) | Percent error |
|---|---|---|
| huIL-33 (mm2) | 0.351 (0.202-0.526) | 1.36 |
| hu IL-33 (WT + DTT) | 4.04 (2.60-5.76) | 0.90 |

Table 13. Affinity determinations were made using the fixed-antigen assay format. 7E8 Fab was titrated from 15 fM to 0.25 nM into fixed concentrations of 4 pM and 100 pM huIL-33 (mm2), and it was titrated from 244 fM to 2 nM into fixed concentrations of 100 pM and 500 pM hu IL-33 (WT). The 95% confidence interval, shown in parentheses with the kD, and percent error are calculated by KinExA software based on a least-squares fit of the theoretical binding equation to the measured signals.

Example 11 Paratope Determination of Anti-IL-33 Antibodies by Augmented Binary Substitution Three methods were used to identify amino acids critical for function of antibody 7E8. First, a systematic examination of the CDR residues that differ between the rat mAb CDR sequences and the human germline CDR sequences was carried out to determine which positions require the original rat sequence and which tolerate change. This method addressed sequences in CDR-H1 and CDR-H2 in the heavy chain and light chain CDR-L1, CDR-L2, and CDR-L3. A second method (Example 12) addressed tolerance for sequence variation in CDR-H3, which is not encoded in the germline. Sequence variation present in splenic B cells of the immunized rat from which parental 7E8 was derived was determined by next-generation sequencing (NGS), and the frequency of variation at each position of CDR-H3 was determined. Function of a subset of variant CDR sequences was tested to determine the impact of observed sequence changes. A third method that examined functional CDR residues was the examination of specific engineered amino acid variants in the course of antibody engineering (see Examples 14-16).

A method for determining critical CDR residues has been described, by which functional antibody variants are selected from a library containing either the human germline residue or the corresponding rodent residue at each CDR position except for CDR-H3 (Townsend et al., 2015). A phage scFv library was constructed in which all CDR positions of 7E8 that differed from the human germline (DP54/DPK9) were randomized such that approximately 50% of the clones encoded the rat 7E8 amino acid and approximately 50% encoded the human germline amino acid at that position (Table 14). Libraries were prepared and subjected to 3-4 rounds of selection on human IL-33 (mm2).

Clones that retained binding to IL-33 were recovered and their sequences determined. From this experiment, positions at which the human sequence was observed in less than approximately 20% of the binding clones were defined as essential rat residues. Rat residues were preferentially retained at 11 positions (heavy chain residues Y35, S50, T52, and P53; light chain residues H32, D34, F50, N53, Y91, G94, and W95) indicating that replacement of these residues by human germline residues was strongly disfavored. Replacement of F50 in the light chain with A was not observed, indicating that F is the strongly preferred amino acid at this position. Rat and human residues were found with similar frequency at heavy chain residues 54 (N/D), 56, (G/S), 57 (N/E), 58 (T/K), and 61 (P/V) and light chain residues 24 (K/R), 28 (N/S), 30 (N/S), 31 (K/S), 52 (N/S), 56 (T/S), 89 (F/Q), 92 (N/Y), and 93 (N/S), indicating that the rat sequence at these positions is not critical. Position 51 in the light chain encoded a threonine residue in the rat 7E8 clone, but the alanine encoded in the human DPK9 germline sequence was favored, being incorporated in 86% of the binding clones (Table 14). While the starting frequency of alanine codons at position 51 in the library was 68%, higher than most but similar to several other residues, other positions with similar starting bias (e.g., 65% arginine codons at position L24 and 63% serine codons at position L30 in the starting library) had a nearly-equal distribution of amino acids in the selected clones. This observation suggests that alanine is strongly favored at position 51.

TABLE 14

Frequency of incorporation of human amino acids in 7E8 CDR positions tested by augmented binary substitution

| Site | 7E8 rat AA | human germline AA | starting library % human | binding clones % human |
|---|---|---|---|---|
| H35 | Y | S | 52 | 5.88 |
| H50 | S | N | 37 | 7.84 |
| H52 | T | K | 51 | 2.6 |
| H53 | P | Q | 48 | 5.22 |
| H54 | N | D | 56 | 43.13 |
| H56 | G | S | 40 | 49.0 |
| H57 | N | E | 54 | 48.36 |
| H58 | T | K | 53 | 51.63 |
| H61 | P | V | 47 | 48.36 |
| L24 | K | R | 65 | 48.36 |
| L28 | N | S | 52 | 42.48 |

TABLE 14-continued

Frequency of incorporation of human amino acids in 7E8 CDR positions tested by augmented binary substitution

| Site | 7E8 rat AA | human germline AA | starting library % human | binding clones % human |
|---|---|---|---|---|
| L30 | N | S | 63 | 49.67 |
| L31 | K | S | 36 | 33.98 |
| L32 | H | Y | 42 | 16.99 |
| L34 | D | N | 41 | 13.72 |
| L50 | F | A | 55 | 0 |
| L51 | T | A | 68 | 86.27 |
| L52 | N | S | 47 | 48.36 |
| L53 | N | S | 46 | 20.26 |
| L56 | T | S | 45 | 59.48 |
| L89 | F | Q | 56 | 54.25 |
| L91 | Y | S | 43 | 16.33 |
| L92 | N | Y | 52 | 54.9 |
| L93 | N | S | 65 | 49.01 |
| L94 | G | T | 56 | 20.26 |
| L95 | W | L | 36 | 7.10 |

Table 14. Sites are numbered as heavy chain (H) or light chain (L) variable regions based on SEQ ID NO: 94 and SEQ ID NO: 91, respectively.

Example 12 Tolerated Variations in Anti-IL-33 Antibody CDR-H3 Sequences in Rats Immunized with Human IL33

Tolerance of CDR H3 sequence variation by antibodies related to the IL-33 neutralizing antibodies described in Example 1 was examined by sequencing of the immune repertoire of the same animal from which the antibodies were derived. RNA was isolated from spleen tissue from the immunized rat, prepared by reverse transcription-RACE PCR as described in Example 2, and subjected to next-generation sequencing on a Roche FLX+ instrument. From 62,484 sequence reads, sets of VH genes with CDR3 sequences related to those of the neutralizing antibodies in Example 1 were identified. Within the set of unique CDR3 sequences, the frequencies with which amino acids diverged from the neutralizing antibody sequences at each position were calculated, without adjustment for the frequency of each CDR3 sequence in the population (Table 15). Strongly-conserved sequences in CDR3 from both 7E8 and 9B3 (<15% variation in unweighted sample) were G99, H100, Y101, Y103, S105, Y106, and S107. Variations in Y106 were not observed among the 72 sequence variants identified in the rat repertoire, and variations from Y103, S105, and S107 were observed in fewer than 3 percent of sequences.

TABLE 15

Frequency of amino acid differences from 7E8 and 9B3 CDR-H3 found among variants present in immunized rat immune repertoire

| 7E8 CDR H3 | G99 | H100 | Y101 | Y102 | Y103 | T104 | S105 | Y106 | S107 | L108 | G109 | Y110 |
|---|---|---|---|---|---|---|---|---|---|---|---|---|
| Frequency of differences from 7E8 | 4.2 | 6.9 | 8.3 | 27.8 | 1.4 | 73.6 | 1.4 | 0 | 2.8 | 87.5 | 65.3 | 30.6 |

| 9B3 CDR H3 | G99 | H100 | Y101 | S102 | Y103 | S104 | S105 | Y106 | S107 | F108 | S109 | Y110 |
|---|---|---|---|---|---|---|---|---|---|---|---|---|
| Frequency of differences from 9B3 | 4.2 | 6.9 | 8.3 | 73.6 | 1.4 | 31.9 | 1.4 | 0 | 2.8 | 25 | 97.2 | 30.6 |

Table 15. Numbers represent the frequencies of amino acid changes observed at each position of CDR H3 within the set of unique 7E8- and 9B3-related CDR H3 sequences identified in the repertoire of the immunized rat from which these antibodies were obtained. The frequency with which a given CDR H3 sequence was observed in the repertoire was not taken into account in this calculation.

A subset of CDRH3 sequences related to 9B3 and 7E8, shown in Table 16, were cloned into the framework of the chimeric 9B3 heavy chain, generating heavy chains designated by SEQ ID NOs: 116, 120, 123, 125, 128, 131, 134, 137, 140, 143, 146, 149, 151, 154, 157, and 160. These heavy chains were cotransfected with the chimeric 9B3 light chain (SEQ ID NO:117) and the resulting antibodies expressed, purified and analyzed for IL-33 dissociation rate by BIAcore analysis and inhibition of IL-33 signaling in the HEK293 ST2 NFkB reporter assay. Dissociation rates were measured following binding to 125 nM IL-33 (mm2) using intact IgG captured by an immobilized anti-human Fc antibody as described in Example 9. Both assays showed that most of the CDRH3 sequence variants present in the rat variants with minimal functional effects. Substitution of two highly-conserved amino acids with chemically-similar side chains (aromatic side chain substitution Y101F in antibody 9B3-22 and the positively-charged side chain substitution H100R in antibody 9B3-7) did not lead to significant changes in antibody function in the context of additional substitutions in these antibodies. Taken together, the amino acid sequence variation observed in the immunized repertoire suggests that residues G99, H100, Y101, Y103, S105, Y106, and S107 or residues with chemically-similar side chains are favored in the CDR H3 of antibody 9B3 and its close relative 7E8.

TABLE 16

IL-33 neutralization activity and dissociation rates of 9B3 chimera variants containing CDR-H3s identified from immunized rat repertoire.

| Antibody | HC SEQ NO | LC SEQ NO | frequency | end FW3 (lower case) + CDR H3 | HEK293 ST2 NFkB assay estimated IC$_{50}$ (nM) | Dissociation rate (kd; 1/s) |
|---|---|---|---|---|---|---|
| 9B3-1 | 116 | 117 | 1 | cakGHYYYSSYSLGY | 0.039 | 5.69E-04 |
| 9B3-2A | 120 | 117 | 2 | cakGHYSYSSYSFGY | 0.056 | 4.37E-04 |
| 9B3-26 | 123 | 117 | 2 | cvkGHYSYSSYSIDY | 0.048 | 5.06E-04 |
| 9B3-3 | 125 | 117 | 3 | cakGHYSYSSYSIDY | 0.048 | 4.24E-04 |
| 9B3-5 | 128 | 117 | 5 | cakGHYSYTSYSFGY | 0.106 | 3.25E-04 |
| 9B3-7 | 131 | 117 | 7 | cakGRYYYSSYSFAY | 0.069 | 5.89E-04 |
| 9B3 chimera huJseg | 40 | 83 | 8 | cakGHYSYSSYSFSY | 0.061 | 4.51E-04 |
| 9B3-13 | 134 | 117 | 13 | carGHYYYNSYSFAH | 0.175 | 3.26E-04 |
| 9B3015 | 137 | 117 | 15 | cakGHYSYSSYSFAN | 0.101 | 4.79E-04 |
| 9B3-17 | 140 | 117 | 17 | caeGHYYYSSYSFGS | 0.040 | 5.09E-04 |
| 9B3-22 | 143 | 117 | 22 | cakGHFSYTSYSFAN | 0.153 | 5.31E-04 |
| 9B3-31v2 | 146 | 117 | 31 | cakGHYYYSSYSFAF | 0.202 | 7.06E-04 |
| 9B3-36 | 149 | 117 | 36 | cakGHYYYTSYSFAY | 0.251 | 2.89E-04 |
| 9B3-79 | 151 | 117 | 79 | carGHYYYTSYSFAY | 0.063 | 5.43E-04 |
| 9B3-124 | 154 | 117 | 124 | cakGHYYYTSYSLGF | 0.081 | 3.98E-04 |
| 9B3-162 | 157 | 117 | 162 | cakGHYYYSSYSFGY | 0.067 | 6.42E-04 |
| 7E8H/963K | 28 | 117 | 234 | cakGHYYYTSYSLGY | 0.015 | 3.85E-04 |
| 963-563 | 160 | 117 | 563 | cakGHYYYSSYSFAY | 0.177 | 1.09E-03 |

Table 16. IL-33 neutralization activity and dissociation rate of 9B3 chimera variants containing CDR-H3s identified from immunized rat repertoire. Frequency refers to the number of times the CDR3 sequence was obtained in a next-generation sequencing run from the immunized rat repertoire. Sequences diverging from 9B3 are shown in bold underlined text.
Sequences at C terminal end of Framework 3 are shown in lower-case text.

repertoire conferred little or no change in dissociation rate or neutralization potency compared to that of parental 9B3, indicating that the observed sequence variations are well-tolerated changes. The dissociation rates of all 18 antibodies tested were within 2.5-fold of that of 9B3. Cell-based potency reductions up to four-fold were observed in four of the 18 antibodies. The larger changes in potency could not be attributed to specific single changes, since all four of these antibodies contained mutations observed in other

Example 13 Assessment of Non-Specific Binding of Anti-IL-33 Antibodies

Nonspecific binding of antibodies to molecules other than their targets has been proposed to be a mechanism of rapid clearance in vivo (Hötzel et al., 2010, MAbs 4(6):753-760). Evidence for such polyreactive non-target binding can be obtained through measurement of binding to membrane preparations (Xu et al., 2013, Protein Eng. Des. Select.

26(10):663-70;), baculovirus particles (Hötzel et al., 2012, mAbs 4:753-60), or negatively-charged substrates such as DNA, insulin, and heparin (Tiller et al., 2008, J. Immunol. Methods 329(1-2):112-124).

The ELISA for DNA and insulin used a low-stringency protocol originally developed for detection of low-affinity autoantibodies from lupus patients (Tiller et al., 2008). Insulin at 5 µg/ml or single-stranded or double-stranded DNA at 10 µg/ml in PBS were coated onto Nunc Maxisorp ELISA plates overnight. Wells were washed 3× with water, then blocked with ELISA buffer (PBS/0.05% Tween/1 mM EDTA) 1 hr room temperature. Antibodies at 3-10 µg/ml in ELISA buffer were incubated in the wells for 1 hr at room temperature, and the wells were washed 3× with water, incubated with HRP-conjugated goat anti-human IgG 1:5000 in ELISA buffer for 1 hr room temperature. Following 3 washes with water, color was developed with TMB for 5 mins and the reaction stopped with 0.1M sulfuric acid. The ELISA for binding to baculovirus (BV) particles was based on the method described in Hotzel, 2012. Antigen was immobilized in Nunc Maxisorp ELISA plates by adding a 4% BV suspension in 50 mM sodium carbonate buffer pH 9.6 to each well and allowing the particles to adsorb to the plates overnight at 4° C. The wells were blocked with blocking buffer (PBS/0.5% BSA) 1 h at room temperature. After 3 washes with PBS, antibodies at 10 µg/ml in blocking buffer were added to the ELISA wells and incubated for 1 h at room temperature. Plates were washed 6 times with PBS and incubated with 20 ng/ml HRP-goat anti-human antibody (Jackson ImmunoResearch Cat No. 109-035-008) for 1 h at room temperature. Plates were washed 6 times in PBS, and 25 µl of TMB substrate was added to each well and allowed to develop for 15 min and then stopped by adding 1 M phosphoric acid to each well. Detergents were not added to buffers in any step. A450 signals at 10 µg/ml Ab were normalized to the signal from a blank well for comparison of samples.

Chimeric and CDR-grafted 7E8 were found to have moderate binding to DNA and insulin in the low-stringency polyreactivity ELISAs, while chimeric 9B3 showed DNA and insulin binding close to that of a negative control antibody despite sequence similarity to 7E8 (Table 17). Replacement of CDR-H2 of 7E8 by its 9B3 counterpart produces a partial reduction in polyreactivity, while replacement of CDR H1 or CDR H3 had minimal effect.

The human IL-33 (mm2) blocking activity of 9B3 is lower than that of 7E8 (0.264 nM in the HEK293 ST2 NFkB assay for 9B3 vs 0.059 nM for 7E8). The difference is more pronounced in inhibition of cynomolgus monkey IL-33: 7E8 inhibits with a potency (0.131 nM) similar to its potency on human IL-33, while 9B3 is substantially weaker on cynomolgus IL-33, blocking only partially at 20 nM. Replacement of the 7E8 CDR H2 with the 9B3 CDR H2 leads to a large loss in potency against cynomolgus monkey IL-33 (0.131 nM $IC_{50}$ reduced to 3.46 nM), and similarly, replacement of the 7E8 CDR H3 with the 9B3 CDR H3 leads to a loss of cynomolgus monkey IL-33 potency (7.65 nM). Thus, CDR H2 carries determinants of both specific and nonspecific activity of the 7E8/9B3 family of IL-33 neutralizing antibodies, and CDR H3 carries determinants of specific activity.

TABLE 17

DNA binding activity and neutralization of human and cynomolgus monkey IL-33 by CDR graft variants of 7E8

| Antibody | HC SEQ NO | LC SEQ NO | VH description | VL description | 2.2 nM Ab DNA binding normalized to blank ± SEM (n) | 6.7 nM Ab DNA binding normalized to blank ± SEM (n) | 20 nM Ab DNA binding normalized to blank ± SEM (n) | HEK293 ST2 NFkB human IL-33 (mm2) $IC_{50}$ (nM) ± SEM (n) | HEK293 ST2 NFkB cyno IL-33 $IC_{50}$ (nM) ± SEM (n) |
|---|---|---|---|---|---|---|---|---|---|
| 7E8 chimera | 28 | 31 | 7E8 chimera | 7E8 chimera | 20.12 | 20.39 | 26.82 | | |
| 9B3 chimera | 40 | 42 | 9B3 chimera | 9B3 chimera | 6.26 | 7.64 | 11.98 | | |
| 9B3 chimera/hu J | 40 | 83 | 9B3 chimera | 9B3 chimera/ human J segment | 3.19 | 5.91 | 9.54 | 0.264 ± 0.029 (2) | 71.6% @ 20 nM |
| 7E8 CDR graft | 92 | 93 | 7E8 CDR graft | 7E8 CDR graft | 23.54 | 24.68 | 27.19 | 0.059 ± 0.001 (2) | 0.131 ± 0.008 (2) |
| IL33-10 | 95 | 93 | 7E8 CDR graft | 7E8 CDR graft | 25.40 | 25.16 | 27.51 | 0.017 | 0.132 |
| IL33-11 | 162 | 93 | 7E8 VH with 9B3 H1 | 7E8 CDR graft | 24.02 | 24.29 | 26.71 | 0.090 | 0.204 |
| IL33-12 | 164 | 93 | 7E8 VH with 9B3 H2 | 7E8 CDR graft | 12.64 | 19.21 | 24.68 | 0.144 | 3.460 |
| IL33-13 | 166 | 93 | 7E8 with 9B3 H3 | 7E8 CDR graft | 23.14 | 22.50 | 25.89 | 0.220 | 7.651 |
| Polyreactivity negative control (8.8) | | | | | 2.52 ± 0.11 (2) | 4.49 ± 0.81 (2) | 8.08 ± 0.46 (2) | | |
| Polyreactivity positive control (scFv-Fc) | | | | | 15.69 | 20.84 | 26.22 | | |

Example 14 Assessment of Non-Specific Binding and Activity of CDR Variants of 7E8

Polyreactivity has been linked to imbalance of positive charge in CDRs (Datta-Mannan et al., 2015, MAbs 7(3): 483-493). No charge differences exist between light chains of 7E8 and 9B3. Inspection of the CDR-H2 and CDR-H3 sequences of 7E8 and 9B3 (SEQ ID NO:17, 34, 18, and 35) showed four CDR-H2 and four CDR-H3 differences, of which only one (at position 54, N in 7E8 and D in 9B3) would lead to a difference in charge. Modification of 7E8 with the N54D mutation to generate IL33-45 (heavy chain SEQ ID NO:169) had only modest effects on polyreactivity but reduced cynomolgus monkey IL-33 neutralization significantly, in a way similar to what was observed with substitution of CDR H2 of 7E8 with that of 9B3 (Table 18). For this reason, additional sequence variants were required in order to identify sequence changes that would allow retention of 7E8 activity on both human and cynomolgus monkey IL-33 while reducing the polyreactivity of 7E8.

TABLE 18

DNA binding activity and neutralization of human and cynomolgus monkey IL-33 by variants of 7E8 incorporating CDR H2 sequences from 9B3

| Antibody | HC SEQ NO | LC SEQ NO | VH description | VL description | 2.22 nM Ab DNA binding normalized to blank | 6.67 nM Ab DNA binding normalized to blank | 20 nM Ab DNA binding normalized to blank | HEK293 ST2 NFkB mm2 $IC_{50}$ (nM) | HEK293 ST2 NFkB cyno IL-33 $IC_{50}$ (nM) |
|---|---|---|---|---|---|---|---|---|---|
| 7E8 CDR-grafted | 92 | 93 | Parental 7E8 CDR graft | 7E8 CDR graft | 28.20 | 30.33 | 30.66 | 0.057 | 0.077 |
| 9B3 chimera/hu J | 40 | 83 | 9B3 chimera | 9B3 chimera/ human J segment | 8.40 | 13.40 | 18.48 | ND | ND |
| IL33-12 | 164 | 93 | 7E8 VH with 9B3 H2 | 9B3 CDR graft | 25.47 | 29.34 | 29.03 | 0.140 | 0.943 |
| IL33-45 | 169 | 93 | N54D | 7E8 CDR graft | 17.36 | 24.44 | 29.20 | 0.325 | 0.535 |
| Polyreactivity negative control (8.8) | | | | | 1.95 | 4.41 | 7.17 | | |
| Polyreactivity positive control (MJ4-2 v1.1/P33) | | | | | 28.09 | 35.44 | 35.43 | | |

Example 15 Optimization of Anti-IL-33 Antibody 7E8

A series of mutations was made in 7E8 in order to identify changes that would reduce polyreactivity without loss of activity. While substitution of N54 in CDR H2 with aspartic acid slightly reduced polyreactivity but led to reduced cell-based activity, replacement of N54 with other amino acids (I, L, V, W, Y) increased nonspecific binding to baculovirus while leaving cell-based activity intact.

Replacement of the CDR H2 residue N57 with either of two negatively-charged residues, aspartic acid or glutamic acid, led to significant reductions in polyreactivity as measured by binding to baculovirus particles, DNA, or insulin, but these mutations did not reduce neutralization activity (Table 19). Surprisingly, addition of negative charge to CDR3 of the heavy chain (S105D) led to undesirable changes in both polyreactivity and cell-based activity, and addition of negative charges to the light chain (mutations N30D, K31D, T56D, or T56E) increased polyreactivity. The N57D and N57E variants are therefore unusual in that they improve polyreactivity without impairing neutralization of human or cynomolgus monkey IL-33. These results suggest that the position of negative charges and not simply the total charge on the variable domain is significant.

TABLE 19

Baculovirus binding activity and neutralization of human and cynomolgus monkey IL-33 by single amino acid variants of CDR-grafted 7E8

| Antibody | HC SEQ NO | LC SEQ NO | VH description | VL description | Baculovirus binding normalized to blank | HEK293 ST2 NFkB human IL-33 (mm2) $IC_{50}$ (nM) | HEK293 ST2 NFkB cyno IL-33 $IC_{50}$ (nM) |
|---|---|---|---|---|---|---|---|
| 7E8 CDR graft | 92 | 93 | 7E8 CDR graft | 7E8 CDR graft | 1.27 | 0.040 | 0.054 |
| IL33-12 | 164 | 93 | 7E8 VH with 9B3 H2 | 7E8 CDR graft | 0.51 | | |
| IL33-55 | 172 | 93 | N57D | 7E8 CDR graft | 0.97 | 0.084 | 0.19 |
| IL33-56 | 175 | 93 | N57E | 7E8 CDR graft | 1.00 | 0.053 | 0.104 |
| IL33-57 | 178 | 93 | S105D | 7E8 CDR graft | 3.17 | 0.310 | |
| IL33-58 | 181 | 93 | N54L | 7E8 CDR graft | 5.04 | 0.027 | |
| IL33-61 | 183 | 93 | N57E S105D | 7E8 CDR graft | 2.48 | 0.595 | |
| IL33-62 | 185 | 93 | N57D S105D | 7E8 CDR graft | 2.48 | 0.885 | |
| IL33-68 | 188 | 93 | S105A | 7E8 CDR graft | 1.73 | 0.046 | 0.062 |
| IL33-74 | 95 | 191 | 7E8 CDR graft | K31D | 4.02 | 0.174 | |
| IL33-75 | 95 | 194 | 7E8 CDR graft | N30D | 5.14 | 0.156 | |
| IL33-80 | 95 | 197 | 7E8 CDR graft | T56D | 3.49 | 0.161 | |
| IL33-81 | 95 | 200 | 7E8 CDR graft | T56E | 4.68 | 0.168 | |
| Negative polyreactivity control (bevacizumab) | | | | | 0.52 | | |
| Positive polyreactivity control (MJ4-2 VH1.1/P33) | | | | | 5.83 | | |

A series of additional heavy chain CDR mutations predicted to introduce negative charge, remove hydrophobic residues, or modify residues in proximity to position 57 was examined in conjunction with N57E. Polyreactivity of 7E8 with the N57E mutation remained generally low with the incorporation of individual mutations in CDR-H2 (S50A, T58D; Table 20), and in the HEK293 ST2 NFkB cell-based assay (Table 21), potency of 7E8 with the N57E mutation was largely unchanged by the incorporation of S50A or T58D. Similarly, polyreactivity of 7E8 with the N57E mutation remained generally low with the incorporation of additional individual mutations in CDR H1 (T28E), H2 (G56H, T58D, D62E, S63A, or K65Q) or H3 (H100Y, Y102H, Y103H, Y103W, T104N, or T104S). Likewise, in the HEK293 ST2 NFkB cell-based assay, potency of 7E8 with the N57E mutation was largely unchanged by the incorporation of additional individual mutations in CDR H1 (T28E), H2 (K65Q) or H3 (H100Y, T104N, or T104S).

IL-33 can stimulate the production of IFNγ in human whole blood with the costimulation by IL-12 in a format nearly identical to that used for the PBMC assay described in Example 8, except that a higher concentration of IL-33 (100 pM) is required for the whole blood response, compared to 5 pM IL-33 for PBMCs. Similar to the results observed in the HEK293 ST2 NFkB assay, the whole-blood potency of 7E8 with the N57E mutation was largely unchanged by the incorporation of individual mutations 550A or T58D (Table 21). Likewise, potency of 7E8 with the N57E mutation was largely unchanged by the incorporation of additional individual mutations in CDR H1 (T28E), H2 (S63A or K65Q) or H3 (Y103H, T104N or T104S).

A mutation designed to eliminate a potential site of posttranslational modification (light chain N93Q, which removes a potential NG asparagine deamidation site (Chelius et al., 2005, Anal. Chem. 77(18):6004-6011) was combined with the heavy chain mutation N57E in antibody IL33-136 and found to lead to retention of cell-based activity (Table 21) with a partial retention of improved polyreactivity (Table 20).

TABLE 20

Binding to baculovirus, DNA, and insulin by CDR H2 and CDR L3 variants of CDR-grafted 7E8

| Antibody | HC SEQ NO | LC SEQ NO | VH description | VL description | DNA binding normalized to blank ± SEM (n) | Insulin binding normalized to blank ± SEM (n) | baculovirus binding normalized to blank ± SEM (n) |
|---|---|---|---|---|---|---|---|
| IL33-10 | 95 | 93 | 7E8 CDR graft | 7E8 CDR graft | 13.22 ± 2.06 (4) | 16.6 ± 1.77 (4) | 2.32 ± 0.29 (5) |
| IL33-12 | 164 | 93 | 7E8 VH with 9B3 H2 | 7E8 CDR graft | 5.76 ± 0.44 (4) | 7.79 ± 0.47 (4) | 1.57 ± 0.29 (5) |
| IL33-45 | 169 | 93 | N54D | 7E8 CDR graft | 6.91 ± 0.7 (4) | 8.6 ± 1.69 (4) | 3.93 ± 0.61 (5) |
| IL33-55 | 172 | 93 | N57D | 7E8 CDR graft | 4.94 ± 0.67 (4) | 6.96 ± 0.68 (4) | 1.14 ± 0.09 (5) |
| IL33-56 | 175 | 93 | N57E | 7E8 CDR graft | 6.13 ± 0.96 (4) | 8.81 ± 0.87 (4) | 1.5 ± 0.34 (5) |
| IL33-103 | 203 | 93 | N57E S50A | 7E8 CDR graft | 6.09 ± 1.01 (4) | 9.1 ± 0.64 (4) | 1.44 ± 0.24 (5) |
| IL33-117 | 206 | 93 | N57E T58D | 7E8 CDR graft | 6.46 ± 0.99 (4) | 8.96 ± 1.5 (4) | 1.47 ± 0.18 (5) |
| IL33-136 | 175 | 209 | N57E | N93Q | 11.33 ± 2.14 (4) | 13.9 ± 1.4 (4) | 4.34 ± 1.59 (5) |
| Negative polyreactivity control (8.8) | | | | | 5.71 ± 1.12 (4) | 7.17 ± 0.87 (4) | 2.19 ± 0.21 (5) |
| Positive polyreactivity control (MJ4-2 VH1.1/P33) | | | | | 35.06 ± 4.1 (4) | 39.06 ± 1.33 (4) | 10.54 ± 1.68 (5) |

TABLE 21

Cell-based activity of CDR H2 and CDR L3 variants of CDR-grafted 7E8

| Antibody | HC SEQ NO | LC SEQ NO | VH description | VL description | HEK293 ST2 NFkB mm2 IC$_{50}$ (nM) | HEK293 ST2 NFkB cyno IL-33 IC$_{50}$ (nM) | HEK293 ST2 NFkB WT IL-33 IC$_{50}$ (nM) | Whole blood IC$_{50}$ (nM) |
|---|---|---|---|---|---|---|---|---|
| IL33-10 | 95 | 93 | 7E8 CDR graft | 7E8 CDR graft | 0.031 | 0.059 | 0.117 | 0.121 ± 0.025 (4) |
| IL33-103 | 203 | 93 | N57E S50A | 7E8 CDR graft | 0.028 | 0.07 | 0.178 | 0.104 ± 0.008 (4) |
| IL33-117 | 206 | 93 | N57E T58D | 7E8 CDR graft | | 0.052 | 0.155 | 0.106 ± 0.014 (2) |
| IL33-136 | 175 | 209 | N57E | N93Q | | | 0.037 | 0.098 ± 0.033 (4) |

Combinations of these mutations and two additional heavy chain mutations (G55A, which allowed removal of a potential NG asparagine deamidation site, and D62E, which removes a potential DS aspartic acid isomerization site; (Chelius, D., et al. (2005) were examined for activity and polyreactivity, and a set of clones with cell-based activity (in the HEK293 ST2 NFkB reporter assay, human whole blood, and human PBMC assays) within approximately two-fold of the starting clone 7E8 CDR graft and polyreactivity within two-fold of the negative control antibody was identified (Table 22, Table 23).

TABLE 22

Binding to baculovirus, DNA, and insulin by variants of CDR-grafted 7E8 containing multiple CDR H2 and CDR L3 mutations

| Antibody | HC SEQ NO | LC SEQ NO | VH description | VL description | DNA binding normalized to blank ± SEM (n) | Insulin binding normalized to blank ± SEM (n) | baculovirus binding normalized to blank ± SEM (n) |
|---|---|---|---|---|---|---|---|
| IL33-153 | 212 | 209 | G55A N57E T58D | N93Q | 4.6 ± 0.4 (2) | 6.67 ± 1.14 (2) | 1.42 (1) |
| IL33-154 | 215 | 209 | G55A N57E T58D D62E | N93Q | 4.94 ± 0 (2) | 6.21 ± 1.65 (2) | 1.25 (1) |
| IL33-155 | 218 | 209 | S50A N57E T58D | N93Q | 4.05 ± 0.29 (2) | 5.18 ± 0.9 (2) | 1.25 (1) |

TABLE 22-continued

Binding to baculovirus, DNA, and insulin by variants of CDR-grafted 7E8 containing multiple CDR H2 and CDR L3 mutations

| Antibody | HC SEQ NO | LC SEQ NO | VH description | VL description | DNA binding normalized to blank ± SEM (n) | Insulin binding normalized to blank ± SEM (n) | baculovirus binding normalized to blank ± SEM (n) |
|---|---|---|---|---|---|---|---|
| IL33-156 | 221 | 209 | S50A N57E T58D D62E | N93Q | 4.32 ± 0.04 (2) | 5.75 ± 1.32 (2) | 1.15 (1) |
| IL33-157 | 224 | 209 | S50A G55A N57E T58D | N93Q | 4.74 ± 0.16 (2) | 5.71 ± 1.67 (2) | 1.55 (1) |
| IL33-158 | 227 | 209 | S50A G55A N57E T58D D62E | N93Q | 5.25 ± 0.09 (2) | 6.42 ± 1.82 (2) | 1.43 (1) |
| IL33-167 | 212 | 93 | G55A N57E T58D | 7E8 CDR graft | 5.71 ± 0.8 (2) | 8.01 ± 2.63 (2) | 1.47 (1) |
| IL33-168 | 215 | 93 | G55A N57E T58D D62E | 7E8 CDR graft | 4.58 ± 0.07 (2) | 6.26 ± 0.95 (2) | 1.03 (1) |
| IL33-169 | 218 | 93 | S50A N57E T58D | 7E8 CDR graft | 5.71 ± 1.63 (2) | 6.34 ± 1.84 (2) | 1.24 (1) |
| IL33-170 | 221 | 93 | S50A N57E T58D D62E | 7E8 CDR graft | 5.91 ± 0.89 (2) | 6.35 ± 2.29 (2) | 0.96 (1) |
| IL33-171 | 224 | 93 | S50A G55A N57E T58D | 7E8 CDR graft | 5.4 ± 0.83 (2) | 5.45 ± 0.99 (2) | 1.15 (1) |
| IL33-172 | 227 | 93 | S50A G55A N57E T58D D62E | 7E8 CDR graft | 5.4 ± 1.16 (2) | 6.2 ± 1.4 (2) | 1.51 (1) |
| IL33-175 | 230 | 93 | S50A G55A N57E D62E | 7E8 CDR graft | 6.2 ± 0.28 (2) | 8.55 ± 2.19 (2) | 1.57 (1) |
| IL33-186 | 233 | 209 | S50A N57E D62E | N93Q | 4.92 ± 0.11 (2) | 7.77 ± 1.63 (2) | 1.01 (1) |
| IL33-187 | 236 | 209 | S50A G55A N57E | N93Q | 6.43 ± 0.53 (2) | 7.21 ± 1.59 (2) | 0.96 (1) |
| IL33-188 | 230 | 209 | S50A G55A N57E D62E | N93Q | 5.52 ± 0.04 (2) | 7.28 ± 1.35 (2) | 0.92 (1) |
| Polyreactivity negative control (8.8) | | | | | 3.42 ± 1.07 (2) | 3.44 ± 0.86 (2) | 1.36 (1) |
| Polyreactivity positive control (MJ4-2 v1.1/P33) | | | | | 18.19 ± 8.12 (2) | 15.37 ± 3.16 (2) | 4.77 (1) |

TABLE 23

Cell-based activity of variants of CDR-grafted 7E8 containing multiple CDR H2 and CDR L3 mutations

| Antibody | HC SEQ NO | LC SEQ NO | VH description | VL description | HEK293 ST2 NFkB IC$_{50}$ (nM) ± SEM (n) | HEK293 ST2 NFkB cyno IL-33 IC$_{50}$ (nM) ± SEM (n) | Whole blood mm2 IC$_{50}$ (nM) ± SEM (n) | PBMC mm2 IC$_{50}$ (nM) ± SEM (n) |
|---|---|---|---|---|---|---|---|---|
| 7E8 CDR graft | 92 | 93 | 7E8 CDR graft | 7E8 CDR graft | 0.114 ± 0.042 (3) | 0.18 ± 0.015 (2) | 0.009 ± 0.002 (8) | 0.004 ± 0.001 (2) |
| IL33-153 | 212 | 209 | G55A N57E T58D | N93Q | 0.087 (1) | 0.122 (1) | 0.014 ± 0.004 (4) | |
| IL33-154 | 215 | 209 | G55A N57E T58D D62E | N93Q | 0.188 ± 0.061 (3) | 0.133 ± 0.018 (2) | 0.01 ± 0.003 (6) | 0.007 ± 0.002 (2) |
| IL33-155 | 218 | 209 | S50A N57E T58D | N93Q | 0.171 (1) | 0.239 (1) | 0.025 ± 0.008 (4) | |
| IL33-156 | 221 | 209 | S50A N57E T58D D62E | N93Q | 0.116 ± 0.038 (3) | 0.087 ± 0.015 (2) | 0.004 ± 0.001 (6) | 0.004 ± 0.001 (2) |
| IL33-157 | 224 | 209 | S50A G55A N57E T58D | N93Q | 0.118 (1) | 0.161 (1) | 0.016 ± 0.007 (4) | |
| IL33-158 | 227 | 209 | S50A G55A N57E T58D D62E | N93Q | 0.131 ± 0.033 (3) | 0.125 ± 0.033 (2) | 0.007 ± 0.002 (6) | 0.004 ± 0.001 (2) |
| IL33-167 | 212 | 93 | G55A N57E T58D | 7E8 CDR graft | 0.049 ± 0.014 (3) | 0.062 ± 0.01 (2) | 0.008 ± 0.004 (6) | 0.001 ± 0 (2) |
| IL33-168 | 215 | 93 | G55A N57E T58D D62E | 7E8 CDR graft | 0.109 (1) | 0.264 (1) | 0.014 ± 0.005 (4) | |
| IL33-169 | 218 | 93 | S50A N57E T58D | 7E8 CDR graft | 0.071 (1) | 0.176 (1) | 0.009 ± 0.003 (4) | |

TABLE 23-continued

Cell-based activity of variants of CDR-grafted 7E8 containing multiple CDR H2 and CDR L3 mutations

| Antibody | HC SEQ NO | LC SEQ NO | VH description | VL description | HEK293 ST2 NFkB IC$_{50}$ (nM) ± SEM (n) | HEK293 ST2 NFkB cyno IL-33 IC$_{50}$ (nM) ± SEM (n) | Whole blood mm2 IC$_{50}$ (nM) ± SEM (n) | PBMC mm2 IC$_{50}$ (nM) ± SEM (n) |
|---|---|---|---|---|---|---|---|---|
| IL33-170 | 221 | 93 | S50A N57E T58D D62E | 7E8 CDR graft | 0.176 ± 0.091 (2) | 0.218 ± 0.033 (2) | 0.005 ± 0.001 (4) | |
| IL33-171 | 224 | 93 | S50A G55A N57E T58D | 7E8 CDR graft | 0.145 (1) | 0.216 (1) | 0.012 ± 0.004 (4) | |
| IL33-172 | 227 | 93 | S50A G55A N57E T58D D62E | 7E8 CDR graft | 0.201 ± 0.105 (2) | 0.222 ± 0.07 (2) | 0.012 ± 0.004 (4) | |
| IL33-175 | 230 | 93 | S50A G55A N57E D62E | 7E8 CDR graft | 0.059 ± 0.011 (2) | 0.086 (1) | 0.006 ± 0.002 (6) | 0.004 ± 0 (2) |
| IL33-186 | 233 | 209 | S50A N57E D62E | N93Q | 0.109 (1) | 0.144 (1) | 0.012 ± 0.006 (4) | |
| IL33-187 | 236 | 209 | S50A G55A N57E | N93Q | 0.15 (1) | 0.282 (1) | 0.006 ± 0.002 (3) | |
| IL33-188 | 230 | 209 | S50A G55A N57E D62E | N93Q | 0.147 (1) | 0.351 (1) | 0.017 ± 0.01 (3) | |

Example 17 Addition of Half-Life Extension Mutations to Optimized Antibody 7E8 Variants Two heavy-chain variant versions of antibodies IL33-158 and IL33-167 were generated, one a variant Fc (SEQ ID NO:237) containing the mutations L234A L235A and G237A in the Fc to decrease effector function (described in U.S. Pat. No. 5,624,821) and deletion of the lysine residue at the C terminus to reduce product heterogeneity, and the other (SEQ ID NO:238) containing the L234A L235A, and G237A mutations, the C terminal lysine deletion, and the double mutation M432L N438S to enhance binding to the neonatal Fc receptor FcRn at acidic pH, expected to lead to prolonged half-life in vivo (Zalevsky et al., 2010, Nature Biotechnol. 28(2):157-159). Each construct was built in the vector pRY19 and stably transfected into CHO cells. The resulting antibodies were IL33-158-152 (SEQ ID NO:241, SEQ NO: 209), IL33-167-153 (SEQ ID NO:242, SEQ ID NO:93), IL33-158LS (SEQ ID NO:244 SEQ ID NO:209), and IL33-167LS (SEQ ID NO:245, SEQ ID NO:93). Sequence alignments of the variable regions of the optimized antibodies with the corresponding human germline sequences are shown in FIG. 2.

Example 18 Polyreactivity Reduction in Optimized Molecules

The antibodies L33-158LS (SEQ ID NO:244 SEQ ID NO:209) and IL33-167LS (SEQ ID NO:245, SEQ ID NO:93) produced from stably-transfected CHO cells showed polyreactivity levels comparable to those of the negative control monoclonal antibody bevacizumab (Table 24). These levels are comparable to those of IL33-158 (SEQ ID NO:227, SEQ ID NO:209) and IL33-167 (SEQ ID NO:212, SEQ ID NO:93), shown in Table 22, indicating that the addition of the constant region mutations L234A L235A, G237A, M432L and N438S mutations and deletion of the C terminal lysine did not substantially alter the polyreactivity of the resulting molecule.

TABLE 24

Binding to DNA and insulin by optimized variants of CDR-grafted 7E8

| Antibody | HC SEQ NO | LC SEQ NO | VH description | VL description | DNA binding normalized to blank ± SEM (n) | Insulin binding normalized to blank ± SEM (n) |
|---|---|---|---|---|---|---|
| IL33-158LS | 244 | 209 | S50A G55A N57E T58D D62E | N93Q | 7.45 ± 0.10 (8) | 8.08 ± 0.48 (8) |
| IL33-167LS | 245 | 93 | G55A N57E T58D | 7E8 CDR graft | 6.23 ± 0.31 (8) | 5.33 ± 1.05 (8) |
| 7E8 CDR graft | 92 | 93 | 7E8 CDR graft | 7E8 CDR graft | 25.42 ± 0.36 (8) | 14.58 ± 1.93 (8) |
| IL33-10 | 95 | 93 | 7E8 CDR graft | 7E8 CDR graft | 26.92 ± 0.77 (8) | 12.26 ± 0.38 (8) |
| Polyreactivity positive control (MJ4-2 v1.1/P33) | | | | | 39.62 ± 0.24 (8) | 42.20 ± 0.34 (8) |
| Polyreactivity negative control (bevacizumab) | | | | | 7.66 ± 0.36 (8) | 9.87 ± 0.27 (8) |
| Polyreactivity negative control (8.8) | | | | | 1.50 ± 0.06 (6) | 4.47 ± 0.09 (6) |

Example 19 Human and Cynomolgus Monkey IL-33 Neutralization Activity of Optimized Anti-IL-33 Antibodies in Cell-Based Assays The antibodies IL33-158-152 (SEQ ID NO:241, SEQ ID NO:209), IL33-167-153 (SEQ ID NO:242, SEQ ID NO:93), IL33-158LS (SEQ ID NO:244 SEQ ID NO:209), and IL33-167LS (SEQ ID NO:245, SEQ ID NO:93) produced from stably-transfected CHO cells showed neutralization of IL-33 in the HEK293 ST2 NFkB reporter assay similar to that of the parental antibody 7E8 CDR graft (SEQ ID NO:92, SEQ ID NO:93) for human IL-33 (mm2), human IL-33 (WT) and cynomolgus monkey IL-33 (cys mut).

TABLE 25

Neutralization activity of optimized variants of CDR-grafted 7E8 in HEK293 ST2 NFkB reporter cell assay

| Antibody | HC SEQ NO | LC SEQ NO | HEK293 ST2 NFkB hIL-33 (mm2) $IC_{50}$ (nM) ± SEM (n) | HEK293 ST2 NFkB hIL-33 (R&D) $IC_{50}$ (nM) ± SEM (n) | HEK293 ST2 NFkB cynomolgus monkey IL-33 (cys mut) $IC_{50}$ (nM) ± SEM (n) |
|---|---|---|---|---|---|
| IL33-158LS | 244 | 209 | 0.162 ± 0.058 (3) | 0.983 ± 0.149 (2) | 0.198 ± 0.068 (3) |
| IL33-167LS | 245 | 93 | 0.13 ± 0.035 (3) | 0.685 ± 0.089 (2) | 0.162 ± 0.071 (3) |
| IL33-158-152 | 241 | 209 | 0.095 ± 0.032 (3) | 0.62 ± 0.103 (2) | |
| IL33-167-153 | 242 | 93 | 0.129 ± 0.042 (3) | 0.749 ± 0.227 (2) | |
| 7E8 CDR graft | 92 | 93 | 0.093 ± 0.029 (3) | 0.322 ± 0.011 (2) | 0.184 ± 0.056 (3) |

Example 20 IL-33 Neutralization Activity of Optimized Anti-IL-33 Antibodies in PBMCs and Whole Blood The antibodies IL33-158LS (SEQ ID NO:244 SEQ ID NO:209) and IL33-167LS (SEQ ID NO:245, SEQ ID NO:93) produced from stably-transfected CHO cells showed neutralization of IL-33 (mm2) in human PBMCs similar to that of the parental antibody 7E8 CDR graft (SEQ ID NO:92, SEQ ID NO:93).

TABLE 26

Neutralization activity of optimized variants of CDR-grafted 7E8 in human PBMC

| Antibody | HC SEQ NO | LC SEQ NO | $IC_{50}$ (nM) ± SEM (n) |
|---|---|---|---|
| IL33-158LS | 244 | 209 | 0.0014 ± 0.0001 (4) |
| IL33-167LS | 245 | 93 | 0.0011 ± 0.0002 (4) |
| 7E8 CDR graft | 92 | 93 | 0.0014 ± 0.0004 (4) |

Table 26: Neutralization of IFN-γ production in PBMC. Human PBMC were primed with 16.67pM IL-12, then treated with 5 pM human IL-33 (mm2).

The antibodies IL33-158LS (SEQ ID NO:244 SEQ ID NO:209) and IL33-167LS (SEQ ID NO:245, SEQ ID NO:93) produced from stably-transfected CHO cells showed neutralization of IL-33-stimulated INFγ production in human in human whole blood similar to that of the parental antibody 7E8 CDR graft (SEQ ID NO:92, SEQ ID NO:93) for human IL-33 (mm2) and human IL-33 (WT).

TABLE 27

Neutralization activity of optimized variants of CDR-grafted 7E8 in human whole blood

| Antibody | HC SEQ NO | LC SEQ NO | human IL-33 (mm2) $IC_{50}$ (nM) ± SEM (n) | human IL-33 (R&D) $IC_{50}$ (nM) ± SEM (n) |
|---|---|---|---|---|
| IL33-158LS | 244 | 209 | 0.021 ± 0.003 (6) | 0.868 ± 0.235 (2) |
| IL33-167LS | 245 | 93 | 0.013 ± 0.001 (6) | 0.451 ± 0.154 (2) |
| 7E8 CDR graft | 92 | 93 | 0.014 ± 0.002 (6) | 0.387 ± 0.216 (2) |

Table 27: Whole blood was stimulated with IL-12, followed by 125 nM human IL-33 (mm2 or R&D).

The antibody IL33-158LS (SEQ ID NO:244 SEQ ID NO:209) produced from stably-transfected CHO cells showed neutralization of human IL-33 (mm2) and human IL33 (R&D), while the commercially-available Nessy-1 did not show significant neutralization. The commercially-available monoclonal antibody 19G8 showed weaker neutralization of human IL-33 (mm2) than IL33-158LS and comparable neutralization of human IL-33 (R&D) (Table 28). Thus the strongly selective neutralization of the active form of human IL-33 represented by IL-33 (mm2) is a characteristic property of IL33-158LS.

TABLE 28

Neutralization activity of IL33-158LS in HEK293 ST2 NFkB assay compared to that of commercial anti-IL-33 antibodies

| Antibody | HC SEQ NO | LC SEQ NO | IL-33 (mm2) $IC_{50}$ (nM) ± SEM (n) | IL-33 (R&D) $IC_{50}$ (nM) ± SEM (n) |
|---|---|---|---|---|
| IL33-158LS | 244 | 209 | 0.079 ± 0.029 (2) | 2.658 ± 1.243 (2) |
| ALX-804-840-C100 (Nessy-1) | | | no neutralization (1) | no neutralization (1) |
| mabg-hIL-33 (19G8) | | | 0.283 ± 0.001 (2) | 1.952 ± 0.94 (2) |

Conclusions

Humanized, optimized anti-human IL-33 antibodies IL33-158-152, IL33-167-153, IL33-158LS, and IL33-167LS are potent neutralizers of IL-33 bioactivity, in a range of bioassays, utilizing cell lines, primary human monocytes, and human whole blood.

Example 21 Kinetic Evaluation of Optimized Anti-IL-33 Antibodies Using Surface Plasmon Resonance Biacore kinetic assays were conducted at 37° C. at a collection rate of 1 Hz on a Biacore T200 instrument (GE Healthcare). Human IL33 (mm2), cynomolgus monkey IL-33, and reduced huIL33 wt were covalently coupled to a CM5 sensor chip (catalogue number BR100530, GE Healthcare) using an amine coupling kit (catalogue number BR100050, GE Healthcare) according to the manufacturer's protocol. Immobilization levels were 260 RU of human IL-33 (mm2), 85 RU of cynomolgus monkey IL-33, and 108-225 RU of reduced human IL-33 (WT), Flow cell 1 was activated and blocked for use as a reference flow cell. Titration series of the lead anti-IL-33 Fabs 158LS, 167LS and parental Fab 7E8 were injected at a flow rate of 50 ul per min and the dissociation was monitored for 3600 seconds. The dilution and running buffer was HBS-EP+(10 mM HEPES pH 7.4, 0.15M NaCl, 3 mM EDTA, 0.05% P-20). Rate constants and affinities were determined by fitting the resulting sensorgram data to a 1:1 model in Biacore T200 Evaluation software version 1.0 (GE Healthcare).

The affinity of Fab fragments of the optimized antibodies IL33-158LS and IL33-167LS were measured by surface plasmon resonance as described in Example 10, with IL-33 immobilized on the sensor chip and Fab fragments in solution phase. Both optimized antibodies showed binding affinities to human IL-33 (mm2), human IL33 (WT), and cynomolgus monkey IL-33 comparable to the affinities exhibited by the parental CDR grafted-7E8 Fab (Table 29).

TABLE 29

Kinetic parameters of Fab fragments of 7E8 CDR graft, IL33-158LS, and IL33-167LS binding to human and cynomolgus monkey IL-33 measured by surface plasmon resonance

| Fab | IL-33 form | ka (1/Ms) ± SEM | kd (1/s) ± SEM | kD (pM) ± SEM (n) |
|---|---|---|---|---|
| 7E8 CDR graft | huIL-33 (mm2) | 2.74E+06 ± 1.15E+05 | 4.17E−05 ± 3.82E−06 | 15.48 ± 2.10 (4) |
| 7E8 CDR graft | hu IL-33 (WT + DTT) | 3.05E+06 ± 2.15E+05 | 5.79E−05 ± 5.10E−06 | 19.05 ± 0.35 (2) |
| 7E8 CDR graft | cyno IL-33 (cys mut) | 2.81E+06 ± 2.50E+04 | 4.07E−05 ± 5.25E−06 | 14.45 ± 1.75 (2) |
| IL33-158LS | huIL-33 (mm2) | 2.42E+06 ± 3.75E+05 | 3.09E−05 ± 2.20E−06 | 13.00 ± 1.10 (2) |
| IL33-158LS | hu IL-33 (WT + DTT) | 1.86E+06 ± 2.65E+04 | 1.29E−04 ± 2.73E−06 | 69.57 ± 2.46 (3) |
| IL33-158LS | cyno IL-33 (cys mut) | 1.64E+06 ± 4.50E+04 | 1.71E−05 ± 7.00E−07 | 10.45 ± 0.15 (2) |
| IL33-167LS | huIL-33 (mm2) | 4.75E+06 ± 3.00E+04 | 4.80E−05 ± 7.90E−06 | 10.11 ± 1.59 (2) |
| IL33-167LS | hu IL-33 (WT + DTT) | 1.45E+06 ± 3.00E+04 | 6.56E−05 ± 2.50E−07 | 45.25 ± 0.85 (2) |
| IL33-167LS | cyno IL-33 (cys mut) | 1.57E+06 ± 6.00E+04 | 2.09E−05 ± 1.00E−07 | 13.35 ± 0.45 (2) |

Example 22 Cytokine Specificity of Anti-IL-33

Figure 3A:
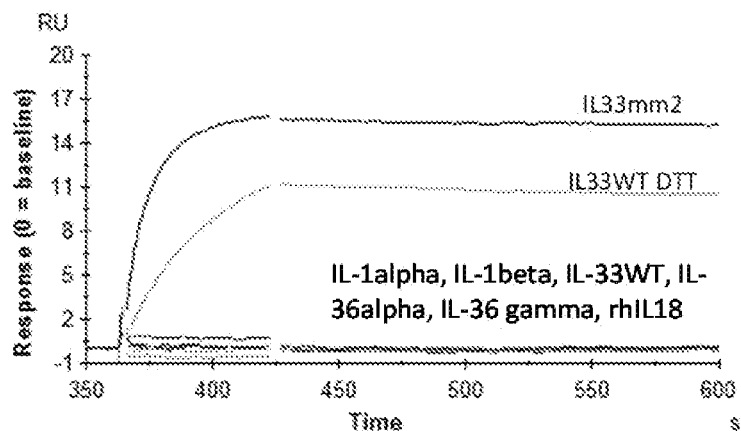
FIGS. 3A-3B are panels showing binding of cytokines to antibodies on the invention immobilized on a chip.
Figure 3B:
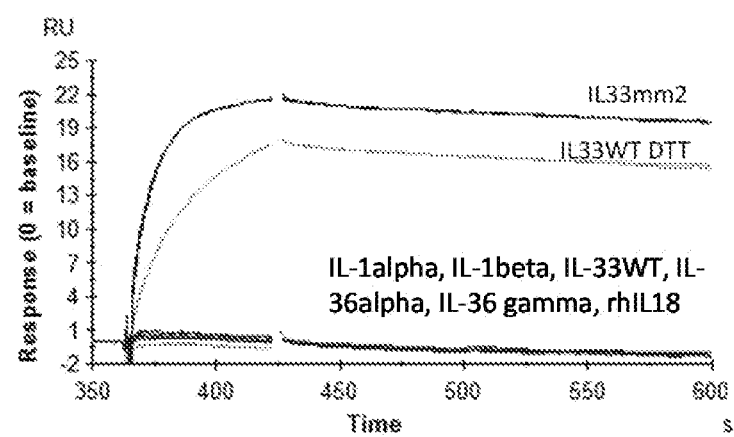

To evaluate the cytokine specificity of anti-IL-33 antibodies 7E8 and IL33-158LS, a panel of non-target cytokines was evaluated for binding to these antibodies by surface plasmon resonance with a BIAcore T-200. The panel of cytokines included IL-1α, IL-1β, IL-18, IL-36α, and IL-36γ. Results (Table 30, FIG. 3) showed that there was no binding of the unrelated cytokines at 100 nM, while anti-IL-33 antibodies 7E8 and IL33-158LS bind IL-33 mm2 and reduced IL-33 WT at very similar % Rmax values. No binding was observed to IL-33 in the absence of reduction.

TABLE 30

Cytokine selectivity of 7E8 and IL33-158LS

| Cytokine | % Rmax 7E8 Fab | % Rmax IL33-158LS Fab |
|---|---|---|
| IL-33 mm2 | 61 | 65 |
| IL-33 WT | NB | NB |
| IL-33 WT + DTT | 52 | 52 |
| IL-1α | NB | NB |
| IL-1β | NB | NB |
| IL-18 | NB | NB |
| IL-36α | NB | NB |
| IL-36γ | NB | NB |

Table 30. Binding of the indicated Fab to 100 nM cytokine was measured by suface plasmon resonance. The Fabs were captured using the Human Fab Capture Kit (GE Healthcare) and each cytokine was injected over the captured Fab at 100 nM. Binding is indicated by the % Rmax value. % Rmax is the ratio of experimentally-observed Rmax to theoretical Rmax (assuming 100% binding), expressed as a percentage, and theoretical Rmax is the Resonance Units of captured Fab multiplied by the ratio of the molecular weights of the cytokine and the Fab. NB, no binding.

Example 23 Competition with Human ST2 for Binding to IL33

The ability of IL33-158LS to block the binding of the ST2 receptor to IL-33 was tested in an Octet binding assay. Antibodies or human ST2-Fc (SEQ ID NO:6) were captured on Octet tips coated with anti human Fc, free binding sites were blocked with an excess of human IgG1 control antibody, and a mixture of IL-33 (R&D) and a second antibody or ST2-Fc was applied to the tips. The complex of IL33-158LS and human IL-33 was able to bind to a control non-neutralizing anti-IL-33 antibody, IL33-271 (SEQ ID NO:254, SEQ ID NO:256) captured on the Octet tip, and conversely, a complex of IL33-271 and human IL-33 was able to bind to immobilized IL33-158LS. Likewise, human ST2-Fc and IL33-271 were able to bind human IL-33 simultaneously in either orientation. However, immobilized IL33-158LS was not able to bind to a complex of IL-33 and ST2-Fc, and conversely, immobilized ST2-Fc was not able to bind to a complex of IL-33 and IL33-158LS. These results indicate that IL33-158LS and ST2-Fc compete for overlapping binding sites on IL-33.

TABLE 31

Competition of IL33-158LS with the IL-33
receptor ST2 for binding to IL-33

| Molecule catpured on anti-Fc tip | HC SEQ NO | LC SEQ NO | IL33-158LS + IL-33 | hST2-Fc + IL-33 | IL33-271 + IL-33 | IL-33 alone |
|---|---|---|---|---|---|---|
| IL33-158LS | 244 | 209 | – | – | + | + |
| hST2-Fc | | 2 | – | – | + | + |
| IL33-271 | 256 | 256 | + | + | – | + |

Table 31: A (+) indicates that the complex of the second antibody and IL-33 bound to the first antibody that had been captured on the Octet tip. A (−) indicates that no increase in signal was observed upon addition of the mixture of IL-33 and the second antibody.

Example 24 Thermal Stability of Optimized Anti-IL-33 Antibodies

Differential scanning calorimetry was used to determine the stability of IL33-158-152, IL33-158LS, IL33-167-153, and IL33-167LS. For this analysis, samples at 0.3 mg/ml were dispensed into the sample tray of a MicroCal VP-Capillary DSC with Autosampler (Malvern Instruments, Inc.), equilibrated for 5 mins at 10° C. and then scanned up to 110° C. at a rate of 100° C. per hr. A filtering period of 16 secs was selected. Raw data was baseline corrected and the protein concentration was normalized. Origin Software 7.0 (OriginLab Corporation, Northampton, Mass.) was used to fit the data to an MN2-State Model with an appropriate number of transitions. Table 32 below shows the melting temperatures ($T_m1$-$T_m3$) of the molecules in 20 mM Histidine pH5.8, 8.5% sucrose, 0.05 mg/ml EDTA. All four molecules show good stability, with the first transition in the CH2 domain ($T_m1$) of greater than 65° C. Additionally, the introduction of the LS mutation has a very small impact (≤1° C.) on the stability of the molecules.

TABLE 32

Thermal stability of optimized 7E8 variants

| Antibody | HC SEQ NO | LC SEQ NO | $T_m1$ | $T_m2$ | $T_m3$ |
|---|---|---|---|---|---|
| IL33-158-152 | 241 | 209 | 71.35 ± 0.09 | 83.58 ± 0.61 | 85.93 ± 0.15 |
| IL33-167-153 | 242 | 93 | 71.13 ± 0.03 | 82.71 ± 0.08 | 84.31 ± 0.04 |
| IL33-158LS | 244 | 209 | 70.26 ± 0.11 | 82.20 ± 0.38 | 85.81 ± 0.06 |
| IL33-167LS | 245 | 93 | 70.45 ± 0.10 | 81.38 ± 0.43 | 84.03 ± 0.10 |

Table 32: thermal transitions for IL33-158 and IL33-167-derived molecules in 20 mM Histidine pH5.8, 8.5% sucrose, 0.05 mg/ml EDTA determined by differential scanning calorimetry.

Example 25 Capture of Cynomolgus Monkey IL-33 by Anti-IL-33 Antibodies Administered In Vivo IL33-158LS was tested for its ability to capture native cynomolgus monkey IL-33. Following intravenous dosing of cynomolgus monkeys at 0.14 or 14 mg/kg of IL33-158LS, aluminum hydroxide (alum) was administered by intraperitoneal injection (1 mg in 0.1 ml). Blood samples were drawn up to 72 hrs post alum. Total cynomolgus monkey IL-33 bound to IL33-158LS was measured using an immunoaffinity LC\MS\MS method. Biotin-conjugated anti-human Fc antibodies were incubated with each plasma sample and incubated overnight at 4° C. in order to bind all cytokine bound to the anti-IL-33 antibody. Streptavidin beads were added to each sample and incubated for 30 mins, washed, and then the cytokine was released from the antibodies using a low pH elution buffer, followed by neutralization with Tris buffer. Extended stable isotope-labeled peptides with signature sequences for IL-33 were then added to each sample, and then all samples were reduced with DTT, alkylated with iodoacetamide and digested with trypsin. The tryptic peptides were then identified with a 2D nano UPLC tandem mass spectrometer system. The limit of quantitation for this assay is 50 pg/mL for cynomolgus monkey IL-33 using 20 μL of plasma. Measurements of IL-33 bound to IL33-158LS increased over time following administration of 14.3 mg/kg and alum challenge as compared to the low dose of 0.14 mg/kg of IL33-158LS (Table 33). These results indicate that IL33-158LS binds to native cynomolgus monkey IL-33 in a dose-dependent manner and produces measurable effects that could be used to model pharmacodynamics in humans.

The terminal serum half-life of IL33-158LS in cynomolgus monkeys was 18 days, which permitted the parameterization of a two-compartment PK model. Allometric scaling of the rate constants with an allometric exponent of 0.75 for clearance resulted in a predicted human serum terminal half-life of 41 days. This is significantly longer compared to the typical observed half-life of 20 days for antibodies in humans (Brekke and Sandlie (2003), Nature Reviews, Vol 2, pp 52-62) and 17 days for human or humanized biotherapeutic IgG antibodies (derived from PK parameters reported in Singh, et al. (Chapter 5. Application of mechanistic pharmacokinetic-pharmacodynamic modeling towards the development of biologics. In: Kumar S, Kumar Singh S, editors. Developability of Biotherapeutics: Computational Approaches. CRC Press; 2015: p. 109-34).

Surprisingly, preliminary evaluation in healthy human volunteers indicates that the serum elimination (β phase) half-life of IL33-158LS is at least 50 days. In some aspects of the invention the terminal half-life of the antibody or antigen binding portion thereof is at least about 50 days. In some aspects of the invention the terminal half-life of the antibody or antigen binding portion thereof is at least about 55 days. In some aspects of the invention the terminal half-life of the antibody or antigen binding portion thereof is at least about 60 days. In some aspects of the invention the terminal half-life of the antibody or antigen binding portion thereof is at least about 65 days. In some aspects of the invention the terminal half-life of the antibody or antigen binding portion thereof is at least about 70 days. In some aspects of the invention the terminal half-life of the antibody or antigen binding portion thereof is at least about 75 days. In some aspects of the invention the terminal half-life of the antibody or antigen binding portion thereof is at least about 80 days. In some aspects of the invention the terminal half-life of the antibody or antigen binding portion thereof is at least about 85 days. In some aspects of the invention the terminal half-life of the antibody or antigen binding portion thereof is at least about 90 days. The unexpectedly high half-life may be due to modifications in the variable and CDR regions, as well as the Fc domain.

TABLE 33

Time course of total circulating IL-33 concentration in cynomolgus monkeys dosed with IL33-158LS and challenged with aluminum hydroxide (Alum)

| Time After Alum Challenge (hrs) | 0.14 mg/kg Dose IL-33 Bound to IL33-158LS (pg/ml) Average (n = 3 +/− SEM) | 14.3 mg/kg Dose IL-33 Bound to IL33-158LS (pg/ml) Average (n = 3 +/− SEM) |
|---|---|---|
| 0 | 52.0 ± 12.7 | 64.5 ± 12.7 |
| 1 | 62.5 ± 3.6 | 52.5 ± 8.4 |
| 2 | 61 ± 4.0 | 59.1 ± 11.5 (n = 2) |
| 4 | 71.3 ± 8.9 | 45.5 ± 2.0 |
| 8 | 84 ± 23.3 | 63.5 ± 4.7 |
| 10 | 48 ± 10.7 (n = 2) | 84.2 ± 11.9 (n = 2) |
| 24 | 61.7 ± 18.7 | 137.3 ± 16.0 |
| 48 | 47.8 ± 17.8 | 217 ± 22.8 |
| 72 | 54.8 ± 11.0 | 311.3 ± 10.4 |

Example 26 Generation and Testing of Comparator IL-33 Antibodies

IgG1 versions of a number of hIgG4 antibodies described in WO2014164959 were generated (Table 35) (binding properties of the isolated Fab fragment are independent of the Fc region, and binding properties of the intact IgG4 are expected to be essentially identical in the IgG1). H4H9675P (corresponding to IL33-265), H4H9659P (corresponding to IL33-266), and H4H9665P (corresponding to IL33-267) are disclosed as having the highest affinity against human IL-33 at 37° C. or monkey 11-33 (Tables 3 & 6 of WO2014164959). Initial functional assessment showed IL33-267 to be less potent than IL33-265 and IL33-266. A more detailed assessment showed that IL33-265 is 8-10-fold more potent than IL33-266 (Table 36). BIAcore analysis of IgG binding to immobilized wild-type human IL-33 showed that IL33-265 bound only to the reduced form of IL-33 and not non-reduced IL-33.

TABLE 35

| Antibody (IgG1) | SEQ ID HC | SEQ ID VL | Antibody (IgG4) | WO2014164959 SEQ ID VH | WO2014164959 SEQ ID VL | WO2014164959 SEQ ID VH- DNA | WO2014164959 SEQ ID VL- DNA |
|---|---|---|---|---|---|---|---|
| IL33-265 | 282 | 283 | H4H9675P | 274 | 282 | 273 | 281 |
| IL33-266 |  |  | H4H9659P | 98 | 106 | 97 | 105 |
| IL33-267 |  |  | H4H9665P | 178 | 186 | 177 | 185 |

TABLE 36

|  | Titration vs. 0.1 ng/ml pur mm2 | | | Titration vs. 0.1 ng/ml R&D rhIL-33 | | |
|---|---|---|---|---|---|---|
|  | IC50 | SEM | n | IC50 | SEM | n |
| IL33-265 | 0.061 | 0.021 | 3 | 0.128 | 0.018 | 3 |
| IL33-266 | 0.719 | 0.159 | 2 | 0.998 | 0.076 | 2 |

IgG1 antibody IL33-310 (SEQ ID NO:287 (HC) and SEQ ID NO:288 (LC)) was generated, and is derived from 10C12.38.H6. 87Y.581 IgG4 of WO2016077381, which is disclosed as having the high affinity to human and cynomolgus monkey IL-33.

10C12.38.H6. 87Y.581 consists of SEQ ID NO: 306 (HC) and SEQ ID NO: 307 (LC) of WO2016077381. To obtain nucleotide sequences for use in expression, the variable region sequences were reverse translated using Vector NTI software. The nucleotide sequence of a standard constant kappa region, which encodes an identical amino acid sequence to that of SEQ ID NO:307 of WO2016077381, was used for the expression construct. The nucleotide sequence of a standard constant IgG4 region encoded an amino acid sequence with three differences from that of SEQ ID NO: 306 of WO2016077381 and was modified in these three codons to encode the constant region of SEQ ID NO: 306 of WO2016077381. A nucleotide sequence encoding a leader sequence SEQ ID NO:402 was placed in-frame upstream of the VH and VL coding sequences. Table 37 shows cell-based assay data comparing IL-167/LS, IL-158/LS, IL33-265, and IL33-310.

TABLE 37

|  | Titration vs 0.1 ng/ml mm2 CYS human IL-33 | | | Titration vs. 0.1 ng/ml cyIL33_3cys | | | cyno: human IC50 ratio: cys mutant | Titration vs. 0.1 ng/ml R&D rhIL-33 (+10 mM DTT pretreat) | | | Titration vs 0.1 ng/ml pfe cyno WT IL-33 (+10 mM DTT pretreat) | | | cyno: human IC50 ratio: WT |
|---|---|---|---|---|---|---|---|---|---|---|---|---|---|---|
|  | IC50 (nM) | SEM | n | IC50 (nM) | SEM | n |  | IC50 (nM) | SEM | n | IC50 (nM) | SEM | n |  |
| IL33-167/LS | 0.037 | 0.012 | 2 | 0.036 | 0.006 | 3 | 1.0 | 0.250 | 0.019 | 4 | 1.560 | 0.317 | 7 | 6.2 |
| IL33-158/LS | 0.019 | 0.004 | 3 | 0.034 | 0.009 | 3 | 1.8 | 0.331 | 0.085 | 5 | 1.391 | 0.331 | 7 | 4.2 |
| IL33-265 | 0.014 | 0.003 | 5 | 1.562 | 0.243 | 4 | 108.9 | 0.050 | 0.010 | 6 | 12.691 | 2.484 | 5 | 255.7 |
| IL33-310 | 0.018 | 0.002 | 3 | 0.590 | 0.041 | 3 | 32.5 | 0.061 | 0.011 | 3 | 1.644 | 0.421 | 4 | 27.1 |

IgG1 antibody IL33-244 is based on APE04909 disclosed as SEQ ID NO:136 and SEQ ID NO: 171 of WO2015/106080. APE04909 is a neutralizing antibody described in detail, e.g. in example 2 (in vitro cell-based assays) and example 5 (in vivo study of human IL-33 dependent proliferation of eosinophils in mice, example 5). However, when an antibody was generated according to SEQ ID NOs:136/171 of WO2015/106080, it expressed poorly and had a heterogeneous SEC profile. To eliminate the possibility that that poor codon usage contributed to poor expression, DNA sequences from similar, well-expressed antibodies were used as a starting point and adjusted to encode the sequences above using high-frequency human codons where changes were necessary. However, expression was still poor after this step, and SEC patterns still showed heterogeneity (Table 38).

TABLE 38

| Antibody name | VH SEQ ID NO: | VL SEQ ID NO: | Protein yield (mg/L) | Area % (SEC) | IC50 vs 0.1 ng/ml human IL33 mm2 in 239 ST2 NFkB assay expt rts16-42 |
|---|---|---|---|---|---|
| IL33-244 | 136 | 171 | 9 | too low to integrate | 10.9 |

IL33-248 was described in WO2015/099175 as 3H04 and A25 (see FIG. 8), and IL33-247 was described in WO2015/099175 as 1C04 and A10 (see FIG. 9). Variable region nucleotide sequences from WO 2015/099175 were synthesized and cloned into human IgG1 and human lambda expression vectors (see Table 39 for sequences from WO2015/099175). IL33-247 and IL33-248 have a distinct epitope IL-158/LS and IL33-167/LS, and yielded 90.75 mgL CM and an area under the curve of 100% for IL33-247 and 36 mg/L CM and an area under the curve of 85.3% for IL33-248, which also showed an asymmetrical peak with a wide retention time.

TABLE 39

| | | WO2015/099175 SEQ ID | | | |
|---|---|---|---|---|---|
| Antibody (IgG1) | Antibody (IgG4) | VH | VL | VH-DNA | VL-DNA |
| IL33-247 | 1C04/A10 | 105 | 79 | 254 | 228 |
| IL33-248 | 3H04/A25 | 115 | 92 | 264 | 241 |

IgG1 antibody IL33-312 is based on 33_640087-7B of WO16156440 (SEQ ID NO: 615 and SEQ ID NO: 617) (see e.g., FIG. 52, & Example 11-12). IgG1 antibody IL33-313 is based on 33 640237-2B of WO16156440 (SEQ ID NO: 623 and SEQ ID NO: 625).

Example 27 Human and Cynomolgus Monkey IL-33 Neutralization Activity of Optimized Anti-IL-33 Antibodies and Comparator Antibodies in Cell-Based Assays The antibodies IL33-158LS (SEQ ID NO:244 SEQ ID NO:209), IL33-167LS (SEQ ID NO:245, SEQ ID NO:93), IL33-265 (SEQ ID NO:403 SEQ ID NO:404), and IL33-310 (SEQ ID NO:405 SEQ ID NO:406), were tested in the HEK293 ST2 NFkB reporter assay for neutralization of human and cynomolgus monkey IL-33 (Table 40). IL33-158LS (SEQ ID NO:244 SEQ ID NO:209) showed similar neutralization potency against the cysteine mutant forms of human and cynomolgus IL-33 (with a monkey IC50:human IC50 ratio of 1.8). Likewise, the neutralization potency of IL33-158LS (SEQ ID NO:244 SEQ ID NO:209) against wild-type human and cynomolgus monkey IL-33 (SEQ ID NO:397) was similar (with a monkey IC50:human IC50 ratio of 4.2). IL33-167LS (SEQ ID NO:245, SEQ ID NO:93) showed similarly close neutralization of monkey and human IL-33. Two other antibodies, IL33-265 (SEQ ID NO:403 SEQ ID NO:404), and IL33-310 (SEQ ID NO:405 SEQ ID NO:406) showed a wider difference between neutralization of human and cynomolgus monkey IL-33 (monkey IC50: human IC50 ratios ranging from 28.7 to over 250).

In a second experiment, IL33-158LS (SEQ ID NO:244, SEQ ID NO:209), IL33-310 (SEQ ID NO:405, SEQ ID NO:406), IL33-312 (SEQ ID NO:407, SEQ ID NO:408), and IL33-313 (SEQ ID NO:409, SEQ ID NO:410), were tested in the HEK293 ST2 NFkB reporter assay for neutralization of human and cynomolgus monkey IL-33 (Table 41). IL33-158LS and IL33-312 had similarly close relative neutralization of monkey and human cysteine mutant IL-33 (cynomolgus monkey IC50: human IC50 ratios of 1.4, and 1.1, respectively). Relative neutralization of wild-type human and cynomolgus monkey IL-33 was also similar for IL33-158LS and IL33-312 (cynomolgus monkey IC50: human IC50 ratios of 9.2 and 5.4, respectively). IL33-310 and IL33-313 showed a wider difference between human and cynomolgus monkey IC50s (monkey IC50:human IC50 ratios ranging from 29.2 to 528.1; Table 41). Together, the data show that IL33-158LS (SEQ ID NO:244 SEQ ID NO:209) has among the most highly similar neutralization of wild-type human and cynomolgous monkey IL-33 within this panel of high-potency anti human IL-33 antibodies, comparable to IL33-312.

TABLE 40

Neutralization of human and cynomolgus monkey IL-33 in HEK293 ST2 NFkB reporter cell assay

| Antibody | HC SEQ NO | LC SEQ NO | HEK293 ST2 NFkB hIL-33 (mm2) IC$_{50}$ (nM) ± SEM (n) | HEK293 ST2 NFkB cynomolgus monkey IL-33 (cys mut) IC50 (nM) ± SEM (n) | Cynomolgus monkey: human IC50 ratio: cysteine mutant IL-33 | HEK293 ST2 NFkB hIL-33 (R&D) IC$_{50}$ (nM) ± SEM (n) | HEK293 ST2 NFkB cynomolgus monkey IL-33 (wild-type) IC$_{50}$ (nM) ± SEM (n) | Cynomolgus monkey: human IC50 ratio: wild-type IL-33 |
|---|---|---|---|---|---|---|---|---|
| IL33-158LS | 244 | 209 | 0.019 ± 0.004(3) | 0.034 ± 0.009(3) | 1.8 | 0.331 ± 0.085(5) | 1.391 ± 0.331(7) | 4.2 |
| IL33-167LS | 245 | 93 | 0.037 ± 0.012(2) | 0.036 ± 0.006(3) | 1.0 | 0.250 ± 0.019(4) | 1.560 ± 0.317(7) | 6.2 |
| IL33-265 | 403 | 404 | 0.014 ± 0.003(5) | 1.562 ± 0.243(4) | 108.9 | 0.050 ± 0.010(6) | 12.691 ± 2.484(5) | 255.7 |
| IL33-310 | 405 | 406 | 0.018 ± 0.002(3) | 0.590 ± 0.041(3) | 32.5 | 0.061 ± 0.011(3) | 1.644 ± 0.421(4) | 27.1 |

TABLE 41

Neutralization of human and cynomolgus monkey IL-33 in HEK293 ST2 NFkB reporter cell assay

| Antibody | HC SEQ NO | LC SEQ NO | HEK293 ST2 NFkB hIL-33 (mm2) IC$_{50}$ (nM) | HEK293 ST2 NFkB cynomolgus monkey IL-33 (cys mut) IC50 (nM) | Cynomolgus monkey: human IC50 ratio: cysteine mutant IL-33 | HEK293 ST2 NFkB hIL-33 (R&D) IC$_{50}$ (nM) | HEK293 ST2 NFkB cynomolgus monkey IL-33 (wild-type) IC$_{50}$ (nM) | Cynomolgus monkey: human IC50 ratio: wild-type IL-33 |
|---|---|---|---|---|---|---|---|---|
| IL33-158LS | 244 | 209 | 0.009 | 0.013 | 1.4 | 0.061 | 0.562 | 9.2 |
| IL33-310 | 405 | 406 | 0.007 | 0.213 | 29.2 | 0.021 | 2.185 | 103.5 |
| IL33-312 | 407 | 408 | 0.003 | 0.003 | 1.1 | 0.008 | 0.043 | 5.4 |
| IL33-313 | 409 | 410 | 0.006 | 1.197 | 206.2 | 0.027 | 14.131 | 528.1 | n = 1

Example 28 Kinetic Evaluation of Anti-IL-33 Antibodies Using Surface Plasmon Resonance Biacore kinetic assays were conducted at 37° C. at a collection rate of 1 Hz on a Biacore T200 instrument (GE Healthcare). Reduced and non-reduced wild-type human IL-33 and reduced wild-type cynomolgus monkey IL-33 were covalently coupled to a CM5 sensor chip (catalogue number BR100530, GE Healthcare) using an amine coupling kit (catalogue number BR100050, GE Healthcare) according to the manufacturer's protocol. Flow cell 1 was activated and blocked for use as a reference flow cell. In one experiment, immobilization levels were 218 RU of reduced wild-type human IL-33 and 248 RU of reduced wild-type cynomolgus monkey IL-33. In this experiment, titration series of the anti-IL-33 Fabs 158LS and 167LS were injected at a flow rate of 50 ul per min and the dissociation was monitored for 3600 seconds. In a second experiment, immobilization levels were 130 RU of reduced wild-type human IL-33, 97 RU of non-reduced wild-type human IL-33, and 88 RU of reduced wild-type cynomolgus monkey IL-33. In this experiment, titration series of the anti-IL-33 Fabs 158LS, 167LS, and IL33-265 were injected at a flow rate of 50 ul per min and the dissociation was monitored for 900 seconds. The dilution and running buffer was HBS-EP+ (10 mM HEPES pH 7.4, 0.15M NaCl, 3 mM EDTA, 0.05% P-20). Rate constants and affinities were determined by fitting the resulting sensorgram data to a 1:1 model in Biacore T200 Evaluation software version 1.0 (GE Healthcare). Intact IL33-0310 IgG was also tested in this format and was observed to bind with rapid association and very slow dissociation to reduced human IL-33 and reduced cynomolgus monkey IL-33, but it did not bind to non-reduced human IL-33 (Table Y). Kinetic properties of the bivalent IgG cannot be directly compared to those of monovalent Fab fragments and are not presented here.

The anti-IL-33 Fabs 158LS, 167LS, IL33-265, and the anti-IL33 IgG IL33-310 all bound strongly to DTT-treated wild-type human and cynomolgus monkey IL-33. By contrast, none of these antibodies bound to non-reduced wild-type human IL-33 (Table 42).

The affinities of the Fab of IL33-158LS (SEQ ID NO:244 SEQ ID NO:209) to wild-type human and cynomolgus monkey IL-33 (SEQ ID NO:397) were similar (with a monkey $K_D$:human $K_D$ ratio of 1.3 and 2.3 in two independent experiments). IL33-167LS (SEQ ID NO:245, SEQ ID NO:93) showed similarly close affinity to monkey and human IL-33. IL33-265 (SEQ ID NO:403 SEQ ID NO:1003) showed a wider difference between affinity to wild-type human and cynomolgus monkey IL-33, with a monkey KD:human KD ratio of 57.8 (Table 42).

TABLE 42

Kinetic parameters of Fab fragments of Fabs 158LS, 167LS, and IL33-265 binding to wild-type human and cynomolgus monkey IL-33 measured by surface plasmon resonance

| Fab | IL-33 form | ka (1/Ms) ± SEM | kd (1/s) ± SEM | kD (pM) ± SEM (n) | Ratio of cynomolgus monkey KD/ human KD |
|---|---|---|---|---|---|
| Experiment 1 | | | | | |
| IL33-158LS | huIL-33 (WT + DTT) | 3.13E+06 ± 3.00E+05 | 3.30E−04 ± 5.00E−07 | 106 ± 11 | 1.3 |
| IL33-158LS | cyno IL-33 (WT + DTT) | 4.50E+06 ± 5.05E+05 | 6.20E−04 ± 3.65E−05 | 139 ± 8 | |
| IL33-167LS | huIL-33 (WT + DTT) | 3.03E+06 ± 8.50E+04 | 2.76E−04 ± 1.50E−05 | 91 ± 2 | 1.5 |
| IL33-167LS | cyno IL-33 (WT + DTT) | 4.81E+06 ± 2.80E+05 | 6.65E−04 ± 3.20E−05 | 139 ± 2 | |
| Experiment 2 | | | | | |
| IL33-158LS | huIL-33 (WT no DTT) | | | (no binding) | |
| IL33-158LS | huIL-33 (WT + DTT) | 4.11E+06 ± 5.00E3 | 4.17E−04 ± 3.30E−05 | 101 ± 8 | 2.3 |
| IL33-158LS | cyno IL-33 (WT + DTT) | 5.32E+06 ± 4.82E+05 | 1.21E−03 ± 1.01E−04 | 228 ± 2 | |

TABLE 42-continued

Kinetic parameters of Fab fragments of Fabs 158LS, 167LS, and IL33-265 binding to wild-type human and cynomolgus monkey IL-33 measured by surface plasmon resonance

| Fab | IL-33 form | ka (1/Ms) ± SEM | kd (1/s) ± SEM | kD (pM) ± SEM (n) | Ratio of cynomolgus monkey KD/ human KD |
|---|---|---|---|---|---|
| IL33-167LS | huIL-33 (WT no DTT) | | | (no binding) | |
| IL33-167LS | huIL-33 (WT + DTT) | 3.96E+06 ± 5.00E+03 | 3.50E−04 ± 1.30E−05 | 89 ± 3 | 2.5 |
| IL33-167LS | cyno IL-33 (WT + DTT) | 5.50E+06 ± 5.30E+05 | 1.19E−03 ± 1.04E−04 | 218 ± 2 | |
| IL33-265 | huIL-33 (WT no DTT) | | | (no binding) | |
| IL33-265 | huIL-33 (WT + DTT) | 2.89E+06 ± 6.00E+04 | 8.07E−05 ± 1.27E−05 | 28 ± 5 | 57.8 |
| IL33-265 | cyno IL-33 (WT + DTT) | 2.58E+06 ± 5.59E+05 | 3.80E−03 ± 1.60E−04 | 1618 ± 342 | |
| IL33-310 IgG | huIL-33 (WT no DTT) | | | (no binding) | |

Example 29 Self-Interaction and Polyreactivity of Optimized Anti-IL-33 Antibodies and Comparator Antibodies The antibodies IL33-158 (SEQ ID NO:227 SEQ ID NO:209), IL33-158LS (SEQ ID NO:244 SEQ ID NO:209), and IL33-312 (SEQ ID NO: 407 SEQ ID NO: 408) were tested for binding to DNA and insulin, and in addition were tested for self-interaction in an AC-SINS assay (affinity-capture self-interaction nanoparticle spectroscopy; Liu et al., 2014, mAbs 6:483-92). In the AC-SINS assay, mAbs captured on gold nanospheres will induce a shift in the absorbance maximum if they bind to one another and thereby cause the beads to cluster, and high scores in this assay have been suggested to correlate with solubility and nonspecific membrane interactions (Liu et al., 2014, mAbs 6:483-92). IL33-158 and IL33-158LS had very low AC-SINS scores, comparable to those of the negative control, while IL33-312 had a score comparable to the positive control (Table 43). IL33-312 also had a high DNA-binding score, comparable to the positive control, while IL33-158 and IL33-158LS showed more moderate scores. Taken together, these results indicate that IL33-158 and IL33-158LS had substantially lower indicators of nonspecific binding than did IL33-312.

TABLE 43

Non-specific binding and self-interaction of IL-33 antibodies

| Antibody | HC SEQ NO | LC SEQ NO | AC-SINS (wavelength of maximum absorbance relative to blank, nm) | DNA binding normalized to blank | Insulin binding normalized to blank |
|---|---|---|---|---|---|
| IL33-158 | 227 | 209 | 0 | 5.25 ± 0.09 (2) | 6.42 ± 1.82 (2) |
| L33-158LS | 244 | 209 | 0 | 7.45 ± 0.10 (8) | 8.08 ± 0.48 (8) |
| IL33-312 | 407 | 408 | 18 ± 0.22 | 19.93 | 8.83 |
| Polyreactivity negative control (8.8) | | | 1 ± 0.07 | 2.14 | 3.22 |
| Polyreactivity positive control (MJ4-2 v1.1/P33) | | | 22 ± 1.11 | 21.78 | 14.77 |

The invention thus has been disclosed broadly and illustrated in reference to representative embodiments described above. Those skilled in the art will recognize that various modifications can be made to the present invention without departing from the spirit and scope thereof. All publications, patent applications, and issued patents, are herein incorporated by reference to the same extent as if each individual publication, patent application or issued patent were specifically and individually indicated to be incorporated by reference in its entirety. Definitions that are contained in text incorporated by reference are excluded to the extent that they contradict definitions in this disclosure.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention. In particular, any aspect of the invention described in the claims, alone or in combination with one or more additional claims and/or aspects of the description, is to be understood as being combinable with other aspects of the invention set out elsewhere in the claims and/or description and/or sequence listings and/or drawings.

In so far as specific examples found herein do not fall within the scope of an invention, said specific example may be explicitly disclaimed.

The use of the term "or" in the claims is used to mean "and/or" unless explicitly indicated to refer to alternatives only or the alternatives are mutually exclusive, although the disclosure supports a definition that refers to only alternatives and "and/or." As used herein the specification, "a" or "an" may mean one or more, unless clearly indicated otherwise. As used herein in the claim(s), when used in conjunction with the word "comprising", the words "a" or "an" may mean one or more than one. As used herein "another" may mean at least a second or more. Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The words "comprises/comprising" and the words "having/including" when used herein with reference to the present invention are used to specify the presence of stated features, integers, steps or components but does not preclude the presence or addition of one or more other features, integers, steps, components or groups thereof.

Although the disclosed teachings have been described with reference to various applications, methods, and compositions, it will be appreciated that various changes and modifications can be made without departing from the teachings herein and the claimed invention below. The examples are provided to better illustrate the disclosed teachings and are not intended to limit the scope of the teachings presented herein. While the present teachings have been described in terms of these exemplary embodiments, numerous variations and modifications of these exemplary embodiments are possible without undue experimentation. All such variations and modifications are within the scope of the current teachings.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The description and examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

TABLE 34

SUMMARY OF ANTIBODY SEQ IDS

| Antibody | Heavy Chain (HC) | | | | | | | | | |
|---|---|---|---|---|---|---|---|---|---|---|
| | HC CDR1 | HC CDR2 | HC CDR3 | JH | $V_H$ | CH1 | HINGE | CH2 | CH3 | HC |
| 7E8_chimera | 16 | 17 | 18 | 23 | 14 | 24 | 25 | 26 | 27 | 28 |
| 9B3_chimera | 33 | 34 | 35 | 39 | 32 | 24 | 25 | 26 | 27 | 40 |
| 12F9_chimera | 44 | 45 | 46 | 8 | 43 | 24 | 25 | 26 | 27 | 51 |
| 14D8_chimera | 44 | 55 | 46 | 8 | 54 | 24 | 25 | 26 | 27 | 59 |
| 30A1_chimera | 62 | 63 | 64 | 8 | 61 | 24 | 25 | 26 | 27 | 69 |
| 30B11_chimera | 73 | 74 | 75 | 8 | 72 | 24 | 25 | 26 | 27 | 78 |
| 9B3_chimera_huJseg | 33 | 34 | 35 | 39 | 32 | 24 | 25 | 26 | 27 | 40 |
| 14D8_chimera_huJseg | 44 | 55 | 45 | 8 | 54 | 24 | 25 | 26 | 27 | 59 |
| 30A1_chimera_huJseg | 62 | 63 | 64 | 8 | 61 | 24 | 25 | 26 | 27 | 69 |
| 30B11_chimera_huJseg | 73 | 74 | 75 | 8 | 72 | 24 | 25 | 26 | 27 | 78 |
| 7E8 CDR graft | 16 | 17 | 18 | 8 | 90 | 24 | 25 | 26 | 27 | 92 |
| IL33-10 | 16 | 17 | 18 | 8 | 94 | 24 | 25 | 96 | 27 | 95 |
| 9B3 CDR graft | 33 | 34 | 35 | 8 | 97 | 24 | 25 | 26 | 27 | 99 |
| 12F9 CDR graft | 102 | 45 | 46 | 8 | 101 | 24 | 25 | 26 | 27 | 104 |
| 30B11 CDR graft | 107 | 74 | 75 | 8 | 106 | 24 | 25 | 26 | 27 | 109 |
| 30B11 CDR graft_R71V | 107 | 74 | 75 | 8 | 111 | 24 | 25 | 26 | 27 | 112 |
| 9B3_1 | 33 | 34 | 114 | 39 | 113 | 24 | 25 | 26 | 27 | 116 |
| 9B3_2A | 33 | 34 | 119 | 39 | 118 | 24 | 25 | 26 | 27 | 120 |
| 9B3_2B | 33 | 34 | 122 | 39 | 121 | 24 | 25 | 26 | 27 | 123 |
| 9B3_3 | 33 | 34 | 122 | 39 | 124 | 24 | 25 | 26 | 27 | 125 |
| 9B3_5 | 33 | 34 | 127 | 39 | 126 | 24 | 25 | 26 | 27 | 128 |
| 9B3_7 | 33 | 34 | 130 | 39 | 129 | 24 | 25 | 26 | 27 | 131 |
| 9B3_13 | 33 | 34 | 133 | 39 | 132 | 24 | 25 | 26 | 27 | 134 |
| 9B3_15 | 33 | 34 | 136 | 39 | 135 | 24 | 25 | 26 | 27 | 137 |
| 9B3_17 | 33 | 34 | 139 | 39 | 138 | 24 | 25 | 26 | 27 | 140 |
| 9B3_22 | 33 | 34 | 142 | 39 | 141 | 24 | 25 | 26 | 27 | 143 |
| 9B3_31V2 | 33 | 34 | 145 | 39 | 144 | 24 | 25 | 26 | 27 | 146 |
| 9B3_36 | 33 | 34 | 148 | 39 | 147 | 24 | 25 | 26 | 27 | 149 |
| 9B3_79 | 33 | 34 | 148 | 39 | 150 | 24 | 25 | 26 | 27 | 151 |
| 9B3_124 | 33 | 34 | 153 | 39 | 152 | 24 | 25 | 26 | 27 | 154 |
| 9B3_162 | 33 | 34 | 156 | 39 | 155 | 24 | 25 | 26 | 27 | 157 |
| 7E8H/9B3K | 16 | 17 | 18 | 23 | 14 | 24 | 25 | 26 | 27 | 28 |
| 9B3_563 | 33 | 34 | 159 | 39 | 158 | 24 | 25 | 26 | 27 | 160 |
| IL33-11 | 33 | 17 | 18 | 8 | 161 | 24 | 25 | 96 | 27 | 162 |
| IL33-12 | 16 | 34 | 18 | 8 | 163 | 24 | 25 | 96 | 27 | 164 |
| IL33-13 | 16 | 17 | 35 | 8 | 165 | 24 | 25 | 96 | 27 | 166 |
| IL33-45 | 16 | 168 | 18 | 8 | 167 | 24 | 25 | 96 | 27 | 169 |
| IL33-55 | 16 | 171 | 18 | 8 | 170 | 24 | 25 | 96 | 27 | 172 |
| IL33-56 | 16 | 174 | 18 | 8 | 173 | 24 | 25 | 96 | 27 | 175 |
| IL33-57 | 16 | 17 | 177 | 8 | 176 | 24 | 25 | 96 | 27 | 178 |
| IL33-58 | 16 | 180 | 18 | 8 | 179 | 24 | 25 | 96 | 27 | 181 |
| IL33-61 | 16 | 174 | 177 | 8 | 182 | 24 | 25 | 96 | 27 | 183 |

TABLE 34-continued

SUMMARY OF ANTIBODY SEQ IDS

| | | | | | | | | | | |
|---|---|---|---|---|---|---|---|---|---|---|
| IL33-62 | 16 | 171 | 177 | 8 | 184 | 24 | 25 | 96 | 27 | 185 |
| IL33-68 | 16 | 17 | 187 | 8 | 186 | 24 | 25 | 96 | 27 | 188 |
| IL33-74 | 16 | 17 | 18 | 8 | 94 | 24 | 25 | 96 | 27 | 95 |
| IL33-75 | 16 | 17 | 18 | 8 | 94 | 24 | 25 | 96 | 27 | 95 |
| IL33-80 | 16 | 17 | 18 | 8 | 94 | 24 | 25 | 96 | 27 | 95 |
| IL33-81 | 16 | 17 | 18 | 8 | 94 | 24 | 25 | 96 | 27 | 95 |
| IL33-103 | 16 | 202 | 18 | 8 | 201 | 24 | 25 | 96 | 27 | 203 |
| IL33-117 | 16 | 205 | 18 | 8 | 204 | 24 | 25 | 96 | 27 | 206 |
| IL33-136 | 16 | 174 | 18 | 8 | 173 | 24 | 25 | 96 | 27 | 175 |
| IL33-153 | 16 | 211 | 18 | 8 | 210 | 24 | 25 | 26 | 27 | 212 |
| IL33-154 | 16 | 214 | 18 | 8 | 213 | 24 | 25 | 26 | 27 | 215 |
| IL33-155 | 16 | 217 | 18 | 8 | 216 | 24 | 25 | 26 | 27 | 218 |
| IL33-156 | 16 | 220 | 18 | 8 | 219 | 24 | 25 | 26 | 27 | 221 |
| IL33-157 | 16 | 223 | 18 | 8 | 222 | 24 | 25 | 26 | 27 | 224 |
| IL33-158 | 16 | 226 | 18 | 8 | 225 | 24 | 25 | 26 | 27 | 227 |
| IL33-167 | 16 | 211 | 18 | 8 | 210 | 24 | 25 | 26 | 27 | 212 |
| IL33-168 | 16 | 214 | 18 | 8 | 213 | 24 | 25 | 26 | 27 | 215 |
| IL33-169 | 16 | 217 | 18 | 8 | 216 | 24 | 25 | 26 | 27 | 218 |
| IL33-170 | 16 | 220 | 18 | 8 | 219 | 24 | 25 | 26 | 27 | 221 |
| IL33-171 | 16 | 223 | 18 | 8 | 222 | 24 | 25 | 26 | 27 | 224 |
| IL33-172 | 16 | 226 | 18 | 8 | 225 | 24 | 25 | 26 | 27 | 227 |
| IL33-175 | 16 | 229 | 18 | 8 | 228 | 24 | 25 | 26 | 27 | 230 |
| IL33-186 | 16 | 232 | 18 | 8 | 231 | 24 | 25 | 26 | 27 | 233 |
| IL33-187 | 16 | 235 | 18 | 8 | 234 | 24 | 25 | 26 | 27 | 236 |
| IL33-188 | 16 | 229 | 18 | 8 | 228 | 24 | 25 | 26 | 27 | 230 |
| IL33-158-152 | 16 | 226 | 18 | 8 | 225 | 24 | 25 | 26 | 240 | 241 |
| IL33-167-153 | 16 | 211 | 18 | 8 | 210 | 24 | 25 | 26 | 240 | 242 |
| IL33-158LS | 16 | 226 | 18 | 8 | 225 | 24 | 25 | 26 | 243 | 244 |
| IL33-167LS | 16 | 211 | 18 | 8 | 210 | 24 | 25 | 26 | 243 | 245 |
| IL33-271 | 247 | 248 | 249 | 8 | 246 | 24 | 25 | 26 | 27 | 254 |

| | Light Chain (LC) | | | | | | |
|---|---|---|---|---|---|---|---|
| Antibody | LC CDR1 | LC CDR2 | LC CDR3 | JK | $V_L$ | CL | LC |
| 7E8_chimera | 20 | 21 | 22 | 29 | 19 | 30 | 31 |
| 9B3_chimera | 37 | 21 | 38 | 41 | 36 | 30 | 42 |
| 12F9_chimera | 48 | 49 | 50 | 52 | 47 | 30 | 53 |
| 14D8_chimera | 57 | 58 | 50 | 41 | 56 | 30 | 60 |
| 30A1_chimera | 66 | 67 | 68 | 70 | 65 | 30 | 71 |
| 30B11_chimera | 77 | 67 | 68 | 79 | 76 | 30 | 80 |
| 9B3_chimera_huJseg | 37 | 21 | 38 | 82 | 81 | 30 | 83 |
| 14D8_chimera_huJseg | 57 | 58 | 50 | 82 | 84 | 30 | 85 |
| 30A1_chimera_huJseg | 66 | 67 | 68 | 12 | 86 | 30 | 87 |
| 30B11_chimera_huJseg | 77 | 67 | 68 | 12 | 88 | 30 | 89 |
| 7E8 CDR graft | 20 | 21 | 22 | 12 | 91 | 30 | 93 |
| IL33-10 | 20 | 21 | 22 | 12 | 91 | 30 | 93 |
| 9B3 CDR graft | 37 | 21 | 33 | 12 | 98 | 30 | 100 |
| 12F9 CDR graft | 48 | 49 | 50 | 12 | 103 | 30 | 105 |
| 30B11 CDR graft | 77 | 67 | 68 | 12 | 108 | 30 | 110 |
| 30B11 CDR graft_R71V | 77 | 67 | 68 | 12 | 108 | 30 | 110 |
| 9B3_1 | 37 | 21 | 38 | 82 | 115 | 30 | 117 |
| 9B3_2A | 37 | 21 | 38 | 82 | 115 | 30 | 117 |
| 9B3_2B | 37 | 21 | 38 | 82 | 115 | 30 | 117 |
| 9B3_3 | 37 | 21 | 38 | 82 | 115 | 30 | 117 |
| 9B3_5 | 37 | 21 | 38 | 82 | 115 | 30 | 117 |
| 9B3_7 | 37 | 21 | 38 | 82 | 115 | 30 | 117 |
| 9B3_13 | 37 | 21 | 38 | 82 | 115 | 30 | 117 |
| 9B3_15 | 37 | 21 | 38 | 82 | 115 | 30 | 117 |
| 9B3_17 | 37 | 21 | 38 | 82 | 115 | 30 | 117 |
| 9B3_22 | 37 | 21 | 38 | 82 | 115 | 30 | 117 |
| 9B3_31V2 | 37 | 21 | 38 | 82 | 115 | 30 | 117 |
| 9B3_36 | 37 | 21 | 38 | 82 | 115 | 30 | 117 |
| 9B3_79 | 37 | 21 | 38 | 82 | 115 | 30 | 117 |
| 9B3_124 | 37 | 21 | 38 | 82 | 115 | 30 | 117 |
| 9B3_162 | 37 | 21 | 38 | 82 | 115 | 30 | 117 |
| 7E8H/9B3K | 37 | 21 | 38 | 82 | 115 | 30 | 117 |
| 9B3_563 | 37 | 21 | 38 | 82 | 115 | 30 | 117 |
| IL33-11 | 20 | 21 | 22 | 12 | 91 | 30 | 93 |
| IL33-12 | 20 | 21 | 22 | 12 | 91 | 30 | 93 |
| IL33-13 | 20 | 21 | 22 | 12 | 91 | 30 | 93 |
| IL33-45 | 20 | 21 | 22 | 12 | 91 | 30 | 93 |
| IL33-55 | 20 | 21 | 22 | 12 | 91 | 30 | 93 |
| IL33-56 | 20 | 21 | 22 | 12 | 91 | 30 | 93 |
| IL33-57 | 20 | 21 | 22 | 12 | 91 | 30 | 93 |
| IL33-58 | 20 | 21 | 22 | 12 | 91 | 30 | 93 |
| IL33-61 | 20 | 21 | 22 | 12 | 91 | 30 | 93 |

TABLE 34-continued

SUMMARY OF ANTIBODY SEQ IDS

| | | | | | | | |
|---|---|---|---|---|---|---|---|
| IL33-62 | 20 | 21 | 22 | 12 | 91 | 30 | 93 |
| IL33-68 | 20 | 21 | 22 | 12 | 91 | 30 | 93 |
| IL33-74 | 190 | 21 | 22 | 12 | 189 | 30 | 191 |
| IL33-75 | 193 | 21 | 22 | 12 | 192 | 30 | 194 |
| IL33-80 | 20 | 196 | 22 | 12 | 195 | 30 | 197 |
| IL33-81 | 20 | 199 | 22 | 12 | 198 | 30 | 200 |
| IL33-103 | 20 | 21 | 22 | 12 | 91 | 30 | 93 |
| IL33-117 | 20 | 21 | 22 | 12 | 91 | 30 | 93 |
| IL33-136 | 20 | 21 | 208 | 12 | 207 | 30 | 209 |
| IL33-153 | 20 | 21 | 208 | 12 | 207 | 30 | 209 |
| IL33-154 | 20 | 21 | 208 | 12 | 207 | 30 | 209 |
| IL33-155 | 20 | 21 | 208 | 12 | 207 | 30 | 209 |
| IL33-156 | 20 | 21 | 208 | 12 | 207 | 30 | 209 |
| IL33-157 | 20 | 21 | 208 | 12 | 207 | 30 | 209 |
| IL33-158 | 20 | 21 | 208 | 12 | 207 | 30 | 209 |
| IL33-167 | 20 | 21 | 22 | 12 | 91 | 30 | 93 |
| IL33-168 | 20 | 21 | 22 | 12 | 91 | 30 | 93 |
| IL33-169 | 20 | 21 | 22 | 12 | 91 | 30 | 93 |
| IL33-170 | 20 | 21 | 22 | 12 | 91 | 30 | 93 |
| IL33-171 | 20 | 21 | 22 | 12 | 91 | 30 | 93 |
| IL33-172 | 20 | 21 | 22 | 12 | 91 | 30 | 93 |
| IL33-175 | 20 | 21 | 22 | 12 | 91 | 30 | 93 |
| IL33-186 | 20 | 21 | 208 | 12 | 207 | 30 | 209 |
| IL33-187 | 20 | 21 | 208 | 12 | 207 | 30 | 209 |
| IL33-188 | 20 | 21 | 208 | 12 | 207 | 30 | 209 |
| IL33-158-152 | 20 | 21 | 208 | 12 | 207 | 30 | 209 |
| IL33-167-153 | 20 | 21 | 22 | 12 | 91 | 30 | 93 |
| IL33-158LS | 20 | 21 | 208 | 12 | 207 | 30 | 209 |
| IL33-167LS | 20 | 21 | 22 | 12 | 91 | 30 | 93 |
| IL33-271 | 251 | 252 | 253 | 255 | 250 | 30 | 256 |

SEQUENCE LIST

| SEQ | Description | Sequence |
|---|---|---|
| 1 | human IL-33 WT (R&D) C208, C227, C232, and C259, corresponding to C208, C227, C232 and C259 of SEQ ID NO: 396 are underlined and in bold | SITGISPITE YLASLSTYND QSITFALEDE SYEIYVEDLK KDEKKDKVLL SYYESQHPSN ESGDGVDGKM LMVTLSPTKD FWLHANNKEH SVELHKCEKP LPDQAFFVLH NMHSNCVSFE CKTDPGVFIG VKDNHLALIK VDSSENLCTE NILFKLSET |
| 2 | human ST2-Fc-His (R&D) | KFSKQSWGLE NEALIVRCPR QGKPSYTVDW YYSQTNKSIP TQERNRVFAS GQLLKFLPAE VADSGIYTCI VRSPTFNRTG YANVTIYKKQ SDCNVPDYLM YSTVSGSEKN SKIYCPTIDL YNWTAPLEWF KNCQALQGSR YRAHKSFLVI DNVMTEDAGD YTCKFIHNEN GANYSVTATR SFTVKDEQGF SLFPVIGAPA QNEIKEVEIG KNANLTCSAC FGKGTQFLAA VLWQLNGTKI TDFGEPRIQQ EEGQNQSFSN GLACLDMVLR IADVKEEDLL LQYDCLALNL HGLRRHTVRL SRKNPSKECF IEGRMDPKSC DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSRDELTK NQVSLTCLVK GFYPSDIAVE WESNGQPENN YKTTPPVLDS DGSFFLYSKL TVDKSRWQQG NVFSCSVMHE ALHNHYTQKS LSLSPGKHHH HHH |
| 3 | human IL-33 (mm2) Residues corresponding to C208, C227, C232 and C259 of SEQ ID NO: 396 are underlined and in bold | MSITGISPIT EYLASLSTYN DQSITFALED ESYEIYVEDL KKDEKKDKVL LSYYESQHPS NESGDGVDGK MLMVTLSPTK DFWLHANNKE HSVELHKSEK PLPDQAFFVL HNMHSNSVSF ESKTDPGVFI GVKDNHLALI KVDSSENLST ENILFKLSET HHHHHH |
| 4 | human IL-33 WT FLAG residues corresponding to C208, C227, C232 and C259 of SEQ ID NO: 396 are underlined and in bold | SITGISPITE YLASLSTYND QSITFALEDE SYEIYVEDLK KDEKKDKVLL SYYESQHPSN ESGDGVDGKM LMVTLSPTKD FWLHANNKEH SVELHKCEKP LPDQAFFVLH NMHSNCVSFE CKTDPGVFIG VKDNHLALIK VDSSENLCTE NILFKLSETL EDYKDDDDK |

-continued

| SEQ | Description | Sequence |
|---|---|---|
| 5 | cynomolgus monkey IL-33(CID42) Residues corresponding to C208, C227, C232 of SEQ ID NO: 396 underlined and in bold | MSITGISPIT ESLASLSTYN DQSITFALED ESYEIYVEDL KKDKKKDKVL LSYYESQHPS SESGDGVDGK MLMVTLSPTK DFWLQANNKE HSVELHKSEK PLPDQAFFVL HNRSFNSVSF ESKTDPGVFI GVKDNHLALI KVDYSENLGS ENILFKLSEI HHHHHH |
| 6 | human ST2-hIgG2Fc | KFSKQSWGLENEALIVRCPRQGKPSYTVDWYYSQTNKSIPTQERNRVFASGQLL KFLPAAVADSGIYTCIVRSPTFNRTGYANVTIYKKQSDCNVPDYLMYSTVSGSE KNSKIYCPTIDLYNWTAPLEWFKNCQALQGSRYRAHKSFLVIDNVMTEDAGDYT CKFIHNENGANYSVTATRSFTVKDEQGFSLFPVIGAPAQNEIKEVEIGKNANLT CSACFGKGTQFLAAVLWQLNGTKITDFGEPRIQQEEGQNQSFSNGLACLDMVLR LADVKEEDLLLQYDCLALNLHGLRRHTVRLSRKNPSKECFVECPPCPAPPVAGP SVFLFPPKPKDTLMISRTPEVTCVVVDVSHEDPEVQFNWYVDGMEVHNAKTKPR EEQFNSTFRVVSVLTVVHQDWLNGKEYKCKVSNKGLPAPIEKTISKTKGQPREP QVYTLPPSREEMTKNQVSLTCLVKGFYPSDIAVEWESNGQPENNYKTTPPMLDS DGSFFLYSKLTVDKSRWQQGNVFSCSVMHEALHNHYTQKSLSLSPGK |
| 7 | DP-54 framework region (VH3 sub-group) with a JH4 segment | EVQLVESGGGLVQPGGSLRLSCAASGFTFSSYWMSWVRQAPGKGLEWVANIKQD GSEKYYVDSVKGRFTISRDNAKNSLYLQMNSLRAEDTAVYYCARYFDYWGQGTL VTVSS |
| 8 | JH4 | WGQGTLVTVSS |
| 9 | human IgG1 effector function null constant region | ASTKGPSVFPLAPSSKSTSGGTAALGCLVKDYFPEPVTVSWNSGALTSGVHTFP AVLQSSGLYSLSSVVTVPSSSLGTQTYICNVNHKPSNTKVDKKVEPKSCDKTHT CPPCPAPEAAGAPSVFLFPPKPKDTLMISRTPEVTCVVVDVSHEDPEVKFNWYV DGVEVHNAKTKPREEQYNSTYRVVSVLTVLHQDWLNGKEYKCKVSNKALPAPIE KTISKAKGQPREPQVYTLPPSREEMTKNQVSLTCLVKGFYPSDIAVEWESNGQP ENNYKTTPPVLDSDGSFFLYSKLTVDKSRWQQGNVFSCSVMHEALHNHYTQKSL SLSPGK |
| 10 | human IgG1 wild-type constant region | ASTKGPSVFPLAPSSKSTSGGTAALGCLVKDYFPEPVTVSWNSGALTSGVHTFP AVLQSSGLYSLSSVVTVPSSSLGTQTYICNVNHKPSNTKVDKKVEPKSCDKTHT CPPCPAPELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNKALPAPIE KTISKAKGQPREPQVYTLPPSREEMTKNQVSLTCLVKGFYPSDIAVEWESNGQP ENNYKTTPPVLDSDGSFFLYSKLTVDKSRWQQGNVFSCSVMHEALHNHYTQKSL SLSPGK |
| 11 | DPK9 framework (VKI sub-group) with a JK4 segment | DIQMTQSPSSLSASVGDRVTITCRASQSISSYLNWYQQKPGKAPKLLIYAASSL QSGVPSRFSGSGSGTDFTLTISSLQPEDFATYYCQQSYSTPLTFGGGTKVEIK |
| 12 | JK4 | FGGGTKVEIK |
| 13 | human kappa constant domain | RTVAAPSVFIFPPSDEQLKSGTASVVCLLNNFYPREAKVQWKVDNALQSGNSQE SVTEQDSKDSTYSLSSTLTLSKADYEKHKVYACEVTHQGLSSPVTKSFNRGEC |
| 14 | 7E8 chimera VH | EVQLVETGGGLVQPGRSLKLSCKTSGFTFSSYWMYWIRQAPGKGLEWVSSITPN GGNTYYPDSVKGRFTISRDNAENTIYLQMSSLRSEDTATYFCAKGHYYYTSYSL GYWGQGSLVTVSS |
| 15 | 7E8 chimera VH secretory leader | MGWSCIILFLVATATGAHS |
| 16 | 7E8 chimera CDRH1 | GFTFSSYWMY |
| 17 | 7E8 chimera CDRH2 | SITPNGGNTYYPDSVKG |
| 18 | 7E8 chimera CDRH3 | GHYYYTSYSLGY |
| 19 | 7E8 chimera VL | EIQMTQSPSVLSASVGDRVTLSCKASQNINKHLDWYQQKLGEAPKLLIYFTNNL QTGIPSRFSGSGSGTDCTLTINSLQPGDVATYFCFQYNNGWTFGGGTKLELD |
| 20 | 7E8 chimera CDRL1 | KASQNINKHLD |
| 21 | 7E8 chimera CDRL2 | FTNNLQT |
| 22 | 7E8 chimera CDRL3 | FQYNNGWT |
| 23 | 7E8 chimera JH | WGQGSLVTVSS |
| 24 | CH1 hIgG1 WT | ASTKGPSVFPLAPSSKSTSGGTAALGCLVKDYFPEPVTVSWNSGALTSGVHTFP AVLQSSGLYSLSSVVTVPSSSLGTQTYICNVNHKPSNTKVDKKV |

| SEQ | Description | Sequence |
|---|---|---|
| 25 | Human IgG1 hinge | EPKSCDKTHTCPPCP |
| 26 | CH2 hIgG1 effector function null | APEAAGAPSVFLFPPKPKDTLMISRTPEVTCVVVDVSHEDPEVKFNWYVDGVEV HNAKTKPREEQYNSTYRVVSVLTVLHQDWLNGKEYKCKVSNKALPAPIEKTISK AK |
| 27 | CH3 hIgG1 WT | GQPREPQVYTLPPSREEMTKNQVSLTCLVKGFYPSDIAVEWESNGQPENNYKTT PPVLDSDGSFFLYSKLTVDKSRWQQGNVFSCSVMHEALHNHYTQKSLSLSPGK |
| 28 | 7E8 chimera HC | EVQLVETGGGLVQPGRSLKLSCKTSGFTFSSYWMYWIRQAPGKGLEWVSSITPN GGNTYYPDSVKGRFTISRDNAENTIYLQMSSLRSEDTATYFCAKGHYYYTSYSL GYWGQGSLVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVD KKVEPKSCDKTHTCPPCPAPEAAGAPSVFLFPPKPKDTLMISRTPEVTCVVVDV SHEDPEVKFNWYVDGVEVHNAKTKPREEQYNSTYRVVSVLTVLHQDWLNGKEYK CKVSNKALPAPIEKTISKAKGQPREPQVYTLPPSREEMTKNQVSLTCLVKGFYP SDIAVEWESNGQPENNYKTTPPVLDSDGSFFLYSKLTVDKSRWQQGNVFSCSVM HEALHNHYTQKSLSLSPGK |
| 29 | 7E8 chimera JK | FGGGTKLELD |
| 30 | CL | RTVAAPSVFIFPPSDEQLKSGTASVVCLLNNFYPREAKVQWKVDNALQSGNSQE SVTEQDSKDSTYSLSSTLTLSKADYEKHKVYACEVTHQGLSSPVTKSFNRGEC |
| 31 | 7E8 chimera LC | EIQMTQSPSVLSASVGDRVTLSCKASQNINKHLDWYQQKLGEAPKLLIYFTNNL QTGIPSRFSGSGSGTDCTLTINSLQPGDVATYFCQYNNGWTFGGGTKLELDRT VAAPSVFIFPPSDEQLKSGTASVVCLLNNFYPREAKVQWKVDNALQSGNSQESV TEQDSKDSTYSLSSTLTLSKADYEKHKVYACEVTHQGLSSPVTKSFNRGEC |
| 32 | 9B3 chimera VH | EVQLVETGGGLVQPGRSLKLSCVASGFTFSNYWMYWIRQAPGMGLEWVSSINND GGNTYYLDSVKGRFTISRNNAENTVYLQMNSLRSEDTATYYCAKGHYSYSSYSF SYWGQGTLVTVSS |
| 33 | 9B3 chimera CDRH1 | GFTFSNYWMY |
| 34 | 9B3 chimera CDRH2 | SINNDGGNTYYLDSVKG |
| 35 | 9B3 chimera CDRH3 | GHYSYSSYSFSY |
| 36 | 9B3 chimera VL | DIQMTQSPSVLSASVGDRVTLSCKASHNINKHLDWCQQKVGEAPKLLIYFTNNL QTGIPSRFSGSGSGTDYTLTISSLQPEDVATYFCFQYNSGWTFGGGTKLELK |
| 37 | 9B3 chimera CDRL1 | KASHNINKHLD |
| 38 | 9B3 chimera CDRL3 | FQYNSGWT |
| 39 | 9B3 chimera JH | WGQGTLVTVSS |
| 40 | 9B3 chimera HC | EVQLVETGGGLVQPGRSLKLSCVASGFTFSNYWMYWIRQAPGMGLEWVSSINND GGNTYYLDSVKGRFTISRNNAENTVYLQMNSLRSEDTATYYCAKGHYSYSSYSF SYWGQGTLVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVD KKVEPKSCDKTHTCPPCPAPEAAGAPSVFLFPPKPKDTLMISRTPEVTCVVVDV SHEDPEVKFNWYVDGVEVHNAKTKPREEQYNSTYRVVSVLTVLHQDWLNGKEYK CKVSNKALPAPIEKTISKAKGQPREPQVYTLPPSREEMTKNQVSLTCLVKGFYP SDIAVEWESNGQPENNYKTTPPVLDSDGSFFLYSKLTVDKSRWQQGNVFSCSVM HEALHNHYTQKSLSLSPGK |
| 41 | 9B3 chimera JK | FGGGTKLELK |
| 42 | 9B3 chimera LC | DIQMTQSPSVLSASVGDRVTLSCKASHNINKHLDWCQQKVGEAPKLLIYFTNNL QTGIPSRFSGSGSGTDYTLTISSLQPEDVATYFCFQYNSGWTFGGGTKLELKRT VAAPSVFIFPPSDEQLKSGTASVVCLLNNFYPREAKVQWKVDNALQSGNSQESV TEQDSKDSTYSLSSTLTLSKADYEKHKVYACEVTHQGLSSPVTKSFNRGEC |
| 43 | 12F9 chimera VH | EVQLVESGGDLVQPGRSLKLSCVTSGFIFKNYWMTWIRQVPGKGLEWVASITNT GGATYYPDSVKGRFTISRDNSENTLYLQMNSLRSEDTATYYCARDRRYNSGSPF AYWGQGTLVTVSS |
| 44 | 12F9 chimera CDRH1 | GFIFKNYWMT |
| 45 | 12F9 chimera CDRH2 | SITNTGGATYYPDSVKG |
| 46 | 12F9 chimera CDRH3 | DRRYNSGSPFAY |

-continued

| SEQ | Description | Sequence |
|---|---|---|
| 47 | 12F9 chimera VL | DIQLTQSPSTLAASLGERVTISCRASQSISNSLIWFQQKPDGTIKRLIYSSSTL ESGVPSRFSGSGSGTDYSLSISSLESEDFAMYYCLQYATYPWTFGGGTKLELR |
| 48 | 12F9 chimera CDRL1 | RASQSISNSLI |
| 49 | 12F9 chimera CDRL2 | SSSTLES |
| 50 | 12F9 chimera CDRL3 | LQYATYPWT |
| 51 | 12F9 chimera HC | EVQLVESGGDLVQPGRSLKLSCVTSGFIFKNYWMTWIRQVPGKGLEWVASITNT GGATYYPDSVKGRFTISRDNSENTLYLQMNSLRSEDTATYYCARDRRYNSGSPF AYWGQGTLVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVD KKVEPKSCDKTHTCPPCPAPEAAGAPSVFLFPPKPKDTLMISRTPEVTCVVVDV SHEDPEVKFNWYVDGVEVHNAKTKPREEQYNSTYRVVSVLTVLHQDWLNGKEYK CKVSNKALPAPIEKTISKAKGQPREPQVYTLPPSREEMTKNQVSLTCLVKGFYP SDIAVEWESNGQPENNYKTTPPVLDSDGSFFLYSKLTVDKSRWQQGNVFSCSVM HEALHNHYTQKSLSLSPGK |
| 52 | 12F9 chimera JK | FGGGTKLELR |
| 53 | 12F9 chimera LC | DIQLTQSPSTLAASLGERVTISCRASQSISNSLIWFQQKPDGTIKRLIYSSSTL ESGVPSRFSGSGSGTDYSLSISSLESEDFAMYYCLQYATYPWTFGGGTKLELRR TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC |
| 54 | 14D8 chimera VH | EVQLVDSGGDQVQPGRSLKLSCVASGFIFKNYWMTWIRQVPGKGLEWIASITNS GGNTYYPDSVKGRFTISRDNAKDTLYLQMNSLRSEDTATYYCARDRRYNSGSPF AYWGQGTLVTVSS |
| 55 | 14D8 chimera CDRH2 | SITNSGGNTYYPDSVKG |
| 56 | 14D8 chimera VL | DIQLTQSPSTLPASLGERVTISCRTSQSINNNLCWYQQKPDGTVKRLIYSTSTL ESGVPSRFSGSGSGTDYSLSISSLESQDFAMYYCLQYATYPWTFGGGTKLELK |
| 57 | 14D8 chimera CDRL1 | RTSQSINNNLC |
| 58 | 14D8 chimera CDRL2 | STSTLES |
| 59 | 14D8 chimera HC | EVQLVDSGGDQVQPGRSLKLSCVASGFIFKNYWMTWIRQVPGKGLEWIASITNS GGNTYYPDSVKGRFTISRDNAKDTLYLQMNSLRSEDTATYYCARDRRYNSGSPF AYWGQGTLVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVD KKVEPKSCDKTHTCPPCPAPEAAGAPSVFLFPPKPKDTLMISRTPEVTCVVVDV SHEDPEVKFNWYVDGVEVHNAKTKPREEQYNSTYRVVSVLTVLHQDWLNGKEYK CKVSNKALPAPIEKTISKAKGQPREPQVYTLPPSREEMTKNQVSLTCLVKGFYP SDIAVEWESNGQPENNYKTTPPVLDSDGSFFLYSKLTVDKSRWQQGNVFSCSVM HEALHNHYTQKSLSLSPGK |
| 60 | 14D8 chimera LC | DIQLTQSPSTLPASLGERVTISCRTSQSINNNLCWYQQKPDGTVKRLIYSTSTL ESGVPSRFSGSGSGTDYSLSISSLESQDFAMYYCLQYATYPWTFGGGTKLELKR TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC |
| 61 | 30A1 chimera VH | QVNLLQSGATLVKPGASMKMSCKASGYSFTDYWVSWVKQSHGKSLEWIGETYPN SGANNFNKEFKDKATLTVDKSTSTAYMELTRLTSEDSAVYYCTRGPYYYSSQII FAYWGQGTLVTVSS |
| 62 | 30A1 chimera CDRH1 | GYSFTDYWVS |
| 63 | 30A1 chimera CDRH2 | EIYPNSGANNFNKEFKD |
| 64 | 30A1 chimera CDRH3 | GPYYYSSQIIFAY |
| 65 | 30A1 chimera VL | IIVMTQSPKSMSISVGDRVTMNCKASQNVGNNIAWYRQKPGQSPELLIYYASNR YTGVPDRFTGGGYGTDFTLTINSVQAEDAAFYYCQRIYNSPPTFGGGTKVELK |
| 66 | 30A1 chimera CDRL1 | KASQNVGNNIA |
| 67 | 30A1 chimera CDRL2 | YASNRYT |
| 68 | 30A1 chimera CDRL3 | QRIYNSPPT |
| 69 | 30A1 chimera HC | QVNLLQSGATLVKPGASMKMSCKASGYSFTDYWVSWVKQSHGKSLEWIGETYPN SGANNFNKEFKDKATLTVDKSTSTAYMELTRLTSEDSAVYYCTRGPYYYSSQII EAYWGQGTLVTVSSASTKGPSVFPLAPSSKSTSGGTAALGCLVKDYFPEPVTVS |

| SEQ | Description | Sequence |
|---|---|---|
| | | WNSGALTSGVHTFPAVLQSSGLYSLSSVVTVPSSSLGTQTYICNVNHKPSNTKV<br>DKKVEPKSCDKTHTCPPCPAPEAAGAPSVFLEPPKPKDTLMISRTPEVTCVVVD<br>VSHEDPEVKFNWYVDGVEVHNAKTKPREEQYNSTYRVVSVLTVLHQDWLNGKEY<br>KCKVSNKALPAPIEKTISKAKGQPREPQVYTLPPSREEMTKNQVSLTCLVKGFY<br>PSDIAVEWESNGQPENNYKTTPPVLDSDGSFFLYSKLTVDKSRWQQGNVFSCSV<br>MHEALHNHYTQKSLSLSPGK |
| 70 | 30A1 chimera JK | FGGGTKVELK |
| 71 | 30A1 chimera LC | IIVMTQSPKSMSISVGDRVTMNCKASQNVGNNIAWYRQKPGQSPELLIYYASNR<br>YTGVPDRFTGGGYGTDFTLTINSVQAEDAAFYYCQRIYNSPPTFGGGTKVELKR<br>TVAAPSVFIFPPSDEQLKSGTASVVCLLNNEYPREAKVQWKVDNALQSGNSQES<br>VTEQDSKDSTYSLSSTLTLSKADYEKHKVYACEVTHQGLSSPVTKSFNRGEC |
| 72 | 30B11 chimera VH | QVKLLQSGAALVKPGASVKMSCATSGFSFTDYWVSWVKQSHGKGLEWIGETYPN<br>SGADNFNENFKGKATLTVDKSTSTAYMELSRLTSEDSAIYYCTRGPYYYSTQII<br>EAYWGQGTLVTVSS |
| 73 | 30B11 chimera CDRH1 | GFSFTDYWVS |
| 74 | 30B11 chimera CDRH2 | EIYPNSGADNFNENFKG |
| 75 | 30B11 chimera CDRH3 | GPYYYSTQIIFAY |
| 76 | 30B11 chimera VL | NIVMTQSPKSMSISVGDRVTMNCKASQNVGNNLAWYQQKPGQSPKLLIYYASNR<br>YTGVPDRFTGGGYGTDFTLTINSVQAEDAAFYYCQRIYNSPPTFGGGTKVELR |
| 77 | 30B11 chimera CDRL1 | KASQNVGNNLA |
| 78 | 30B11 chimera HC | QVKLLQSGAALVKPGASVKMSCATSGFSFTDYWVSWVKQSHGKGLEWIGETYPN<br>SGADNFNENFKGKATLTVDKSTSTAYMELSRLTSEDSAIYYCTRGPYYYSTQII<br>EAYWGQGTLVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTKV<br>DKKVEPKSCDKTHTCPPCPAPEAAGAPSVFLEPPKPKDTLMISRTPEVTCVVVD<br>VSHEDPEVKFNWYVDGVEVHNAKTKPREEQYNSTYRVVSVLTVLHQDWLNGKEY<br>KCKVSNKALPAPIEKTISKAKGQPREPQVYTLPPSREEMTKNQVSLTCLVKGFY<br>PSDIAVEWESNGQPENNYKTTPPVLDSDGSFFLYSKLTVDKSRWQQGNVFSCSV<br>MHEALHNHYTQKSLSLSPGK |
| 79 | 30B11 chimera JK | FGGGTKVELR |
| 80 | 30B11 chimera LC | NIVMTQSPKSMSISVGDRVTMNCKASQNVGNNLAWYQQKPGQSPKLLIYYASNR<br>YTGVPDRFTGGGYGTDFTLTINSVQAEDAAFYYCQRIYNSPPTFGGGTKVELRR<br>TVAAPSVFIFPPSDEQLKSGTASVVCLLNNEYPREAKVQWKVDNALQSGNSQES<br>VTEQDSKDSTYSLSSTLTLSKADYEKHKVYACEVTHQGLSSPVTKSFNRGEC |
| 81 | 9B3 chimera/hu J VL | DIQMTQSPSVLSASVGDRVTLSCKASHNINKHLDWCQQKVGEAPKLLIYFTNNL<br>QTGIPSRFSGSGSGTDYTLTISSLQPEDVATYFCFQYNSGWTFGQGTKVEIK |
| 82 | 9B3 chimera/hu J JK | FGQGTKVEIK |
| 83 | 9B3 chimera/hu J LC | DIQMTQSPSVLSASVGDRVTLSCKASHNINKHLDWCQQKVGEAPKLLIYFTNNL<br>QTGIPSRFSGSGSGTDYTLTISSLQPEDVATYFCFQYNSGWTFGQGTKVEIKRT<br>VAAPSVFIFPPSDEQLKSGTASVVCLLNNFYPREAKVQWKVDNALQSGNSQESV<br>TEQDSKDSTYSLSSTLTLSKADYEKHKVYACEVTHQGLSSPVTKSFNRGEC |
| 84 | 14D8 chimera/hu J VL | DIQLTQSPSTLPASLGERVTISCRTSQSINNNLCWYQQKPDGTVKRLIYSTSTL<br>ESGVPSRFSGSGSGTDYSLSISSLESQDFAMYYCLQYATYPWTFGQGTKVEIK |
| 85 | 14D8 chimera/hu J LC | DIQLTQSPSTLPASLGERVTISCRTSQSINNNLCWYQQKPDGTVKRLIYSTSTL<br>ESGVPSRFSGSGSGTDYSLSISSLESQDFAMYYCLQYATYPWTFGQGTKVEIKR<br>TVAAPSVFIFPPSDEQLKSGTASVVCLLNNEYPREAKVQWKVDNALQSGNSQES<br>VTEQDSKDSTYSLSSTLTLSKADYEKHKVYACEVTHQGLSSPVTKSFNRGEC |
| 86 | 30A1 chimera/hu J VL | IIVMTQSPKSMSISVGDRVTMNCKASQNVGNNIAWYRQKPGQSPELLIYYASNR<br>YTGVPDRFTGGGYGTDFTLTINSVQAEDAAFYYCQRIYNSPPTFGGGTKVEIK |
| 87 | 30A1 chimera/hu J LC | IIVMTQSPKSMSISVGDRVTMNCKASQNVGNNIAWYRQKPGQSPELLIYYASNR<br>YTGVPDRFTGGGYGTDFTLTINSVQAEDAAFYYCQRIYNSPPTFGGGTKVEIKR<br>TVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| 88 | 30B11 chimera/hu J VL | NIVMTQSPKSMSISVGDRVTMNCKASQNVGNNLAWYQQKPGQSPKLLIYYASNR<br>YTGVPDRFTGGGYGTDFTLTINSVQAEDAAFYYCQRIYNSPPTFGGGTKVEIK |

-continued

| SEQUENCE LIST | | |
|---|---|---|
| SEQ | Description | Sequence |
| 89 | 30B11 chimera/hu J LC | NIVMTQSPKSMSISVGDRVTMNCKASQNVGNNLAWYQQKPGQSPKLLIYYASNR<br>YTGVPDRFTGGGYGTDFTLTINSVQAEDAAFYYCQRIYNSPPTFGGGTKVEIKR<br>TVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| 90 | 7E8 CDR graft VH | HSEVQLVESGGGLVQPGGSLRLSCAASGFTFSSYWMYWVRQAPGKGLEWVASIT<br>PNGGNTYYPDSVKGRFTISRDNAKNSLYLQMNSLRAEDTAVYYCARGHYYYTSY<br>SLGYWGQGTLVTVSS |
| 91 | 7E8 CDR graft VL | DIQMTQSPSSLSASVGDRVTITCKASQNINKHLDWYQQKPGKAPKLLIYFTNNL<br>QTGVPSRFSGSGSGTDFTLTISSLQPEDFATYYCFQYNNGWTFGGGTKVEIK |
| 92 | 7E8 CDR graft HC | HSEVQLVESGGGLVQPGGSLRLSCAASGFTFSSYWMYWVRQAPGKGLEWVASIT<br>PNGGNTYYPDSVKGRFTISRDNAKNSLYLQMNSLRAEDTAVYYCARGHYYYTSY<br>SLGYWGQGTLVTVSSASTKGPSVFPLAPSSKSTSGGTAALGCLVKDYFPEPVTV<br>SWNSGALTSGVHTFPAVLQSSGLYSLSSVVTVPSSSLGTQTYICNVNHKPSNTK<br>VDKKVEPKSCDKTHTCPPCPAPEAAGAPSVFLFPPKPKDTLMISRTPEVTCVVV<br>DVSHEDPEVKFNWYVDGVEVHNAKTKPREEQYNSTYRVVSVLTVLHQDWLNGKE<br>YKCKVSNKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQQGNVFSCS<br>VMHEALHNHYTQKSLSLSPGK |
| 93 | 7E8 CDR graft LC | DIQMTQSPSSLSASVGDRVTITCKASQNINKHLDWYQQKPGKAPKLLIYFTNNL<br>QTGVPSRFSGSGSGTDFTLTISSLQPEDFATYYCFQYNNGWTFGGGTKVEIKRT<br>VAAPSVFIFPPSDEQLKSGTASVVCLLNNFYPREAKVQWKVDNALQSGNSQESV<br>TEQDSKDSTYSLSSTLTLSKADYEKHKVYACEVTHQGLSSPVTKSFNRGEC |
| 94 | IL33-10 VH | EVQLVESGGGLVQPGGSLRLSCAASGFTFSSYWMYWVRQAPGKGLEWVASITPN<br>GGNTYYPDSVKGRFTISRDNAKNSLYLQMNSLRAEDTAVYYCARGHYYYTSYSL<br>GYWGQGTLVTVSS |
| 95 | IL33-10 HC | EVQLVESGGGLVQPGGSLRLSCAASGFTFSSYWMYWVRQAPGKGLEWVASITPN<br>GGNTYYPDSVKGRFTISRDNAKNSLYLQMNSLRAEDTAVYYCARGHYYYTSYSL<br>GYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVD<br>KKVEPKSCDKTHTCPPCPAPELLGGPSVFLFPPKPKDTLMISRTPEVTCVVVDV<br>SHEDPEVKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLTCLVKGFYP<br>SDIAVEWESNGQPENNYKTTPPVLDSDGSFFLYSKLTVDKSRWQQGNVFSCSVM<br>HEALHNHYTQKSLSLSPGK |
| 96 | CH2 hIgG1 WT | APELLGGPSVFLFPPKPKDTLMISRTPEVTCVVVDVSHEDPEVKFNWYVDGVEV<br>HNAKTKPREEQYNSTYRVVSVLTVLHQDWLNGKEYKCKVSNKALPAPIEKTISK<br>AK |
| 97 | 9B3 CDR graft VH | EVQLVESGGGLVQPGGSLRLSCAASGFTFSNYWMYWVRQAPGKGLEWVASINND<br>GGNTYYLDSVKGRFTISRDNAKNSLYLQMNSLRAEDTAVYYCARGHYSYSSYSF<br>SYWGQGTLVTVSS |
| 98 | 9B3 CDR graft VL | DIQMTQSPSSLSASVGDRVTITCKASHNINKHLDWYQQKPGKAPKLLIYFTNNL<br>QTGVPSRFSGSGSGTDFTLTISSLQPEDFATYYCFQYNSGWTFGGGTKVEIK |
| 99 | 9B3 CDR graft HC | EVQLVESGGGLVQPGGSLRLSCAASGFTFSNYWMYWVRQAPGKGLEWVASINND<br>GGNTYYLDSVKGRFTISRDNAKNSLYLQMNSLRAEDTAVYYCARGHYSYSSYSF<br>SYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVD<br>KKVEPKSCDKTHTCPPCPAPEAAGAPSVFLFPPKPKDTLMISRTPEVTCVVVDV<br>SHEDPEVKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLTCLVKGFYP<br>SDIAVEWESNGQPENNYKTTPPVLDSDGSFFLYSKLTVDKSRWQQGNVFSCSVM<br>HEALHNHYTQKSLSLSPGK |
| 100 | 9B3 CDR graft LC | DIQMTQSPSSLSASVGDRVTITCKASHNINKHLDWYQQKPGKAPKLLIYFTNNL<br>QTGVPSRFSGSGSGTDFTLTISSLQPEDFATYYCFQYNSGWTFGGGTKVEIKRT<br>VAAPSVFIFPPSDEQLKSGTASVVCLLNNFYPREAKVQWKVDNALQSGNSQESV<br>TEQDSKDSTYSLSSTLTLSKADYEKHKVYACEVTHQGLSSPVTKSFNRGEC |
| 101 | 12F9 CDR graft VH | EVQLVESGGGLVQPGGSLRLSCAASGFTFKNYWMTWVRQAPGKGLEWVASITNT<br>GGATYYPDSVKGRFTISRDNAKNSLYLQMNSLRAEDTAVYYCARDRRYNSGSPF<br>AYWGQGTLVTVSS |
| 102 | 12F9 CDR graft CDRH1 | GFTFKNYWMT |
| 103 | 12F9 CDR graft VL | DIQMTQSPSSLSASVGDRVTITCRASQSISNSLIWYQQKPGKAPKLLIYSSSTL<br>ESGVPSRFSGSGSGTDFTLTISSLQPEDFATYYCLQYATYPWTFGGGTKVEIK |

| SEQ | Description | Sequence |
|---|---|---|
| 104 | 12F9 CDR graft HC | EVQLVESGGGLVQPGGSLRLSCAASGFTFKNYWMTWVRQAPGKGLEWVASITNT<br>GGATYYPDSVKGRFTISRDNAKNSLYLQMNSLRAEDTAVYYCARDRRYNSGSPF<br>AYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVD<br>KKVEPKSCDKTHTCPPCPAPEAAGAPSVFLFPPKPKDTLMISRTPEVTCVVVDV<br>SHEDPEVKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLTCLVKGFYP<br>SDIAVEWESNGQPENNYKTTPPVLDSDGSFFLYSKLTVDKSRWQQGNVFSCSVM<br>HEALHNHYTQKSLSLSPGK |
| 105 | 12F9 CDR graft LC | DIQMTQSPSSLSASVGDRVTITCRASQSISNSLIWYQQKPGKAPKLLIYSSSTL<br>ESGVPSRFSGSGSGTDFTLTISSLQPEDFATYYCLQYATYPWTFGGGTKVEIKR<br>TVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| 106 | 30B11 CDR graft VH | EVQLVESGGGLVQPGGSLRLSCAASGFTFTDYWVSWVRQAPGKGLEWVAETYPN<br>SGADNFNENFKGRFTISRDNAKNSLYLQMNSLRAEDTAVYYCARGPYYYSTQII<br>FAYWGQGTLVTVSS |
| 107 | 30B11 CDR graft CDRH1 | GFTFTDYWVS |
| 108 | 30B11 CDR graft VL | DIQMTQSPSSLSASVGDRVTITCKASQNVGNNLAWYQQKPGKAPKLLIYYASNR<br>YTGVPSRFSGSGSGTDFTLTISSLQPEDFATYYCQRIYNSPPTFGGGTKVEIK |
| 109 | 30B11 CDR graft HC | EVQLVESGGGLVQPGGSLRLSCAASGFTFTDYWVSWVRQAPGKGLEWVAETYPN<br>SGADNFNENFKGRFTISRDNAKNSLYLQMNSLRAEDTAVYYCARGPYYYSTQII<br>FAYWGQGTLVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTKV<br>DKKVEPKSCDKTHTCPPCPAPEAAGAPSVFLFPPKPKDTLMISRTPEVTCVVVD<br>VSHEDPEVKFNWYVDGVEVHNAKTKPREEQYNSTYRVVSVLTVLHQDWLNGKEY<br>KCKVSNKALPAPIEKTISKAKGQPREPQVYTLPPSREEMTKNQVSLTCLVKGFY<br>PSDIAVEWESNGQPENNYKTTPPVLDSDGSFFLYSKLTVDKSRWQQGNVFSCSV<br>MHEALHNHYTQKSLSLSPGK |
| 110 | 30B11 CDR graft LC | DIQMTQSPSSLSASVGDRVTITCKASQNVGNNLAWYQQKPGKAPKLLIYYASNR<br>YTGVPSRFSGSGSGTDFTLTISSLQPEDFATYYCQRIYNSPPTFGGGTKVEIKR<br>TVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| 111 | 30B11_R71V CDR graft VH | EVQLVESGGGLVQPGGSLRLSCAASGFTFTDYWVSWVRQAPGKGLEWVAETYPN<br>SGADNFNENFKGRFTISVDNAKNSLYLQMNSLRAEDTAVYYCARGPYYYSTQII<br>FAYWGQGTLVTVSS |
| 112 | 30B11_R71V CDR graft HC | EVQLVESGGGLVQPGGSLRLSCAASGFTFTDYWVSWVRQAPGKGLEWVAETYPN<br>SGADNFNENFKGRFTISVDNAKNSLYLQMNSLRAEDTAVYYCARGPYYYSTQII<br>FAYWGQGTLVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNTKV<br>DKKVEPKSCDKTHTCPPCPAPEAAGAPSVFLFPPKPKDTLMISRTPEVTCVVVD<br>VSHEDPEVKFNWYVDGVEVHNAKTKPREEQYNSTYRVVSVLTVLHQDWLNGKEY<br>KCKVSNKALPAPIEKTISKAKGQPREPQVYTLPPSREEMTKNQVSLTCLVKGFY<br>PSDIAVEWESNGQPENNYKTTPPVLDSDGSFFLYSKLTVDKSRWQQGNVFSCSV<br>MHEALHNHYTQKSLSLSPGK |
| 113 | 9B3-1 VH | EVQLVETGGGLVQPGRSLKLSCVASGFTFSNYWMYWIRQAPGMGLEWVSSINND<br>GGNTYYLDSVKGRFTISRNNAENTVYLQMNSLRSEDTATYYCAKGHYYYSSYSL<br>GYWGQGTLVTVSS |
| 114 | 9B3-1 CDRH3 | GHYYYSSYSLGY |
| 115 | 9B3-1 VL | DIQMTQSPSVLSASVGDRVTLSCKASHNINKHLDWYQQKVGEAPKLLIYFTNNL<br>QTGIPSRFSGSGSGTDYTLTISSLQPEDVATYFCFQYNSGWTFGQGTKVEIK |
| 116 | 9B3-1 HC | EVQLVETGGGLVQPGRSLKLSCVASGFTFSNYWMYWIRQAPGMGLEWVSSINND<br>GGNTYYLDSVKGRFTISRNNAENTVYLQMNSLRSEDTATYYCAKGHYYYSSYSL<br>GYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVD<br>KKVEPKSCDKTHTCPPCPAPEAAGAPSVFLFPPKPKDTLMISRTPEVTCVVVDV<br>SHEDPEVKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLTCLVKGFYP<br>SDIAVEWESNGQPENNYKTTPPVLDSDGSFFLYSKLTVDKSRWQQGNVFSCSVM<br>HEALHNHYTQKSLSLSPGK |
| 117 | 9B3-1 LC | DIQMTQSPSVLSASVGDRVTLSCKASHNINKHLDWYQQKVGEAPKLLIYFTNNL<br>QTGIPSRFSGSGSGTDYTLTISSLQPEDVATYFCFQYNSGWTFGQGTKVEIKRT |

| SEQ | Description | Sequence |
|---|---|---|
| | | VAAPSVFIFPPSDEQLKSGTASVVCLLNNFYPREAKVQWKVDNALQSGNSQESV<br>TEQDSKDSTYSLSSTLTLSKADYEKHKVYACEVTHQGLSSPVTKSFNRGEC |
| 118 | 9B3-2A VH | EVQLVETGGGLVQPGRSLKLSCVASGFTFSNYWMYWIRQAPGMGLEWVSSINND<br>GGNTYYLDSVKGRFTISRNNAENTVYLQMNSLRSEDTATYYCAKGHYSYSSYSF<br>GYWGQGTLVTVSS |
| 119 | 9B3-2A CDRH3 | GHYSYSSYSFGY |
| 120 | 9B3-2A HC | EVQLVETGGGLVQPGRSLKLSCVASGFTFSNYWMYWIRQAPGMGLEWVSSINND<br>GGNTYYLDSVKGRFTISRNNAENTVYLQMNSLRSEDTATYYCAKGHYSYSSYSF<br>GYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVD<br>KKVEPKSCDKTHTCPPCPAPEAAGAPSVFLFPPKPKDTLMISRTPEVTCVVVDV<br>SHEDPEVKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLTCLVKGFYP<br>SDIAVEWESNGQPENNYKTTPPVLDSDGSFFLYSKLTVDKSRWQQGNVFSCSVM<br>HEALHNHYTQKSLSLSPGK |
| 121 | 9B3-2B VH | EVQLVETGGGLVQPGRSLKLSCVASGFTFSNYWMYWIRQAPGMGLEWVSSINND<br>GGNTYYLDSVKGRFTISRNNAENTVYLQMNSLRSEDTATYYCVKGHYSYSSYSI<br>DYWGQGTLVTVSS |
| 122 | 9B3-2B CDRH3 | GHYSYSSYSIDY |
| 123 | 9B3-2B HC | EVQLVETGGGLVQPGRSLKLSCVASGFTFSNYWMYWIRQAPGMGLEWVSSINND<br>GGNTYYLDSVKGRFTISRNNAENTVYLQMNSLRSEDTATYYCVKGHYSYSSYSI<br>DYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVD<br>KKVEPKSCDKTHTCPPCPAPEAAGAPSVFLFPPKPKDTLMISRTPEVTCVVVDV<br>SHEDPEVKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLTCLVKGFYP<br>SDIAVEWESNGQPENNYKTTPPVLDSDGSFFLYSKLTVDKSRWQQGNVFSCSVM<br>HEALHNHYTQKSLSLSPGK |
| 124 | 9B3-3 VH | EVQLVETGGGLVQPGRSLKLSCVASGFTFSNYWMYWIRQAPGMGLEWVSSINND<br>GGNTYYLDSVKGRFTISRNNAENTVYLQMNSLRSEDTATYYCAKGHYSYSSYSI<br>DYWGQGTLVTVSS |
| 125 | 9B3-3 HC | EVQLVETGGGLVQPGRSLKLSCVASGFTFSNYWMYWIRQAPGMGLEWVSSINND<br>GGNTYYLDSVKGRFTISRNNAENTVYLQMNSLRSEDTATYYCAKGHYSYSSYSI<br>DYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVD<br>KKVEPKSCDKTHTCPPCPAPEAAGAPSVFLFPPKPKDTLMISRTPEVTCVVVDV<br>SHEDPEVKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLTCLVKGFYP<br>SDIAVEWESNGQPENNYKTTPPVLDSDGSFFLYSKLTVDKSRWQQGNVFSCSVM<br>HEALHNHYTQKSLSLSPGK |
| 126 | 9B3-5 VH | EVQLVETGGGLVQPGRSLKLSCVASGFTFSNYWMYWIRQAPGMGLEWVSSINND<br>GGNTYYLDSVKGRFTISRNNAENTVYLQMNSLRSEDTATYYCAKGHYSYTSYSF<br>GYWGQGTLVTVSS |
| 127 | 9B3-5 CDRH3 | GHYSYTSYSFGY |
| 128 | 9B3-5 HC | EVQLVETGGGLVQPGRSLKLSCVASGFTFSNYWMYWIRQAPGMGLEWVSSINND<br>GGNTYYLDSVKGRFTISRNNAENTVYLQMNSLRSEDTATYYCAKGHYSYTSYSF<br>GYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVD<br>KKVEPKSCDKTHTCPPCPAPEAAGAPSVFLFPPKPKDTLMISRTPEVTCVVVDV<br>SHEDPEVKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLTCLVKGFYP<br>SDIAVEWESNGQPENNYKTTPPVLDSDGSFFLYSKLTVDKSRWQQGNVFSCSVM<br>HEALHNHYTQKSLSLSPGK |
| 129 | 9B3-7 VH | EVQLVETGGGLVQPGRSLKLSCVASGFTFSNYWMYWIRQAPGMGLEWVSSINND<br>GGNTYYLDSVKGRFTISRNNAENTVYLQMNSLRSEDTATYYCAKGRYYYSSYSF<br>AYWGQGTLVTVSS |
| 130 | 9B3-7 CDRH3 | GRYYYSSYSFAY |
| 131 | 9B3-7 HC | EVQLVETGGGLVQPGRSLKLSCVASGFTFSNYWMYWIRQAPGMGLEWVSSINND<br>GGNTYYLDSVKGRFTISRNNAENTVYLQMNSLRSEDTATYYCAKGRYYYSSYSF<br>AYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVD |

| SEQ | Description | Sequence |
|---|---|---|
| | | KKVEPKSCDKTHTCPPCPAPEAAGAPSVFLFPPKPKDTLMISRTPEVTCVVVDV SHEDPEVKFNWYVDGVEVHNAKTKPREEQYNSTYRVVSVLTVLHQDWLNGKEYK CKVSNKALPAPIEKTISKAKGQPREPQVYTLPPSREEMTKNQVSLTCLVKGFYP SDIAVEWESNGQPENNYKTTPPVLDSDGSFFLYSKLTVDKSRWQQGNVFSCSVM HEALHNHYTQKSLSLSPGK |
| 132 | 9B3-13 VH | EVQLVETGGGLVQPGRSLKLSCVASGFTFSNYWMYWIRQAPGMGLEWVSSINND GGNTYYLDSVKGRFTISRNNAENTVYLQMNSLRSEDTATYYCARGHYYYNSYSF AHWGQGTLVTVSS |
| 133 | 9B3-13 CDRH3 | GHYYYNSYSFAH |
| 134 | 9B3-13 HC | EVQLVETGGGLVQPGRSLKLSCVASGFTFSNYWMYWIRQAPGMGLEWVSSINND GGNTYYLDSVKGRFTISRNNAENTVYLQMNSLRSEDTATYYCARGHYYYNSYSF AHWGQGTLVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVD KKVEPKSCDKTHTCPPCPAPEAAGAPSVFLFPPKPKDTLMISRTPEVTCVVVDV SHEDPEVKFNWYVDGVEVHNAKTKPREEQYNSTYRVVSVLTVLHQDWLNGKEYK CKVSNKALPAPIEKTISKAKGQPREPQVYTLPPSREEMTKNQVSLTCLVKGFYP SDIAVEWESNGQPENNYKTTPPVLDSDGSFFLYSKLTVDKSRWQQGNVFSCSVM HEALHNHYTQKSLSLSPGK |
| 135 | 9B3-15 VH | EVQLVETGGGLVQPGRSLKLSCVASGFTFSNYWMYWIRQAPGMGLEWVSSINND GGNTYYLDSVKGRFTISRNNAENTVYLQMNSLRSEDTATYYCAKGHYSYSSYSF ANWGQGTLVTVSS |
| 136 | 9B3-15 CDRH3 | GHYSYSSYSFAN |
| 137 | 9B3-15 HC | EVQLVETGGGLVQPGRSLKLSCVASGFTFSNYWMYWIRQAPGMGLEWVSSINND GGNTYYLDSVKGRFTISRNNAENTVYLQMNSLRSEDTATYYCAKGHYSYSSYSF ANWGQGTLVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVD KKVEPKSCDKTHTCPPCPAPEAAGAPSVFLFPPKPKDTLMISRTPEVTCVVVDV SHEDPEVKFNWYVDGVEVHNAKTKPREEQYNSTYRVVSVLTVLHQDWLNGKEYK CKVSNKALPAPIEKTISKAKGQPREPQVYTLPPSREEMTKNQVSLTCLVKGFYP SDIAVEWESNGQPENNYKTTPPVLDSDGSFFLYSKLTVDKSRWQQGNVFSCSVM HEALHNHYTQKSLSLSPGK |
| 138 | 9B3-17 VH | EVQLVETGGGLVQPGRSLKLSCVASGFTFSNYWMYWIRQAPGMGLEWVSSINND GGNTYYLDSVKGRFTISRNNAENTVYLQMNSLRSEDTATYYCARGHYYYSSYSF GSWGQGTLVTVSS |
| 139 | 9B3-17 CDRH3 | GHYYYSSYSFGS |
| 140 | 9B3-17 HC | EVQLVETGGGLVQPGRSLKLSCVASGFTFSNYWMYWIRQAPGMGLEWVSSINND GGNTYYLDSVKGRFTISRNNAENTVYLQMNSLRSEDTATYYCARGHYYYSSYSF GSWGQGTLVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVD KKVEPKSCDKTHTCPPCPAPEAAGAPSVFLFPPKPKDTLMISRTPEVTCVVVDV SHEDPEVKFNWYVDGVEVHNAKTKPREEQYNSTYRVVSVLTVLHQDWLNGKEYK CKVSNKALPAPIEKTISKAKGQPREPQVYTLPPSREEMTKNQVSLTCLVKGFYP SDIAVEWESNGQPENNYKTTPPVLDSDGSFFLYSKLTVDKSRWQQGNVFSCSVM HEALHNHYTQKSLSLSPGK |
| 141 | 9B3-22 VH | EVQLVETGGGLVQPGRSLKLSCVASGFTFSNYWMYWIRQAPGMGLEWVSSINND GGNTYYLDSVKGRFTISRNNAENTVYLQMNSLRSEDTATYYCAKGHFSYTSYSF AYWGQGTLVTVSS |
| 142 | 9B3-22 CDRH3 | GHFSYTSYSFAY |
| 143 | 9B3-22 HC | EVQLVETGGGLVQPGRSLKLSCVASGFTFSNYWMYWIRQAPGMGLEWVSSINND GGNTYYLDSVKGRFTISRNNAENTVYLQMNSLRSEDTATYYCAKGHFSYTSYSF AYWGQGTLVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVD KKVEPKSCDKTHTCPPCPAPEAAGAPSVFLFPPKPKDTLMISRTPEVTCVVVDV SHEDPEVKFNWYVDGVEVHNAKTKPREEQYNSTYRVVSVLTVLHQDWLNGKEYK CKVSNKALPAPIEKTISKAKGQPREPQVYTLPPSREEMTKNQVSLTCLVKGFYP SDIAVEWESNGQPENNYKTTPPVLDSDGSFFLYSKLTVDKSRWQQGNVFSCSVM HEALHNHYTQKSLSLSPGK |
| 144 | 9B3-31V2 VH | EVQLVETGGGLVQPGRSLKLSCVASGFTFSNYWMYWIRQAPGMGLEWVSSINND GGNTYYLDSVKGRFTISRNNAENTVYLQMNSLRSEDTATYYCAKGHYYYSSYSF AFWGQGTLVTVSS |
| 145 | 9B3-31V2 CDRH3 | GHYYYSSYSFAF |

| SEQ | Description | Sequence |
|---|---|---|
| 146 | 9B3-31V2 HC | EVQLVETGGGLVQPGRSLKLSCVASGFTFSNYWMYWIRQAPGMGLEWVSSINND GGNTYYLDSVKGRFTISRNNAENTVYLQMNSLRSEDTATYYCAKGHYYYSSYSF AFWGQGTLVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVD KKVEPKSCDKTHTCPPCPAPEAAGAPSVFLFPPKPKDTLMISRTPEVTCVVVDV SHEDPEVKFNWYVDGVEVHNAKTKPREEQYNSTYRVVSVLTVLHQDWLNGKEYK CKVSNKALPAPIEKTISKAKGQPREPQVYTLPPSREEMTKNQVSLTCLVKGFYP SDIAVEWESNGQPENNYKTTPPVLDSDGSFFLYSKLTVDKSRWQQGNVFSCSVM HEALHNHYTQKSLSLSPGK |
| 147 | 9B3-36 VH | EVQLVETGGGLVQPGRSLKLSCVASGFTFSNYWMYWIRQAPGMGLEWVSSINND GGNTYYLDSVKGRFTISRNNAENTVYLQMNSLRSEDTATYYCAKGHYYYTSYSF AYWGQGTLVTVSS |
| 148 | 9B3-36 CDRH3 | GHYYYTSYSFAY |
| 149 | 9B3-36 HC | EVQLVETGGGLVQPGRSLKLSCVASGFTFSNYWMYWIRQAPGMGLEWVSSINND GGNTYYLDSVKGRFTISRNNAENTVYLQMNSLRSEDTATYYCAKGHYYYTSYSF AYWGQGTLVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVD KKVEPKSCDKTHTCPPCPAPEAAGAPSVFLFPPKPKDTLMISRTPEVTCVVVDV SHEDPEVKFNWYVDGVEVHNAKTKPREEQYNSTYRVVSVLTVLHQDWLNGKEYK CKVSNKALPAPIEKTISKAKGQPREPQVYTLPPSREEMTKNQVSLTCLVKGFYP SDIAVEWESNGQPENNYKTTPPVLDSDGSFFLYSKLTVDKSRWQQGNVFSCSVM HEALHNHYTQKSLSLSPGK |
| 150 | 9B3-79 VH | EVQLVETGGGLVQPGRSLKLSCVASGFTFSNYWMYWIRQAPGMGLEWVSSINND GGNTYYLDSVKGRFTISRNNAENTVYLQMNSLRSEDTATYYCARGHYYYTSYSF AYWGQGTLVTVSS |
| 151 | 9B3-79 HC | EVQLVETGGGLVQPGRSLKLSCVASGFTFSNYWMYWIRQAPGMGLEWVSSINND GGNTYYLDSVKGRFTISRNNAENTVYLQMNSLRSEDTATYYCARGHYYYTSYSF AYWGQGTLVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVD KKVEPKSCDKTHTCPPCPAPEAAGAPSVFLFPPKPKDTLMISRTPEVTCVVVDV SHEDPEVKFNWYVDGVEVHNAKTKPREEQYNSTYRVVSVLTVLHQDWLNGKEYK CKVSNKALPAPIEKTISKAKGQPREPQVYTLPPSREEMTKNQVSLTCLVKGFYP SDIAVEWESNGQPENNYKTTPPVLDSDGSFFLYSKLTVDKSRWQQGNVFSCSVM HEALHNHYTQKSLSLSPGK |
| 152 | 9B3-124 VH | EVQLVETGGGLVQPGRSLKLSCVASGFTFSNYWMYWIRQAPGMGLEWVSSINND GGNTYYLDSVKGRFTISRNNAENTVYLQMNSLRSEDTATYYCAKGHYYYTSYSF GYWGQGTLVTVSS |
| 153 | 9B3-124 CDRH3 | GHYYYTSYSFGY |
| 154 | 9B3-124 HC | EVQLVETGGGLVQPGRSLKLSCVASGFTFSNYWMYWIRQAPGMGLEWVSSINND GGNTYYLDSVKGRFTISRNNAENTVYLQMNSLRSEDTATYYCAKGHYYYTSYSF GYWGQGTLVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVD KKVEPKSCDKTHTCPPCPAPEAAGAPSVFLFPPKPKDTLMISRTPEVTCVVVDV SHEDPEVKFNWYVDGVEVHNAKTKPREEQYNSTYRVVSVLTVLHQDWLNGKEYK CKVSNKALPAPIEKTISKAKGQPREPQVYTLPPSREEMTKNQVSLTCLVKGFYP SDIAVEWESNGQPENNYKTTPPVLDSDGSFFLYSKLTVDKSRWQQGNVFSCSVM HEALHNHYTQKSLSLSPGK |
| 155 | 9B3-162 VH | EVQLVETGGGLVQPGRSLKLSCVASGFTFSNYWMYWIRQAPGMGLEWVSSINND GGNTYYLDSVKGRFTISRNNAENTVYLQMNSLRSEDTATYYCAKGHYYYSSYSF GYWGQGTLVTVSS |
| 156 | 9B3-162 CDRH3 | GHYYYSSYSFGY |
| 157 | 9B3-162 HC | EVQLVETGGGLVQPGRSLKLSCVASGFTFSNYWMYWIRQAPGMGLEWVSSINND GGNTYYLDSVKGRFTISRNNAENTVYLQMNSLRSEDTATYYCAKGHYYYSSYSF GYWGQGTLVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVD KKVEPKSCDKTHTCPPCPAPEAAGAPSVFLFPPKPKDTLMISRTPEVTCVVVDV SHEDPEVKFNWYVDGVEVHNAKTKPREEQYNSTYRVVSVLTVLHQDWLNGKEYK CKVSNKALPAPIEKTISKAKGQPREPQVYTLPPSREEMTKNQVSLTCLVKGFYP SDIAVEWESNGQPENNYKTTPPVLDSDGSFFLYSKLTVDKSRWQQGNVFSCSVM HEALHNHYTQKSLSLSPGK |
| 158 | 9B3-563 VH | EVQLVETGGGLVQPGRSLKLSCVASGFTFSNYWMYWIRQAPGMGLEWVSSINND GGNTYYLDSVKGRFTISRNNAENTVYLQMNSLRSEDTATYYCAKGHYYYSSYSF AYWGQGTLVTVSS |

| SEQ | Description | Sequence |
|---|---|---|
| 159 | 9B3-563 CDRH3 | GHYYYSSYSFAY |
| 160 | 9B3-563 HC | EVQLVETGGGLVQPGRSLKLSCVASGFTFSNYWMYWIRQAPGMGLEWVSSINND<br>GGNTYYLDSVKGRFTISRNNAENTVYLQMNSLRSEDTATYYCAKGHYYYSSYSF<br>AYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVD<br>KKVEPKSCDKTHTCPPCPAPEAAGAPSVFLFPPKPKDTLMISRTPEVTCVVVDV<br>SHEDPEVKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLTCLVKGFYP<br>SDIAVEWESNGQPENNYKTTPPVLDSDGSFFLYSKLTVDKSRWQQGNVFSCSVM<br>HEALHNHYTQKSLSLSPGK |
| 161 | IL33-11 VH | EVQLVESGGGLVQPGGSLRLSCAASGFTFSNYWMYWVRQAPGKGLEWVASITPN<br>GGNTYYPDSVKGRFTISRDNAKNSLYLQMNSLRAEDTAVYYCARGHYYYTSYSL<br>GYWGQGTLVTVSS |
| 162 | IL33-11 HC | EVQLVESGGGLVQPGGSLRLSCAASGFTFSNYWMYWVRQAPGKGLEWVASITPN<br>GGNTYYPDSVKGRFTISRDNAKNSLYLQMNSLRAEDTAVYYCARGHYYYTSYSL<br>GYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVD<br>KKVEPKSCDKTHTCPPCPAPELLGGPSVFLFPPKPKDTLMISRTPEVTCVVVDV<br>SHEDPEVKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLTCLVKGFYP<br>SDIAVEWESNGQPENNYKTTPPVLDSDGSFFLYSKLTVDKSRWQQGNVFSCSVM<br>HEALHNHYTQKSLSLSPGK |
| 163 | IL33-12 VH | EVQLVESGGGLVQPGGSLRLSCAASGFTFSSYWMYWVRQAPGKGLEWVASINND<br>GGNTYYLDSVKGRFTISRDNAKNSLYLQMNSLRAEDTAVYYCARGHYYYTSYSL<br>GYWGQGTLVTVSS |
| 164 | IL33-12 HC | EVQLVESGGGLVQPGGSLRLSCAASGFTFSSYWMYWVRQAPGKGLEWVASINND<br>GGNTYYLDSVKGRFTISRDNAKNSLYLQMNSLRAEDTAVYYCARGHYYYTSYSL<br>GYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVD<br>KKVEPKSCDKTHTCPPCPAPELLGGPSVFLFPPKPKDTLMISRTPEVTCVVVDV<br>SHEDPEVKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLTCLVKGFYP<br>SDIAVEWESNGQPENNYKTTPPVLDSDGSFFLYSKLTVDKSRWQQGNVFSCSVM<br>HEALHNHYTQKSLSLSPGK |
| 165 | IL33-13 VH | EVQLVESGGGLVQPGGSLRLSCAASGFTFSSYWMYWVRQAPGKGLEWVASITPN<br>GGNTYYPDSVKGRFTISRDNAKNSLYLQMNSLRAEDTAVYYCARGHYSYSSYSF<br>SYWGQGTLVTVSS |
| 166 | IL33-13 HC | EVQLVESGGGLVQPGGSLRLSCAASGFTFSSYWMYWVRQAPGKGLEWVASITPN<br>GGNTYYPDSVKGRFTISRDNAKNSLYLQMNSLRAEDTAVYYCARGHYSYSSYSF<br>SYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVD<br>KKVEPKSCDKTHTCPPCPAPELLGGPSVFLFPPKPKDTLMISRTPEVTCVVVDV<br>SHEDPEVKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLTCLVKGFYP<br>SDIAVEWESNGQPENNYKTTPPVLDSDGSFFLYSKLTVDKSRWQQGNVFSCSVM<br>HEALHNHYTQKSLSLSPGK |
| 167 | IL33-45 VH | EVQLVESGGGLVQPGGSLRLSCAASGFTFSSYWMYWVRQAPGKGLEWVASITPD<br>GGNTYYPDSVKGRFTISRDNAKNSLYLQMNSLRAEDTAVYYCARGHYYYTSYSL<br>GYWGQGTLVTVSS |
| 168 | IL33-45 CDRH2 | SITPDGGNTYYPDSVKG |
| 169 | IL33-45 HC | EVQLVESGGGLVQPGGSLRLSCAASGFTFSSYWMYWVRQAPGKGLEWVASITPD<br>GGNTYYPDSVKGRFTISRDNAKNSLYLQMNSLRAEDTAVYYCARGHYYYTSYSL<br>GYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVD<br>KKVEPKSCDKTHTCPPCPAPELLGGPSVFLFPPKPKDTLMISRTPEVTCVVVDV<br>SHEDPEVKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLTCLVKGFYP<br>SDIAVEWESNGQPENNYKTTPPVLDSDGSFFLYSKLTVDKSRWQQGNVFSCSVM<br>HEALHNHYTQKSLSLSPGK |
| 170 | IL33-55 VH | EVQLVESGGGLVQPGGSLRLSCAASGFTFSSYWMYWVRQAPGKGLEWVASITPN<br>GGDTYYPDSVKGRFTISRDNAKNSLYLQMNSLRAEDTAVYYCARGHYYYTSYSL<br>GYWGQGTLVTVSS |
| 171 | IL33-55 CDRH2 | SITPNGGDTYYPDSVKG |

-continued

| SEQ | Description | Sequence |
|---|---|---|
| 172 | IL33-55 HC | EVQLVESGGGLVQPGGSLRLSCAASGFTFSSYWMYWVRQAPGKGLEWVASITPN<br>GGDTYYPDSVKGRFTISRDNAKNSLYLQMNSLRAEDTAVYYCARGHYYYTSYSL<br>GYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVD<br>KKVEPKSCDKTHTCPPCPAPELLGGPSVFLFPPKPKDTLMISRTPEVTCVVVDV<br>SHEDPEVKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLTCLVKGFYP<br>SDIAVEWESNGQPENNYKTTPPVLDSDGSFFLYSKLTVDKSRWQQGNVFSCSVM<br>HEALHNHYTQKSLSLSPGK |
| 173 | IL33-56 VH | EVQLVESGGGLVQPGGSLRLSCAASGFTFSSYWMYWVRQAPGKGLEWVASITPN<br>GGETYYPDSVKGRFTISRDNAKNSLYLQMNSLRAEDTAVYYCARGHYYYTSYSL<br>GYWGQGTLVTVSS |
| 174 | IL33-56 CDRH2 | SITPNGGETYYPDSVKG |
| 175 | IL33-56 HC | EVQLVESGGGLVQPGGSLRLSCAASGFTFSSYWMYWVRQAPGKGLEWVASITPN<br>GGETYYPDSVKGRFTISRDNAKNSLYLQMNSLRAEDTAVYYCARGHYYYTSYSL<br>GYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVD<br>KKVEPKSCDKTHTCPPCPAPELLGGPSVFLFPPKPKDTLMISRTPEVTCVVVDV<br>SHEDPEVKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLTCLVKGFYP<br>SDIAVEWESNGQPENNYKTTPPVLDSDGSFFLYSKLTVDKSRWQQGNVFSCSVM<br>HEALHNHYTQKSLSLSPGK |
| 176 | IL33-57 VH | EVQLVESGGGLVQPGGSLRLSCAASGFTFSSYWMYWVRQAPGKGLEWVASITPN<br>GGNTYYPDSVKGRFTISRDNAKNSLYLQMNSLRAEDTAVYYCARGHYYYTDYSL<br>GYWGQGTLVTVSS |
| 177 | IL33-57 CDRH3 | GHYYYTDYSLGY |
| 178 | IL33-57 HC | EVQLVESGGGLVQPGGSLRLSCAASGFTFSSYWMYWVRQAPGKGLEWVASITPN<br>GGNTYYPDSVKGRFTISRDNAKNSLYLQMNSLRAEDTAVYYCARGHYYYTDYSL<br>GYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVD<br>KKVEPKSCDKTHTCPPCPAPELLGGPSVFLFPPKPKDTLMISRTPEVTCVVVDV<br>SHEDPEVKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLTCLVKGFYP<br>SDIAVEWESNGQPENNYKTTPPVLDSDGSFFLYSKLTVDKSRWQQGNVFSCSVM<br>HEALHNHYTQKSLSLSPGK |
| 179 | IL33-58 VH | EVQLVESGGGLVQPGGSLRLSCAASGFTFSSYWMYWVRQAPGKGLEWVASITPL<br>GGNTYYPDSVKGRFTISRDNAKNSLYLQMNSLRAEDTAVYYCARGHYYYTSYSL<br>GYWGQGTLVTVSS |
| 180 | IL33-58 CDRH2 | SITPLGGNTYYPDSVKG |
| 181 | IL33-58 HC | EVQLVESGGGLVQPGGSLRLSCAASGFTFSSYWMYWVRQAPGKGLEWVASITPL<br>GGNTYYPDSVKGRFTISRDNAKNSLYLQMNSLRAEDTAVYYCARGHYYYTSYSL<br>GYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVD<br>KKVEPKSCDKTHTCPPCPAPELLGGPSVFLFPPKPKDTLMISRTPEVTCVVVDV<br>SHEDPEVKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLTCLVKGFYP<br>SDIAVEWESNGQPENNYKTTPPVLDSDGSFFLYSKLTVDKSRWQQGNVFSCSVM<br>HEALHNHYTQKSLSLSPGK |
| 182 | IL33-61 VH | EVQLVESGGGLVQPGGSLRLSCAASGFTFSSYWMYWVRQAPGKGLEWVASITPN<br>GGETYYPDSVKGRFTISRDNAKNSLYLQMNSLRAEDTAVYYCARGHYYYTDYSL<br>GYWGQGTLVTVSS |
| 183 | IL33-61 HC | EVQLVESGGGLVQPGGSLRLSCAASGFTFSSYWMYWVRQAPGKGLEWVASITPN<br>GGETYYPDSVKGRFTISRDNAKNSLYLQMNSLRAEDTAVYYCARGHYYYTDYSL<br>GYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVD<br>KKVEPKSCDKTHTCPPCPAPELLGGPSVFLFPPKPKDTLMISRTPEVTCVVVDV<br>SHEDPEVKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLTCLVKGFYP<br>SDIAVEWESNGQPENNYKTTPPVLDSDGSFFLYSKLTVDKSRWQQGNVFSCSVM<br>HEALHNHYTQKSLSLSPGK |
| 184 | IL33-62 VH | EVQLVESGGGLVQPGGSLRLSCAASGFTFSSYWMYWVRQAPGKGLEWVASITPN<br>GGDTYYPDSVKGRFTISRDNAKNSLYLQMNSLRAEDTAVYYCARGHYYYTDYSL<br>GYWGQGTLVTVSS |

-continued

SEQUENCE LIST

| SEQ | Description | Sequence |
|---|---|---|
| 185 | IL33-62 HC | EVQLVESGGGLVQPGGSLRLSCAASGFTFSSYWMYWVRQAPGKGLEWVASITPN<br>GGDTYYPDSVKGRFTISRDNAKNSLYLQMNSLRAEDTAVYYCARGHYYYTDYSL<br>GYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVD<br>KKVEPKSCDKTHTCPPCPAPELLGGPSVFLFPPKPKDTLMISRTPEVTCVVVDV<br>SHEDPEVKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLTCLVKGFYP<br>SDIAVEWESNGQPENNYKTTPPVLDSDGSFFLYSKLTVDKSRWQQGNVFSCSVM<br>HEALHNHYTQKSLSLSPGK |
| 186 | IL33-68 VH | EVQLVESGGGLVQPGGSLRLSCAASGFTFSSYWMYWVRQAPGKGLEWVASITPN<br>GGNTYYPDSVKGRFTISRDNAKNSLYLQMNSLRAEDTAVYYCARGHYYYTAYSL<br>GYWGQGTLVTVSS |
| 187 | IL33-68 CDRH3 | GHYYYTAYSLGY |
| 188 | IL33-68 HC | EVQLVESGGGLVQPGGSLRLSCAASGFTFSSYWMYWVRQAPGKGLEWVASITPN<br>GGNTYYPDSVKGRFTISRDNAKNSLYLQMNSLRAEDTAVYYCARGHYYYTAYSL<br>GYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVD<br>KKVEPKSCDKTHTCPPCPAPELLGGPSVFLFPPKPKDTLMISRTPEVTCVVVDV<br>SHEDPEVKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLTCLVKGFYP<br>SDIAVEWESNGQPENNYKTTPPVLDSDGSFFLYSKLTVDKSRWQQGNVFSCSVM<br>HEALHNHYTQKSLSLSPGK |
| 189 | IL33-74 VL | DIQMTQSPSSLSASVGDRVTITCKASQNINDHLDWYQQKPGKAPKLLIYFTNNL<br>QTGVPSRFSGSGSGTDFTLTISSLQPEDFATYYCFQYNNGWTFGGGTKVEIK |
| 190 | IL33-74 CDRL1 | KASQNINDHLD |
| 191 | IL33-74 LC | DIQMTQSPSSLSASVGDRVTITCKASQNINDHLDWYQQKPGKAPKLLIYFTNNL<br>QTGVPSRFSGSGSGTDFTLTISSLQPEDFATYYCFQYNNGWTFGGGTKVEIKRT<br>VAAPSVFIFPPSDEQLKSGTASVVCLLNNFYPREAKVQWKVDNALQSGNSQESV<br>TEQDSKDSTYSLSSTLTLSKADYEKHKVYACEVTHQGLSSPVTKSFNRGEC |
| 192 | IL33-75 VL | DIQMTQSPSSLSASVGDRVTITCKASQNIDKHLDWYQQKPGKAPKLLIYFTNNL<br>QTGVPSRFSGSGSGTDFTLTISSLQPEDFATYYCFQYNNGWTFGGGTKVEIK |
| 193 | IL33-75 CDRL1 | KASQNIDKHLD |
| 194 | IL33-75 LC | DIQMTQSPSSLSASVGDRVTITCKASQNIDKHLDWYQQKPGKAPKLLIYFTNNL<br>QTGVPSRFSGSGSGTDFTLTISSLQPEDFATYYCFQYNNGWTFGGGTKVEIKRT<br>VAAPSVFIFPPSDEQLKSGTASVVCLLNNFYPREAKVQWKVDNALQSGNSQESV<br>TEQDSKDSTYSLSSTLTLSKADYEKHKVYACEVTHQGLSSPVTKSFNRGEC |
| 195 | IL33-80 VL | DIQMTQSPSSLSASVGDRVTITCKASQNINKHLDWYQQKPGKAPKLLIYFTNNL<br>QDGVPSRFSGSGSGTDFTLTISSLQPEDFATYYCFQYNNGWTFGGGTKVEIK |
| 196 | IL33-80 CDRL2 | FTNNLQD |
| 197 | IL33-80 LC | DIQMTQSPSSLSASVGDRVTITCKASQNINKHLDWYQQKPGKAPKLLIYFTNNL<br>QDGVPSRFSGSGSGTDFTLTISSLQPEDFATYYCFQYNNGWTFGGGTKVEIKRT<br>VAAPSVFIFPPSDEQLKSGTASVVCLLNNFYPREAKVQWKVDNALQSGNSQESV<br>TEQDSKDSTYSLSSTLTLSKADYEKHKVYACEVTHQGLSSPVTKSFNRGEC |
| 198 | IL33-81 VL | DIQMTQSPSSLSASVGDRVTITCKASQNINKHLDWYQQKPGKAPKLLIYFTNNL<br>QEGVPSRFSGSGSGTDFTLTISSLQPEDFATYYCFQYNNGWTFGGGTKVEIK |
| 199 | IL33-81 CDRL2 | FTNNLQE |
| 200 | IL33-81 LC | DIQMTQSPSSLSASVGDRVTITCKASQNINKHLDWYQQKPGKAPKLLIYFTNNL<br>QEGVPSRFSGSGSGTDFTLTISSLQPEDFATYYCFQYNNGWTFGGGTKVEIKRT<br>VAAPSVFIFPPSDEQLKSGTASVVCLLNNFYPREAKVQWKVDNALQSGNSQESV<br>TEQDSKDSTYSLSSTLTLSKADYEKHKVYACEVTHQGLSSPVTKSFNRGEC |
| 201 | IL33-103 VH | EVQLVESGGGLVQPGGSLRLSCAASGFTFSSYWMYWVRQAPGKGLEWVAAITPN<br>GYWGQGTLVTVSS |
| 202 | IL33-103 CDRH2 | AITPNGGETYYPDSVKG |
| 203 | IL33-103 HC | EVQLVESGGGLVQPGGSLRLSCAASGFTFSSYWMYWVRQAPGKGLEWVAAITPN<br>GGETYYPDSVKGRFTISRDNAKNSLYLQMNSLRAEDTAVYYCARGHYYYTSYSL<br>GYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVD |

| SEQ | Description | Sequence |
|---|---|---|
| | | KKVEPKSCDKTHTCPPCPAPELLGGPSVFLFPPKPKDTLMISRTPEVTCVVVDV SHEDPEVKFNWYVDGVEVHNAKTKPREEQYNSTYRVVSVLTVLHQDWLNGKEYK CKVSNKALPAPIEKTISKAKGQPREPQVYTLPPSREEMTKNQVSLTCLVKGFYP SDIAVEWESNGQPENNYKTTPPVLDSDGSFFLYSKLTVDKSRWQQGNVFSCSVM HEALHNHYTQKSLSLSPGK |
| 204 | IL33-117 VH | EVQLVESGGGLVQPGGSLRLSCAASGFTFSSYWMYWVRQAPGKGLEWVASITPN GGEDYYPDSVKGRFTISRDNAKNSLYLQMNSLRAEDTAVYYCARGHYYYTSYSL GYWGQGTLVTVSS |
| 205 | IL33-117 CDRH2 | SITPNGGEDYYPDSVKG |
| 206 | IL33-117 HC | EVQLVESGGGLVQPGGSLRLSCAASGFTFSSYWMYWVRQAPGKGLEWVASITPN GGEDYYPDSVKGRFTISRDNAKNSLYLQMNSLRAEDTAVYYCARGHYYYTSYSL GYWGQGTLVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVD KKVEPKSCDKTHTCPPCPAPELLGGPSVFLFPPKPKDTLMISRTPEVTCVVVDV SHEDPEVKFNWYVDGVEVHNAKTKPREEQYNSTYRVVSVLTVLHQDWLNGKEYK CKVSNKALPAPIEKTISKAKGQPREPQVYTLPPSREEMTKNQVSLTCLVKGFYP SDIAVEWESNGQPENNYKTTPPVLDSDGSFFLYSKLTVDKSRWQQGNVFSCSVM HEALHNHYTQKSLSLSPGK |
| 207 | IL33-136 VL | DIQMTQSPSSLSASVGDRVTITCKASQNINKHLDWYQQKPGKAPKLLIYFTNNL QTGVPSRFSGSGSGTDFTLTISSLQPEDFATYYCFQYNQGWTFGGGTKVEIK |
| 208 | IL33-136 CDRL3 | FQYNQGWT |
| 209 | IL33-136 LC | DIQMTQSPSSLSASVGDRVTITCKASQNINKHLDWYQQKPGKAPKLLIYFTNNL QTGVPSRFSGSGSGTDFTLTISSLQPEDFATYYCFQYNQGWTFGGGTKVEIKRT VAAPSVFIFPPSDEQLKSGTASVVCLLNNFYPREAKVQWKVDNALQSGNSQESV TEQDSKDSTYSLSSTLTLSKADYEKHKVYACEVTHQGLSSPVTKSFNRGEC |
| 210 | IL33-153 VH | EVQLVESGGGLVQPGGSLRLSCAASGFTFSSYWMYWVRQAPGKGLEWVASITPN AGEDYYPDSVKGRFTISRDNAKNSLYLQMNSLRAEDTAVYYCARGHYYYTSYSL GYWGQGTLVTVSS |
| 211 | IL33-153 CDRH2 | SITPNAGEDYYPDSVKG |
| 212 | IL33-153 HC | EVQLVESGGGLVQPGGSLRLSCAASGFTFSSYWMYWVRQAPGKGLEWVASITPN AGEDYYPDSVKGRFTISRDNAKNSLYLQMNSLRAEDTAVYYCARGHYYYTSYSL GYWGQGTLVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVD KKVEPKSCDKTHTCPPCPAPEAAGAPSVFLFPPKPKDTLMISRTPEVTCVVVDV SHEDPEVKFNWYVDGVEVHNAKTKPREEQYNSTYRVVSVLTVLHQDWLNGKEYK CKVSNKALPAPIEKTISKAKGQPREPQVYTLPPSREEMTKNQVSLTCLVKGFYP SDIAVEWESNGQPENNYKTTPPVLDSDGSFFLYSKLTVDKSRWQQGNVFSCSVM HEALHNHYTQKSLSLSPGK |
| 213 | IL33-154 VH | EVQLVESGGGLVQPGGSLRLSCAASGFTFSSYWMYWVRQAPGKGLEWVASITPN AGEDYYPESVKGRFTISRDNAKNSLYLQMNSLRAEDTAVYYCARGHYYYTSYSL GYWGQGTLVTVSS |
| 214 | IL33-154 CDRH2 | SITPNAGEDYYPESVKG |
| 215 | IL33-154 HC | EVQLVESGGGLVQPGGSLRLSCAASGFTFSSYWMYWVRQAPGKGLEWVASITPN AGEDYYPESVKGRFTISRDNAKNSLYLQMNSLRAEDTAVYYCARGHYYYTSYSL GYWGQGTLVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVD KKVEPKSCDKTHTCPPCPAPEAAGAPSVFLFPPKPKDTLMISRTPEVTCVVVDV SHEDPEVKFNWYVDGVEVHNAKTKPREEQYNSTYRVVSVLTVLHQDWLNGKEYK CKVSNKALPAPIEKTISKAKGQPREPQVYTLPPSREEMTKNQVSLTCLVKGFYP SDIAVEWESNGQPENNYKTTPPVLDSDGSFFLYSKLTVDKSRWQQGNVFSCSVM HEALHNHYTQKSLLSPGK |
| 216 | IL33-155 VH | EVQLVESGGGLVQPGGSLRLSCAASGFTFSSYWMYWVRQAPGKGLEWVAAITPN GGEDYYPDSVKGRFTISRDNAKNSLYLQMNSLRAEDTAVYYCARGHYYYTSYSL GYWGQGTLVTVSS |
| 217 | IL33-155 CDRH2 | AITPNGGEDYYPDSVKG |
| 218 | IL33-155 HC | EVQLVESGGGLVQPGGSLRLSCAASGFTFSSYWMYWVRQAPGKGLEWVAAITPN GGEDYYPDSVKGRFTISRDNAKNSLYLQMNSLRAEDTAVYYCARGHYYYTSYSL GYWGQGTLVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVD KKVEPKSCDKTHTCPPCPAPEAAGAPSVFLFPPKPKDTLMISRTPEVTCVVVDV |

| SEQ | Description | Sequence |
|---|---|---|
| | | SHEDPEVKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLTCLVKGFYP<br>SDIAVEWESNGQPENNYKTTPPVLDSDGSFFLYSKLTVDKSRWQQGNVFSCSVM<br>HEALHNHYTQKSLSLSPGK |
| 219 | IL33-156 VH | EVQLVESGGGLVQPGGSLRLSCAASGFTFSSYWMYWVRQAPGKGLEWVAAITPN<br>GGEDYYPESVKGRFTISRDNAKNSLYLQMNSLRAEDTAVYYCARGHYYYTSYSL<br>GYWGQGTLVTVSS |
| 220 | IL33-156 CDRH2 | AITPNGGEDYYPESVKG |
| 221 | IL33-156 HC | EVQLVESGGGLVQPGGSLRLSCAASGFTFSSYWMYWVRQAPGKGLEWVAAITPN<br>GGEDYYPESVKGRFTISRDNAKNSLYLQMNSLRAEDTAVYYCARGHYYYTSYSL<br>GYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVD<br>KKVEPKSCDKTHTCPPCPAPEAAGAPSVFLFPPKPKDTLMISRTPEVTCVVVDV<br>SHEDPEVKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLTCLVKGFYP<br>SDIAVEWESNGQPENNYKTTPPVLDSDGSFFLYSKLTVDKSRWQQGNVFSCSVM<br>HEALHNHYTQKSLSLSPGK |
| 222 | IL33-157 VH | EVQLVESGGGLVQPGGSLRLSCAASGFTFSSYWMYWVRQAPGKGLEWVAAITPN<br>AGEDYYPDSVKGRFTISRDNAKNSLYLQMNSLRAEDTAVYYCARGHYYYTSYSL<br>GYWGQGTLVTVSS |
| 223 | IL33-157 CDRH2 | AITPNAGEDYYPDSVKG |
| 224 | IL33-157 HC | EVQLVESGGGLVQPGGSLRLSCAASGFTFSSYWMYWVRQAPGKGLEWVAAITPN<br>AGEDYYPDSVKGRFTISRDNAKNSLYLQMNSLRAEDTAVYYCARGHYYYTSYSL<br>GYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVD<br>KKVEPKSCDKTHTCPPCPAPEAAGAPSVFLFPPKPKDTLMISRTPEVTCVVVDV<br>SHEDPEVKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLTCLVKGFYP<br>SDIAVEWESNGQPENNYKTTPPVLDSDGSFFLYSKLTVDKSRWQQGNVFSCSVM<br>HEALHNHYTQKSLSLSPGK |
| 225 | IL33-158 VH | EVQLVESGGG LVQPGGSLRL SCAASGFTFS SYWMYWVRQA PGKGLEWVAA<br>ITPNAGEDYY PESVKGRFTI SRDNAKNSLY LQMNSLRAED TAVYYCARGH<br>YYYTSYSLGY WGQGTLVTVSS |
| 226 | IL33-158 CDRH2 | AITPNAGEDYYPESVKG |
| 227 | IL33-158 HC | EVQLVESGGGLVQPGGSLRLSCAASGFTFSSYWMYWVRQAPGKGLEWVAAITPN<br>AGEDYYPESVKGRFTISRDNAKNSLYLQMNSLRAEDTAVYYCARGHYYYTSYSL<br>GYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVD<br>KKVEPKSCDKTHTCPPCPAPEAAGAPSVFLFPPKPKDTLMISRTPEVTCVVVDV<br>SHEDPEVKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLTCLVKGFYP<br>SDIAVEWESNGQPENNYKTTPPVLDSDGSFFLYSKLTVDKSRWQQGNVFSCSVM<br>HEALHNHYTQKSLSLSPGK |
| 228 | IL33-175 VH | EVQLVESGGGLVQPGGSLRLSCAASGFTFSSYWMYWVRQAPGKGLEWVAAITPN<br>AGETYYPESVKGRFTISRDNAKNSLYLQMNSLRAEDTAVYYCARGHYYYTSYSL<br>GYWGQGTLVTVSS |
| 229 | IL33-175 CDRH2 | AITPNAGETYYPESVKG |
| 230 | IL33-175 HC | EVQLVESGGGLVQPGGSLRLSCAASGFTFSSYWMYWVRQAPGKGLEWVAAITPN<br>AGETYYPESVKGRFTISRDNAKNSLYLQMNSLRAEDTAVYYCARGHYYYTSYSL<br>GYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVD<br>KKVEPKSCDKTHTCPPCPAPEAAGAPSVFLFPPKPKDTLMISRTPEVTCVVVDV<br>SHEDPEVKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLTCLVKGFYP<br>SDIAVEWESNGQPENNYKTTPPVLDSDGSFFLYSKLTVDKSRWQQGNVFSCSVM<br>HEALHNHYTQKSLSLSPGK |
| 231 | IL33-186 VH | EVQLVESGGGLVQPGGSLRLSCAASGFTFSSYWMYWVRQAPGKGLEWVAAITPN<br>GGETYYPESVKGRFTISRDNAKNSLYLQMNSLRAEDTAVYYCARGHYYYTSYSL<br>GYWGQGTLVTVSS |
| 232 | IL33-186 CDRH2 | AITPNGGETYYPESVKG |

| SEQ | Description | Sequence |
|---|---|---|
| 233 | IL33-186 HC | EVQLVESGGGLVQPGGSLRLSCAASGFTFSSYWMYWVRQAPGKGLEWVAAITPN<br>GGETYYPESVKGRFTISRDNAKNSLYLQMNSLRAEDTAVYYCARGHYYYTSYSL<br>GYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVD<br>KKVEPKSCDKTHTCPPCPAPEAAGAPSVFLFPPKPKDTLMISRTPEVTCVVVDV<br>SHEDPEVKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLTCLVKGFYP<br>SDIAVEWESNGQPENNYKTTPPVLDSDGSFFLYSKLTVDKSRWQQGNVFSCSVM<br>HEALHNHYTQKSLSLSPGK |
| 234 | IL33-187 VH | EVQLVESGGGLVQPGGSLRLSCAASGFTFSSYWMYWVRQAPGKGLEWVAAITPN<br>AGETYYPDSVKGRFTISRDNAKNSLYLQMNSLRAEDTAVYYCARGHYYYTSYSL<br>GYWGQGTLVTVSS |
| 235 | IL33-187 CDRH2 | AITPNAGETYYPDSVKG |
| 236 | IL33-187 HC | EVQLVESGGGLVQPGGSLRLSCAASGFTFSSYWMYWVRQAPGKGLEWVAAITPN<br>AGETYYPDSVKGRFTISRDNAKNSLYLQMNSLRAEDTAVYYCARGHYYYTSYSL<br>GYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVD<br>KKVEPKSCDKTHTCPPCPAPEAAGAPSVFLFPPKPKDTLMISRTPEVTCVVVDV<br>SHEDPEVKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLTCLVKGFYP<br>SDIAVEWESNGQPENNYKTTPPVLDSDGSFFLYSKLTVDKSRWQQGNVFSCSVM<br>HEALHNHYTQKSLSLSPGK |
| 237 | human IgG1 effector function null constant region, lysine deleted | ASTKGPSVFPLAPSSKSTSGGTAALGCLVKDYFPEPVTVSWNSGALTSGVHTFP<br>AVLQSSGLYSLSSVVTVPSSSLGTQTYICNVNHKPSNTKVDKKVEPKSCDKTHT<br>CPPCPAPEAAGAPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPAPIE<br>KTISKAKGQPREPQVYTLPPSREEMTKNQVSLTCLVKGFYPSDIAVEWESNGQP<br>ENNYKTTPPVLDSDGSFFLYSKLTVDKSRWQQGNVFSCSVMHEALHNHYTQKSL<br>SLSPG |
| 238 | human IgG1 effector function null constant region, lysine deleted, LS | ASTKGPSVFPLAPSSKSTSGGTAALGCLVKDYFPEPVTVSWNSGALTSGVHTFP<br>AVLQSSGLYSLSSVVTVPSSSLGTQTYICNVNHKPSNTKVDKKVEPKSCDKTHT<br>CPPCPAPEAAGAPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPAPIE<br>KTISKAKGQPREPQVYTLPPSREEMTKNQVSLTCLVKGFYPSDIAVEWESNGQP<br>ENNYKTTPPVLDSDGSFFLYSKLTVDKSRWQQGNVFSCSVLHEALHSHYTQKSL<br>SLSPG |
| 239 | IL33-158-152 VH secretory leader | MGWSCIILFLVATATGVHS |
| 240 | CH3 hIgG1 delta K | GQPREPQVYTLPPSREEMTKNQVSLTCLVKGFYPSDIAVEWESNGQPENNYKTT<br>PPVLDSDGSFFLYSKLTVDKSRWQQGNVFSCSVMHEALHNHYTQKSLSLSPG |
| 241 | IL33-158-152 HC | EVQLVESGGGLVQPGGSLRLSCAASGFTFSSYWMYWVRQAPGKGLEWVAAITPN<br>AGEDYYPESVKGRFTISRDNAKNSLYLQMNSLRAEDTAVYYCARGHYYYTSYSL<br>GYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVD<br>KKVEPKSCDKTHTCPPCPAPEAAGAPSVFLFPPKPKDTLMISRTPEVTCVVVDV<br>SHEDPEVKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLTCLVKGFYP<br>SDIAVEWESNGQPENNYKTTPPVLDSDGSFFLYSKLTVDKSRWQQGNVFSCSVM<br>HEALHNHYTQKSLSLSPG |
| 242 | IL33-167-153 HC | EVQLVESGGGLVQPGGSLRLSCAASGFTFSSYWMYWVRQAPGKGLEWVASITPN<br>AGEDYYPDSVKGRFTISRDNAKNSLYLQMNSLRAEDTAVYYCARGHYYYTSYSL<br>GYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVD<br>KKVEPKSCDKTHTCPPCPAPEAAGAPSVFLFPPKPKDTLMISRTPEVTCVVVDV<br>SHEDPEVKFNWYVDGVEVHNAKTKPREEQYNSTYRVVSVLTVLHQDWLNGKEYK<br>CKVSNKALPAPIEKTISKAKGQPREPQVYTLPPSREEMTKNQVSLTCLVKGFYP<br>SDIAVEWESNGQPENNYKTTPPVLDSDGSFFLYSKLTVDKSRWQQGNVFSCSVM<br>HEALHNHYTQKSLSLSPG |
| 243 | CH3 hIgG1 LS | GQPREPQVYTLPPSREEMTKNQVSLTCLVKGFYPSDIAVEWESNGQPENNYKTT<br>PPVLDSDGSFFLYSKLTVDKSRWQQGNVFSCSVLHEALHSHYTQKSLSLSPG |
| 244 | IL33-158L5 HC | EVQLVESGGGLVQPGGSLRLSCAASGFTFSSYWMYWVRQAPGKGLEWVAAITPN<br>AGEDYYPESVKGRFTISRDNAKNSLYLQMNSLRAEDTAVYYCARGHYYYTSYSL<br>GYWGQGTLVTVSSASTKGPSVFPLAPSSKSTSGGTAALGCLVKDYFPEPVTVSW<br>NSGALTSGVHTFPAVLQSSGLYSLSSVVTVPSSSLGTQTYICNVNHKPSNTKVD<br>KKVEPKSCDKTHTCPPCPAPEAAGAPSVFLFPPKPKDTLMISRTPEVTCVVVDV<br>SHEDPEVKFNWYVDGVEVHNAKTKPREEQYNSTYRVVSVLTVLHQDWLNGKEYK |

| SEQ | Description | Sequence |
|---|---|---|
| | | CKVSNKALPAPIEKTISKAKGQPREPQVYTLPPSREEMTKNQVSLTCLVKGFYP SDIAVEWESNGQPENNYKTTPPVLDSDGSFFLYSKLTVDKSRWQQGNVFSCSVL HEALHSHYTQKSLSLPG |
| 245 | IL33-167LS HC | EVQLVESGGGLVQPGGSLRLSCAASGFTFSSYWMYWVRQAPGKGLEWVASITPN AGEDYYPDSVKGRFTISRDNAKNSLYLQMNSLRAEDTAVYYCARGHYYYTSYSL GYWGQGTLVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVD KKVEPKSCDKTHTCPPCPAPEAAGAPSVFLFPPKPKDTLMISRTPEVTCVVVDV SHEDPEVKFNWYVDGVEVHNAKTKPREEQYNSTYRVVSVLTVLHQDWLNGKEYK CKVSNKALPAPIEKTISKAKGQPREPQVYTLPPSREEMTKNQVSLTCLVKGFYP SDIAVEWESNGQPENNYKTTPPVLDSDGSFFLYSKLTVDKSRWQQGNVFSCSVL HEALHSHYTQKSLSLSPG |
| 246 | IL33-271 VH | QVLLVQSGAEVKKPGATVKVSCHASGSTFTGYYMHWVRQAPGQGLEWMGWINPN NGGTNYAQKFQGRVTMTRDTSISTAYMELSRLRSDDTAVYYCARELRYNWKSWG QGTLVTVSS |
| 247 | IL33-271 CDRH1 | GSTFTGYYMH |
| 248 | IL33-271 CDRH2 | WINPNNGGTNYAQKFQG |
| 249 | IL33-271 CDRH3 | ELRYNWKS |
| 250 | IL33-271 VL | EIVLTQSPGTLSLSPGERVTLSCRASQSVGRPYLAWYQQIPGQAPRLLIYGASS RATDIPDRFSGNGSGTDFTLTISRLEPEDFAVYYCQQYDNSPYTFGQGTRLEIK |
| 251 | IL33-271 CDRL1 | RASQSVGRPYLA |
| 252 | IL33-271 CDRL2 | GASSRAT |
| 253 | IL33-271 CDRL3 | QQYDNSPYT |
| 254 | IL33-271 HC | QVLLVQSGAEVKKPGATVKVSCHASGSTFTGYYMHWVRQAPGQGLEWMGWINPN NGGTNYAQKFQGRVTMTRDTSISTAYMELSRLRSDDTAVYYCARELRYNWKSWG QGTLVTVSSASTKGPSVFPLAPSSKSTSGGTAALGCLVKDYFPEPVTVSWNSGA LTSGVHTFPAVLQSSGLYSLSSVVTVPSSSLGTQTYICNVNHKPSNTKVDKKVE PKSCDKTHTCPPCPAPEAAGAPSVFLFPPKPKDTLMISRTPEVTCVVVDVSHED PEVKFNWYVDGVEVHNAKTKPREEQYNSTYRVVSVLTVLHQDWLNGKEYKCKVS NKALPAPIEKTISKAKGQPREPQVYTLPPSREEMTKNQVSLTCLVKGFYPSDIA VEWESNGQPENNYKTTPPVLDSDGSFFLYSKLTVDKSRWQQGNVFSCSVMHEAL HNHYTQKSLSLSPGK |
| 255 | IL33-271 JK | FGQGTRLEIK |
| 256 | IL33-271 LC | EIVLTQSPGTLSLSPGERVTLSCRASQSVGRPYLAWYQQIPGQAPRLLIYGASS RATDIPDRFSGNGSGTDFTLTISRLEPEDFAVYYCQQYDNSPYTFGQGTRLEIK RTVAAPSVFIFPPSDEQLKSGTASVVCLLNNFYPREAKVQWKVDNALQSGNSQE SVTEQDSKDSTYSLSSTLTLSKADYEKHKVYACEVTHQGLSSPVTKSFNRGEC |
| 257 | Consensus CDR L1 Broad | (K/S/H/T/Q/W/Y/F/R) (A/S/G) (S/A/D) (Q/H/S/E/D/T) (N/S/D/ R/K/Y/E/G) (I/V) (N/F/K/H/R/L/M/I/E/S) (K/Q/E/R/W/F/Y/ N/A/S/H) (H/F/R/W) (L/I/V/A) (D/S/A) |
| 258 | Consensus CDR L1 7E8 9B3 germline ABS mutagenesis | (K/R)AS(Q/H)(N/S)(I/V)(N/S)(K/S/N)HLD |
| 259 | Consensus CDR L1 7E8 9B3 ABS mutagenesis | (K/R)AS(Q/H)(N/S)I(N/S)(K/S)HLD |
| 260 | Consensus CDR L1 7E8 ABS | (K/R)ASQ(N/S)I(N/S)(K/S)HLD |
| 261 | Consensus CDR L2 Broad | (F/W/Y/D/E/G/S) (T/G/R/A/N/V) (N/W/Y/R/F/K/Q/E/D/H/S) (N/ F/Y/I/M/Q/L/A/R/G/P/S) (L/I/V/R) (Q/R/K/F/H/L/W/Y/A/E) (T/S/N/Y) |
| 262 | Consensus CDR L2 7E8 germline ABS mutagenesis | (F/Y)(A/T)(N/S)(N/S)L(Q/E)(T/S) |
| 263 | Consensus CDR L2 7E8 ABS mutagenesis | F(T/A)(N/S)(N/S)LQ(T/S) |

| SEQ | Description | Sequence |
|---|---|---|
| 264 | Consensus CDR L2 7E8 ABS | F(A/T)(N/S)NLQ(T/S) |
| 265 | Consensus CDR L3 Broad | (F/Q/W/H/A)(Q/S/T/A)(Y/H/F)(N/W/F/Y/R/K/H/D)(N/S/Q/W/K/R/H/Y/D/G/T/V)(G/R/P/K/W/F/I/N/Q)(W/H)(T/S/Q) |
| 266 | Consensus CDR L3 7E8 9B3 ABS mutagenesis | (F/Q)Q(Y/F)(N/Y)(N/S/Q/R/Y)GWT |
| 267 | Consensus CDR L3 7E8 9B3 ABS | (F/Q)QY(N/Y)(N/S/Q/R)GWT |
| 268 | Consensus CDR L3 7E8 ABS | (F/Q)QY(N/Y)(N/S/Q)GWT |
| 269 | Consensus CDR H1 Broad | G(F/Y/H)(T/Q/N/S/E/D/R/Y)(F/Y/H)(S/E/D/T/W)(N/S/T/E/D/H/L/I/Y/R/K/G)(Y/F/H)(W/H/Y/A/G)(M/E/Q/I)(Y/F/H/N) |
| 270 | Consensus CDR H1 7E8 9B3 ABS mutagenesis | GF(T/E)F(S/E)(N/S)YWMY |
| 271 | Consensus CDR H1 7E8 9B3 ABS | GFTFS(N/S)YWMY |
| 272 | Consensus CDR H2 Broad | (S/A/T)(I/V)(T/H/N/S)(P/N/F/M)(N/I/D/Y/W)(G/A)(G/H/D/E/R/K/Y/S)(N/Y/D/E/Q/H)(T/K/E/S/I/A/D)(Y/H/W)(Y/F/H)(P/V/L/D/S)(D/E/Q/A)(S/A/N/D)(V/D/T)(K/N/D/S/E/Q)G |
| 273 | Consensus CDR H2 7E8 9B3 ABS mutagenesis | (S/A)I(T/N)(P/N)(N/D)(G/A)(G/S/H)(N/D/E)(T/K/D/E)YY(P/V/L)(D/E)SV(K/Q)G |
| 274 | Consensus CDR H2 7E8 9B3 ABS | (S/A)I(T/N)(P/N)(N/D)(G/A)(G/S)(N/E)(T/K/D)YY(P/V/L)(D/E)SVKG |
| 275 | Consensus CDR H2 7E8 ABS | (S/A)ITP(N/D)(G/A)(G/S)(N/E)(T/K/D)YY(P/V)(D/E)SVKG |
| 276 | Consensus CDR H3 Broad | (G/S/A/T/D)(H/K/R/Y)(Y/H/F/S)(Y/H/R/S)(Y/H/W/F/R/S)(T/N/V/I/S/A/G/Y)(S/N/A/Q/D/G/R/Y)(Y/W/H/F/G/D/N)(S/A/G)(L/M/F/I)(G/A/Y/S/D)(Y/N/S/F/E/D/H/I/V) |
| 277 | Consensus CDR H3 7E8 9B3 mutagenesis and repertoire | G(H/R/Y)(Y/F)(Y/S)(Y/H)(T/S/N)(S/A)YS(L/F/I)(G/S/A)(Y/H/N/S/F) |
| 278 | Consensus CDR H3 7E8 9B3 mutagenesis | G(H/Y)Y(Y/S)(Y/H)(T/S/N)(S/A)YS(L/F)(G/S)Y |
| 279 | Consensus CDR H3 7E8 9B3 | GHY(Y/S)Y(T/S)SYS(L/F)(G/S)Y |
| 396 | Full length human IL-33 Swiss Prot O95760-1. Residues C208, C227, C232, and C259 are bold and underlined | MKPKMKYSTN KISTAKWKNT ASKALCFKLG KSQQKAKEVC PMYFMKLRSG LMIKKEACYF PRETTKRRSL KTGRKHKRHL VLAACQQQST VECFAFGISG VQKYTRALHD SSITGISPIT EYLASLSTYN DQSITFALED ESYEIYVEDL KKDEKKDKVL LSYYESQHPS NESGDGVDCK MLMVTLSPTK DFWLHANNKE HSVELHKCEK PLPDQAFFVL HNMHSNCVSF ECKTDPGVFI GVKDNHLALI KVDSSENLCT ENILFKLSET |
| 397 | Wild-type cynomolgus monkey IL-33 | SITGISPITE SLASLSTYND QSITFALEDE SYEIYVEDLK KDKKKDKVLL SYYESQHPSS ESGDGVDGKM LMVTLSPTKD FWLQANNKEH SVELHKCEKP LPDQAFFVLH NRSFNCVSFE CKTDPGVFIG VKDNHLALIK VDYSENLGSE NILFKLSEIH HHHHH |
| 398 | DNA sequence encoding light chain IL33-158LS | GACATCCAGATGACCCAGTCCCCCTCTTCTCTGTCTGCCTCTGTGGGCGACAGA GTGACCATCACCTGTAAAGCAAGTCAGAGATATTAATAAACACTTAGACTGGTAT CAGCAGAAGCCTGGCAAGGCTCCCAAGCTGCTGATCTACTTTACAAACAATTTA CAAACTGGCGTGCCTTCCAGATTCTCCGGCTCTGGCTCTGGCACCGATTTCACC CTGACCATCTCCTCCCTCCAGCCTGAGGATTTCGCCACCTACTACTGCTTTCAG TATAACCAGGGGTGGACCTTTGGCGGCGGAACAAAGGTGGAGATCAAGCGTACG GTGGCTGCACCATCTGTCTTCATCTTCCCGCCATCTGATGAGCAGTTGAAATCT GGAACTGCCTCTGTTGTGTGCCTGCTGAATAACTTCTATCCCAGAGAGGCCAAA GTACAGTGGAAGGTGGATAACGCCCTCCAATCGGGTAACTCCCAGGAGAGTGTC ACAGAGCAGGACAGCAAGGACAGCACCTACAGCCTCAGCAGCACCCTGACGCTG AGCAAAGCAGACTACGAGAAACACAAAGTCTACGCCTGCGAAGTCACCCATCAG GGCCTGAGCTCGCCCGTCACAAAGAGCTTCAACAGGGGAGAGTGT |

| SEQ | Description | Sequence |
|---|---|---|
| 399 | DNA sequence encoding heavy chain IL33-158LS | GAGGTGCAGCTGGTGGAGTCTGGCGGCGGACTGGTGCAGCCTGGCGGCTCTCTG<br>AGACTGTCTTGTGCCGCCTCCGGCTTCACCTTCAGTTCCTACTGGATGTACTGG<br>GTGAGGCAGGCCCCTGGCAAGGGCCTGGAGTGGGTGGCCGCCATTACTCCTAAT<br>GCCGGTGAGGACTACTATCCAGAGTCTGTGAAAGGCCGGTTCACCATCTCCAGG<br>GACAACGCCAAGAACTCCCTGTACCTCCAGATGAACTCCCTGAGGGCCGAGGAT<br>ACCGCCGTGTACTACTGTGCCAGAGGCCATTATTACTATACCAGCTATTCGCTT<br>GGATACTGGGGCCAGGGCACCCTGGTGACCGTGTCCTCTGCGTCGACCAAGGGC<br>CCATCGGTCTTCCCCCTGGCACCCTCCTCCAAGAGCACCTCTGGGGGCACAGCG<br>GCCCTGGGCTGCCTGGTCAAGGACTACTTCCCCGAACCGGTGACGGTGTCGTGG<br>AACTCAGGCGCCCTGACCAGCGGCGTGCACACCTTCCCGGCTGTCCTACAGTCC<br>TCAGGACTCTACTCCCTCAGCAGCGTGGTGACCGTGCCCTCCAGCAGCTTGGGC<br>ACCCAGACCTACATCTGCAACGTGAATCACAAGCCCAGCAACACCAAGGTGGAC<br>AAGAAAGTTGAGCCCAAATCTTGTGACAAAACTCACACATGCCCACCGTGCCCA<br>GCACCTGAAGCCGCTGGGGCACCGTCAGTCTTCCTCTTCCCCCCAAAACCCAAG<br>GACACCCTCATGATCTCCCGGACCCCTGAGGTCACATGCGTGGTGGTGGACGTG<br>AGCCACGAAGACCCTGAGGTCAAGTTCAACTGGTACGTGGACGGCGTGGAGGTG<br>CATAATGCCAAGACAAAGCCGCGGGAGGAGCAGTACAACAGCACGTACCGTGTG<br>GTCAGCGTCCTCACCGTCCTGCACCAGGACTGGCTGAATGGCAAGGAGTACAAG<br>TGCAAGGTCTCCAACAAAGCCCTCCCAGCCCCCATCGAGAAAACCATCTCCAAA<br>GCCAAAGGGCAGCCCCGAGAACCACAGGTGTACACCCTGCCCCCATCCCGGGAG<br>GAGATGACCAAGAACCAGGTCAGCCTGACCTGCCTGGTCAAAGGCTTCTATCCC<br>AGCGACATCGCCGTGGAGTGGGAGAGCAATGGGCAGCCGGAGAACAACTACAAG<br>ACCACGCCTCCCGTGCTGGACTCCGACGGCTCCTTCTTCCTCTATAGCAAGCTC<br>ACCGTGGACAAGAGCAGGTGGCAGCAGGGGAACGTCTTCTCATGCTCCGTGTTG<br>CATGAGGCTCTGCACTCCCACTACACGCAGAAGAGCCTCTCCCTGTCCCCGGGA |
| 400 | DNA sequence encoding light chain IL33-167LS | GACATCCAGATGACCCAGTCCCCCTCTTCTCTGTCTGCCTCTGTGGGCGACAGA<br>GTGACCATCACCTGTAAAGCAAGTCAGAATATTAATAAACACTTAGACTGGTAT<br>CAGCAGAAGCCTGGCAAGGCTCCCAAGCTGCTGATCTACTTTACAAACAATTTA<br>CAAACTGGCGTGCCTTCCAGATTCTCCGGCTCTGGCTCTGGCACCGATTTCACC<br>CTGACCATCTCCTCCCTCCAGCCTGAGGATTTCGCCACCTACTACTGCTTTCAG<br>TATAACAATGGGTGGACCTTTGGCGGCGGAACAAAGGTGGAGATCAAGCGTACG<br>GTGGCTGCACCATCTGTCTTCATCTTCCCGCCATCTGATGAGCAGTTGAAATCT<br>GGAACTGCCTCTGTTGTGTGCCTGCTGAATAACTTCTATCCCAGAGAGGCCAAA<br>GTACAGTGGAAGGTGGATAACGCCCTCCAATCGGGTAACTCCCAGGAGAGTGTC<br>ACAGAGCAGGACAGCAAGGACAGCACCTACAGCCTCAGCAGCACCCTGACGCTG<br>AGCAAAGCAGACTACGAGAAACACAAAGTCTACGCCTGCGAAGTCACCCATCAG<br>GGCCTGAGCTCGCCCGTCACAAAGAGCTTCAACAGGGGAGAGTGT |
| 401 | DNA sequence encoding heavy chain IL33-167LS | GAGGTGCAGCTGGTGGAGTCTGGCGGCGGACTGGTGCAGCCTGGCGGCTCTCTG<br>AGACTGTCTTGTGCCGCCTCCGGCTTCACCTTCAGTTCCTACTGGATGTACTGG<br>GTGAGGCAGGCCCCTGGCAAGGGCCTGGAGTGGGTGGCCTACTACTCCTAAT<br>GCCGGTGAGGACTACTATCCAGAGTCTGTGAAAGGCCGGTTCACCATCTCCAGG<br>GACAACGCCAAGAACTCCCTGTACCTCCAGATGAACTCCCTGAGGGCCGAGGAT<br>ACCGCCGTGTACTACTGTGCCAGAGGCCATTATTACTATACCAGCTATTCGCTT<br>GGATACTGGGGCCAGGGCACCCTGGTGACCGTGTCCTCTGCGTCGACCAAGGGC<br>CCATCGGTCTTCCCCCTGGCACCCTCCTCCAAGAGCACCTCTGGGGGCACAGCG<br>GCCCTGGGCTGCCTGGTCAAGGACTACTTCCCCGAACCGGTGACGGTGTCGTGG<br>AACTCAGGCGCCCTGACCAGCGGCGTGCACACCTTCCCGGCTGTCCTACAGTCC<br>TCAGGACTCTACTCCCTCAGCAGCGTGGTGACCGTGCCCTCCAGCAGCTTGGGC<br>ACCCAGACCTACATCTGCAACGTGAATCACAAGCCCAGCAACACCAAGGTGGAC<br>AAGAAAGTTGAGCCCAAATCTTGTGACAAAACTCACACATGCCCACCGTGCCCA<br>GCACCTGAAGCCGCTGGGGCACCGTCAGTCTTCCTCTTCCCCCCAAAACCCAAG<br>GACACCCTCATGATCTCCCGGACCCCTGAGGTCACATGCGTGGTGGTGGACGTG<br>AGCCACGAAGACCCTGAGGTCAAGTTCAACTGGTACGTGGACGGCGTGGAGGTG<br>CATAATGCCAAGACAAAGCCGCGGGAGGAGCAGTACAACAGCACGTACCGTGTG<br>GTCAGCGTCCTCACCGTCCTGCACCAGGACTGGCTGAATGGCAAGGAGTACAAG<br>TGCAAGGTCTCCAACAAAGCCCTCCCAGCCCCCATCGAGAAAACCATCTCCAAA<br>GCCAAAGGGCAGCCCCGAGAACCACAGGTGTACACCCTGCCCCCATCCCGGGAG<br>GAGATGACCAAGAACCAGGTCAGCCTGACCTGCCTGGTCAAAGGCTTCTATCCC<br>AGCGACATCGCCGTGGAGTGGGAGAGCAATGGGCAGCCGGAGAACAACTACAAG<br>ACCACGCCTCCCGTGCTGGACTCCGACGGCTCCTTCTTCCTCTATAGCAAGCTC<br>ACCGTGGACAAGAGCAGGTGGCAGCAGGGGAACGTCTTCTCATGCTCCGTGTTG<br>CATGAGGCTCTGCACTCCCACTACACGCAGAAGAGCCTCTCCCTGTCCCCGGGA |
| 402 | Leader Sequence | MGWSCIILFL VATATGAHS |
| 403 | IL33-265 heavy chain, based on H4H9675P in US 2014/0271658, SEQ ID NO: 274 | EVQLVESGGN LEQPGGSLRL SCTASGFTFS RSAMNWVRRA PGKGLEWVSG<br>ISGSGGRTYY ADSVKGRFTI SRDNSKNTLY LQMNSLSAED TAAYYCAKDS<br>YTTSWYGGMD VWGHGTTVTV SSASTKGPSV FPLAPSSKST SGGTAALGCL<br>VKDYFPEPVT VSWNSGALTS GVHTFPAVLQ SSGLYSLSSV VTVPSSSLGT<br>QTYICNVNHK PSNTKVDKKV EPKSCDKTHT CPPCPAPEAA GAPSVFLFPP<br>KPKDTLMISR TPEVTCVVVD VSHEDPEVKF NWYVDGVEVH NAKTKPREEQ<br>YNSTYRVVSV LTVLHQDWLN GKEYKCKVSN KALPAPIEKT ISKAKGQPRE |

| SEQ | Description | Sequence |
|---|---|---|
| | | PQVYTLPPSR EEMTKNQVSL TCLVKGFYPS DIAVEWESNG QPENNYKTTP PVLDSDGSFF LYSKLTVDKS RWQQGNVFSC SVMHEALHNH YTQKSLSLSP GK |
| 404 | IL33-265 light chain, based on H4H9675P in US 2014/0271658, SEQ ID NO: 282 | DIQMTQSPSS VSASVGDRVT ITCRASQGIF SWLAWYQQKP GKAPKLLIYA ASSLQSGVPS RFSGSGSGTD FTLTISSLQP EDFAIYYCQQ ANSVPITFGQ GTRLEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 405 | IL33-310 heavy chain, based on 10C12.38.H6.87Y.581 IgG4 in U.S. 2016/0168242, SEQ ID NO: 306 | EVQLVESGGG LVQPGGSLRL SCAASGFTFS SFSMSWVRQA PGKGLEWVAT ISGGKTFTDY VDSVKGRFTI SRDDSKNTLY LQMNSLRAED TAVYYCTRAN YGNWFFEVWG QGTLVTVSSA STKGPSVFPL APCSRSTSES TAALGCLVKD YFPEPVTVSW NSGALTSGVH TFPAVLQSSG LYSLSSVVTV PSSSLGTKTY TCNVDHKPSN TKVDKRVESK YGPPCPPCPA PEFLGGPSVF LFPPKPKDTL MISRTPEVTC VVVDVSQEDP EVQFNWYVDG VEVHNAKTKP REEQFNSTYR VVSVLTVLHQ DWLNGKEYKC KVSNKGLPSS IEKTISKAKG QPREPQVYTL PPSQEEMTKN QVSLSCAVKG FYPSDIAVEW ESNGQPENNY KTTPPVLDSD GSFFLVSRLT VDKSRWQEGN VFSCSVMHEA LHNHYTQKSL SLSLG |
| 406 | IL33-310 light chain, based on 10C12.38.H6.87Y.581 IgG4 in U.S. 2016/0168242, SEQ ID NO: 307 | EIVLTQSPAT LSLSPGERAT LSCRASESVA KYGLSLLNWF QQKPGQPPRL LIFAASNRGS GIPARFSGSG SGTDFTLTIS SLEPEDFAVY YCQQSKEVPF TFGQGTKVEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 407 | IL33-312 heavy chain, based on 33_640087-7B in WO16156440, SEQ ID NO: 615 | EVQLLESGGG LVQPGGSLRL SCAASGFTFS SYAMSWVRQA PGKGLEWVSG ISAIDQSTYY ADSVKGRFTI SRDNSKNTLY LQMNSLRAED TAVYYCARQK FMQLWGGGLR YPFGYWGQGT MVTVSSASTK GPSVFPLAPS SKSTSGGTAA LGCLVKDYFP EPVTVSWNSG ALTSGVHTFP AVLQSSGLYS LSSVVTVPSS SLGTQTYICN VNHKPSNTKV DKRVEPKSCD KTHTCPPCPA PEFEGGPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAS IEKTISKAKG QPREPQVYTL PPSREEMTKN QVSLTCLVKG FYPSDIAVEW ESNGQPENNY KTTPPVLDSD GSFFLYSKLT VDKSRWQQGN VFSCSVMHEA LHNHYTQKSL SLSPGK |
| 408 | IL33-312 light chain, based on 33_640087-7B in WO16156440, SEQ ID NO: 617 | SYVLTQPPSV SVSPGQTASI TCSGEGMGDK YAAWYQQKPG QSPVLVIYRD TKRPSGIPER FSGSNSGNTA TLTISGTQAM DEADYYCGVI QDNTGVFGGG TKLTVLGQPK AAPSVTLFPP SSEELQANKA TLVCLISDFY PGAVTVAWKA DSSPVKAGVE TTTPSKQSNN KYAASSYLSL TPEQWKSHRS YSCQVTHEGS TVEKTVAPTE CS |
| 409 | IL33-313 heavy chain, based on 33 640237-2B in WO16156440, SEQ ID NO: 623 | EVQLLESGGG LVQPGGSLRL SCAASGFTFS SYAMSWVRQA PGKGLEWVSG IADDFTSTYY ADPVKGRFTI SRDNSKNTLY LQMNSLRAED TAVYYCARDL WMMNYAGGLR YPFGYWGQGT MVTVSSASTK GPSVFPLAPS SKSTSGGTAA LGCLVKDYFP EPVTVSWNSG ALTSGVHTFP AVLQSSGLYS LSSVVTVPSS SLGTQTYICN VNHKPSNTKV DKRVEPKSCD KTHTCPPCPA PEFEGGPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAS IEKTISKAKG QPREPQVYTL PPSREEMTKN QVSLTCLVKG FYPSDIAVEW ESNGQPENNY KTTPPVLDSD GSFFLYSKLT VDKSRWQQGN VFSCSVMHEA LHNHYTQKSL SLSPGK |
| 410 | IL33-313 light chain, based on 33 640237-2B in WO16156440, SEQ ID NO: 625 | SYVLTQPPSV SVSPGQTASI TCSGERMGDK YAAWYQQKPG QSPVLVIYRD TKRPSGIPER FSGSNSGNTA TLTISGTQAM DEADYYCGVL KQDTGVFGGG TKLTVLGQPK AAPSVTLFPP SSEELQANKA TLVCLISDFY PGAVTVAWKA DSSPVKAGVE TTTPSKQSNN KYAASSYLSL TPEQWKSHRS YSCQVTHEGS TVEKTVAPTE CS |

See Tables 2 and 3 for SEQ ID NOs 280-352 and 353-395 respectively.

The invention claimed is:

1. An antibody, or antigen binding fragment thereof, that specifically binds to human IL-33, comprising one from each of (i)-(vi)
   (i) a light chain complementarity determining region 1 (CDR-L1) selected from the group consisting of SEQ ID NO:20, 37, 190, 193, 257, 258, 259, and 260 according to Kabat numbering,
   (ii) a CDR-L2 selected from the group consisting of SEQ ID NO:21, 196, 199, 261, 262, 263, and 264 according to Kabat numbering,
   (iii) a CDR-L3 selected from the group consisting of SEQ ID NO:22, 38, 208, 265, 26, 267, and 268, according to Kabat numbering,
   (iv) a heavy chain complementarity determining region 1 (CDR-H1) selected from the group consisting of SEQ ID NO:16, 33, 269, 270, and 271 according to Kabat numbering,
   (v) a CDR-H2 selected from the group consisting of SEQ ID NO:17, 34, 168, 171, 174, 180, 202, 205, 211, 214, 217, 220, 223, 226, 229, 232, 235, 272, 273, 274, and 275 according to Kabat numbering, and
   (vi) a CDR-H3 selected from the group consisting of SEQ ID NO:18, 35, 114, 119, 122, 127, 130, 133, 136, 139, 142, 145, 148, 153, 156, 159, 177, 187, 276, 277, 278, and 279 according to Kabat numbering.

2. An antibody, or antigen binding fragment thereof comprising the CDR-H1, CDR-H2, and CDR-H3 sequences of SEQ ID NO:225, and the CDR-L1, CDR-L2, and CDR-L3 sequences of SEQ ID NO:207.

3. The antibody, or antigen binding fragment thereof, as claimed in claim 2, comprising
   (i) a CDR-L1 comprising SEQ ID NO:20 according to Kabat numbering,
   (ii) a CDR-L2 comprising SEQ ID NO:21 according to Kabat numbering,
   (iii) a CDR-L3 comprising SEQ ID NO:208 according to Kabat numbering,
   (iv) a CDR-H1 comprising SEQ ID NO:16 according to Kabat numbering,
   (v) a CDR-H2 comprising SEQ ID NO:226 according to Kabat numbering,
   (vi) a CDR-H3 comprising SEQ ID NO: 18 according to Kabat numbering.

4. The antibody, or antigen binding fragment thereof, of claim 2, comprising a VL framework sequence and a VH framework sequence, and wherein one or both of the VL framework sequence or VH framework sequence is at least 90%, 91%, 92%, 93%, 94%, 95%, 96%, 97%, 98%, or 99% identical to the human germline sequence from which it was derived, and wherein the human germline VL sequence from which the VL framework sequence is derived is selected from the group consisting of DPK9, DPK12, DPK18, DPK24, HK102 _V1, DPK1, DPK8, DPK3, DPK21, Vg_38K, DPK22, DPK15, DPL16, DPL8, V1-22, Vλ consensus, Vλ1 consensus, Vλ3 consensus, Vκ$_1$ consensus, Vκ1 consensus, Vκ2 consensus, and Vκ3, and wherein the human germline VH sequence from which the VH framework sequence is derived is selected from the group consisting of DP54, DP47, DP50, DP31, DP46, DP71, DP75, DP10, DP7, DP49, DP51, DP38, DP79, DP78, DP73, VH3, VH5, VH1, and VH4.

5. The antibody, or antigen binding fragment thereof of claim 2, comprising a VH comprising an amino acid sequence at least 90% identical to SEQ ID NO:225, and a VL comprising an amino acid sequence at least 90% identical to SEQ ID NO:207.

6. The antibody, or antigen binding fragment thereof, of claim 2, comprising an Fc domain, and wherein the Fc domain is the Fc domain of an $IgA_1$ $IgA_2$, IgD, IgE, IgM, $IgG_1$, $IgG_2$, $IgG_3$, or $IgG_4$.

7. The antibody, or antigen binding fragment thereof, of claim 2, comprising a heavy chain comprising an amino acid sequence at least 90% identical to SEQ ID NO:244, and a light chain comprising an amino acid sequence at least 90% identical to SEQ ID NO:209.

8. The antibody, or antigen binding fragment thereof, of claim 2, comprising a heavy chain comprising the amino acid sequence of SEQ ID NO:244, and a light chain comprising the amino acid sequence of SEQ ID NO:209.

9. The antibody, or antigen binding fragment thereof, of claim 2, comprising the VH amino acid sequence encoded by the insert of the plasmid deposited at the ATCC and having ATCC Accession No. PTA-122724, and the VL amino acid sequence encoded by the insert of the plasmid deposited at the ATCC and having ATCC Accession No. PTA-122725.

10. The antibody, or antigen binding fragment thereof, of claim 2, wherein the antibody, or antigen binding fragment thereof, binds human IL-33 with a $K_D$ about or less than a value selected from the group consisting of about 10 nM, 5 nM, 2 nM, 1 nM, 900 pM, 800 pM, 700 pM, 600 pM, 500 pM, 400 pM, 300 pM, 250 pM, 200 pM, 150 pM, 100 pM, 50 pM, 40 pM, 30 pM, 25 pM, 20 pM, 15 pM, 10 pM, 5 pM, and 1 pM, and optionally, wherein the antibody, or antigen binding fragment thereof, binds cynomologus monkey IL-33 with a $K_D$ about or less than a value selected from the group consisting of about 10 nM, 5 nM, 2 nM, 1 nM, 900 pM, 800 pM, 700 pM, 600 pM, 500 pM, 400 pM, 300 pM, 250 pM, 200 pM, 150 pM, 100 pM, 50 pM, 40 pM, 30 pM, 25 pM, 20 pM, 15 pM, 13 pM, 10 pM, 5 pM, and 1 pM.

11. The antibody, or antigen binding fragment thereof, of claim 2, wherein the binding $K_D$ of the antibody, or antigen binding fragment, to cynomologous IL-33 is within 10-fold of the binding $K_D$ to human IL-33.

12. The antibody, or antigen binding fragment thereof, of claim 2, wherein the terminal half life in humans is at least about 31 days.

13. A pharmaceutical composition comprising the antibody, or antigen binding fragment thereof, of claim 2, and a pharmaceutically acceptable carrier or excipient.

14. The antibody, or antigen-binding fragment thereof, of claim 2, comprising a VH framework sequence derived from a human germline DP54 sequence.

15. The antibody, or antigen-binding fragment thereof, of claim 2, comprising a VL framework sequence derived from a human germline DPK9 sequence.

16. The antibody, or antigen-binding fragment thereof, of claim 2, wherein the ratio of binding $K_D$ of the antibody or antigen binding fragment to human IL-33 compared with the binding to cynomologous IL-33 is between 5:1 and 1:5.

17. The antibody, or antigen-binding fragment thereof, of claim 2, wherein the $K_D$ of the antibody, or antigen binding fragment thereof, binding to active IL-33 is at least 10, 100, $1\times10^3$, $1\times10^4$, $1\times10^5$, $1\times10^6$, $1\times10^7$ times lesser than the $K_D$ of the antibody, or antigen binding fragment thereof, binding to an inactive form of IL-33.

18. The antibody, or antigen-binding fragment thereof, of claim 2, wherein the terminal half life in cynomologous monkeys is at least about 15 days.

\* \* \* \* \*